(12) United States Patent
Maynard

(10) Patent No.: US 10,273,333 B2
(45) Date of Patent: Apr. 30, 2019

(54) SUBSTITUTED POLYESTERS BY THIOL-ENE MODIFICATION: RAPID DIVERSIFICATION FOR THERAPEUTIC PROTEIN STABILIZATION

(71) Applicant: THE REGENTS OF THE UNIVERSITY OF CALIFORNIA, Oakland, CA (US)

(72) Inventor: Heather D. Maynard, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/394,483

(22) Filed: Dec. 29, 2016

(65) Prior Publication Data

US 2018/0112034 A1 Apr. 26, 2018

Related U.S. Application Data

(63) Continuation-in-part of application No. PCT/US2015/044973, filed on Aug. 13, 2015.

(60) Provisional application No. 62/036,973, filed on Aug. 13, 2014.

(51) Int. Cl.

| | |
|---|---|
| C08G 63/91 | (2006.01) |
| C07H 3/04 | (2006.01) |
| C08G 63/78 | (2006.01) |
| A61K 47/34 | (2017.01) |
| A61K 38/19 | (2006.01) |
| C12P 19/12 | (2006.01) |
| C08B 37/00 | (2006.01) |
| A61K 47/30 | (2006.01) |
| C08G 63/685 | (2006.01) |
| C08G 63/688 | (2006.01) |
| C08G 63/08 | (2006.01) |
| C08F 220/28 | (2006.01) |
| A61K 38/00 | (2006.01) |

(52) U.S. Cl.
CPC .......... *C08G 63/912* (2013.01); *A61K 38/193* (2013.01); *A61K 47/30* (2013.01); *A61K 47/34* (2013.01); *C07H 3/04* (2013.01); *C08B 37/0006* (2013.01); *C08G 63/08* (2013.01); *C08G 63/688* (2013.01); *C08G 63/6852* (2013.01); *C08G 63/6882* (2013.01); *C08G 63/78* (2013.01); *C08G 63/91* (2013.01); *C12P 19/12* (2013.01); *A61K 38/00* (2013.01); *C08F 2220/285* (2013.01); *C08F 2438/03* (2013.01); *C08G 2230/00* (2013.01)

(58) Field of Classification Search
None
See application file for complete search history.

(56) References Cited

U.S. PATENT DOCUMENTS

| | | |
|---|---|---|
| 2007/0059828 A1 | 3/2007 | Yamaoka et al. |
| 2009/0124534 A1 | 5/2009 | Reineke et al. |
| 2012/0142649 A1 | 6/2012 | Gray et al. |
| 2013/0028857 A1* | 1/2013 | Gao .................... A61K 39/385 424/78.29 |
| 2014/0017676 A1 | 1/2014 | Morhet et al. |
| 2014/0113879 A1 | 4/2014 | Carie et al. |

FOREIGN PATENT DOCUMENTS

| | | |
|---|---|---|
| EP | 0668294 | 8/1995 |
| WO | 2013112897 | 8/2013 |
| WO | WO-2013112897 A1 * | 8/2013 ............. C07H 17/04 |

OTHER PUBLICATIONS

Mancini, R.J.; Lee, J.; Maynard, H.D. J. Am. Chem. Soc., 2012, 134, 8474-8479.
Alconcel, S. N. S.; Baas, A. S.; Maynard, H. D. Polymer Chemistry 2011, 2, 1442.
Agarwal, S. Polym. Chem. 2010, 1, 953-964.
Bailey, W. J.; Wu, S. R.; Ni, Z. Makromolekulare Chemie-Macromolecular Chemistry and Physics 1982, 183, 1913.
Bailey, W. J.; Ni, Z.; Wu, S. R. Macromolecules 1982, 15, 711.
Bat, E.; Lee, J.; Lau, U. Y.; Maynard, H. D. Nature Communications 2015, 6.
Bentley, M. D.; Roberts, M. J.; Harris, J. M. J. Pharm. Sci. 1998, 87, 1446.
Besheer, A.; Liebner, R.; Meyer, M.; Winter, G. In Tailored Polymer Architectures for Pharmaceutical and Biomedical Applications; Scholz, C., Kressler, J., Eds.; Amer Chemical Soc: Washington, 2013; vol. 1135, p. 215. (Book chapter).
Campos, L. M.; Killops, K. L.; Sakai, R.; Paulusse, J. M. J.; Damiron, D.; Drockenmuller, E.; Messmore, B. W.; Hawker, C. J. Macromolecules 2008, 41, 7063.
Cerritelli, S.; Velluto, D.; Hubbell, J. A. Biomacromolecules 2007, 8, 1966.
Chi, E. Y.; Krishnan, S.; Randolph, T. W.; Carpenter, J. F. Pharm. Res. 2003, 20, 1325.
Congdon, T.; Notman, R.; Gibson, M. I. Biomacromolecules 2013, 14, 1578.
Congdon, T.; Wilmet, C.; Williams, R.; Polt, J.; Lilliman, M.; Gibson, M. I. European Polymer Journal 2015, 62, 352.
Decker, C. G.; Maynard, H. D. European Polymer Journal 2015, 65, 305.
Delplace, V.; Tardy, A.; Harrisson, S.; Mura, S.; Gigmes, D.; Guillaneuf, Y.; Nicolas, J. Biomacromolecules 2013, 14, 3769.

(Continued)

*Primary Examiner* — Christopher M Rodd
(74) *Attorney, Agent, or Firm* — Quarles & Brady LLP

(57) ABSTRACT

Structures and methods of making biodegradable trehalose co-polymers are disclosed. Specifically, biodegradable trehalose co-polymers consist of the general structure $R_5$—$[R_1R_2C$—$CR_3R_4]_n$-$[DG]_m$—$R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), wherein DG is a biodegradable group, and wherein $R_5$ and $R_6$ are end groups.

20 Claims, 86 Drawing Sheets

(56) References Cited

OTHER PUBLICATIONS

Dingels, C.; Muller, S. S.; Steinbach, T.; Tonhauser, C.; Frey, H. Biomacromolecules 2013, 14, 448.
Duro-Castano, A.; Conejos-Sánchez, I.; Vicent, M. Polymers 2014, 6, 515.
Ende, A. E. v. d.; Kravitz, E. J.; Harth, E. Journal of the American Chemical Society 2008, 130, 8706.
Gaertner, H. F.; Offord, R. E. Bioconjugate Chemistry 1996, 7, 38.
Gao, W.; Liu, W.; Christensen, T.; Zalutsky, M. R.; Chilkoti, A. Proceedings of the National Academy of Sciences 2010, 107, 16432.
Garman, A. J.; Barret Kalindjian, S. FEBS Letters 1987, 223, 361.
Gestwicki, J. E.; Cairo, C. W.; Strong, L. E.; Oetjen, K. A.; Kiessling, L. L. J. Am. Chem. Soc. 2002, 124, 14922.
Grover, G. N.; Maynard, H. D. Current Opinion in Chemical Biology 2010, 14, 818.
D'Ayala, G G.; Malinconico, M.; Laurienzo, P.; Tardy, A.; Guillaneuf, Y.; Lansalot, M.; D'Agosto, F.; Charleux, B. J. Polym. Sci., A, Polym. Chem. 2014, 52, 104-111.
Hardwicke, J.; Ferguson, E. L.; Moseley, R.; Stephens, P.; Thomas, D. W.; Duncan, R. Journal of Controlled Release 2008, 130, 275.
Hardwicke, J.; Moseley, R.; Stephens, P.; Harding, K.; Duncan, R.; Thomas, D. W. Mol. Pharmaceutics 2010, 7, 699.
Hardwicke, J. T.; Hart, J.; Bell, A.; Duncan, R.; Thomas, D. W.; Moseley, R. J. Controlled Release 2011, 152, 411.
Hedir, G. G.; Bell, C. A.; Ieong, N. S.; Chapman, E.; Collins, I. R.; O'Reilly, R. K.; Dove, A. P. Macromolecules 2014.
Hey, T.; Knoller, H.; Vorstheim, P. "Half-Life Extension through HESylatoin," in Therapeutic Proteins; Wiley-VCH Verlag GmbH & Co. KGaA: 2012, p. 117-140. (Book Chapter).
Hinou, H et al. "Systematic Syntheses and Inhibitory Activities of Bisubstrate-Type Inhibitors of Sialyltransferases" J. Org. Chem., vol. 68, 2003, pp. 5602-5613.
Hu, J.; Zhao, W.; Gao, Y.; Sun, M.; Wei, Y.; Deng, H.; Gao, W. Biomaterials 2015, 47, 13.
Iha, R. K.; van Horn, B. A.; Wooley, K. L. Journal of Polymer Science Part A: Polymer Chemistry 2010, 48, 3553.
Johnson, D. A. Carbohydr. Res. 1992, 237, 313.
Kanai, M.; Mortell, K. H.; Kiessling, L. L. J. Am. Chem. Soc. 1997, 119, 9931.
Keefe, A. J.; Jiang, S. Nat. Chem. 2012, 4, 59.
Knop, K.; Hoogenboom, R.; Fischer, D.; Schubert, U. S. Angew. Chem. Int. Ed. 2010, 49, 6288.
Kobben, S.; Ethirajan, A.; Junkers, T. Journal of Polymer Science Part A: Polymer Chemistry 2014, 52, 1633-1641.
Kozlowski, A.; Milton Harris, J. Journal of Controlled Release 2001, 72, 217.
Ladmiral, V.; Mantovani, G.; Clarkson, G. J.; Cauet, S.; Irwin, J. L.; Haddleton, D. M. J Am Chem Soc 2006, 128, 4823.
Leader, B.; Baca, Q. J.; Golan, D. E. Nat. Rev. Drug Discovery 2008, 7, 39.
Lee, J.; Lin, E.-W.; Lau, U.Y.; Hedrick, J.L.; Bat, E.; Maynard, H.D. Biomacromolecules, 2013, 14, 2561-2569.
Lee, J.; Ko, J. H.; Lin, E.-W.; Wallace, P.; Ruch, F.; Maynard, H. D. Polym. Chem. 2015, 6, 3443.
Li, L.; Xu, Y.; Milligan, I.; Fu, L.; Franckowiak, E. A.; Du, W. Angewandte Chemie-International Edition 2013, 52, 13699.
Li, F.; Pei, D. F.; Huang, Q. R.; Shi, T. F.; Zhang, G. Carbohyd Polym 2014, 99, 728.
Li, L.; Wang, J.; Obrinske, M.; Milligan, I.; O'Hara, K.; Bitterman, L.; Du, W. Chemical Communications 2015, 51, 6972.
Liu, Z.; Dong, C.; Wang, X.; Wang, H.; Li, W.; Tan, J.; Chang, J. ACS Applied Materials & Interfaces 2014, 6(4), 2393.
Lohmeijer, B. G. G.; Pratt, R. C.; Leibfarth, F.; Logan, J. W.; Long, D. A.; Dove, A. P.; Nederberg, F.; Choi, J.; Wade, C.; Waymouth, R. M.; Hedrick, J. L. Macromolecules 2006, 39, 8574.
Lundberg, P.; Lee, B. F.; van den Berg, S. A.; Pressly, E. D.; Lee, A.; Hawker, C. J.; Lynd, N. A. ACS Macro Lett. 2012, 1, 1240.
Lutz, J.-F.; Andrieu, J.; Üzgün, S.; Rudolph, C.; Agarwal, S. Macromolecules 2007, 40, 8540.
Markovsky, E.; Baabur-Cohen, H.; Eldar-Boock, A.; Omer, L.; Tiram, G.; Ferber, S.; Ofek, P.; Polyak, D.; Scomparin, A.; Satchi-Fainaro, R. Journal of Controlled Release 2012, 161, 446.
Yoshiko Miura et al: "Chemoenzymatic synthesis of glycoconjugate polymers starting from non-reducing disaccharides," Journal of Polymer Science Part A: Polymer Chemistry, vol. 42, No. 18, Jan. 1, 2004 (Jan. 1, 2004), pp. 4598-4606.
Nguyen, T. H.; Kim, S.-H.; Decker, C. G.; Wong, D. Y.; Loo, J. A.; Maynard, H. D. Nat. Chem. 2013, 5, 221.
Paz-Alfaro, K. J.; Ruiz-Granados, Y. G.; Uribe-Carvajal, S.; Sampedro, J. G. Journal of Biotechnology 2009, 141, 130.
Parrish, B.; Quansah, J. K.; Emrick, T. Journal of Polymer Science Part A: Polymer Chemistry 2002, 40, 1983.
Parrish, B.; Breitenkamp, R. B.; Emrick, T. Journal of the American Chemical Society 2005, 127, 7404.
Pelegri-O'Day, E. M.; Lin, E.-W.; Maynard, H. D. J. Am. Chem. Soc. 2014, 136, 14323.
Pfister, D.; Morbidelli, M. J. Controlled Release 2014, 180, 134.
Pratt, R. C.; Lohmeijer, B. G. G.; Long, D. A.; Waymouth, R. M.; Hedrick, J. L. Journal of the American Chemical Society 2006, 128, 4556.
Riachi, C.; Schüwer, N.; Klok, H.-A. Macromolecules 2009, 42, 8076.
Roberts, M. J.; Milton Harris, J. Journal of Pharmaceutical Sciences 1998, 87, 1440.
Roberts, M. J.; Bentley, M. D.; Harris, J. M. Advanced Drug Delivery Reviews 2002, 54, 459.
Roy, I. and Jain, N.K. Protein Science, 2009, 24-36.
Siegwart, D. J.; Bencherif, S.A.; Srinivasan, A.; Hollinger, J.0.; Matyjaszewski, K. J. Biomed. Mater. 2008, 87, 345-58.
Silvers, A. L; Chang, C.-C.; Emrick, T. J Polym Sci Pol Chem 2012, 50, 3517.
Sizovs, A.; Xue, L.; Tolstyka, Z. P.; Ingle, N. P.; Wu, Y.; Cortez, M.; Reineke, T. M. Journal of the American Chemical Society 2013, 135, 15417.
Slavin, S.; Burns, J.; Haddleton, D. M.; Becer, C. R. European Polymer Journal 2011, 47, 435.
Stidham, S. E.; Chin, S. L.; Dane, E. L.; Grinstaff, M. W Journal of the American Chemical Society 2014, 136, 9544.
Takasu, A.; Houjyou, T.; Inai, Y.; Hirabayashi, T. Biomacromolecules 2002, 3, 775.
Veronese, F. M.; Largajolli, R.; Boccú, E.; Benassi, C. A.; Schiavon, O. Appl Biochem Biotechnol 1985, 11, 141.
Wada, M.; Miyazawa, Y.; Miura, Y. Polymer Chemistry 2011, 2, 1822.
Wang, R.; Chen, W.; Meng, F.; Cheng, R.; Deng, C.; Feijen, J.; Zhong, Z. Macromolecules 2011, 44, 6009.
Woghiren, C.; Sharma, B.; Stein, S. Bioconjugate Chemistry 1993, 4, 314.
Xiao, N.; Liang, H.; Lu, J. Soft Matter 2011, 7, 10834.
Xiao, NY et al. "Preparations of Well-Defined and Degradable Aldehyde-Functionalized Glycopolymeric Nanospheres" Acta Polymerica Sinica, vol. 8, 2012, pp. 818-824; English translation of abstract only.
Xu, N.; Wang, R.; Du, F.-S.; Li, Z.-C. J Polym Sci Pol Chem 2009, 47, 3583.
Yan-Ling, L.; Yun-Fei, N.; Feng, X.; Ya-Shao, C.; Pei, Z. Journal of Biomaterials Science—Polymer Edition 2010, 21, 1143.
Yurkovetskiy, A.; Choi, S.; Hiller, A.; Yin, M.; McCusker, C.; Syed, S.; Fischman, A. J.; Papisov, M. I. Biomacromolecules 2005, 6, 2648.
Zalipsky, S.; Menon-Rudolph, S. In Poly(ethylene glycol); American Chemical Society: 1997; vol. 680, p. 318. (Book Chapter).
Zhang R.; Jain S.; Rowland, M.; Hussain, N.; Agarwal, M.; Gregoriadis, G. Journal of Diabetes Science and Technology 2010, 4, 532.
Abuchowski, A.; Kazo, G. M.; Verhoest Jr, C. R.; Van Es, T.; Kafkewitz, D.; Nucci, M. L.; Viau, k T.; Davis, F. F. Cancer Biochemistry Biophysics 1984, 7, 175.

* cited by examiner

Figure 81A
Figure 81B
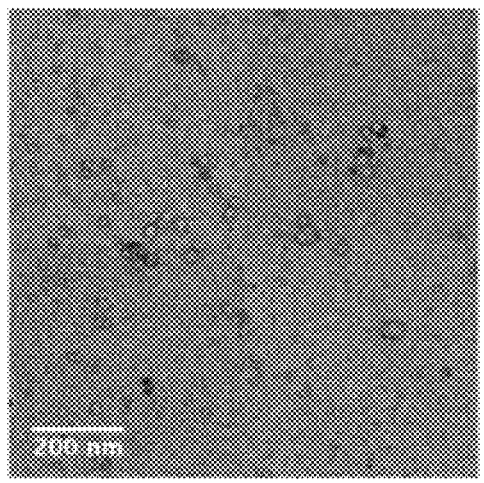
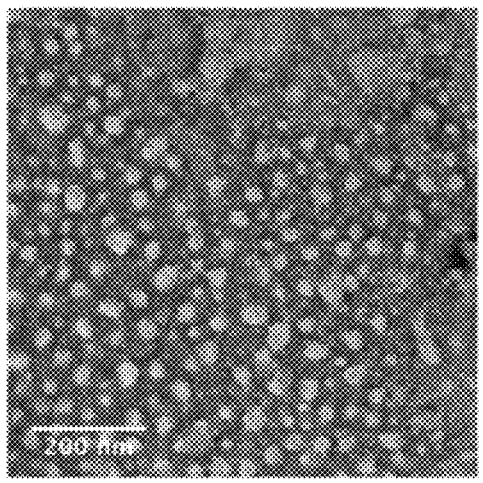
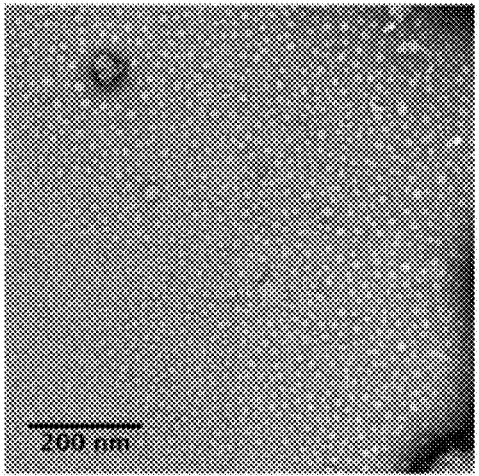
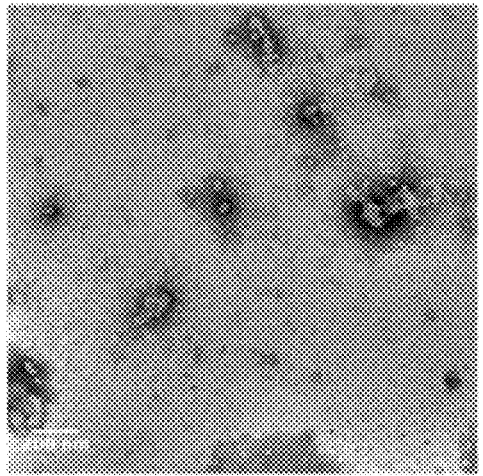
Figure 81C
Figure 81D Scheme 4

Scheme 11

*Protein Protection* — trehalose — *Polymer Degradation*

SUBSTITUTED POLYESTERS BY THIOL-ENE MODIFICATION: RAPID DIVERSIFICATION FOR THERAPEUTIC PROTEIN STABILIZATION

CROSS-REFERENCE TO RELATED APPLICATION(S)

This application is a continuation-in-part of PCT Application No. PCT/US2015/044973, filed on Aug. 13, 2015, which claims benefit from U.S. Provisional Application 62/036,973 filed Aug. 13, 2014, which is incorporated herein by reference for all purposes.

STATEMENT REGARDING FEDERALLY SPONSORED RESEARCH OR DEVELOPMENT

This invention was made with government support under Grant Numbers 1112550 and 1144087, awarded by the National Science Foundation. The government has certain rights in the invention.

FIELD OF THE INVENTION

Compositions and methods for biodegradable trehalose glycopolymers are disclosed. Specifically, the compositions include novel trehalose-based copolymers having biodegradable bonds, wherein the copolymers can be degraded into non-cytotoxic products.

BACKGROUND OF THE INVENTION

Since Adagen was approved by the Food and Drug Administration (FDA) as the first protein-polymer conjugate in 1990, the field of protein-polymer conjugates has grown tremendously. Currently, these biological therapeutics have grown to a market of over $7.4 billion in 2011 (Evaluate Ltd. Drug sales database; www.evaluategroup.com). Protein conjugates have diverse therapeutic applications ranging from enzyme replacement therapy to novel functions such as neutralization of over-active cytokines or receptors (Alconcel et al., 2011). As a result, the treatment duration of a protein conjugate also ranges significantly. Some treatments are temporary, but protein-polymer conjugates are also used in enzyme replacement therapy, requiring injections over an extended period to treat chronic diseases such as severe combined immunodeficiency (SCID) or gout (Alconcel et al., 2011).

While protein-polymer conjugates offer unique solutions to problems of missing or malfunctioning enzymes, their chronic use presents long-term challenges in vivo. Currently, all ten Food and Drug Administration (FDA)-approved therapeutic protein conjugates use poly(ethylene glycol) (PEG) (Pfister and Morbidelli, 2014; Besheer et al., 2013; Pelegri-O'Day et al., 2014). PEG is widely used in many disciplines, yet some deficiencies in its therapeutic application have been observed. These include non-biodegradability causing accumulation in tissue and immunological responses such as accelerated blood clearance upon multiple doses (Besheer et al., 2013; Chi et al., 2003).

Polymer conjugation also typically results in a decrease in bioactivity of the conjugate due to steric shielding of the protein active site. In addition, protein therapeutics often must be formulated with excipients for additional stabilization since proteins are highly susceptible to losses in activity when exposed to temperature fluctuations and other stressors ("FDA Access Data", www.accessdata.fda.gov). While PEGylation often increases stability against environmental stressors, all of protein-PEG conjugates still need to be refrigerated and contain excipients as stabilizers (Leader et al., 2008; Keefe and Jiang, 2012; Nguyen et al., 2013).

PEG alternatives have been developed which improve upon these drawbacks. For instance, previous work in the Maynard group has shown that polymers containing pendant trehalose units stabilize proteins against heat, lyophilization, and electron irradiation (Mancini et al., 2012; Lee et al., 2013; Bat et al., 2015; Lee et al., 2015). Trehalose is a widely used excipient used in the food and cosmetic industries and has been shown to be important in protecting animals and plants against dehydration stress (Jain and Roy, 2009). Other polymers have been shown to exhibit protein-stabilizing properties, including charged polymers, polyols, and other saccharide-based materials (Keefe and Jiang, 2012; Nguyen et al., 2013; Congdon et al., 2013; Stidham et al., 2014; Hu et al., 2015). All these polymers are being actively investigated as PEG alternatives, which also offer stabilization against environmental stressors. However, these examples are still not biodegradable.

Degradable polymers are important to avoid build-up of polymer within the body, especially for enzyme replacement and other chronic therapies. Degradable polysaccharide conjugates have also been prepared by conjugating proteins to biopolymers such as hydroxyethyl starch (HES)(Hey et al., 2012), polysialic acid (Zhang et al., 2010), and dextrin (Hardwicke et al., 2010; Hardwicke et al., 2011). The synthesis of a degradable protein-polymer conjugate by controlled radical polymerization (CRP) has also recently been reported (Decker and Maynard, 2015). Many of these conjugates display increased in vivo half-lives. However, many of these polymers are heterogeneous, which might make FDA approval more difficult, and do not necessarily stabilize proteins.

We sought to prepare well defined polyester backbone and trehalose side chain polymers so that the polymers would stabilize proteins and biodegrade. Previous examples of well-defined biodegradable glycopolymers (none have been reported with trehalose) containing either esters or amides in the main chain backbone were polymerized in two ways: by polymerization of sugar-functionalized monomers, or by post-polymerization modification of polymers containing reactive handles (Xu et al., 2009; Slavin et al., 2011). However, typical polyester or polyamide syntheses require anhydrous conditions, which is compatible with the low solubility of trehalose in typical organic solvents. Therefore, polyesters containing reactive handles were first synthesized, which could be later functionalized with trehalose units after polymerization and purification. While a variety of high-yielding "click" reactions have been demonstrated for the synthesis of glycopolymers, the thiol-ene reaction yields a stable thioether, which can be formed in high yields (Campos et al., 2008).

Polymers may be used as additives to prevent mis-folding and denaturation of proteins. However, the use and development of polymers as food additives and drug component presents its own problems, as polymer longevity causes down-chain problems in waste management and disposal. Due to the wide applicability of polymers in both medical and non-medical fields, interest in developing biodegradable polymers has greatly increased (Agarwal, S. *Polym. Chem.* 2010, 1, 953-964). Moving towards synthesis of easily degradable, "green" polymers will be increasingly important as polymers continue to be used worldwide.

Trehalose is a non-reducing disaccharide formed by α,α-1,1-linked glucose units, which has been proven to exhibit protection against temperature changes and dehydration[2] and is widely used in the food and cosmetic industries. Applicants' previous work has shown that glycopolymers with pendant trehalose groups offer superior protection to both heat burden and lyophilization, better than free (non-polymeric) trehalose and poly(ethylene glycol) (PEG) (Mancini et al., 2012; Lee et al., 2013). These polymers are promising for a variety of applications, but Applicants herein develop techniques to make the polymers degradable.

Needed in the art are biodegradable polymers that stabilize proteins and biodegrade and that can be readily synthesized with reasonable production. Needed in the art are degradable trehalose glycopolymers that stabilize proteins and other biomolecules (e.g., to the lyophilization process and to heat burden) and also can be degraded through simple processes such as ester hydrolysis.

SUMMARY OF THE INVENTION

In one aspect, the present invention relates to a biodegradable trehalose co-polymer. The co-polymer consists of the general structure:

$R_5$—[$R_1R_2C$—$CR_3R_4$]$_n$-[DG]$_m$—$R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), wherein DG is a biodegradable group, and wherein $R_5$ and $R_6$ are end groups.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one embodiment, $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), and biomolecules.

In one embodiment, DG comprises at least one ester group.

In one embodiment, the ester group is in the backbone of the co-polymer.

In one embodiment, the ester group is produced from a cyclic ketene acetal through ring-opening polymerization.

In one embodiment, the cyclic ketene acetal has the structure of

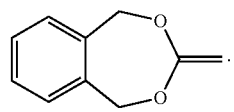

In one embodiment, the degradation products of the co-polymer are non-cytotoxic, and the degradation products of the co-polymer do not disrupt cell proliferation.

In one embodiment, the co-polymer has a structure of

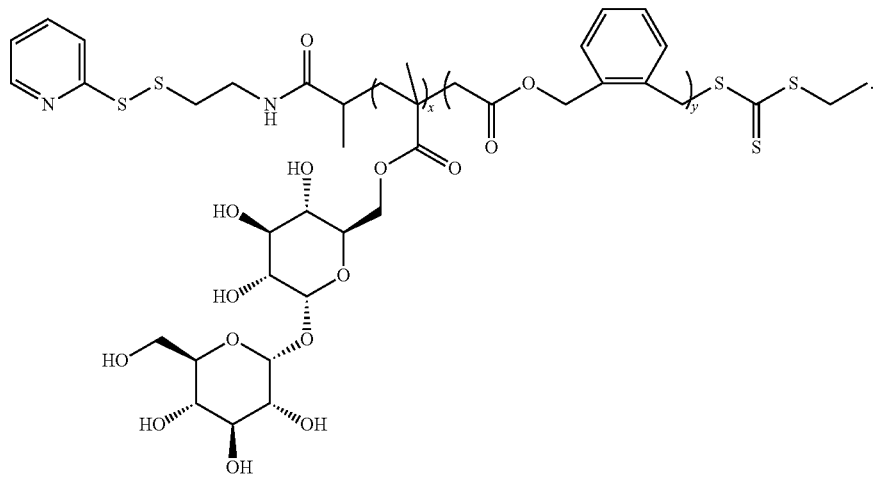

In one embodiment, the co-polymer is degradable under basic conditions or by hydrolysis in vitro or in vivo.

In one embodiment, the co-polymer has a structure of

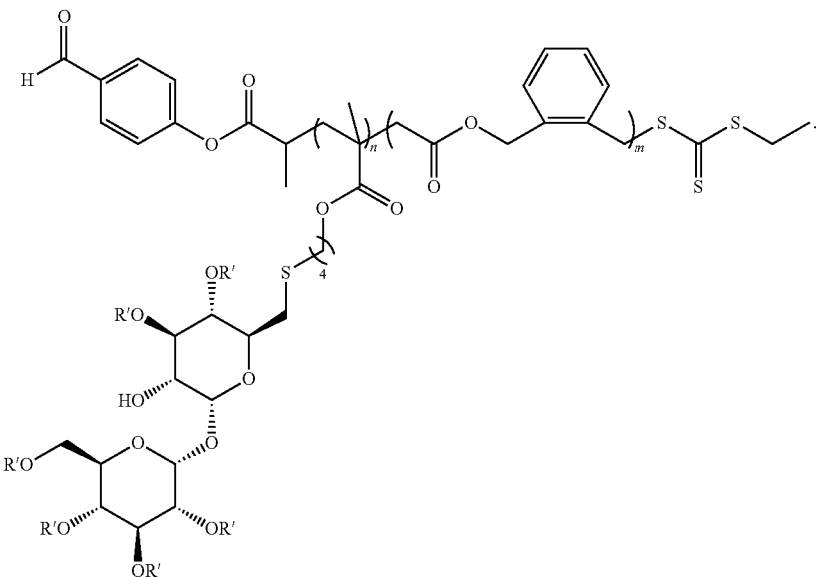

In one aspect, the present invention discloses a biodegradable trehalose co-polymer, wherein the polymer consists of the general structure:

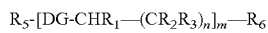

wherein $R_1$-$R_3$ are independently selected from hydrogen or a side chain comprising at least one carbon atom, and wherein at least one of $R_1$-$R_3$ is a side chain comprising -L-trehalose, wherein L is a linker molecule that links trehalose to the co-polymer through at least one of the trehalose hydroxyl groups (—OH), wherein DG is a biodegradable group, and wherein $R_5$ and $R_6$ are end groups, and wherein n=0-10, wherein m≥1.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one embodiment, $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO) (Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), and biomolecules.

In one embodiment, DG comprises at least one ester group.

In one embodiment, the ester group is in the backbone of the polymer.

In one aspect, the present invention discloses a method of synthesizing a biodegradable trehalose co-polymer for stabilizing a biomolecule, the method comprising the steps of: (a) incorporating a side chain comprising a trehalose molecule into a polymerizable monomer; and (b) co-polymerizing the resulting monomer with a cyclic ketene acetal to obtain a co-polymer according to claim 1.

In one embodiment, the co-polymer is generated through chemical synthesis.

In one embodiment, the polymerizable monomer is selected from the group consisting of a styrene monomer, an acrylate monomer, a methacrylate monomer, an acrylamide monomer, a methacrylamide monomer, a vinyl monomer, a norborenyl monomer, and a strained cycle alkene monomer.

In one embodiment, the cyclic ketene acetal has the structure of

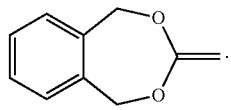

In one embodiment, the step of co-polymerizing the resulting monomer to obtain a homopolymer or copolymer is performed by any one of, but not limited to the following techniques; reversible addition-fragmentation chain transfer (RAFT) polymerization, atom transfer radical polymerization (ATRP), nitroxide mediated polymerization (NMP), cyanoxyl-mediated free radical polymerization, conventional radical polymerization, or ring opening polymerization (ROP).

In one embodiment, the step of co-polymerizing the resulting monomer to obtain a homopolymer or co-polymer is performed by reversible addition-fragmentation chain transfer (RAFT) polymerization.

In one embodiment, one or more of the hydroxyl groups of the trehalose are protected by the formation of an acetal or an ether.

In one aspect, the present invention discloses a method of synthesizing a biodegradable trehalose polymer for stabilizing a biomolecule. The method comprises the steps of: a) polymerizing a cylic ester with an alcohol with to form a polymer, where in the cylic ester includes a pendant functional group; b) preparing a thiolated trehalose monomer; c) reacting the polymer with the thiolated trehalose monomer to form the biodegradable trehalose polymer.

In one embodiment, the cyclic ester is an allyl-functionalized caprolactone (aCL).

In one embodiment, the alcohol is a primary alcohol as an initiator.

In one embodiment, the reaction in step a) is a ROP.

In one embodiment, the reaction in step a) further needs a catalyst.

In one embodiment, the catalyst is triazabicyclodecane (TBD).

In one embodiment, the thiolated trehalose monomer has the structure of:

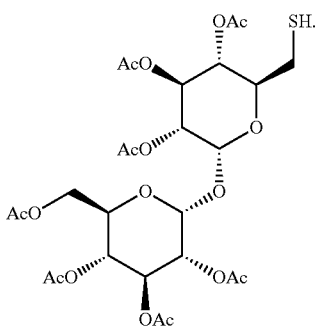 [SMILES: CC(=O)OC[C@H]1O[C@H](O[C@H]2O[C@H](CS)[C@@H](OC(C)=O)[C@H](OC(C)=O)[C@H]2OC(C)=O)[C@H](OC(C)=O)[C@@H](OC(C)=O)[C@@H]1OC(C)=O]

BRIEF DESCRIPTION OF THE DRAWINGS

FIG. 81A is a picture showing transmission electron micrographs of pCL-trehalose$_{80}$.

FIG. 81B is a picture showing transmission electron micrographs of pCL-zwitterion$_{80}$.

FIG. 81C is a picture showing transmission electron micrographs of pCLtrehalose$_{80}$ and G-CSF mixture.

FIG. 81D is a picture showing transmission electron micrographs of pCL-zwitterion$_{80}$ and G-CSF mixture. Solutions contained polymer (1 mg/mL) and G-CSF (0.15 mg/mL) and samples were stained using uranyl acetate as a negative stain.

DETAILED DESCRIPTION OF THE INVENTION

In General

Figure 1:
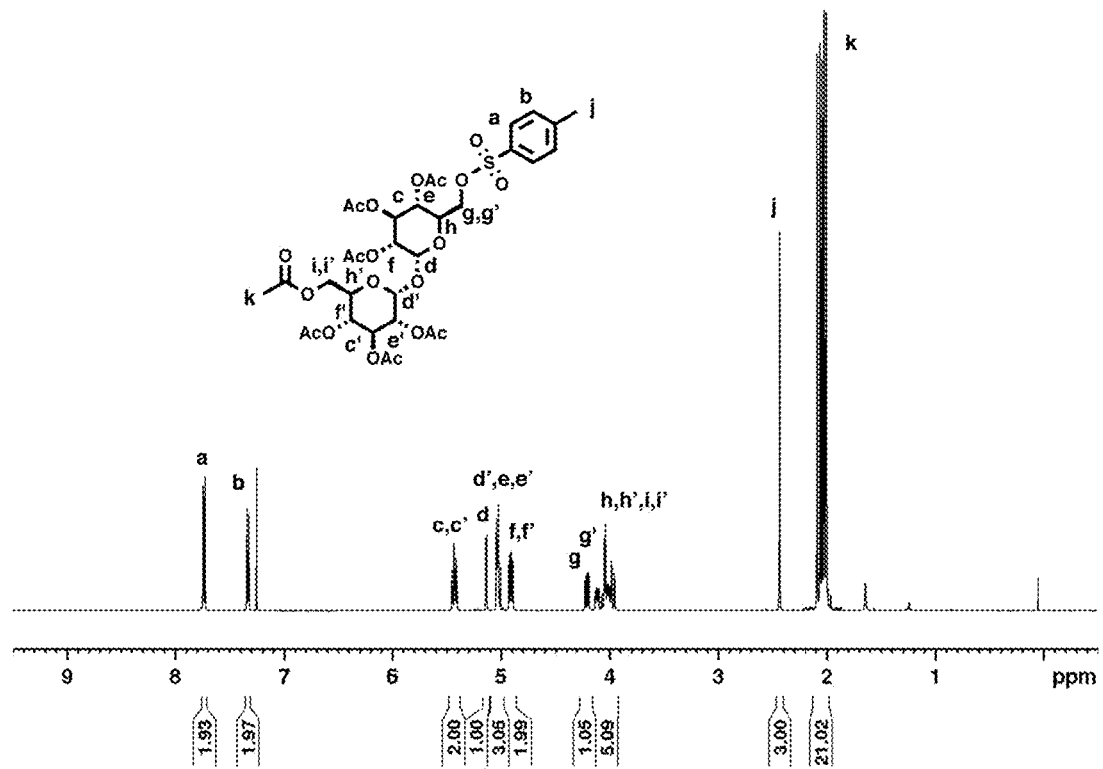
FIG. 1 is a graph showing $^1$H-NMR (500 MHz, CDCl$_3$) of tosylated trehalose 4.

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Definitions

Before the composition and related methods are described, it is to be understood that this invention is not limited to the particular methodology, protocols, materials, and reagents described, as these may vary. The terminology used herein is for the purpose of describing particular embodiments only, and is not intended to limit the scope of the present invention which will be limited only by any later-filed non-provisional applications.

The invention described herein provides compositions and methods for biodegradable trehalose glycopolymers, that have biodegradable bonds. The invention also provides a means for stabilizing biomolecules by protecting or maintaining the structure using effective amounts biodegradable trehalose glycopolymers added or conjugated to the biomolecules.

According to one embodiment of the invention, the as-disclosed trehalose-based copolymers show both biodegradability and stabilization abilities. Biodegradable trehalose-based homopolymer or copolymers are used to stabilize protein molecules against aggregation, conformational changes and/or degradation, such as denaturation of native protein, helping to maintain the protein in the desired configuration in a hostile or stressful environment, and intended function is maintained to be at least equal to the protein in its natural states or is enhanced over a reduced activity that the protein would have in the stressful environment. While proteins can be stabilized against degradation, e.g. by heat, electromagnetic radiation, shear stress, proteolysis, or by chemical modification such as reduction, oxidation, or carbamylation, biodegradable trehalose-based homopolymer or copolymers are degradable under certain conditions and degradation products are non-cytotoxic and do not disrupt cell proliferation.

In some embodiments, biodegradable trehalose-based homopolymers or copolymers may be completely degraded after 24 hours under a base condition (e.g., 5% KOH). In one embodiment, biodegradable trehalose-based homopolymers or copolymers may be degraded slowly in aqueous solution by ester hydrolysis in aqueous solution. The hydrolysis can be accelerated to study the degradation by subjecting to 24 hours under a base condition.

One method for producing biodegradable trehalose-based co-polymers may include a step of cyclic ketene acetals undergoing ring-opening polymerization to produce an ester in the growing polymer backbone. The method may also include a step of co-polymerization of cyclic ketene acetals with one trehalose-based monomer by using ATRP, RAFT, or NMP.

Another method for producing biodegradable trehalose-based co-polymers may include a step of co-polymerization of cyclic ketene acetals with another monomer to produce biodegradable backbone copolymers with active sites. The method may also include a step of attaching trehaloses to the biodegradable backbone co-polymers at the active sites.

One method for producing biodegradable trehalose-based polymers may include the step of polymerizing a cylic ester with an alcohol with to form a polymer, where in the cylic ester includes a pendant functional group. The method may also include a step of reacting the polymer with the thiolated trehalose monomer to form the biodegradable trehalose polymer.

The term "aryl" refers to a carbocyclic (non-heterocyclic or heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "alkyl" refers to optionally substituted straight chain or branched chain hydrocarbon groups. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "alkyl" also encompasses alkyl groups containing one less hydrogen atom such that the group is attached via two positions, i.e., divalent. "$C_{1-4}$alkyl" and "$C_{1-3}$alkyl" including methyl, ethyl, propyl, isopropyl, n-butyl, iso-butyl, sec-butyl and tert-butyl are preferred with methyl being particularly preferred.

The term "biodegradable," as used herein, refers to the capability of being broken down into innocuous products in the normal functioning of the human body, tissues and cells and living organisms (e.g., bacteria).

The term "biodegradable bonds," as used herein, refer to chemical bonds that are dissociable or broken under biological conditions of the normal functioning of the human body, tissues and cells and living organisms. In one embodiment, the present invention discloses polymers that comprise at least one biodegradable bond, e.g., ester, amide, disulfide, or phosphate linkages bond. In one embodiment, the present copolymers may include at least one biodegradable bond on the backbone of the copolymers.

The term "biodegradable polymers," as used herein refer to a specific type of polymer that breaks down after its intended purpose to result in natural byproducts such as gases ($CO_2$, $N_2$), water, other small molecule organic or inorganic byproducts, biomass, and inorganic salts. In one embodiment, the biodegradable polymers are synthetically made, and largely consist of ester, amide, disulfide, acetal, imine, oxime, Diels-Alder adduct, orthoester, hydrazone, cis-aconitryl, carbonate, carbamate, carbamide, glycosidic saccharide linkages, anhydride, phosphoester, phosphoanhydride, iminocarbonate, cyanoacrylate, phosphazene, phosphoramidate, amide-enamine, urea, urethane or any functional group which can degrade in a Natural system. The biodegradable polymers may often be synthesized by condensation reactions, ring opening polymerization, and metal catalysts. In one embodiment, the biodegradable polymers of the present invention include trehaloses that can stabilize proteins or any other biomolecules. In one embodiment, biodegradable polymers (e.g., caprolactone polymers) may be produced by using a ring opening reaction. In one embodiment, biodegradable polymers (e.g., BMDO polymers) may be produced by using radical polymerizations.

The term "pendant functional group," as used herein refers to a functional group that is a pendant branch from the backbone of a co-polymer. In one embodiment, the pendant functional group provides a location where additional functional groups, e.g., trehalose, can be attached to the backbone of co-polymers.

The term "stressful environment," as used herein, means an environment which will reduce a functional property or activity of a biomolecule. For example, the environment may reduce a functional property or activity of a protein over a native protein or that which the protein has in its natural state. A stressful environment may include temperatures which create adverse thermal environments which could be elevated or reduced temperatures, solvents such as an organic solvent, the presence of proteases, pH and/or lack of buffer.

The term "biomolecule" as used herein refers, but is not limited to proteins, enzymes, antibodies, DNA, siRNA, and pharmaceutical compositions. Such biomolecules are subject to environmental stresses which include but are not limited to heat, desiccation, light, storage, exposure to enzymes, endo- and exo-nucleases and pH variation.

The term "protein" used herein refers to any compound of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment"

of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be naturally occurring and isolated from its source. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation, e.g., using E. coli lysate, wheat germ extract, or rabbit reticulocyte. Cell free in vitro translation methods can be employed following in vitro transcription, e.g., following phage or ribosome display.

Examples of proteins include, without limitation, Lysozyme, Adenosine deaminase, L-Asparaginase, Mammalian urate oxidase, Interferons, Anti-TNF a Fab, granulocyte colony stimulated factor (G-CSF), Continuous erythropoietin receptor activator, hGH antagonist B2036, Insulin, Insulin human inhalation, Insulin aspart, Insulin glulisine, Insulin lispro, Isophane insulin, Insulin detemir, Insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIIa, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

The term "stability" refers to the maintenance of a protein or other biomolecule's native bioactivity function after storage. The present invention will provide stability of at least 70%, and preferably at least 80%, of the protein's function as compared to storage without a trehalose stabilizing agent under identical environmental conditions. It is envisioned that, for example, when a protein like insulin is conjugated with a trehalose-based polymer or copolymer as described here, the insulin protein retains at least 70%, 75%, 80%, 85%, 90% or greater percentage of its native bioactivity compared to insulin by itself, which may retain only 20% of its original bioactivity at best. Those skilled in the art appreciate that the percent of bioactivity that is retained is protein and stress dependent. Furthermore, the length of time that a conjugated protein is able to maintain its bioactivity or function compared to a naked/unmodified protein varies depending on the environmental stressors it is subjected to. It is envisioned the conjugated proteins as described here can retain bioactivity for at least 5, 10, 20, 30, 40, 50, 60, 70, 80, 90, or 100 times longer than an unconjugated native protein under identical environmental conditions.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain trans gene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies can also comprise a murine variable region and a human constant region. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted above for chimeric and bifunctional antibodies.

The term "human antibody" includes antibodies having variable and constant regions derived from human germline immunoglobulin sequences. The variable heavy chain is preferably derived from germline sequence DP-50 and the variable light chain is derived from germline sequence L6. The constant regions of the antibody are constant regions of human IgG 1 type.

The term "recombinant human antibody" includes all human antibodies that are prepared, expressed, created or isolated by recombinant means, such as antibodies isolated from a host cell such as an SP2-0, NS0 or CHO cell (like CHO K1) or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "antibody" also includes "antibody fragments" or "antibody-derived fragments" which comprise an antigen binding domain are also included. The term "antibody fragment" as used herein is intended to include any appropriate antibody fragment that displays antigen binding function, for example, Fab, Fab', F(ab')$_2$, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "sugar polymer" as used herein encompasses polymeric and oligomeric saccharide molecules comprising three or more mono-, di- or tri-saccharide units. The sugar polymer can be a linear or non-linear amphipathic sugar polymer derivative. Specifically, sugar polymers comprise one or more sugar(s) including, without limitation, trehalose, erythrose, threose, ribose, arabinose, xylose, lyxose, allose, altrose, glucose, mannose, gulose, idose, galactose, talose, psicose, fructose, sorbose, tagatose, xylulose and ribulose. The sugar polymers can be a dextran, cellulose, amylose, starch, pullulan, mannan, chitin, chitosan, inulin, levan, xylan, cyclodextrin (provided that it is not an alpha, beta or gamma cyclodextrin), cycloamylose or a derivative thereof.

Sugar polymers, specifically trehalose-based homopolymer or copolymers suitable for use in the invention are those which, at an appropriate concentration and in appropriate conditions, can (1) maintain a native biomolecule in its native state to retain a functional property of the native biomolecule in a stressful environment or (2) maintain a denatured biomolecule in a non-native state as desired by the researcher. Suitable trehalose-based homopolymer or copolymers are those which are capable of shielding hydrophobic amino acid side chains or modifying the net biomolecule charge or hydrogen bonding characteristics. Suitable trehalose-based homopolymer or copolymers may also comprise those capable of water entrapment, or those having hydrogen bonding characteristics.

As used herein, the term "glycopolymer" refers to any polymer that comprises one or more saccharide moieties, for example, a polysaccharide, or a glycosaminoglycan.

The term "trehalose-based monomer," as used herein, refers to a monomer including at least one trehalose which is covalently bound to the side chain of the monomer.

The term "ring-opening polymerization" or "ROP," as used herein, refers to a form of chain-growth polymerization, in which the terminal end of a polymer chain acts as a reactive center where further cyclic monomers can react by opening its ring system and form a longer polymer chain. The propagating center can be radical, anionic or cationic. Some cyclic monomers such as norbornene or cyclooctadiene can be polymerized to high molecular weight polymers by using metal catalysts. ROP continues to be a versatile method of synthesis of major groups of biopolymers, particularly when they are required in quantity. In one embodiment, the caprolactone polymer in the present invention may be produced by ROP.

The term "physiological conditions," as used herein, refers to conditions of the external or internal milieu that may occur in nature for that organism or cell system, in contrast to artificial laboratory conditions. A temperature range of 20-40 degrees Celsius, atmospheric pressure of 1, pH of 4-8, glucose concentration of 1-20 mM, atmospheric oxygen concentration, and earth gravity are examples of physiological conditions for most earth organisms.

The term "Atom transfer radical polymerization" or "ATRP," as used herein, refers to an example of a reversible-deactivation radical polymerization, wherein a carbon-carbon bond forms through a transition metal catalyst. The atom transfer step is the key step in the reaction responsible for uniform polymer chain growth.

The term "Reversible Addition-Fragmentation chain Transfer" or "RAFT," as used herein, refers to one of several kinds of Reversible-deactivation radical polymerization wherein a chain transfer agent in the form of a thiocarbonylthio compound (or a similar RAFT agent) is used to afford control over the generated molecular weight and polydispersity during a free-radical polymerization.

The term "Nitroxide-mediated radical polymerization" or "NMP," refers to a method of radical polymerization that makes use of an alkoxyamine initiator to generate polymers with well controlled stereochemistry and a very low polydispersity index.

The term "ring-opening polymerization" or "ROP," as used herein, refers to a form of chain-growth polymerization, in which the terminal end of a polymer chain acts as a reactive center where further cyclic monomers can react by opening its ring system and form a longer polymer chain. The propagating center may be radical, anionic or cationic.

In one embodiment, the ROP of the present invention may be an anionic ring-opening polymerizations (AROP).

The term "anionic ring-opening polymerizations" or "AROP," as used herein, refers to ring-opening polymerizations that involve nucleophilic reagents as initiators.

Ring-opening may be triggered by the nucleophilic attack of the initiator to the carbon, forming a new species that will act as a nucleophile. The sequence may repeat until the polymer is formed.

A typical example of anionic ROP is that of ε-caprolactone, initiated by an alkoxide functional group.

The term "zwitterion" or "zwitterionic," as used herein, refers to a neutral molecule with both positive and negative electrical charges. Zwitterions may also be called dipolar ions or inner salts, which are different from molecules that have dipoles at different locations within the molecule.

In one embodiment, zwitterions may be amino acids. Amino acids contains an ammonium and a carboxylate group, and can be viewed as arising via a kind of intramolecular acid-base reaction: The amine group deprotonates the carboxylic acid.

Many other compounds may also be used as zwitterions. For example, bicine and tricine, containing a basic secondary or tertiary amine fragment together with a carboxylic acid fragment, may be used as zwitterions. Further, many alkaloids, such as LSD and psilocybin, may also be used as zwitterions as they contain carboxylates and ammonium centres.

Many zwitterions may contain quaternary ammonium cations. Because it lacks N—H bonds, the ammonium center cannot participate in tautomerization. The membrane-forming phospholipids may also be zwitterions. The polar head groups in phospholipids may be zwitterions, resulting from the presence of the anionic phosphate and cationic quaternary ammonium centres.

The term "poly(caprolactone)," "polycaprolactone" or "pCL," as used herein, refers to a biodegradable polyester having the general structure of $-[(CH_2)_m-COO]_n-$ or $-[O(CH_2)_m-CO]_n-$. PCL may also be called (1,7)-polyoxepan-2-one, 2-Oxepanone homopolymer, or 6-Caprolactone polymer. PCL may be prepared by ring opening polymerization of ε-caprolactone using a catalyst such as stannous octoate.

PCL has been approved by the Food and Drug Administration (FDA) in specific applications used in the human body as (for example) a drug delivery device, suture (sold under the brand name MONOCRYL or GENERICALLY), or adhesion barrier.

In one embodiment, pCL may be used as the backbone of the biodegradable polymers of the present invention.

The term "backbone," "backbone chain" or "main chain," as used herein, refers to the linear chain to which all other chains, long or short or both, may be regarded as being pendant. The backbone chain or main chain of a polymer may be the series of covalently bounded atoms that together create the continuous chain of the molecule.

The term "side chain" or "pendent chain," as used herein, refers to a chemical group that is attached to a core part of the molecule of main chain or backbone.

In one embodiment, the side chains of the present invention may be trehalose-based side chains.

In another embodiment, the side chains of the present invention may be zwitterion-based side chains.

The term "thiol-ene reaction" or "alkene hydrothiolation," as used herein, refers to an organic reaction between a thiol and an alkene to form an alkyl sulfide.

Thiol-ene additions may proceed through two different mechanisms: free-radical additions and catalyzed Michael additions. Free-radical additions may be initiated by light, heat or radical initiators, which form a thiyl radical species. The radical may then propagate with an ene functional group via an anti-Markovnikov addition to form a carbon-centered radical. A chain-transfer step may remove a hydrogen radical from a thiol, which can subsequently participate in multiple propagation steps.

The term "allyl," as used herein, refers to a substituent with the structural formula $H_2C=CH-CH_2R$, where R is the rest of the molecule. It consists of a methylene bridge ($-CH_2-$) attached to a vinyl group ($-CH=CH_2$).

The term "excipient," as used herein, refers to a substance formulated alongside the active ingredient of a medication. An excipient may be included for the purpose of long-term stabilization, bulking up solid formulations that contain potent active ingredients. An excipient may also be used to confer a therapeutic enhancement on the active ingredient in the final dosage form, such as facilitating drug absorption, reducing viscosity, or enhancing solubility. Excipients may also be referred to as "bulking agents," "fillers," or "diluents."

The term "cytotoxic," as used herein, refers to being toxic to cells.

The Invention

In one aspect, the application discloses biodegradable trehalose-based copolymers and methods of making the copolymers.

In one aspect, the present invention discloses degradable trehalose glycopolymers. Preferably, the trehalose glycopolymers are bio-degradable. The trehalose glycopolymers in the present invention may be co-polymers.

In one embodiment, the present trehalose copolymer consists of the general structure of (1):

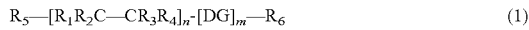

wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose —OH groups, wherein DG is a biodegradable functional group, and wherein $R_5$ and $R_6$ are the end groups.

In some embodiments, the end groups of $R_5$ and $R_6$ are independently selected from the group consisting of activated disulfides, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, alkynes, derivatives thereof, and a combination thereof or any end group that can react with a natural or unnatural functional group of a biomolecule.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one specific embodiment, $R_5$ and $R_6$ are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, and biomolecules.

In one embodiment, any of $R_1$-$R_4$ that is not-L-trehalose is either hydrogen or an alkyl group. In one specific embodiment, the alkyl group is preferably a methyl group.

In one embodiment, one of $R_1$-$R_4$ is an alkyl group and two of $R_1$-$R_4$ are hydrogen. In one specific embodiment, the alkyl group is preferably a methyl group.

In one embodiment, the biodegradable functional groups of DG may include ester, amide, or disulfide groups, acetal, imine, oxime, Diels-Alder adduct, orthoester, hydrazone, cis-aconitryl, carbonate, carbamate, carbamide, glycosidic saccharide linkages, anhydride, phosphoester, phosphoanhydride, iminocarbonate, cyanoacrylate, phosphazene, phosphoramidate, amide-enamine, urea, urethane or any group which can degrade in a Natural system or any other group which can degrade in a natural system. In one preferred embodiment, the biodegradable group of DG comprises at least one ester group. More preferably, the ester group is in the backbone of the co-polymers.

In one embodiment, the co-polymers with biodegradable groups of DG on the backbone may be synthesized through a ring-opening polymerization (ROP) reaction of a cyclic ketene acetal with other monomers. The cyclic ketene acetal provides biodegradable groups of DG, i.e., ester into the backbone of the co-polymers.

In one embodiment, cyclic ketene acetals or monomers that can introduce the degradable group into the co-polymers may include 5,6-benzo-2-methylene-1,3-dioxepane (BMDO), 2-methylene-4-phenyl-1,3-dioxalane (MPDL), 2-methylene-1,3-dioxalane, 2-methylene-4-hexyl-1,3-dioalane, 2-methylene-4-decyl-1,3-dioalane, 2,4-dimethylene-1,3-dioxalane, 2,5-dimethylene-1,3,-dioxane, 2-methylene-1,3-dioxepane (MDO), 2,5-methylene-1,3-dioxane, 4,7-dimethyl-2-methylene-1,3-dioxepane, 4-phenyl-2-propenylene-1,3-dioxalane, 2-methylene-1,3-dioxe-5-pene, 2-ethylidene-4-methyl-1,3-dioxane, 2-ethylidene-4-ethyl-1,3-dioxane, 2-ethylidene-1,3-dioxane, 1-vinyl-4,7-dioxaspiro-[2,4]heptane, 1-vinyl-4,9-dioxaspiro-[2.6]nonane, 1-vinyl-6,7-benzo-4,9-dioxaspiro[2.6]nonane, 9,9-disubstituted-4-methylene-3,5,8,10-tetraoxabicyclo[5.3.0]decane, 3,9-bis-methylene-2,4,8,10-tetraoxa-spiro[5,5]undecane, or 2-methylene-1,3,6-trioxocane.

In one preferred embodiment, the ester group is produced from a cyclic ketene acetal through a ROP reaction. More preferably, the cyclic ketene acetal is BMDO that has the structure of

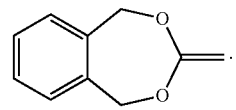

In one embodiment, the copolymers with the general structure of (1) may be produced from a cyclic ketene acetal with another monomer by using any suitable polymerization reactions. In another embodiment, the polymerization reactions may include free radical polymerization, reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROP). In one embodiment, the present degradable trehalose copolymers are synthesized through a RAFT reaction of a cyclic ketene acetal, e.g., BMDO, with another monomer.

In one embodiment, the other monomer comprises a trehalose. Applicants' previous PCT patent application No. PCT/US2013/023235 discloses many trehalose-based monomoers that are suitable for the present invention. Example 2 shows some exemplary monomers and methods of making such monomers.

In one embodiment, the trehalose co-polymers may be degraded under certain physiological conditions. In one embodiment, physiological conditions may include basic conditions or hydrolysis in vitro or in vivo. Applicants envision that other suitable physiological conditions as appreciated by one skilled in the art may also be used for degradation of the trehalose co-polymers. In one preferred embodiment, the degradation products of co-polymers are non-cytotoxic and the products do not disrupt cell proliferation. Scheme 10 in Example 2 shows one exemplary biodegradation of trehalose co-polymers under basic conditions to accelerate the degradation.

In one preferred embodiment, the present trehalose co-polymer has a structure (2) of

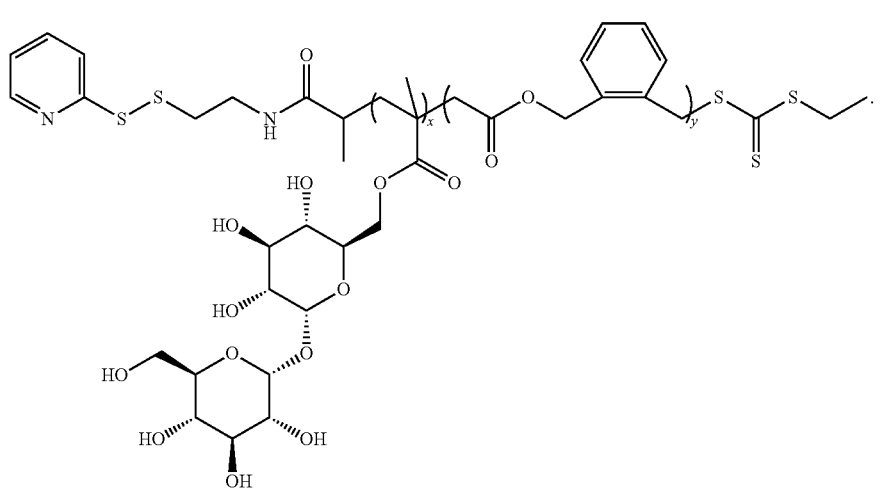

(2)

Example 2 shows a synthetic method of making trehalose co-polymer (2). Scheme 10 shows biodegradation of trehalose co-polymer (2) under basic conditions.

In another preferred embodiment, the present trehalose co-polymer has a structure (3) of:

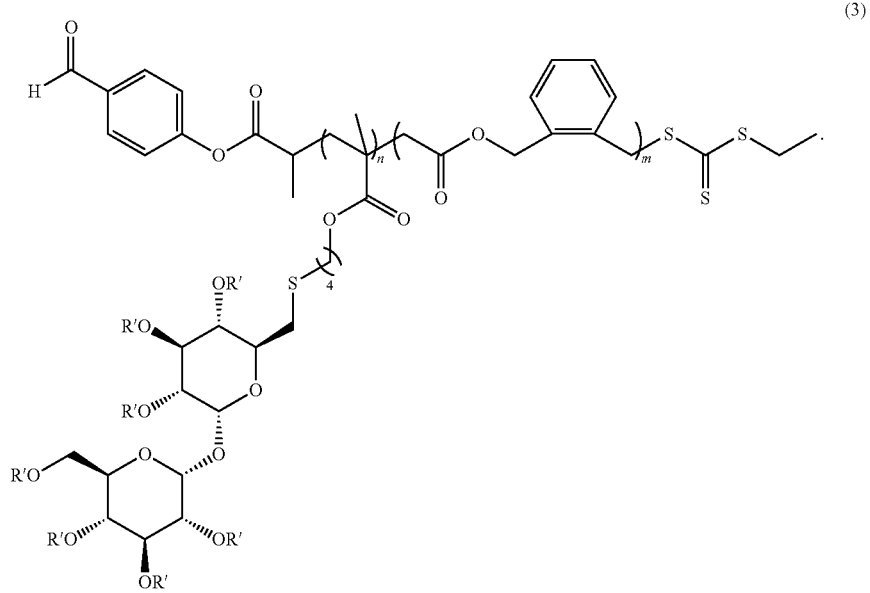

(3)

In one embodiment, the biodegradable trehalose co-polymer may be trehalose-functionalized caprolactones. Poly(caprolactone) is a well-known polymer that is approved by the FDA for in vivo applications (ex: Monocryl® sutures). Applicants demonstrate that modification of poly(caprolactone) with thiolated trehalose via thiol-ene chemistry would produce biodegradable trehalose glycopolymers. Applicants envision that many other methods may also be used to modify the polymers. For example, alkyne/azide click chemistry or any other method as appreciated by one skilled in the art may also be used to modify the polymers.

In one embodiment, the trehalose-functionalized caprolactones may be synthesized through ROP.

In one embodiment, a biodegradable trehalose polymer consists of the general structure:

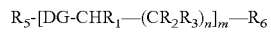

$$R_5\text{-}[DG\text{-}CHR_1\text{—}(CR_2R_3)_n]_m\text{—}R_6$$

wherein $R_1$-$R_3$ are independently selected from hydrogen or a side chain comprising at least one carbon atom, and wherein at least one of $R_1$-$R_3$ is a side chain comprising -L-trehalose, wherein L is a linker molecule that links trehalose to the co-polymer through at least one of the trehalose hydroxyl groups (—OH), wherein DG is a biodegradable group, and wherein $R_5$ and $R_6$ are end groups, and wherein n=0-10,
wherein m≥1.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one specific embodiment, $R_5$ and $R_6$ are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, and biomolecules.

In one embodiment, DG comprises at least one ester group.

In one embodiment, the ester group is in the backbone of the polymer.

In one preferred embodiment, the trehalose-functionalized caprolactones have the structure (4) of:

(4)

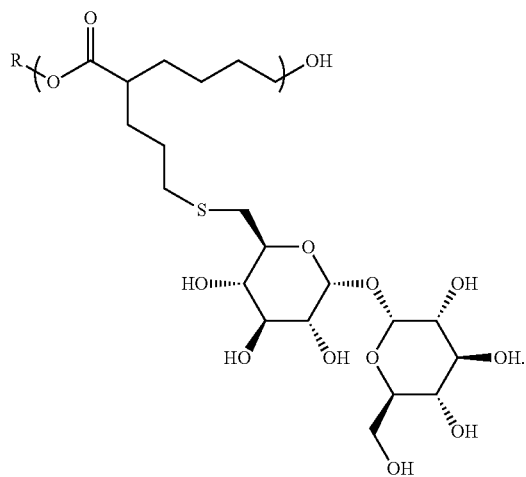

In one embodiment, Applicants envision that other backbone structures may also be used to produce degradable trehalose co-polymers. The specific backbones may include polycaprolactone, polycarbonate, polyurethane, polyanhydrides, Chitosan, hyaluronic acid, poly(amide), or poly(amino acid), poly(lactic acid), poly(glycolic acid), poly(dioxanone), poly(3-hydroxybutyric acid), poly(3-hydroxyvalerate), poly(valerolactone), poly(tartronic acid), poly(β-malonic acid), poly(propylene fumarate), poly(lactide-co-caprolactone), poly(lactic-co-glycolic acid), poly(3-hydroxybutyric acid-co-3-hydroxyvaleric acid), poly[1,4-bis(hydroxyethyl)terephthalate-alt-ethyloxyphosphate], poly[1,6-bis(p-carboxyphenoxy)hexane], poly(sebasic acid), and ethylglycinate polyphosphazene. The chemical structures of some of these suitable backbones are included as below:

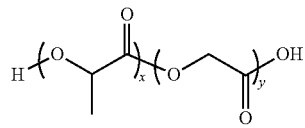

Poly(lactic-co-glycolyc acid)

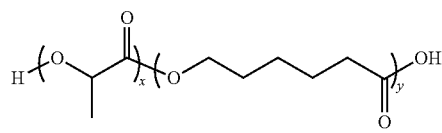

Poly(lactide-co-caprolactone)

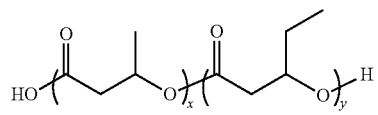

Poly(3-hydroxybutyric acid-co-3-hydroxyvaleric acid)

In one embodiment, the biodegradable trehalose co-polymers show good stabilization properties on biomolecules, e.g., proteins.

In some embodiments, biodegradable trehalose-based homopolymers or copolymers may be completely degraded after 24 hours under a base condition (e.g., 5% KOH). In one embodiment, biodegradable trehalose-based homopolymers or copolymers may be degraded slowly in aqueous solution by ester hydrolysis in aqueous solution. The hydrolysis can be accelerated to study the degradation by subjecting to 24 hours under a base condition.

Figure 85:
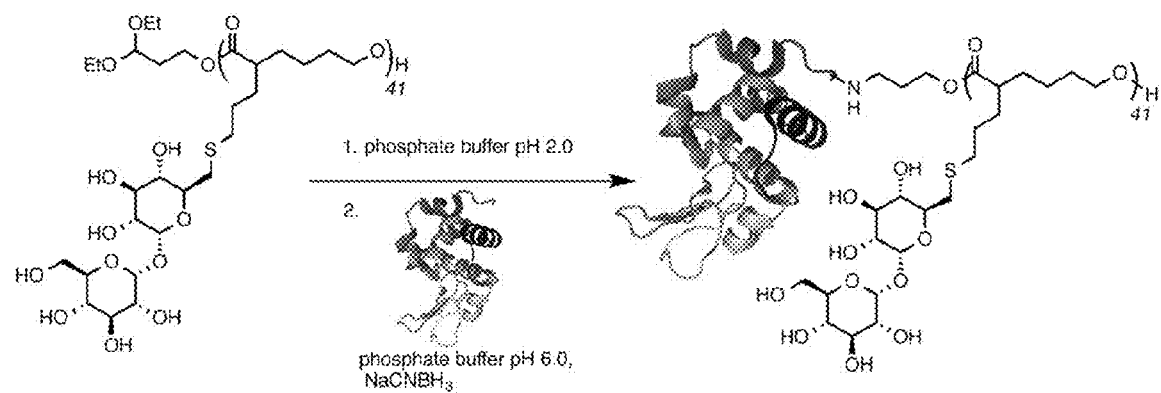
FIG. 85 shows Scheme 4.

In one embodiment, the biodegradable trehalose homo or co-polymers stabilize biomolecules when the biomolecules are chemically conjugated to the homo or co-polymers. Example 1 (e.g., FIG. 85, Scheme 4) shows the stabilization property of a biodegradable trehalose co-polymer over a protein (e.g., lysozyme) upon conjugation.

In one embodiment, the biodegradable trehalose co-polymers can also stabilize biomolecules when they are used as excipients, e.g., in the absence of chemical bond formation. Example 1 (e.g., FIG. 12) shows the stabilization property of a biodegradable trehalose co-polymer over proteins (e.g., lysozyme and 13-Gal) against lyophilization stress when the co-polymers were used as excipients. Thus, similar to those as described in Applicants' previous PCT patent application No. PCT/US2013/023235 (e.g., disclosing many trehalose-based polymers for stabilizing biomolecules), biodegradable trehalose co-polymers show good stabilization properties on biomolecules, e.g., proteins.

In one aspect, the present invention relates to a method or process of synthesizing a biodegradable trehalose co-polymer as discussed above for stabilizing a biomolecule.

Applicants envision that the biodegradable trehalose co-polymers as discussed above may be synthesized by any suitable method as appreciated by one skilled in the art.

For example, as discussed below, one could synthesize one trehalose-based monomer and subsequently co-polymerize the trehalose-based monomer with a cyclic ketene acetal to form the desired biodegradable trehalose co-polymer. Alternatively, one could synthesize the backbone co-polymer with pendant functional groups attached to the backbone. One could then attach trehalose groups to the co-polymer through the pendant functional groups to form the desired biodegradable trehalose co-polymer.

In one embodiment, Applicants note that bromine-functionalized caprolactone monomers could be synthesized and polymerized using tin catalysts (see, e.g., Xu et al., 2009). The pendant bromides could be installed using azide-alkyne "click" chemistry [e.g., displaced by sodium azide and sugar groups (glucose, maltose, and mannose)]. Block copolymers could also be made by copolymerizing with unfunctionalized caprolactone, which then self-assembled into micelles.

Oligosaccharides could also be functionalized with short-chain PEG chains and used as biodegradable backbones for degradable alternatives (Congdon et al., 2015). Dextran could be used as a biodegradable macroinitiator for the ATRP of a disaccharide monomer.[5]

Further, Applicants note that a degradable polymer could be synthesized through copolymerization of a cyclic ketene acetal (CKA) with a galactopyranose-functionalized styrene monomer (Xiao et. al., 2011).

In one embodiment, the biodegradable trehalose copolymer is produced through chemical synthesis. Preferably, the biodegradable trehalose copolymer is produced by using polymerization reactions including RAFT polymerization, ATRP, NMP, cyanoxyl-mediated free radical polymerization, conventional radical polymerization, or ROP. More preferably, the biodegradable trehalose copolymer is produced by using RAFT polymerization, ATRP, NMP, or ROP.

Preferred methods and processes for synthesizing biodegradable trehalose co-polymers are described in Examples 1 and 2.

In one embodiment, a method of synthesizing a biodegradable trehalose co-polymer for stabilizing a biomolecule comprises the steps of (a) incorporating a side chain comprising a trehalose molecule into a polymerizable monomer; and b) co-polymerizing the resulting monomer with a cyclic ketene acetal to obtain a co-polymer or glycopolymer.

In one preferred embodiment, the polymerizable monomer is selected from the group consisting of a styrene monomer, an acrylate monomer, a methacrylate monomer, an acrylamide monomer, a methacrylamide monomer, a vinyl monomer, a norborenyl monomer, and a strained cyclic alkene monomer. More preferably, the polymerizable monomer is a methacrylate monomer.

In one embodiment, the cyclic ketene acetal may include 5,6-benzo-2-methylene-1,3-dioxepane (BMDO), 2-methylene-4-phenyl-1,3-dioxalane (MPDL), 2-methylene-1,3-dioxalane, 2-methylene-4-hexyl-1,3-dioalane, 2-methylene-4-decyl-1,3-dioalane, 2,4-dimethylene-1,3-dioxalane, 2,5-dimethylene-1,3,-dioxane, 2-methylene-1,3-dioxepane (MDO), 2,5-methylene-1,3-dioxane, 4,7-dimethyl-2-methylene-1,3-dioxepane, 4-phenyl-2-propenylene-1,3-dioxalane, 2-methylene-1,3-dioxe-5-pene, 2-ethylidene-4-methyl-1,3-dioxane, 2-ethylidene-4-ethyl-1,3-dioxane, 2-ethylidene-1,3-dioxane, 1-vinyl-4,7-dioxaspiro-[2,4]heptane, 1-vinyl-4,9-dioxaspiro-[2.6]nonane, 1-vinyl-6,7-benzo-4,9-dioxaspiro[2.6]nonane, 9,9-disubstituted-4-methylene-3,5,8,10-tetraoxabicyclo[5.3.0]decane, 3,9-bis-methylene-2,4,8,10-tetraoxa-spiro[5,5]undecane, or 2-methylene-1,3,6-trioxocane.

In one preferred embodiment, the cyclic ketene acetal may be 5,6-benzo-2-methylene-1,3-dioxepane (BMDO).

In one embodiment, the step of co-polymerizing the resulting monomer to obtain biodegradable trehalose co-polymers is performed by any one of, but not limited to the techniques of RAFT polymerization, ATRP, NMP, cyanoxyl-mediated free radical polymerization, conventional radical polymerization, or ROP. Preferably, the step of co-polymerizing the resulting monomer to obtain a homopolymer or copolymer is performed by reversible addition-fragmentation chain transfer (RAFT) polymerization or ROP.

In one embodiment, other methods or processes may also be used to produce the present biodegradable trehalose co-polymers. For example, co-polymers with biodegradable bonds on the backbone and pendant functional groups attached to the backbone may be synthesized and trehalose groups may be later attached to the backbone of the co-polymer through the pendant functional groups.

In one embodiment, a method of synthesizing a biodegradable trehalose co-polymer for stabilizing a biomolecule may comprise the steps of (a) co-polymerizing polymerizable monomers to obtain a non-trehalose co-polymer; and (b) incorporating a side chain comprising a trehalose molecule into the non-trehalose co-polymer or glycopolymer to form the degradable trehalose co-polymer. Applicants envision that there are functional groups on the non-trehalose homopolymer or co-polymer where trehalose may be incorporated into the homopolymer or co-polymer.

In one specific embodiment, a method of synthesizing a biodegradable trehalose polymer for stabilizing a biomolecule may comprise the steps of a) polymerizing a cylic ester with an alcohol with to form a polymer, where in the cylic ester includes a pendant functional group; b) preparing a thiolated trehalose monomer; c) reacting the polymer with the thiolated trehalose monomer to form the biodegradable trehalose polymer.

In one embodiment, the biodegradable trehalose polymer for stabilizing a biomolecule may be a methacrylate-based polymer with a side chain functional group.

In one embodiment, the cylic ester is a caprolactone. Preferably, the cylic ester is allyl-functionalized caprolactone (aCL). Allyl group is used as a pendant functional group wherein trehalose groups can be attached. Example 1 shows that allyl-functionalized caprolactone (aCL) may be synthesized in one step following literature procedures (Ende et al., 2008).

In one embodiment, the alcohol is a primary alcohol. The primary alcohol may be used an initiator for polymerization of aCL.

In one embodiment, the polymerization in step (a) is a ROP. In one embodiment, the ROP in step (a) may further need a catalyst. Preferably, the catalyst is triazabicyclodecane (TBD), an organic catalyst.

In one embodiment, the thiolated trehalose monomer has the structure of:

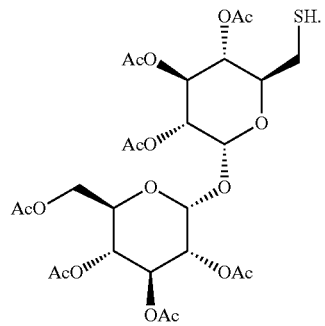 [SMILES: CC(=O)OC[C@H]1O[C@H](O[C@H]2O[C@H](CS)[C@@H](OC(C)=O)[C@H](OC(C)=O)[C@H]2OC(C)=O)[C@H](OC(C)=O)[C@@H](OC(C)=O)[C@@H]1OC(C)=O]

Example 1 (Scheme 1) shows methods and processes for synthesizing thiolated trehalose monomeric unit.

In one embodiment, a thiol-ene reaction was used to connect the co-polymer with the thiolated trehalose monomer to form the biodegradable trehalose co-polymer.

In one embodiment, the present invention discloses a biodegradable trehalose or zwitterion polymer, wherein the polymer consists of the general structure:

R'-[DG-CR$^1$R$^2$—CR$^3$R$^4$—CR$^5$R$^6$—CR$^7$R$^8$—CR$^9$R$^{10}$]$_m$—R".

wherein R$^1$-R$^{10}$ are independently selected from hydrogen or a side chain comprising at least one carbon atom, and wherein at least one of R$^1$-R$^{10}$ is a side chain comprising -L-trehalose or -L- zwitterion, wherein L is a linker molecule that links trehalose or zwitterion to the co-polymer through at least one of the trehalose hydroxyl groups (—OH) or through one end of the zwitterion,
wherein DG is a biodegradable group, and
wherein R' and R" are end groups, and
wherein m≥1.

In one embodiment, only one of R$^1$-R$^{10}$ is a side chain comprising -L-trehalose or -L- zwitterion, wherein L is a linker molecule that links trehalose or zwitterion to the polymer through at least one of the trehalose hydroxyl groups (—OH) or through one end of the zwitterion,
wherein DG is a biodegradable group, and
wherein R' and R" are end groups, and
wherein m≥1.

In one embodiment, two or more of R$^1$-R$^{10}$ are side chains comprising -L-trehalose or -L- zwitterion, wherein L is a linker molecule that links trehalose or zwitterion to the polymer through at least one of the trehalose hydroxyl groups (—OH) or through one end of the zwitterion,
wherein DG is a biodegradable group, and
wherein R' and R" are end groups, and
wherein m≥1.

In one embodiment, DG comprises at least one ester group. In one embodiment, DG comprises one ester group. In one embodiment, the biodegradable trehalose or zwitterion polymer is a pCL-based polymer.

Applicants envision that other degradable backbones may be used for the invention. For example, other types of DGs may be used to make a polymer's degradation faster. Applicants further envision that other backbone structures with fewer methylenes (e.g., lactide) could be used for the biodegradable polymers.

L is a linking molecule as discussed in this application. Applicants envision that many linking molecules as disclosed in this application or anywhere else may be used to connect the side chain to the backbone of the polymer.

In one embodiment, the linking molecules L are methylene groups —(CH$_2$)$_n$— (n=0-1000). In one embodiment, the linking molecules L are methylene groups —(CH$_2$)$_n$— (n=1-100). In one embodiment, the linking molecules L are methylene groups —(CH$_2$)$_n$— (n=1-10). In one embodiment, the linking molecules L are methylene groups —(CH$_2$)$_n$— (n=1-7). In one embodiment, the linking molecules L are methylene groups —(CH$_2$)$_n$— (n=1-5). In one embodiment, the linking molecules L are methylene groups —(CH$_2$)$_n$— (n=2-4). In one embodiment, the linking molecules L are methylene groups —(CH$_2$)$_n$— (n=3).

In one embodiment, R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

In one preferred embodiment, R' and R" are independently comprising —H, -Alkyl, -Alkenyl, -Alkynyl, azide or biomolecules.

In one embodiment, R' and R" are independently selected from the group consisting of —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide and biomolecules.

In one specific embodiment, R' and R" are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, azide and biomolecules.

In one embodiment, when the biodegradable trehalose or zwitterion polymer is a pCL-based polymer, R' and R" are independently selected from the group consisting of -Alkyl, -Alkenyl, -Alkynyl, -Aryl, —(CH$_3$)CHCOO-Aryl, —CH(CH$_3$)—CONH—(CH$_2$)$_n$—SS-Aryl (n=1-10), —H, azide and biomolecules.

In one specific embodiment, R' and R" are independently selected from the group consisting of -Alkyl, -Alkenyl, -Alkynyl, -Aryl, —H, and biomolecules.

In one embodiment, the biodegradable polymer is

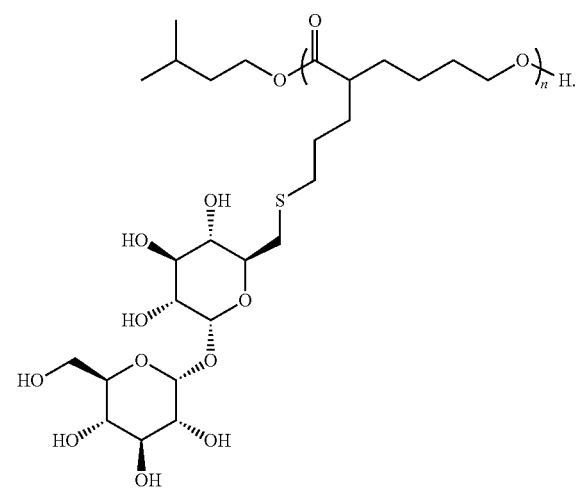

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one specific embodiment, the biodegradable polymer is

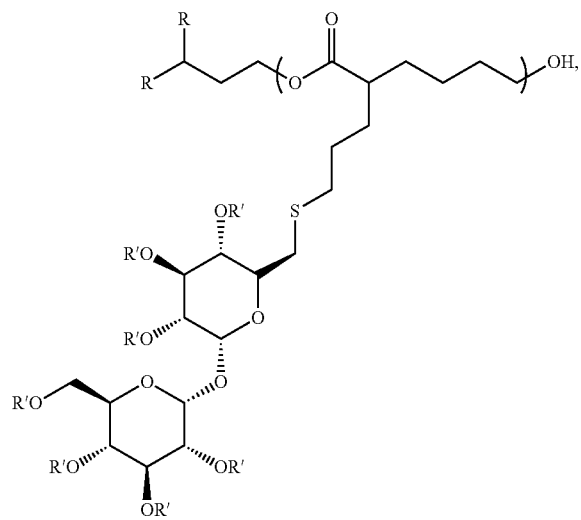

wherein R'=H or Acetyl (Ac).

In one embodiment, R'=Acetyl (Ac).

In another embodiment, the biodegradable polymer is

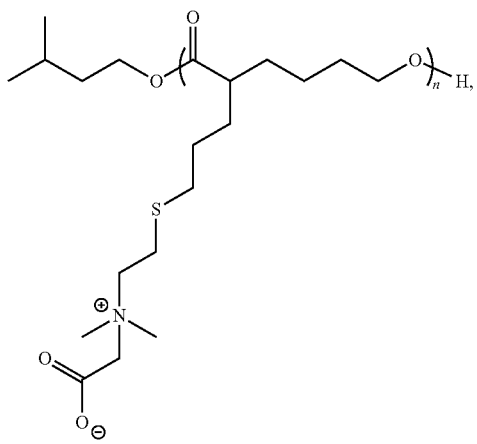

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In another specific embodiment, the biodegradable polymer is

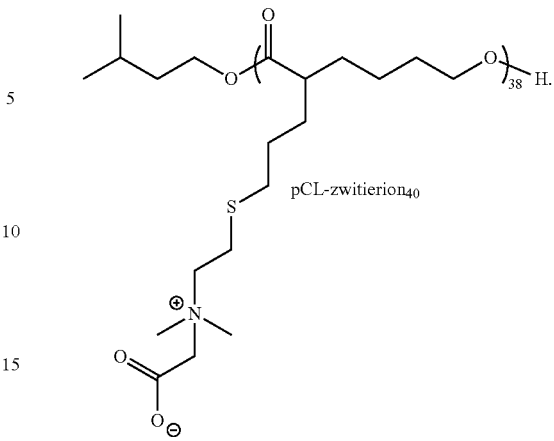

pCL-zwitierion

In one embodiment, the biodegradable polymers of the present invention are pCL backbone polymers. Scheme 2 shows an example of making pCL backbone polymers.

In one embodiment, the pCL backbones of the biodegradable polymers have general structures of —[(CH$_2$)$_m$—CR$^1$R$^2$—COO]$_n$— or —[OOC—(CH$_2$)$_m$—CR$^1$R$^2$]$_n$—, wherein m=0-100, n=1-10000, and R$^1$ and R$^2$ are independently selected from hydrogen or a side chain comprising at least one carbon atom.

In one embodiment, at least one of R$^1$ and R$^2$ is a side chain comprising -L-trehalose or -L- zwitterion. L is a linking molecule as discussed in this application. Applicants envision that many linking molecules as disclosed in this application or anywhere else may be used to connect the side chain to the pCL backbone.

In one embodiment, the linking molecules L are methylene groups —(CH$_2$)$_n$— (n=0-1000). In one embodiment, the linking molecules L are methylene groups —(CH$_2$)$_n$— (n=1-100). In one embodiment, the linking molecules L are methylene groups —(CH$_2$)$_n$— (n=1-10). In one embodiment, the linking molecules L are methylene groups —(CH$_2$)$_n$— (n=1-7). In one embodiment, the linking molecules L are methylene groups —(CH$_2$)$_n$— (n=1-5). In one embodiment, the linking molecules L are methylene groups —(CH$_2$)$_n$— (n=2-4). In one embodiment, the linking molecules L are methylene groups —(CH$_2$)$_n$— (n=3).

In one embodiment, the pCL backbones of the biodegradable polymers further comprise end groups. The general structures may be shown as R'O—[(CH$_2$)$_m$—CR$^1$R$^2$—COO]$_n$—R" or R'—[OOC—(CH$_2$)$_m$—CR$^1$R$^2$]$_n$—OR".

In one embodiment, R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

In one preferred embodiment, R' and R" are independently comprising —H, -Alkyl, -Alkenyl, -Alkynyl, azide or biomolecules.

In one embodiment, R' and R" are independently selected from the group consisting of —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide and biomolecules.

In one specific embodiment, R' and R" are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, azide and biomolecules.

In one embodiment, when the biodegradable trehalose or zwitterion polymer is a pCL-based polymer, R' and R" are independently selected from the group consisting of -Alkyl, -Alkenyl, -Alkynyl, -Aryl, —(CH$_3$)CHCOO-Aryl, —CH(CH$_3$)—CONH—(CH$_2$)$_n$—SS-Aryl (n=1-10), —H, azide and biomolecules.

In one specific embodiment, R' and R" are independently selected from the group consisting of -Alkyl, -Alkenyl, -Alkynyl, -Aryl, —H, azide and biomolecules.

In one embodiment, the end groups R' and R" may be functionalized (e.g., azide functionalized) during the synthesis of pCL backbone polymers. Scheme 21-24 show examples of azide functionalization of the pCL backbone polymers.

In one embodiment, the biodegradable polymer is

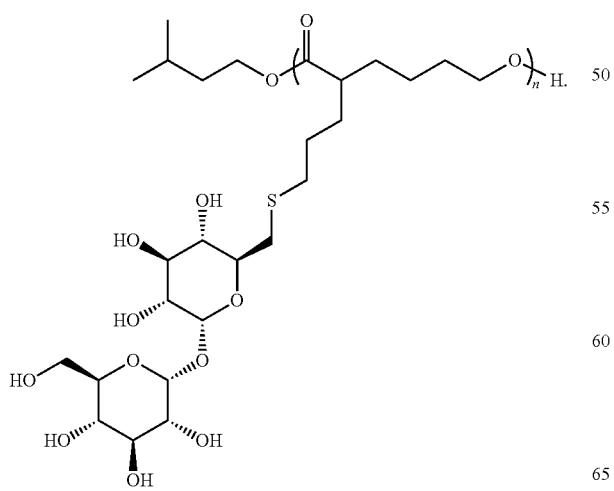

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, the biodegradable trehalose polymer is

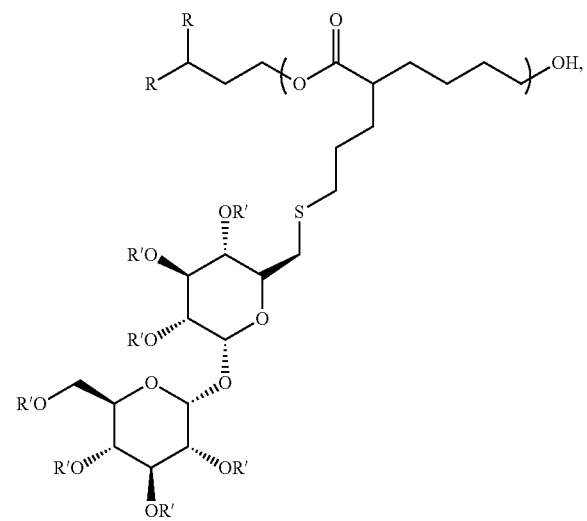

wherein R' is H and R comprises at least one carbon atom.

In one embodiment, R' is acetyl (Ac).

In another embodiment, the biodegradable polymer is

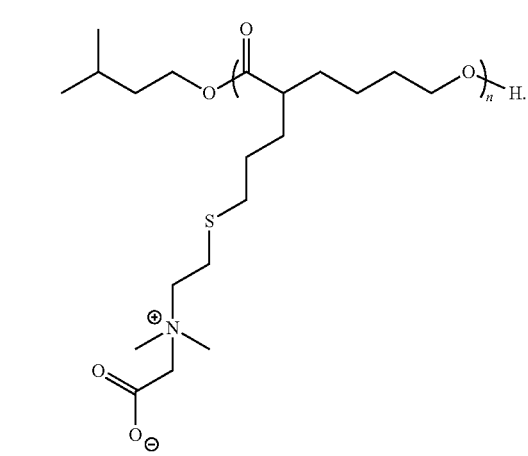

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, the biodegradable polymer is

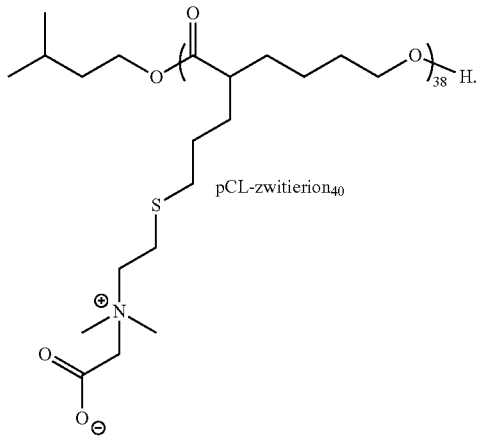

In one embodiment, Applicants demonstrate that the size of the biodegradable pCL trehalose polymers can be controlled by limiting the number of the repeated pCL unit n.

In one embodiment, the repeated pCL unit n is the range of 1-10000, or 1-5000, 1-2000, 1-1000, 1-500, 1-300, or 1-100.

In one preferred embodiment, the repeated pCL unit n is the range of 1-300, or more preferably 1-100.

In one embodiment, the biodegradable polymers of the present invention are pCL backbone polymers. The pCL backbones of the biodegradable polymers have general structures of —[CHR$^1$—CHR$^2$—CHR$^3$—CHR$^4$—CHR$^5$—COO]$_n$— or —[OOC—CHR$^1$—CHR$^2$—CHR$^3$—CHR$^4$—CHR$^5$]$_n$—, wherein m=0-100, n=1-10000, and R$^1$-R$^5$ are independently selected from hydrogen or a side chain comprising at least one carbon atom. In one embodiment, at least one of R$^1$-R$^5$ is a side chain comprising -L-trehalose or -L-zwitterion, wherein L is a linker molecule that links trehalose or zwitterion to the polymer through at least one of the trehalose hydroxyl groups (—OH) or through one end of the zwitterion.

L is a linking molecule as discussed in this application. Applicants envision that many linking molecules as disclosed in this application or anywhere else may be used to connect the side chain to the pCL backbone.

In one embodiment, the linking molecules L are methylene groups —(CH$_2$)$_n$— (n=0-1000). In one embodiment, the linking molecules L are methylene groups —(CH$_2$)$_n$— (n=1-100). In one embodiment, the linking molecules L are methylene groups —(CH$_2$)$_n$— (n=1-10). In one embodiment, the linking molecules L are methylene groups —(CH$_2$)$_n$— (n=1-7). In one embodiment, the linking molecules L are methylene groups —(CH$_2$)$_n$— (n=1-5). In one embodiment, the linking molecules L are methylene groups —(CH$_2$)$_n$— (n=2-4). In one embodiment, the linking molecules L are methylene groups —(CH$_2$)$_n$— (n=3).

In one embodiment, the pCL backbone polymers comprise end groups. The general structures may be shown as R'O—[CHR$^1$—CHR$^2$—CHR$^3$—CHR$^4$—CHR$^5$—COO]$_n$—R" or R'—[OOC—CHR$^1$—CHR$^2$—CHR$^3$—CHR$^4$—CHR]$_n$—OR".

In one embodiment, R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

In one preferred embodiment, R' and R" are independently comprising —H, -Alkyl, -Alkenyl, -Alkynyl, azide or biomolecules.

In one embodiment, R' and R" are independently selected from the group consisting of —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide and biomolecules.

In one specific embodiment, R' and R" are independently selected from the group consisting of -Alkyl, -Alkenyl, -Alkynyl, -Aryl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, azide and biomolecules.

In one embodiment, when the biodegradable trehalose or zwitterion polymer is a pCL-based polymer, R' and R" are independently selected from the group consisting of -Alkyl, -Alkenyl, -Alkynyl, -Aryl, —(CH$_3$)CHCOO-Aryl, —CH(CH$_3$)—CONH—(CH$_2$)$_n$—SS-Aryl (n=1-10), —H, azide and biomolecules.

In one specific embodiment, R' and R" are independently selected from the group consisting of -Alkyl, -Alkenyl, -Alkynyl, -Aryl, —H, azide and biomolecules.

In one embodiment, the end groups R' and R" may be functionalized (e.g., azide functionalized) during the synthesis of pCL backbone polymers. Scheme 21-24 show examples of azide functionalization of the pCL backbone polymers.

In one embodiment, the biodegradable polymer is

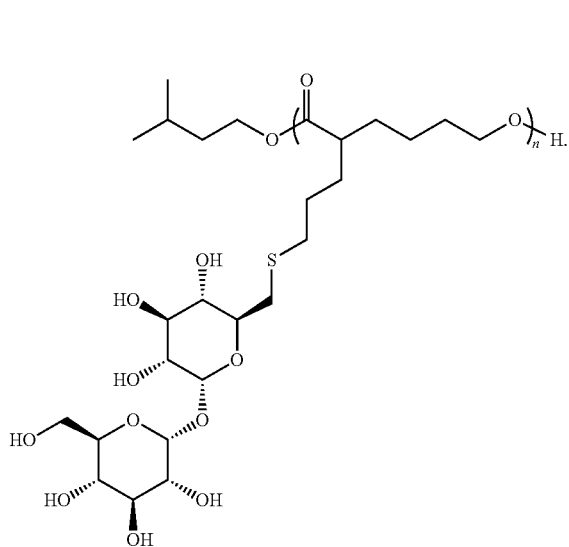

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one specific embodiment, the biodegradable pCL backbone polymer is

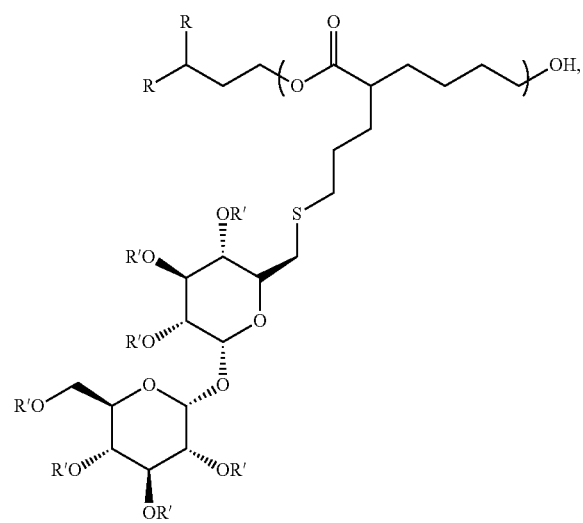

wherein R' is H and R comprises at least one carbon atom.

In one embodiment, R' is an acyl group such as acetyl.

In another embodiment, the biodegradable polymer is

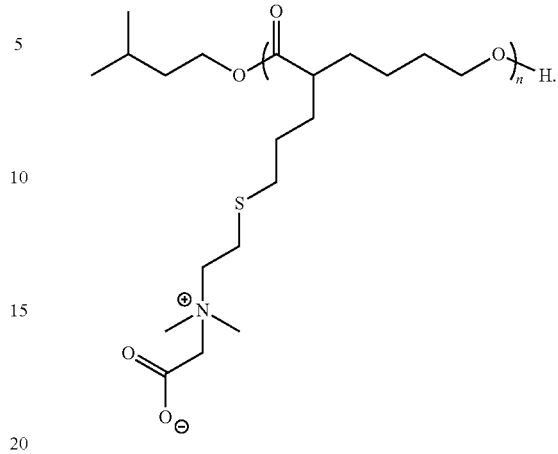

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, Applicants demonstrate that the size of the biodegradable pCL trehalose polymers can be controlled by limiting the number of the repeated pCL unit n.

In one embodiment, the repeated pCL unit n is the range of 1-10000, or 1-5000, 1-2000, 1-1000, 1-500, 1-300, or 1-100.

In one preferred embodiment, the repeated pCL unit n is the range of 1-300, or more preferably 1-100.

Scheme 12 shows the synthetic scheme of thiol-ene modification of pCL-allyl polymers with acetyl-trehalose, acetyl-glucose, acetyl-lactose and PEG thiols with controllable repeat unit numbers, followed by deprotection of the acetylated sugars.

In one aspect, the present invention discloses a biodegradable zwitterion polymer, wherein the polymer consists of the general structure:

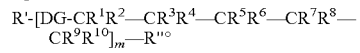

wherein $R^1$-$R^{10}$ are independently selected from hydrogen or a side chain comprising at least one carbon atom, and wherein at least one of $R^1$-$R^{10}$ is a side chain comprising -L- zwitterion, wherein L is a linker molecule that links zwitterion to the polymer through one end of the zwitterion electrical charges, wherein DG is a biodegradable group, and wherein R' and R" are end groups, and wherein m≥1.

In one embodiment, only one of $R^1$-$R^{10}$ is a side chain comprises -L- zwitterion, wherein L is a linker molecule that links zwitterion to the polymer through one end of the zwitterion electrical charges, wherein DG is a biodegradable group, and wherein R' and R" are end groups, and wherein m≥1.

In one embodiment, DG comprises at least one ester group. In one embodiment, DG comprises one ester group. In one embodiment, the biodegradable zwitterion polymer is a pCL-based polymer. Applicants envision that other backbone structures may be used for the biodegradable polymer. For example, other DGs may be used to make the polymer's degradation faster. Applicants further envision that other backbone structures with fewer methylenes (e.g., lactide) could be used for the biodegradable polymers.

L can be any linking molecule as discussed in this application. Applicants envision that many linking molecules as disclosed in this application or anywhere else may be used to connect the side chain to the polymer backbone (e.g., the pCL backbone).

In one embodiment, the linking molecules L are methylene groups —$(CH_2)_n$— (n=0-1000). In one embodiment, the linking molecules L are methylene groups —$(CH_2)_n$— (n=1-100). In one embodiment, the linking molecules L are methylene groups —$(CH_2)_n$— (n=1-10). In one embodiment, the linking molecules L are methylene groups —$(CH_2)_n$— (n=1-7). In one embodiment, the linking molecules L are methylene groups —$(CH_2)_n$— (n=1-5). In one embodiment, the linking molecules L are methylene groups —$(CH_2)_n$— (n=2-4). In one embodiment, the linking molecules L are methylene groups —$(CH_2)_n$— (n=3).

In one embodiment, the end groups R' and R" can be any end groups as discussed in this application.

In one embodiment, R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

In one preferred embodiment, R' and R" are independently comprising —H, -Alkyl, -Alkenyl, -Alkynyl, azide or biomolecules.

In one embodiment, R' and R" are independently selected from the group consisting of —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide and biomolecules.

In one embodiment, R' and R" are independently selected from the group consisting of —H, -Alkyl, -Alkenyl, -Alkynyl, azide and biomolecules.

In one embodiment, the end groups R' and R" may be functionalized (e.g., azide functionalized) during the synthesis of pCL backbone polymers. Scheme 21-24 show examples of azide functionalization of the pCL backbone polymers.

In one embodiment, the zwitterion in the biodegradable zwitterion polymer is an amino acid or an amino acid derivative. Applicants envision many amino acids or amino acid derivatives may be used as a zwitterion in the present invention.

Figure 35:
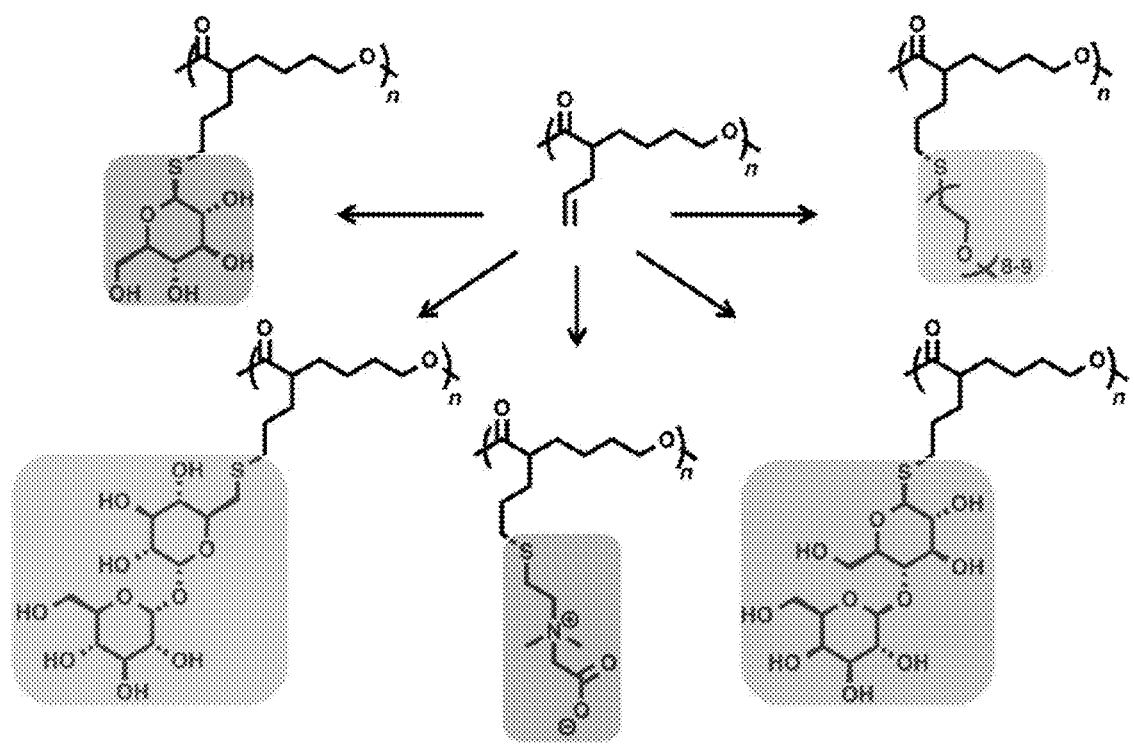
FIG. 35 is a diagram showing illustrative scheme of polymer poly(caprolactone) (pCL) backbone and modification with thiols using thiol-ene chemistry to produce a small library of degradable polymers.

FIG. 35 and Scheme 13 describe synthesis of exemplary biodegradable zwitterion polymers.

For example, one specific biodegradable zwitterion polymer has the structure of

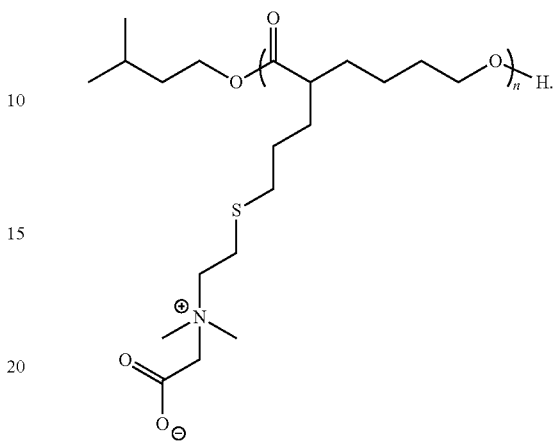

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, Applicants demonstrate that the size of the biodegradable pCL zwitterion polymers can be controlled by limiting the number of the repeated pCL unit n.

In one embodiment, the repeated pCL unit n is the range of 1-10000, or 1-5000, 1-2000, 1-1000, 1-500, 1-300, or 1-100.

In one preferred embodiment, the repeated pCL unit n is the range of 1-300, or more preferably 1-100. The Examples show synthesis and characterization of pCL-zwitterion$_{10}$, pCL-zwitterion$_{20}$, pCL-zwitterion$_{40}$ and pCL-zwitterion$_{80}$.

Scheme 12 shows the synthetic scheme of thiol-ene modification of pCL-allyl polymers with acetyl-trehalose, acetyl-glucose, acetyl-lactose and PEG thiols with controllable repeat unit numbers, followed by deprotection of the acetylated sugars.

In one embodiment, a biodegradable zwitterion polymer of the present invention has general structures of —[$(CH_2)_m$—$CR^1R^2$—$COO$]$_n$— or —[$OOC$—$(CH_2)_m$—$CR^1R^2$]$_n$—, wherein m=0-100, n=1-10000, and $R^1$ and $R^2$ are independently selected from hydrogen or a side chain comprising at least one carbon atom and at least one of $R^1$ and $R^2$ is a side chain comprising -L- zwitterion. L can be any linking molecule as discussed in this application, and L links zwitterion to the polymer through one end of the zwitterion electrical charges.

In one embodiment, only one of $R^1$ and $R^2$ is a side chain comprising -L- zwitterion.

In one embodiment, the linking molecules L are methylene groups —$(CH_2)_n$— (n=0-1000). In one embodiment, the linking molecules L are methylene groups —$(CH_2)_n$— (n=1-100). In one embodiment, the linking molecules L are methylene groups —$(CH_2)_n$— (n=1-10). In one embodiment, the linking molecules L are methylene groups —$(CH_2)_n$— (n=1-7). In one embodiment, the linking molecules L are methylene groups —$(CH_2)_n$— (n=1-5). In one embodiment, the linking molecules L are methylene groups —$(CH_2)_n$— (n=2-4). In one embodiment, the linking molecules L are methylene groups —$(CH_2)_n$— (n=3).

In one embodiment, the biodegradable zwitterion polymer also comprises end groups. The general structures may be shown as R'O—[(CH$_2$)$_m$—CR$^1$R$^2$—COO]$_n$—R" or R'—[OOC—(CH$_2$)$_m$—CR$^1$R$^2$]$_n$—OR". The end groups R' and R" can be any end groups as discussed in this application.

In one embodiment, the zwitterion is an amino acid or an amino acid derivative. In one embodiment, the linking molecule L connects the amino acid zwitterion through the amine group of the amino acid or the amino acid derivative. In one embodiment, the group of -L- zwitterion comprises at least one S—C bond.

As one specific example, the biodegradable zwitterion polymer may have the structure of

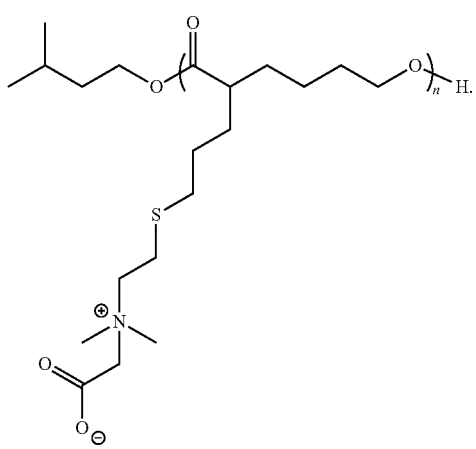

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, Applicants demonstrate that the size of the biodegradable pCL zwitterion polymers can be controlled by limiting the number of the repeated pCL unit n.

In one embodiment, the repeated pCL unit n is the range of 1-10000, or 1-5000, 1-2000, 1-1000, 1-500, 1-300, or 1-100.

In one preferred embodiment, the repeated pCL unit n is the range of 1-300, or more preferably 1-100.

In one embodiment, a biodegradable zwitterion polymer of the present invention has the general structures of R'O—[CHR$^1$—CHR$^2$—CHR$^3$—CHR$^4$—CHR$^5$—COO]$_n$—R" or R'—[OOC—CHR$^1$—CHR$^2$—CHR$^3$—CHR$^4$—CHR]$_n$—OR", wherein R$^1$-R$^5$ are independently selected from hydrogen or a side chain comprising at least one carbon atom, and wherein at least one of R$^1$-R$^5$ is a side chain comprising -L-zwitterion, wherein L is a linker molecule that links zwitterion to the polymer through one end of the zwitterion electrical charge pair, wherein R' and R" are end groups, and wherein n≥1.

In one embodiment, only one of R$^1$-R$^5$ is a side chain comprising -L- zwitterion, wherein L is a linker molecule that links zwitterion to the polymer through one end of the zwitterion electrical charge pair, wherein R' and R" are end groups, and wherein n≥1.

In one embodiment, the end groups R' and R" can be any end groups as discussed in this application.

In one embodiment, R' and R" are independently selected from the group consisting of —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide and biomolecules.

In one embodiment, R' and R" are independently selected from the group consisting of —H, -Alkyl, -Alkenyl, -Alkynyl, azide and biomolecules.

In one embodiment, the end groups R' and R" may be functionalized (e.g., azide functionalized) during the synthesis of pCL backbone polymers. Scheme 21-24 show examples of azide functionalization of the pCL backbone polymers.

In one embodiment, the zwitterion in the biodegradable zwitterion polymer is an amino acid or an amino acid derivative. Applicants envision any amino acid may be used as a zwitterion in the present invention.

In one embodiment, the zwitterion is an amino acid or an amino acid derivative. In one embodiment, the linking molecule L connects the amino acid zwitterion through the amine group of the amino acid or the amino acid derivative. In one embodiment, the group of -L- zwitterion comprises at least one S—C bond.

In one aspect, the present invention discloses methods of making biodegradable pCL polymers of trehalose or zwitterion. As discussed above, the biodegradable pCL polymers may be pCL trehalose polymers or pCL zwitterion polymers.

Example 4 includes detail methods of making pCL trehalose polymers and pCL zwitterion polymers.

In one embodiment, a method for synthesizing a biodegradable trehalose polymer for stabilizing a biomolecule and the method comprises the steps of:
  a) polymerizing a cyclic ester with an alcohol with to form a polymer, wherein the cyclic ester includes a pendant functional group;
  b) preparing a trehalose monomer having a functional group for linking; and
  c) reacting the polymer with the trehalose monomer through the functional group for linking to form the biodegradable trehalose polymer.

Applicants envision that many functional groups for linking may be used for the trehalose monomer depending on the functionality of the polymer. For example, if there was an alkyne side chain on the polymer, one could use an azide trehalose. If there was an activated acid on the side chain, one could use amino trehalose or just trehalose itself, etc.

In one embodiment, the trehalose monomer is a thiolated trehalose monomer.

In the first step (step a), a cyclic ester is polymerized with an alcohol to form a polymer and the cyclic ester was pre-modified to include a pendant functional group.

In one embodiment, the pendant functional group allows the addition of trehalose-based side chains. Applicants envision many functional groups may be used to connect the trehalose-based side chains to the biodegradable trehalose polymers.

In one embodiment, the pendant functional group is an allyl group.

In one embodiment, the first step (step a) may be conducted under a ring-opening polymerization. Examples 4 and 5 describe synthesis of pCL-allyl polymers following a ring-opening polymerization.

In one embodiment, the size of the pCL-allyl polymers may be controlled by limiting the number of allyl groups. For example, the size of the pCL-allyl polymers may be controlled by controlling the monomer to initiator ratio or conversion in the polymerization. Tables 1 and 2 show the properties of different pCL-allyl polymers.

In one embodiment, the cyclic ester is an allyl-functionalized caprolactone (aCL).

In one embodiment, the alcohol is a primary alcohol. The primary alcohol may be used as an initiator for polymerization.

In one embodiment, the first step is a ring-opening polymerization (ROP).

In one embodiment, the reaction in step a) further needs a catalyst.

In one embodiment, the catalyst may be triazabicyclodecane (TBD).

Schemes 2 and 17 show the synthesis of the degradable pCL trehalose polymers by using post-polymerization modification of a biodegradable allylated polymer backbone. Allylated caprolactone is synthesized and polymerized to yield a polyester with pendant allyl groups.

In the second step, a trehalose monomer having a functional group for linking (e.g., a thiolated trehalose monomer) is prepared. Scheme 1 shows the detail step for making a thiolated trehalose monomer.

In one embodiment, the free —OH groups of the thiolated trehalose monomer are protected. For example, the —OH groups of the thiolated trehalose monomer may be protected by acyl groups such as acetyl groups or any other protecting groups suitable for protecting —OH. In one embodiment, the —OH protected trehalose may be deprotected after the formation of the biodegradable trehalose polymers.

In one embodiment, the thiolated trehalose monomer has the structure of:

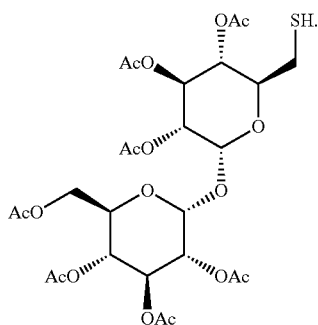

After it is prepared, the trehalose monomer through the functional group for linking (e.g., the thiolated trehalose monomer) reacts with the polymer to form the biodegradable pCL trehalose polymer. In one embodiment, the thiolated trehalose monomer reacts with the polymer to form the biodegradable pCL trehalose polymer via a thiol-ene reaction.

Scheme 2 shows the detail step for making biodegradable pCL trehalose polymer. Scheme 12 shows the synthetic scheme of thiol-ene modification of pCL-allyl polymers with acetyl-trehalose, acetyl-glucose, acetyl-lactose and PEG thiols, followed by deprotection of the acetylated sugars.

In another embodiment, the invention discloses a method for making biodegradable pCL zwitterion polymers.

In one embodiment, the method for making biodegradable pCL zwitterion polymers for stabilizing a biomolecule comprises the steps of:

a) polymerizing a cyclic ester with an alcohol with to form a polymer, where in the cyclic ester includes a pendant functional group;

b) preparing a zwitterion-intermediate monomer having a functional group for linking;

c) reacting the polymer with the zwitterion-intermediate monomer through the functional group for linking to form the zwitterion-intermediate polymer; and d) forming the biodegradable zwitterion polymer.

In one embodiment, the zwitterion-intermediate monomer having a functional group for linking is a thiolated zwitterion-intermediate monomer.

In the first step (step a), a cyclic ester is polymerized with an alcohol with to form a polymer and the cyclic ester was pre-modified to include a pendant functional group.

In one embodiment, the pendant functional group is an allyl group.

In one embodiment, the cyclic ester is an allyl-functionalized caprolactone (aCL).

In one embodiment, the alcohol is a primary alcohol. The primary alcohol may be used as an initiator for polymerization.

In one embodiment, the first step (step a) is a ring-opening polymerization (ROP).

In one embodiment, the reaction in step a) further needs a catalyst.

In one embodiment, the catalyst may be triazabicyclodecane (TBD).

In one embodiment, the as-produced polymer is a pCL allyl polymer.

In the second step (step b), a zwitterion-intermediate monomer is prepared. Scheme 13 shows the detail step for making a zwitterion-intermediate monomer.

The term "zwitterion-intermediate," as used herein, refers to an intermediate compound from which a zwitterion is produced. In one embodiment, when the zwitterion is an amino acid or its derivative, the zwitterion-intermediate may include an amine functional group of the amino acid.

In one embodiment, the zwitterion is an amino acid or an amino acid derivative. The thiolated zwitterion-intermediate monomer is a thiolated amine.

In the third step (step c), the polymer reacts with the thiolated zwitterion-intermediate monomer to form a zwitterion-intermediate polymer.

In one embodiment, the polymer reacts with the thiolated zwitterion-intermediate monomer via a thiol-ene reaction. A zwitterion-intermediate polymer is produced.

In one embodiment, the thiolated zwitterion-intermediate monomer is a thiolated amine.

In one embodiment, a pCL allyl polymer reacts with a thiolated amine to form a zwitterion-intermediate polymer.

As shown in Scheme 13, the zwitterion-intermediate polymer can further form the desired biodegradable pCL zwitterion polymers. Thus, in the last step (step d), the zwitterion-intermediate polymer is further treated to form biodegradable pCL zwitterion polymers.

In one embodiment, one exemplary biodegradable pCL zwitterion polymer has the structure of:

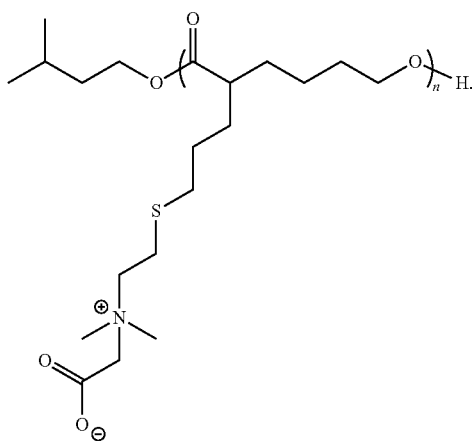

In one embodiment, n=1-10000, 1-5000, 1-2000, 1-1000, 1-500, 1-300, or 1-100. In one embodiment, methyl groups may be substituted with any -Alkyl, -Alkenyl, -Alkynyl, -Aryl, or other functional groups.

In one embodiment, Applicants demonstrate that the size of the biodegradable pCL zwitterion polymers can be controlled by limiting the number of the repeated pCL unit n.

In one embodiment, the repeated pCL unit n is the range of 1-10000, or 1-5000, 1-2000, 1-1000, 1-500, 1-300, or 1-100.

In one preferred embodiment, the repeated pCL unit n is the range of 1-300, or more preferably 1-100.

Scheme 13 shows the scheme for the synthesis of zwitterionic polymer pCL-zwitterion$_{40}$. Tables 1 and 2 show characterization of zwitterionic polymers.

In one aspect, the degradable pCL trehalose polymers and degradable pCL zwitterion polymers can stabilize biomolecules such as proteins, enzymes, antibodies, DNA, siRNA, and pharmaceutical compositions.

In one embodiment, the degradable pCL trehalose polymers and degradable pCL zwitterion polymers may be covalently bonded with the biomolecules.

In another embodiment, the degradable pCL trehalose polymers and degradable pCL zwitterion polymers may also stabilize the biomolecules in the absence of covalent bonding. For example, pCL trehalose and zwitterion polymers may be used as excipients.

Preferably, the degradable pCL trehalose polymers and degradable pCL zwitterion polymers are covalently bonded with the biomolecules for the purpose of stabilization.

In one embodiment, the degradable pCL trehalose polymers and degradable pCL zwitterion polymers may be used as excipients.

In one embodiment, a pharmaceutically effective amount of degradable pCL trehalose polymers or degradable pCL zwitterion polymers may be mixed with biomolecules such as proteins, enzymes, antibodies, DNA, siRNA, and pharmaceutical compositions so that the biomolecules are stabilized.

Figures 37A, 37B:
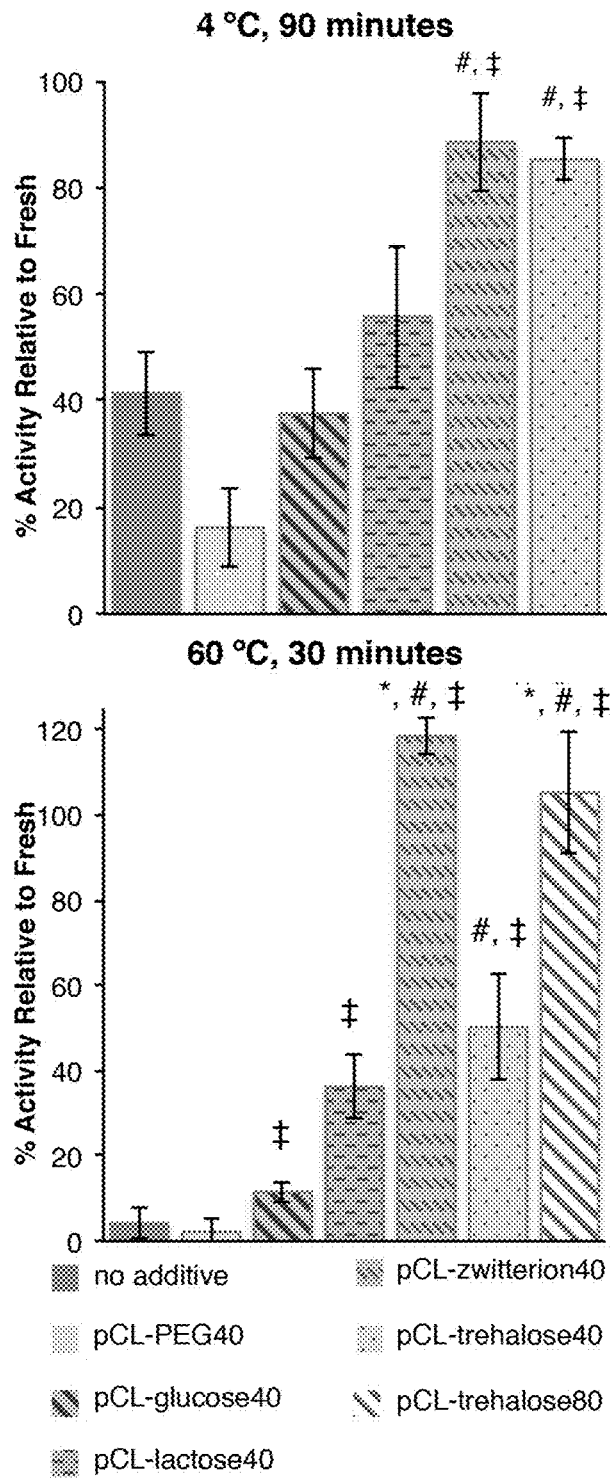
FIG. 37A is a graph showing effect of side chain identity on stabilization of G-CSF at pH 4.0. Storage conditions at 4° C. for 90 minutes.
FIG. 37B is a graph showing effect of side chain identity on stabilization of G-CSF at pH 4.0 thermal stress at 60° C. for 30 minutes. ‡=p<0.01 relative to no stabilizing additive, #=p<0.05 relative to pCL-lactose40, *=p<0.05 relative to trehalose40, Student's t-test. Data shown as the average of six experimental repeats and six well repeats with standard deviation.

FIGS. 37a and 37b demonstrate the stabilization effect of pCL trehalose polymers or pCL zwitterion polymers on an exemplary protein of G-CSF at various conditions, e.g., at 4° C. for 90 minutes and at 60° C. for 30 minutes.

In one embodiment, the stabilization effect of pCL trehalose polymers or pCL zwitterion polymers are molecular weight dependent.

Figure 38A:
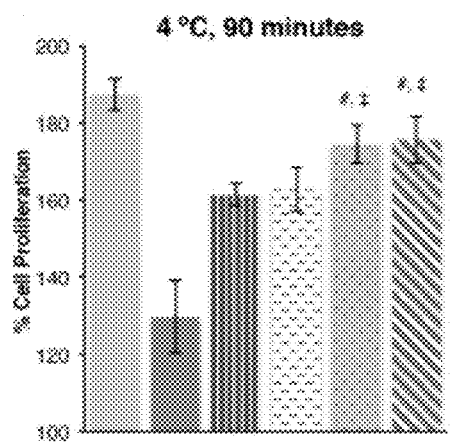
FIG. 38A is a graph showing Effect of pCL-trehalose molecular weight on G-CSF stabilization ability to storage at 4° C. for 90 minutes.
Figure 38B:
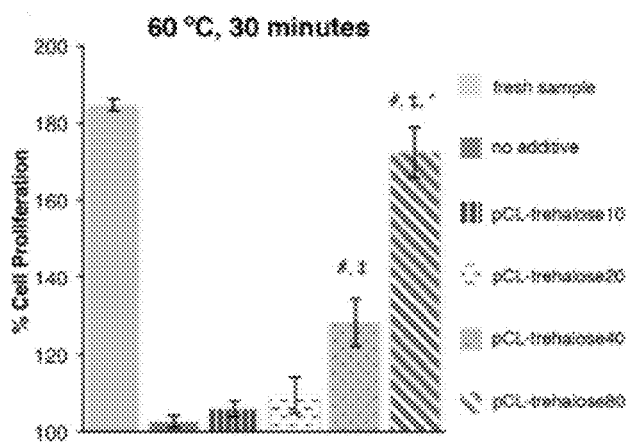
FIG. 38B is a graph showing Effect of pCL-trehalose molecular weight on G-CSF stabilization ability and thermal stress at 60° C. for 30 minutes.

FIG. 38a and FIG. 38b demonstrate the stabilization effect of pCL-trehalose molecular weight on G-CSF stabilization ability at 4° C. for 90 minutes and FIG. 38b and at 60° C. for 30 minutes. All pCL trehalose polymers exhibited statistically significant stabilization (p<0.05) relative to no stabilizing additive. In general, greater molecular weight polymers showed greater stabilization.

In one embodiment, when all other factors are similar, pCL zwitterion polymers show better performance for stabilization of protein than pCL trehalose polymers.

Figure 39:
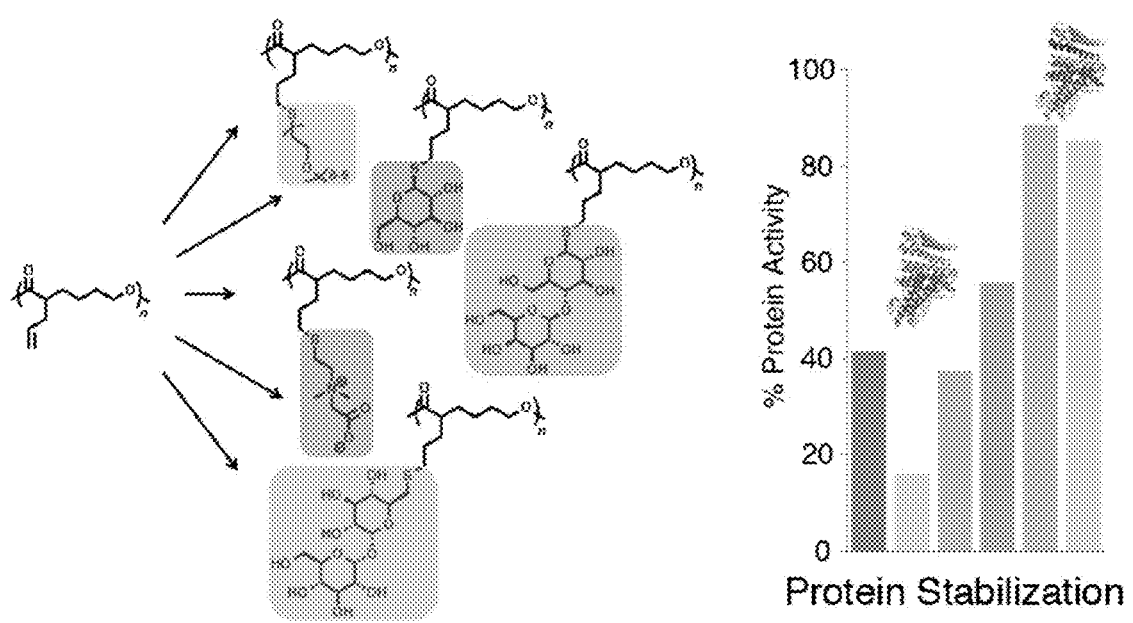
FIG. 39 is a set of diagram and graph showing the synthetic schemes of polymer poly(caprolactone) (pCL) and its characteristic property of protein stabilization.
Figure 40:
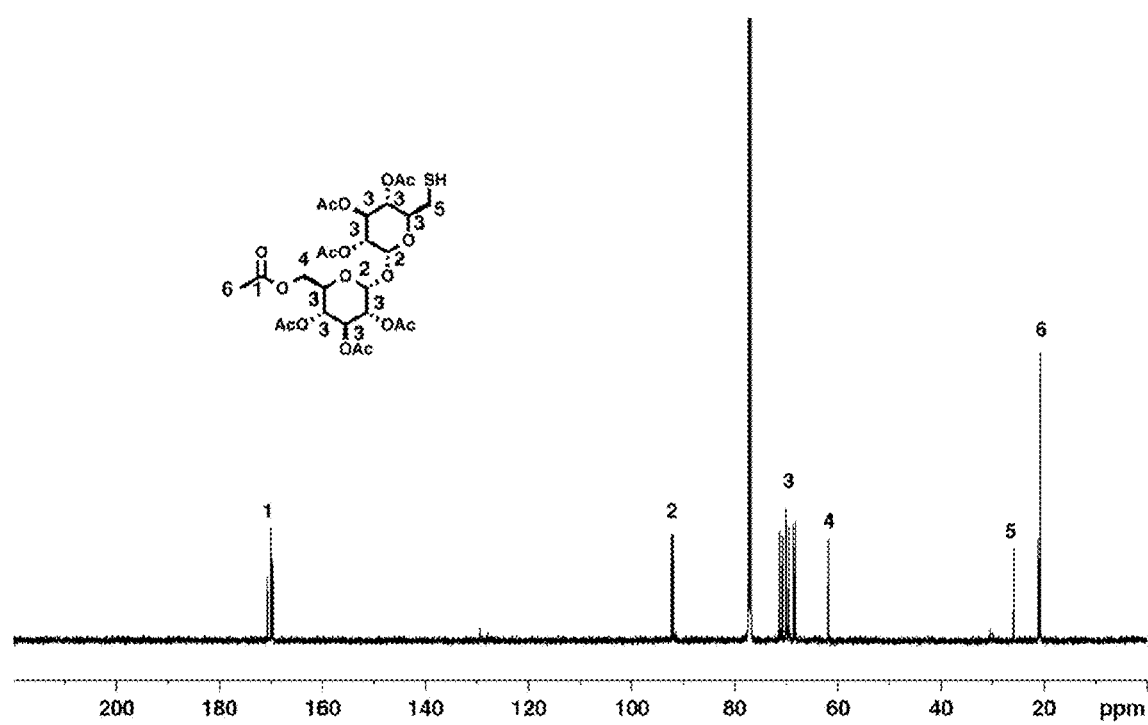
FIG. 40 is a graph showing $^{13}$C-NMR spectrum of thiolated trehalose heptaacetate A (CDCl$_3$, 500 MHz).
Figure 41:
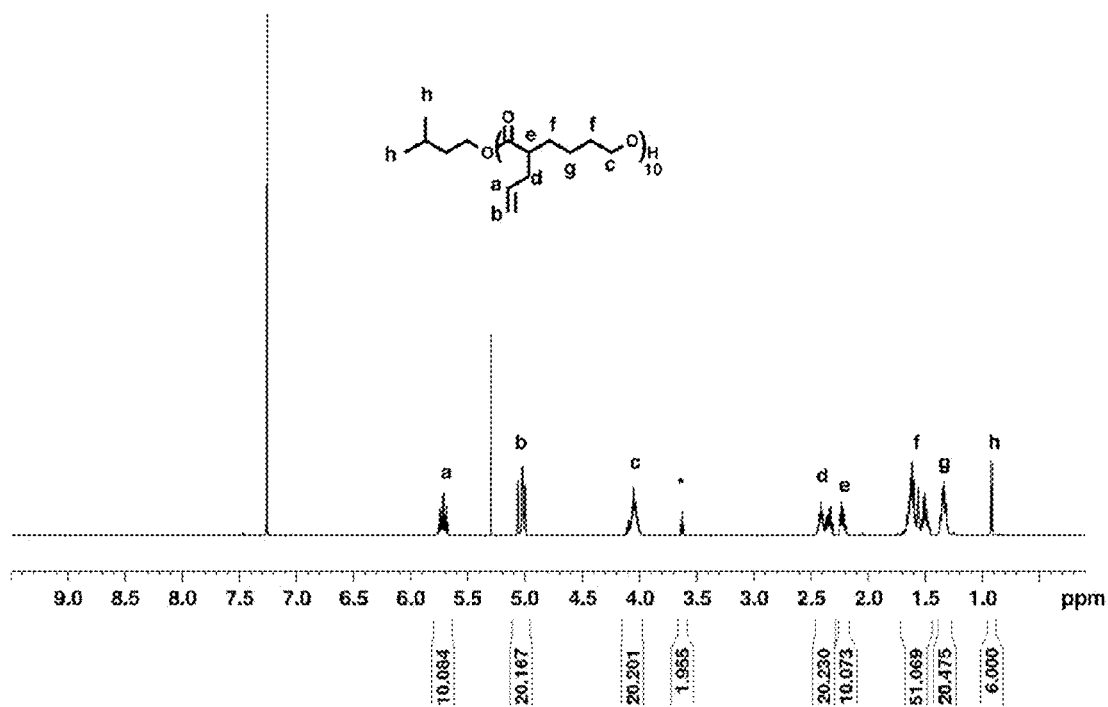
FIG. 41 is a graph showing $^1$H-NMR spectrum of pCL-allyl$_{10}$ (CDCl$_3$, 500 MHz). *=protons from terminal repeat unit on polymer.
Figure 42:
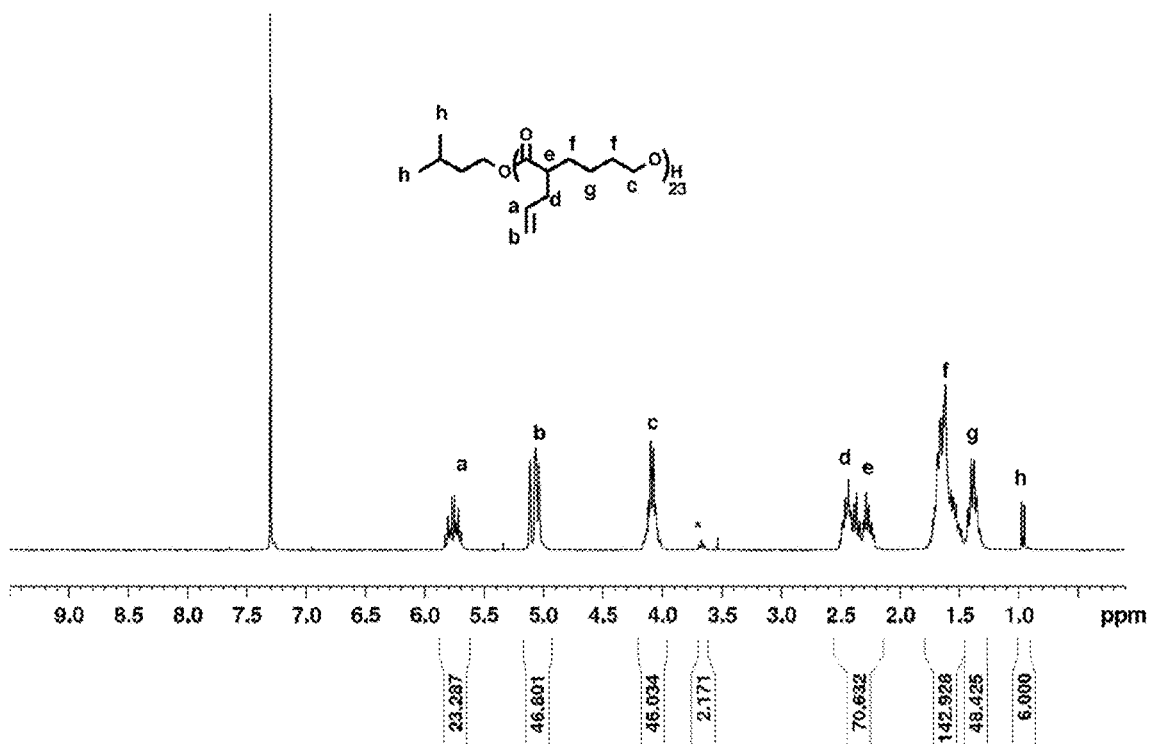
FIG. 42 is a graph showing $^1$H-NMR spectrum of pCL-allyl$_{20}$ (CDCl$_3$, 500 MHz). *=protons from terminal repeat unit on polymer.
Figure 43:
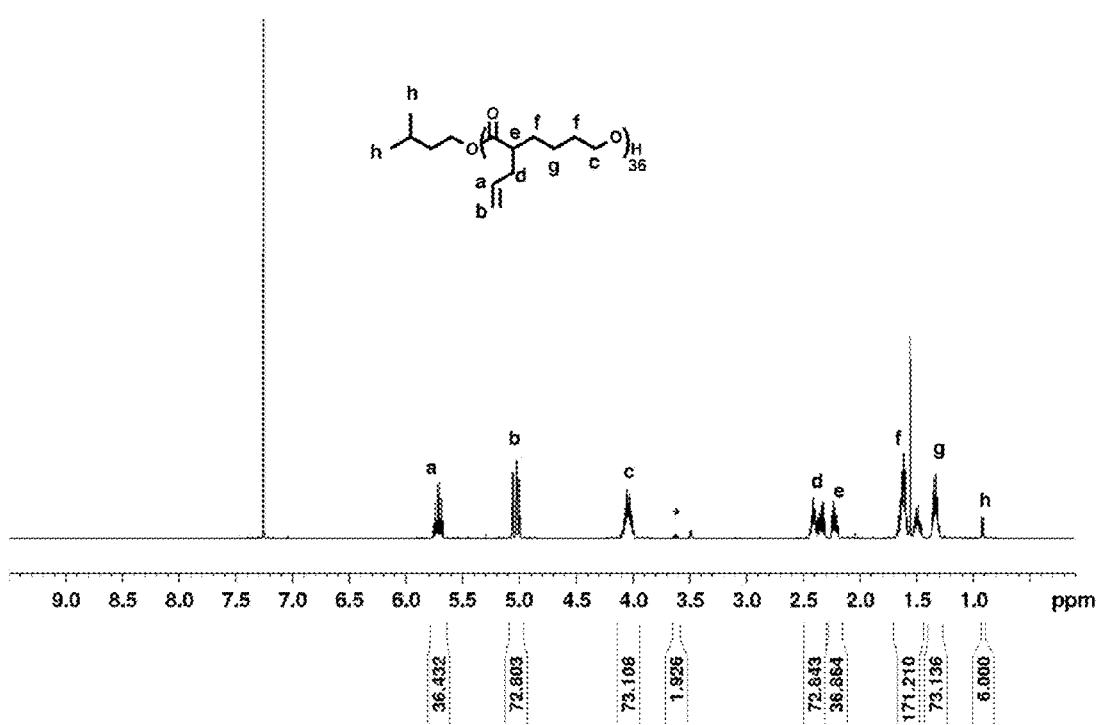
FIG. 43 is a graph showing $^1$H-NMR spectrum of pCL-allyl$_{40}$ (CDCl$_3$, 500 MHz). *=protons from terminal repeat unit on polymer.
Figure 44:
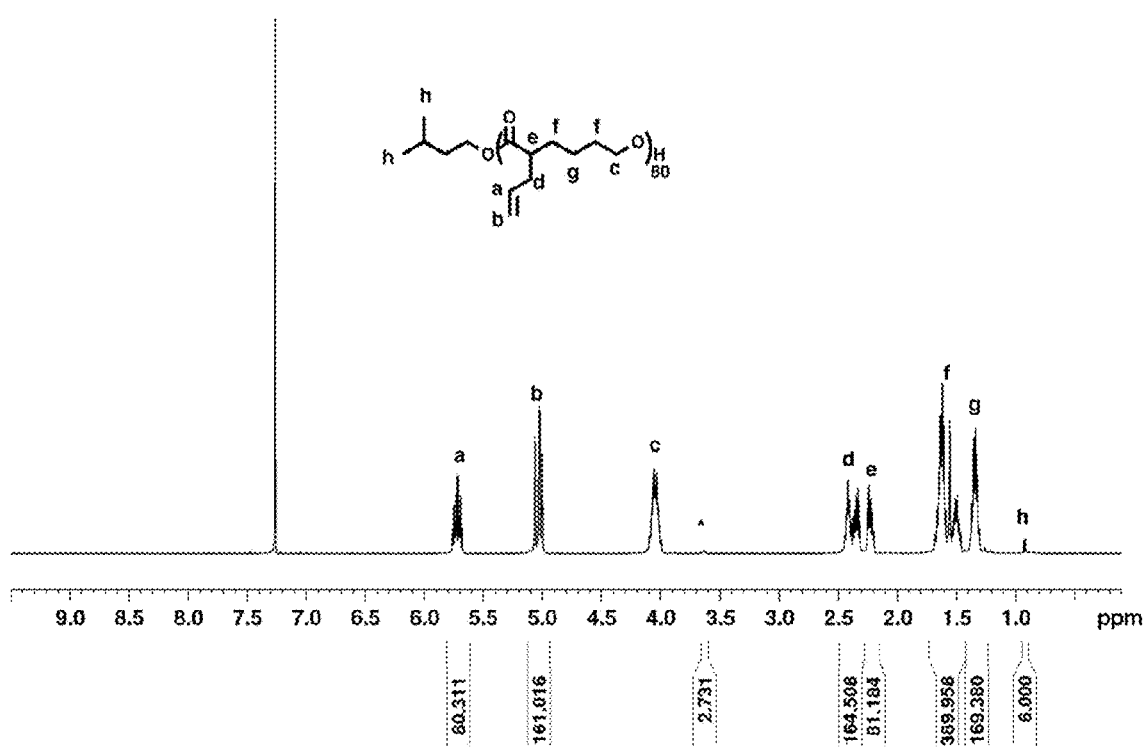
FIG. 44 is a graph showing $^1$H-NMR spectrum of pCL-allyl$_{80}$ (CDCl$_3$, 500 MHz). *=protons from terminal repeat unit on polymer.
Figure 45:
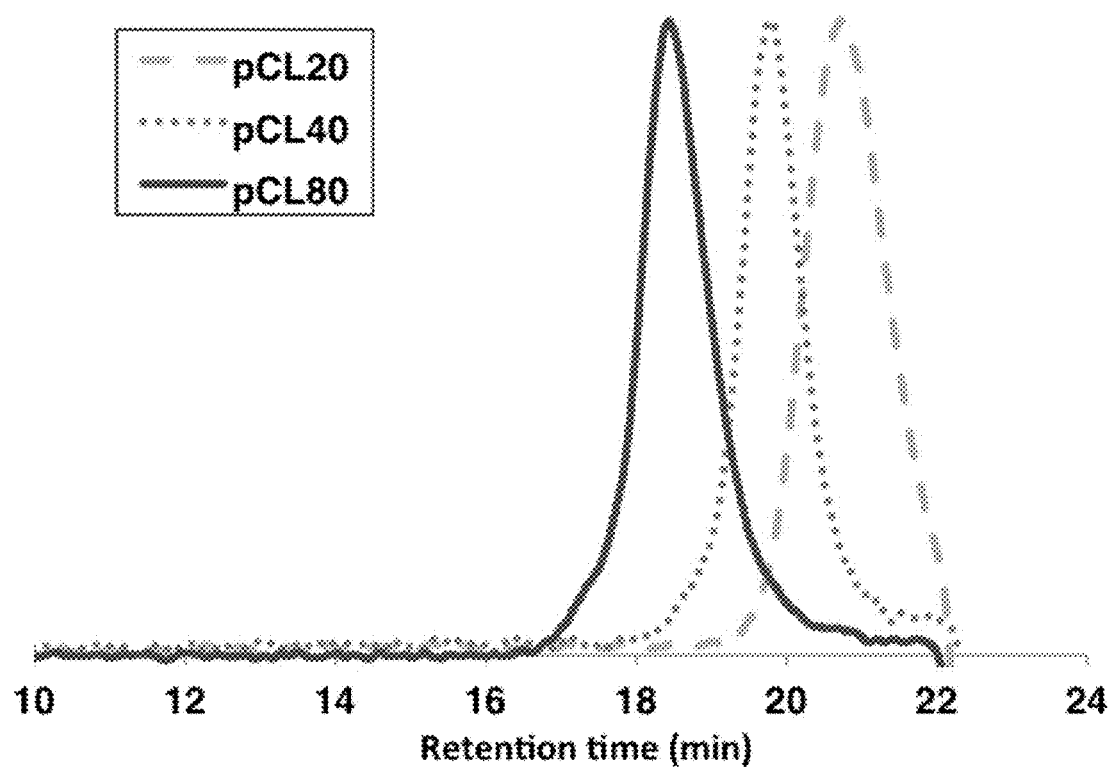
FIG. 45 is a graph showing Gel permeation chromatograms of pCL-allyl$_{20}$, pCL-allyl$_{40}$, pCL-allyl$_{80}$. pCL-allyl$_{10}$ overlapped the solvent peak and was not able to be analyzed by GPC.

FIG. 39 demonstrates that although both the zwitterionic and trehalose side chains significantly outperformed the other control polymers for stabilization of biomolecules, the zwitterionic polymers retained greater activity of the biomolecules than the trehalose side chain polymers of the same size. Larger trehalose side chain polymers were equivalent to smaller zwitterion polymers with regard to stabilization.

The pCL trehalose polymers and the pCL zwitterion polymers may stabilize biomolecules when they are covalently bonded with the biomolecules. Example 1 and scheme 4 (FIG. 85) show conjugation of trehalose-caprolactone to lysozyme via reductive amination and conjugate stabilization of the protein.

In one embodiment, the pCL trehalose polymers or pCL zwitterion polymers are degradable. The backbone of polycaprolactone of the pCL trehalose polymers or pCL zwitterion polymers may be degradable under an aqueous condition or under other conditions. For example, caprolactone polymers are known to degrade more quickly by enzymes.

In one embodiment, the pCL trehalose polymers or pCL zwitterion polymers may be hydrolytically degradable.

In one embodiment, the pCL trehalose polymers or pCL zwitterion polymers may be controlled to be slowly degradable.

Scheme 14 shows hydrolysis of the pCL trehalose polymers. Specifically, pCL-trehalose$_{20}$ was treated with 5% KOH to hydrolytically cleave the backbone esters. However, no hydrolytic degradation was observed under more moderate degradation conditions (cell media at 37° C.) for up to 49 days, consistent with the slow hydrolysis rates observed for polycaprolactone in vivo.

In one embodiment, the pCL trehalose polymers and the pCL zwitterion polymers and their degradation products are not cytotoxic.

Figure 69:
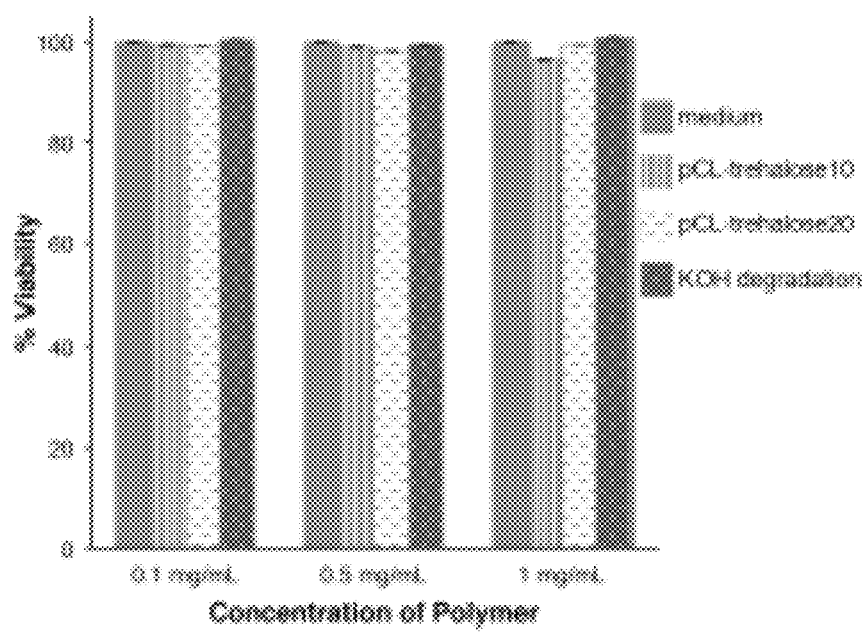
FIG. 69 is a graph showing cytotoxicity assay of pCL-trehalose$_{10}$, pCL-trehalose$_{20}$, and basic degradation products with HUVECs. Data shown as the average of three experimental repeats with standard deviation. There is no statistical difference between groups.
Figure 70:
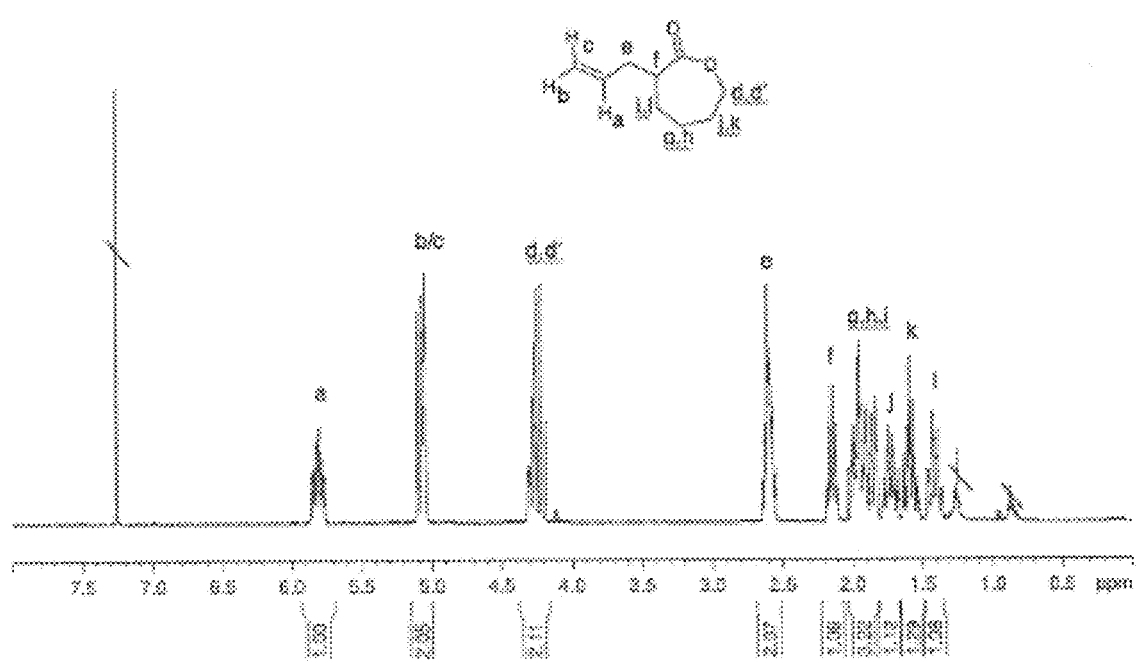
FIG. 70 is a graph showing $^1$H-NMR spectrum of poly(allyl-caprolactone).
Figure 71:
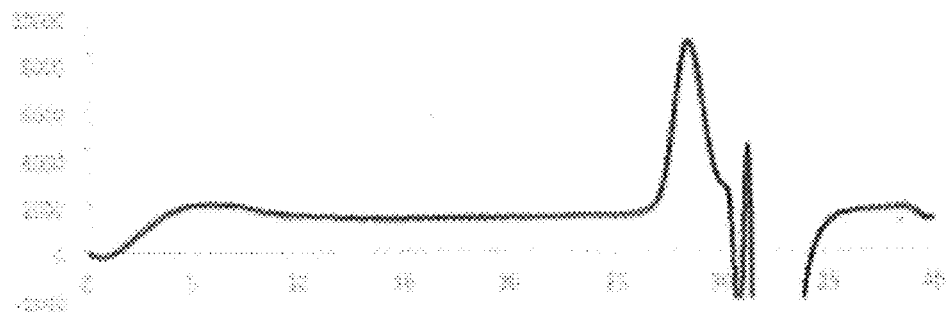
FIG. 71 is a graph showing GPC trace of poly(allyl-caprolactone).
Figure 72:
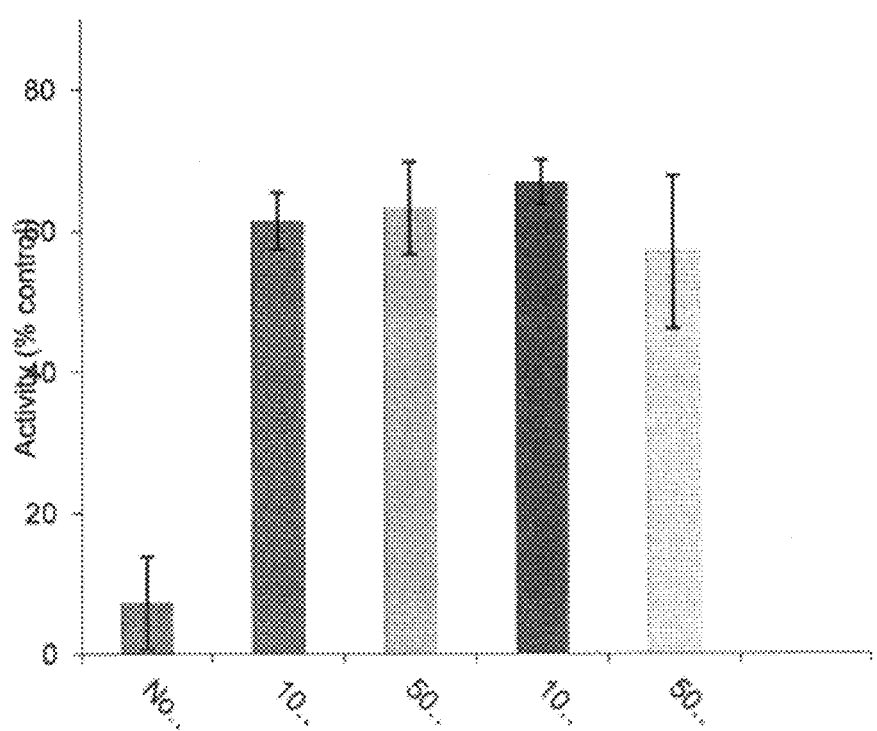
FIG. 72 is a graph showing stabilization of lysozyme against heat stress by trehalose polyester.
Figure 73:
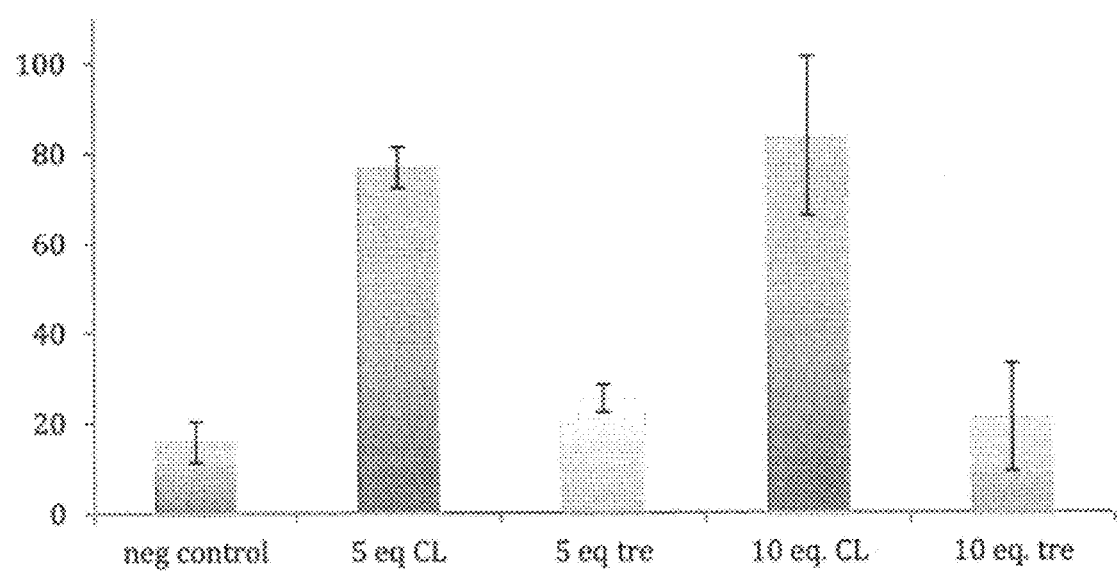
FIG. 73 is a graph showing stabilization of β-Galactosidase against lyophilization stress by trehalose polyester.

FIG. 69 demonstrates that the non-cytotoxicity of pCL-trehalose$_{10}$, pCL-trehalose$_{20}$, and basic degradation products with HUVECs.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

EXAMPLES

Example 1

Caprolactone Polymers

Herein we describe the synthesis of a biodegradable trehalose polymer using ring-opening polymerization (ROP). We show that this polymer when added to proteins stabilizes the biomolecules to stressors such as heating.

Subsequent conjugation to the protein lysozyme was demonstrated using reductive amination. We expect that these polymers can function as improved PEG replacements in protein-polymer therapeutics due to their combination of biodegradability and stabilization abilities. They may also be interesting added as excipients.

Synthetic Methods

Synthesis of Thiolated Trehalose Monomeric Unit.

A thiol-functionalized trehalose molecule was synthesized in 5 steps, with 19% overall yield (Scheme 1; the numericals of compounds are limited in Example 1). Briefly, the primary alcohols of trehalose was selectively functionalized using the bulky trityl protecting group and the remaining hydroxyls converted to the acetate ester using acetic anhydride to form 2. Deprotection of the trityl ether under acidic conditions, followed by tosylation of the exposed alcohol led to tosyl ester 4, which was displaced using the nucleophile potassium thioacetate to yield the thioacetate ester 5. Selective removal of the more labile thioester led to the thiolated trehalose 6.

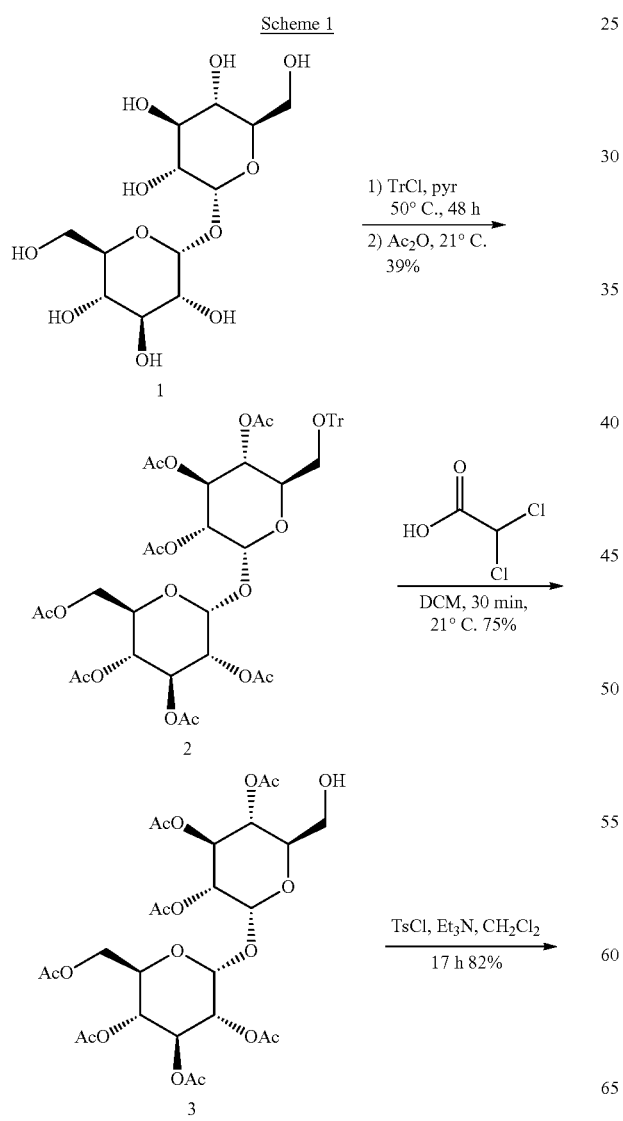

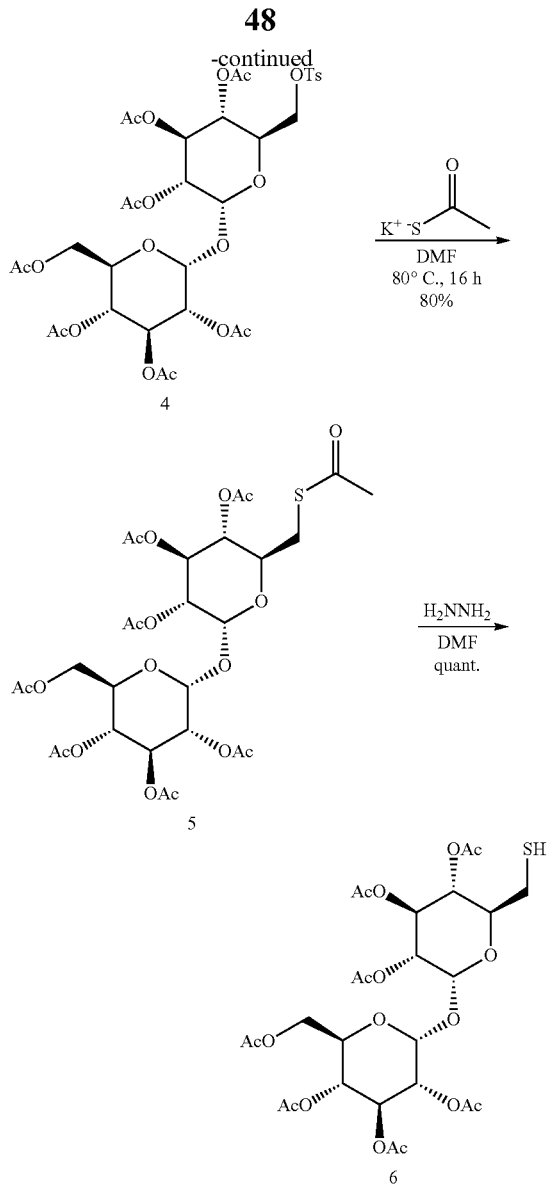

Experimental Details

Tosyl Trehalose 4.

Figure 2:
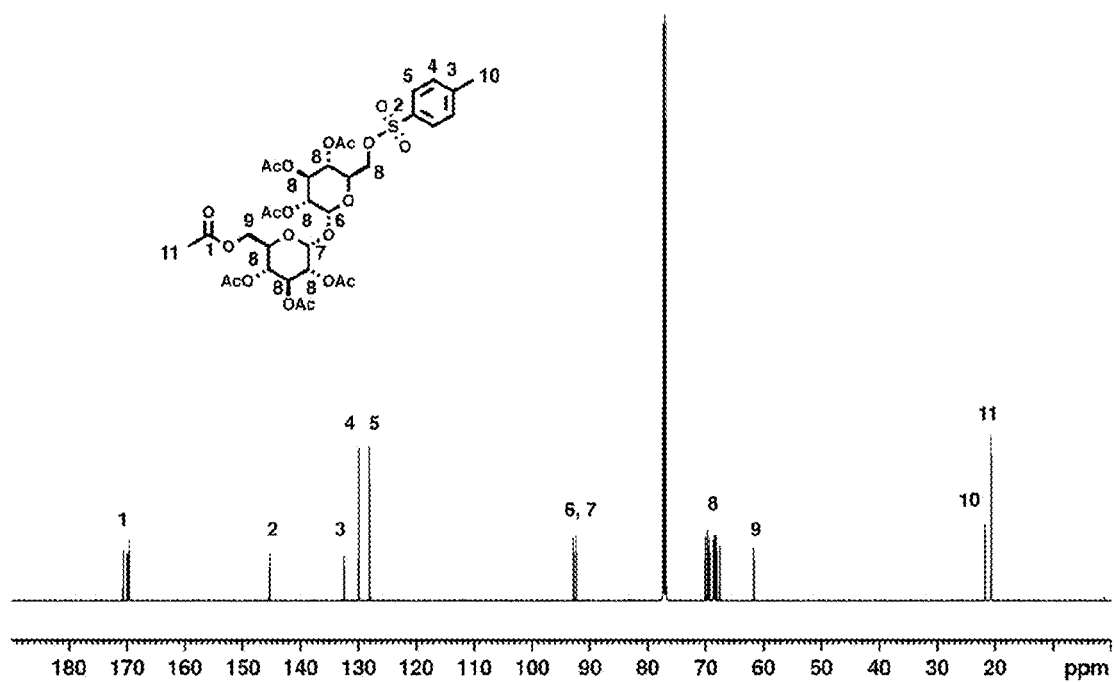
FIG. 2 is a graph showing $^{13}$C-NMR (500 MHz, CDCl$_3$) of tosylated trehalose 4.
Figure 3:
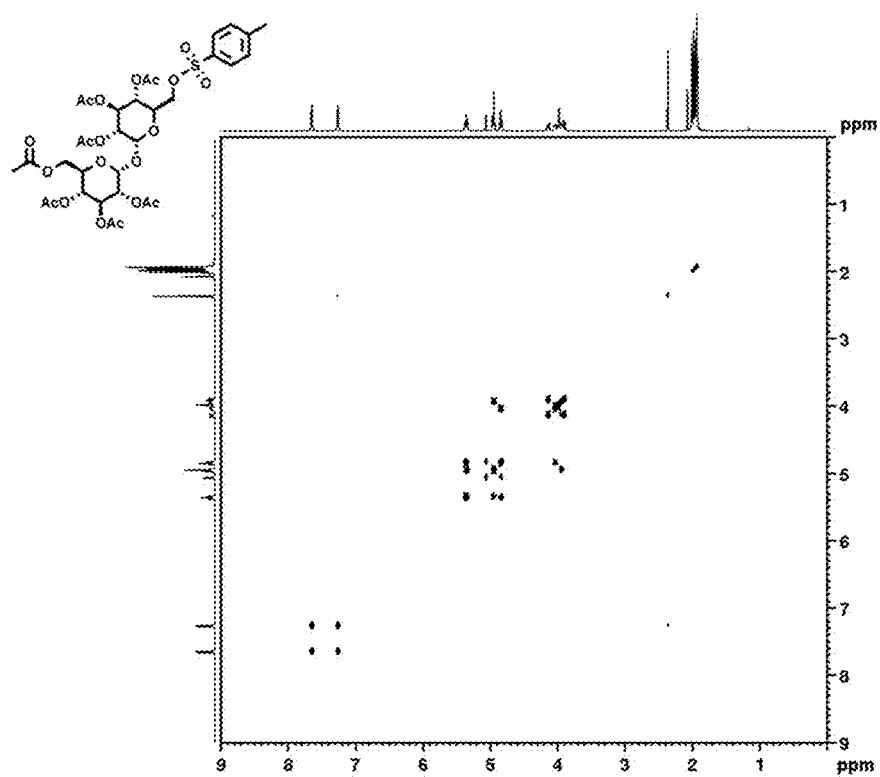
FIG. 3 is a graph showing HSQC 2D-NMR (500 MHz, CDCl$_3$) of tosylated trehalose 4.

In a two-neck round bottom flask, monohydroxylheptaacetyltrehalose (Lee et al., 2013) (1.08 g, 1.69 mmol) was dissolved in anhydrous $CH_2Cl_2$ (10 mL) under argon. Dimethylamino pyridine (DMAP) (41 mg, 0.34 mmol) and anhydrous pyridine ((0.4 mL, 5.1 mmol) were added and the reaction solution cooled to 0° C. in an ice-water bath. Tosyl chloride 970 mg, 5.1 mmol) was added slowly as a solid and the solution stirred for an additional 30 minutes at 0° C. before warming to room temperature for 14 hours. The crude mixture was diluted with additional $CH_2Cl_2$ and washed with water and brine. The organic layer was then dried with MgSO4 and concentrated in vacuo. The crude solid was purified by silica gel flash column chromatography (eluent 4:1 $CH_2Cl_2$:EtOAc) to obtain a crispy white solid (1.062 g, 1.34 mmol, 79.5%). $^1$H-NMR (500 MHz in CDCl3) δ: 7.74 (d, J=8.3 Hz, 2H), 7.34 (d, J=8 Hz, 2H), 5.47-5.41 (m, 2H), 5.14 (d, J=3.9 Hz, 1H), 5.05-5.01 (m, 3H), 4.93-4.89 (m, 2H), 4.21 (dd, J=12.1 Hz, 6.7 Hz, 1H), 4.14-3.94 (m, 5H), 2.44 (s, 3H), 2.09 (s, 3H), 2.06 (s, 3H), 2.05 (s, 3H), 2.03 (s, 3H), 2.02 (s, 3H), 2.01 (s, 3H), 2.00 (s, 3H). $^{13}$C NMR: (500 MHz in CDCl$_3$) δ: 169.0, 169.9, 169.6, 169.6, 169.5, 169.5, 145.3, 132.4, 129.9, 128.0, 92.8, 92.3, 70.0, 69.7, 69.7, 69.3, 68.6, 68.4, 68.2, 68.1, 67.5, 61.7, 21.7, 20.7, 20.7, 20.6, 20.6, 20.6, 20.5. IR: ν=2950, 1744, 1432, 1368, 1221, 1190, 1177, 1138, 1079, 1035, 1016, 988, 911, 862, 805 cm$^{-1}$. HRMS-ESI (m/z) [M+H$_2$O]$^+$ calcd for C$_{33}$H$_{44}$O$_{21}$S, 808.2096; found 808.2226. FIG. 1 shows $^1$H-NMR (500 MHz, CDCl$_3$) of tosylated trehalose 4. FIG. 2 shows $^{13}$C-NMR (500 MHz, CDCl$_3$) of tosylated trehalose 4. FIG. 3 shows HSQC 2D-NMR (500 MHz, CDCl$_3$) of tosylated trehalose 4.

Thioacetate Trehalose 5.

Figure 4:
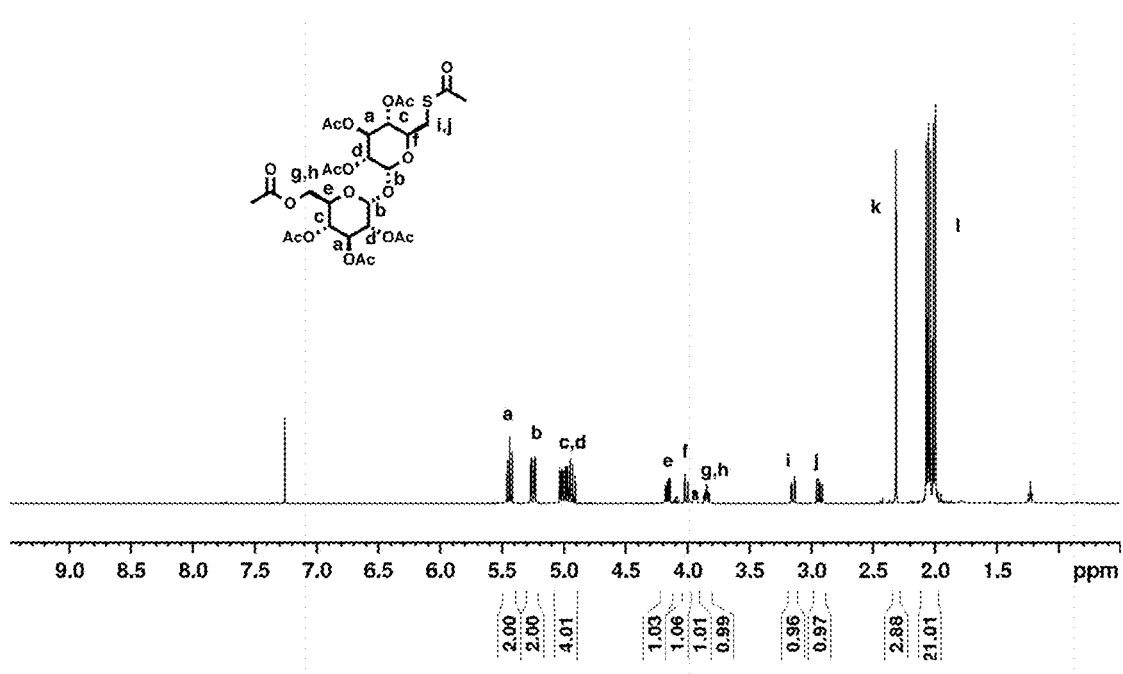
FIG. 4 is a graph showing $^1$H-NMR (500 MHz, CDCl$_3$) of thioacetate trehalose 5.
Figure 5:
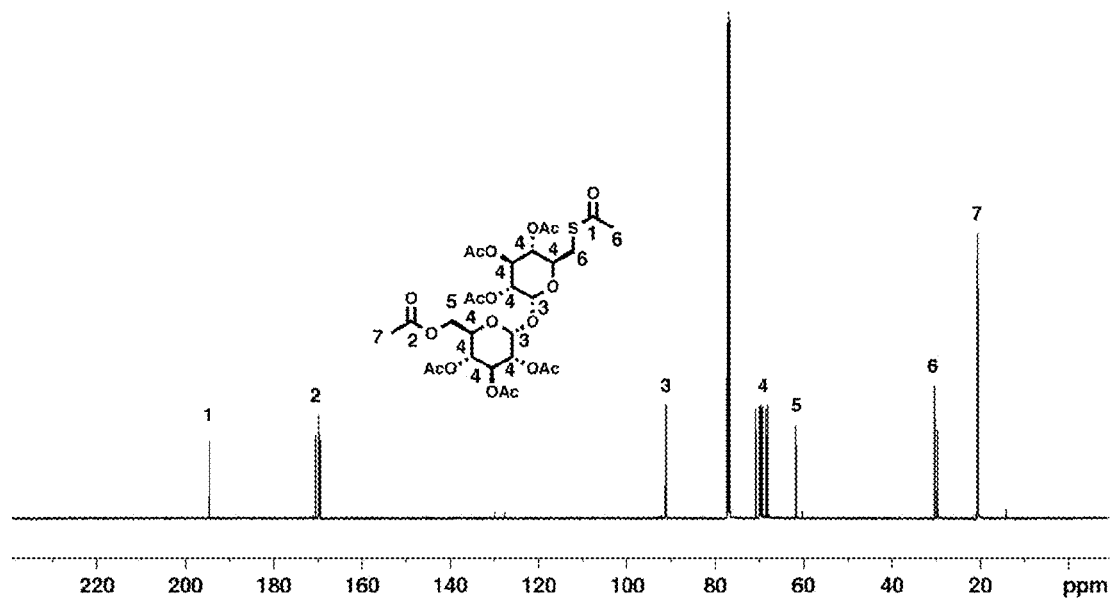
FIG. 5 is a graph showing $^{13}$C-NMR (500 MHz, CDCl$_3$) of thioacetate trehalose 5.

In a two-neck round bottom flask, tosylated trehalose 4 (1.08 g, 1.36 mmol) was dissolved in anhydrous DMF (10 mL) under argon. Potassium thioacetate (480 mg, 4.20 mmol) was added and the reaction solution heated to 80° C. for 14 hours. After cooling to room temperature, DMF was removed in vacuo. The crude brown solid was redissolved in CH$_2$Cl$_2$ and washed with water, sat. NaHCO3 (2×), water, and brine. The organic layer was dried with MgSO4 and concentrated in vacuo. The crude oil was purified by silica gel flash column chromatography (eluent 4:1 CH$_2$Cl$_2$:EtOAc) to obtain 3 as a crispy tan solid (835.2 mg, 1.20 mmol, 89%). $^1$H NMR: (500 MHz in CDCl$_3$) δ: 5.45 (t, J=9.8 Hz, 2H), 5.26 (dd, J=4, 11.2 Hz, 2H), 5.05-4.91 (m, 4H), 5.16 (dd, 1H), 4.00 (dd, 1H), 3.88-3.87 (m, 1H), 3.85 (ddd, 1H), 3.16 (dd, J=2.8, 14.4, 1H), 2.94 (dd, J=7.6, 14.4, 1H), 2.32 (s, 3H), 2.08 (s, 3H), 2.06 (s, 3H), 2.06 (s, 3H), 2.04 (s, 3H), 2.02 (s, 3H), 2.00 (s, 3H), 2.00 (s, 3H). $^{13}$C NMR: (500 MHz, CDCl3) δ: 194.6, 170.6, 169.9, 169.9, 169.9, 169.7, 169.7, 159.6, 91.4, 91.2, 70.9, 70.0, 70.0, 69.8, 69.6, 69.3, 68.5, 68.2, 61.8, 30.4, 29.8, 20.7, 20.6, 20.6, 20.6, 20.5. IR: ν=2957, 1746, 1694, 1431, 1367, 1212, 1161, 1134, 1034, 981, 962, 900, 803 cm$^{-1}$. FIG. 4 shows $^1$H-NMR (CDCl$_3$, 500 MHz) of thioacetate trehalose 5. FIG. 5 shows $^{13}$C-NMR (CDCl$_3$, 500 MHz) of thioacetate trehalose 5.

Thiolated Trehalose 6.

Figure 6:
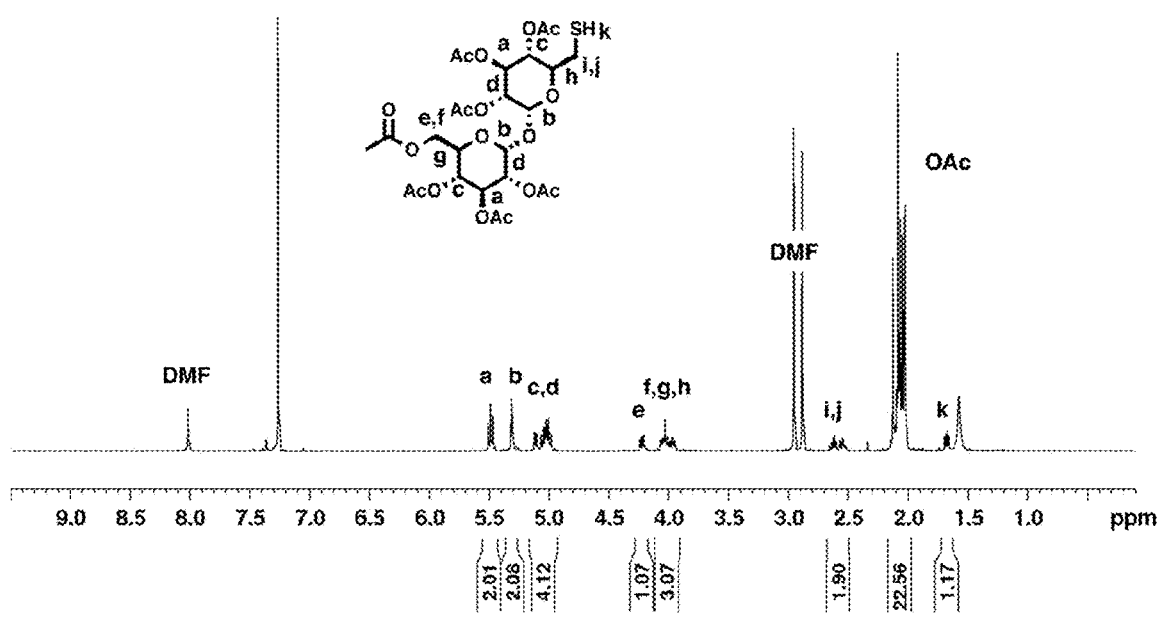
FIG. 6 is a graph showing $^1$H-NMR (500 MHz, CDCl$_3$) of thiol trehalose 6.

In a 20 mL screw-top vial, thioacetylated trehalose 5 (628.3 mg, 0.90 mmol) was dissolved in dry DMF (18 mL) under argon. Acetic acid (51 µL, 0.90 mmol) was added and the solution was stirred for 10 minutes. Hydrazine hydrate (70-82% in H2O, 55 µL, 0.90 mmol) was then added and the reaction solution was stirred at 21° C. for a further 2 hours. Acetone (75 µL) was added to quench the reaction. The solution was diluted with EtOAc, washed 2× with brine, then dried over MgSO4. Solvent and residual DMF were removed in vacuo by freeze-drying from benzene to yield a light tan solid (597 mg, 0.90 mmol, >99%). FIG. 6 shows $^1$H-NMR (CDCl$_3$, 500 MHz) of thiol trehalose 6.

Synthesis of Poly(Caprolactone) with Reactive Pendant Units and Installation of Trehalose Moieties.

Polycaprolactone was selected as the backbone due to its previous use in the medical field and because of the well-developed chemistries for its polymerization and modification (Ende et al., 2008; Silvers et al., 2012; Parrish et al., 2002; Parrish et al., 2005). Allyl-functionalized caprolactone (aCL) was first synthesized in one step following literature procedures (Ende et al., 2008). The ROP of aCL was conducted in toluene with functional alcohols as initiators and triazabicyclodecane (TBD) as organic catalyst (Scheme 2). TBD was selected due to its high activity at room temperature and relative stability to air (Pratt et al., 2006; Lohmeijer et al., 2006). For trehalose polymers to be used as excipients, 2-methylpropanol was used for ease of characterization. For polymers to be used for conjugations, 2,2-diethoxyethanol was used as a protected protein-reactive group.

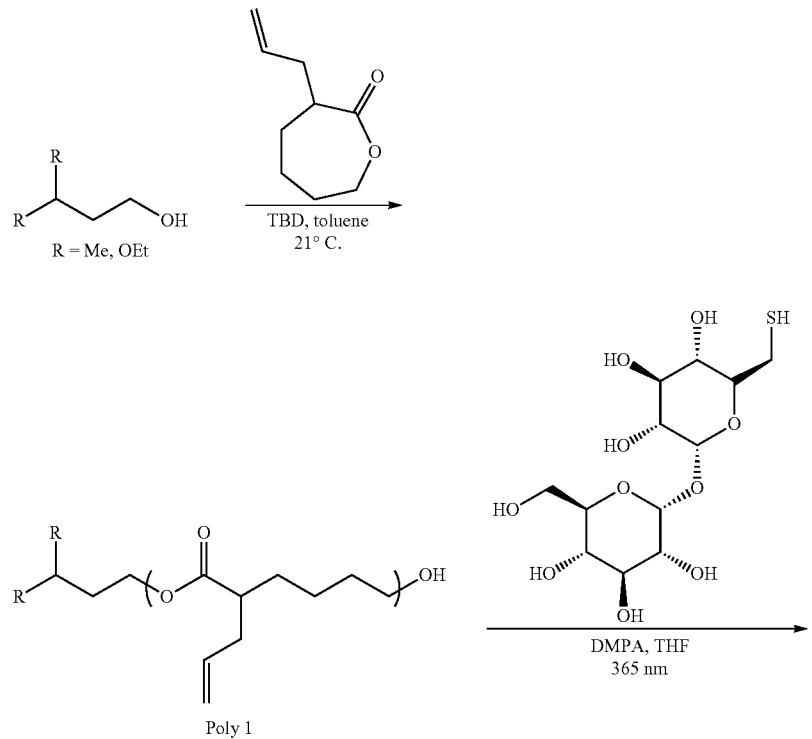

Scheme 2

Poly 1

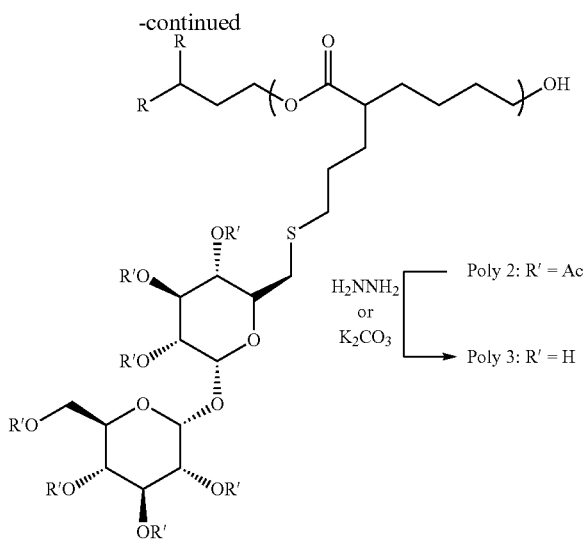

Figures 7A, 7B:
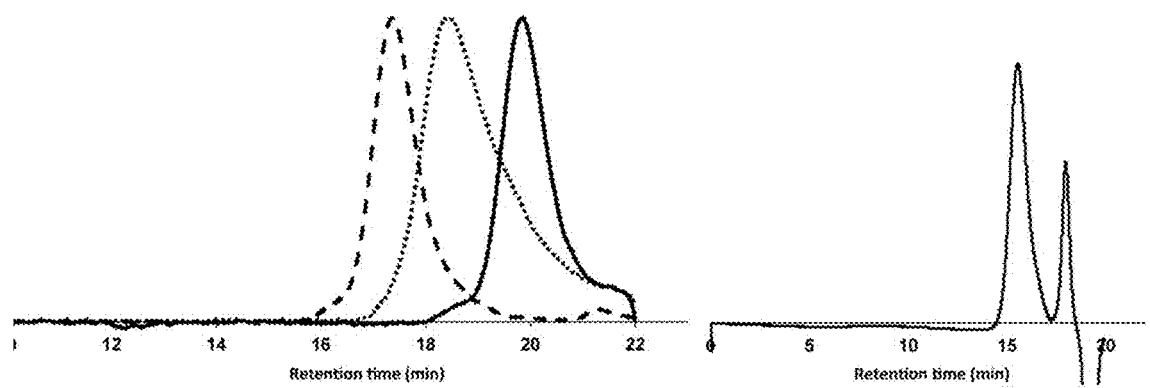
FIG. 7A is a graph showing gel permeation chromatogram of Poly 1-3. Red: Poly 1. Blue: Poly2. Green: Poly3.
FIG. 7B is a graph showing size exclusion chromatography of Poly3.

Acetate-protected trehalose thiol was then installed through a photo-initiated thiol-ene reaction with dimethoxyphenylacetophenone (DMPA) as the photoinitiator (Campos et al., 2008). Full conversion was confirmed by the loss of the allyl peaks at 5.7 ppm in the $^1$H-NMR. The integrity of the polyester backbone was confirmed after each modification by GPC, with an increase in molecular weight and no significant broadening after the attachment of the acetate-protected trehalose units (FIG. 7a).

Removal of the acetate groups could be achieved without hydrolysis of the backbone by either using hydrazine in DMF or 50 mM $K_2CO_3$ in $CHCl_3$/MeOH. A slight broadening was observed when the polymer was analyzed by GPC in organic solvent (FIG. 7a), however when the polymer was analyzed by SEC in aqueous solvent no such increase in D could be seen (FIG. 7b). Therefore the increase in D was hypothesized to be due to interactions between the polysaccharide hydroxyls and the column stationary phase, and not due to any cleavage of the backbone esters.

Modifications to these chemistries could be made. Other protein-reactive functionalities could be used, including thiol-reactive maleimide and pyridyl disulfide groups. These could be installed using a functional alcohol initiator or through post-polymerization esterification with the omega hydroxyl group. A sample post-polymerization modification is shown in Scheme 3, where a methacrylate group was installed via esterification.

Scheme 3

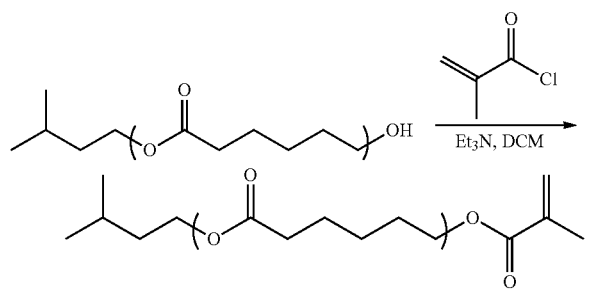

The nature of click chemistry could also be varied. For example, reagent pairs such as azide-alkyne (Parrish et al., 2005) or vinylsulfone-thiol (Wang et al., 2011) could be used to attach the trehalose moieties to the caprolactone backbone.

Experimental Details

Representative Ring-Opening Polymerization of Poly(Allyl-Caprolactone).

Figure 8:
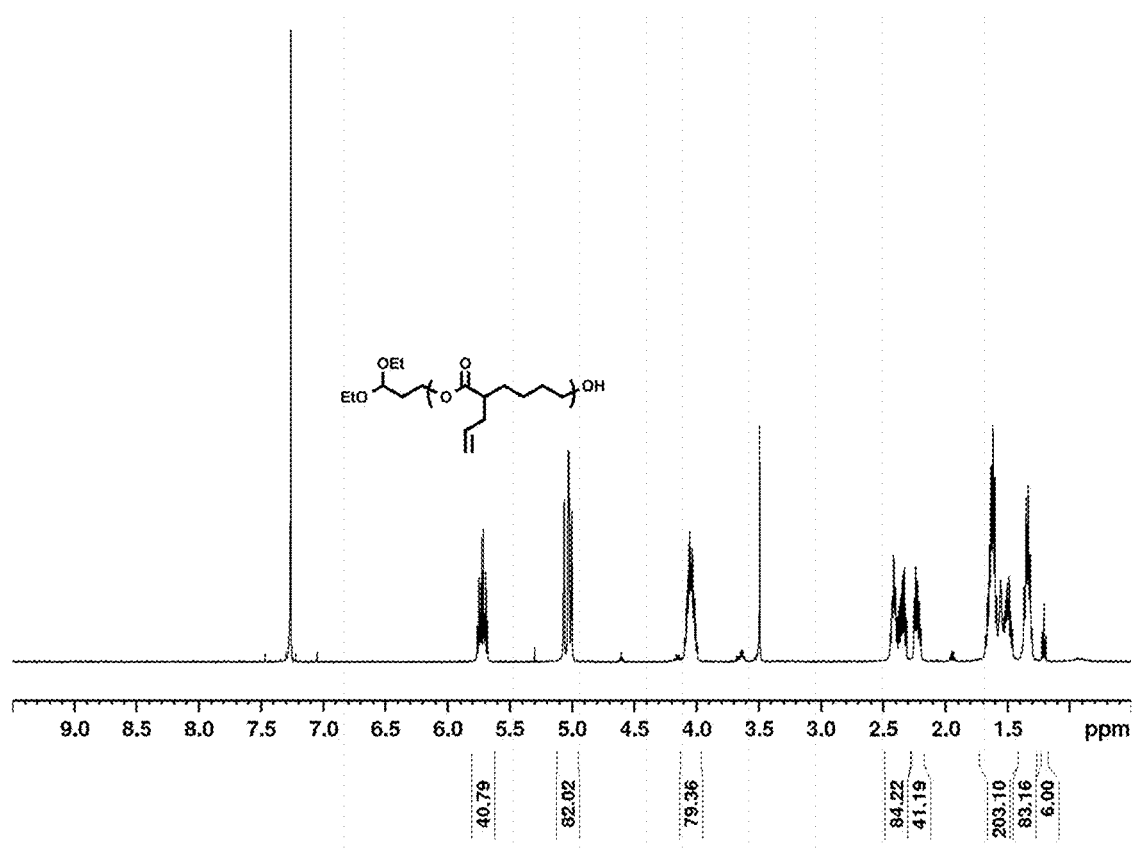
FIG. 8 is a graph showing $^1$H-NMR (CDCl$_3$, 500 MHz) of allyl-functionalized poly(caprolactone).

A 25 mL two-neck round bottom flask was equipped with a stir bar and flame-dried. Triazabicyclodecane (6.6 mg, 47 μmol) added and the flask was evacuated and refilled with nitrogen three times. Anhydrous toluene (600 μL) and 2,2-diethoxyethanol (3.3 mg, 22 μmol in 10 μL toluene) was added via nitrogen-purged syringe and the initiator-catalyst mixture was allowed to stir for 30 minutes at 21° C. before adding allyl-caprolactone (193 mg, 1270 μmol) via nitrogen-purged syringe. The reaction mixture was stirred at 21° C. and aliquots were removed for $^1$H-NMR analysis via syringe. After the desired conversion was achieved (5.5 h), the reaction was quenched with $H_2O$/MeOH and residual monomer and catalyst were removed by dialyzing with Spectra/Por dialysis membrane (MWCO 1 kD) against MeOH to give the polymer as a colorless oil. FIG. 8 shows $^1$H-NMR ($CDCl_3$, 500 MHz) of allyl-functionalized poly (caprolactone).

Synthesis of Functional Polyesters Via Thiol-Ene Reaction.

Figure 9:
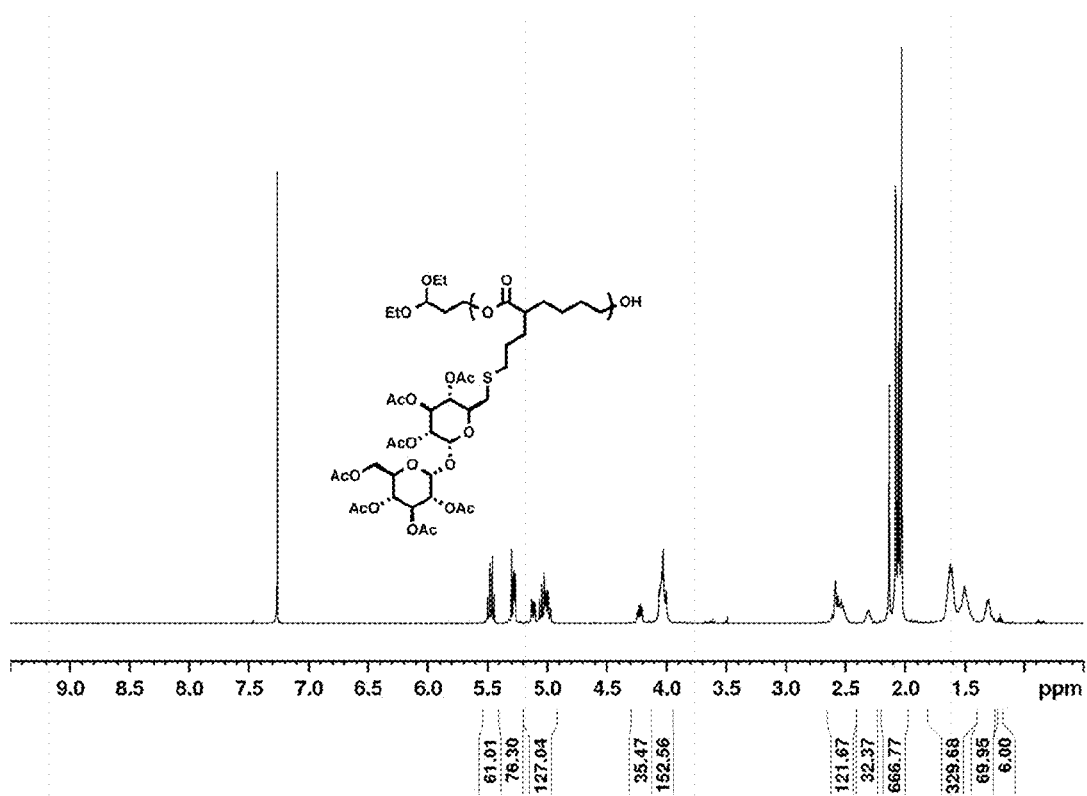
FIG. 9 is a graph showing $^1$H-NMR (CDCl$_3$, 500 MHz) of acetate-protected trehalose-caprolactone polymer.

In a 1.5 mm sample vial, poly(allyl-caprolactone) (15.6 mg) was dissolved in anhydrous THF (700 μL). Thiol trehalose 4 (208 mg) and 2,2-dimethoxy-2-phenylacetophenone (13.5 mg) were added and the vial was sealed with a rubber septum, degassed for 10 minutes, and exposed to a handheld UV lamp (λ=365 nm) for 4 hours. The crude solution was then precipitated into cold MeOH to yield the acetate protected trehalose polyester. FIG. 9 shows $^1$H-NMR ($CDCl_3$, 500 MHz) of acetate-protected trehalose-caprolactone.

Deprotection of Trehalose Polyester.

Figure 10:
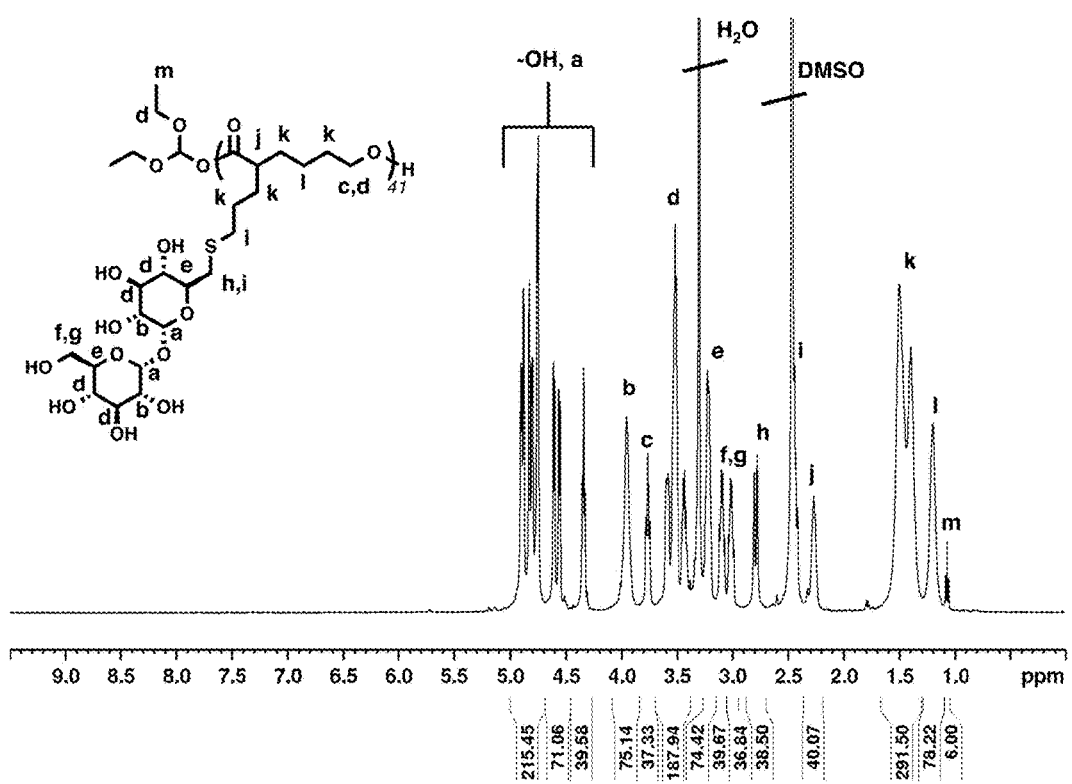
FIG. 10 is a graph showing $^1$H-NMR (500 MHz, DMSO-d$_6$) of acetal-end functionalized trehalose-caprolactone.

Hydrazine was used for global deprotection of the trehalose acetate esters to avoid base-catalyzed hydrolysis of the polyester backbone and to simultaneously expose the hydroxylamine end-group.[34] Alternatively, $K_2CO_3$ could be used as a mild base. In a 20 mL screw-top vial, acetylated trehalose polyester was dissolved in DMF or CHCl$_3$/MeOH. Hydrazine (78-82% in H2O) or K$_2$CO$_3$ (50 mM) was added and the reaction solution was stirred for 20 hours for hydrazine or 3 hours for K$_2$CO$_3$. The formation of hydrazine acetate could be observed as a fine white precipitate as the reaction progressed. To quench these reactions, acetone was added. For all deprotections, the reaction mixture was diluted with H$_2$O and dialyzed against 50% MeOH/H$_2$O with 1 kD MWCO dialysis tubing. FIG. 10 shows $^1$H-NMR (500 MHz, DMSO-d$_6$) of acetal-functionalized trehalose-caprolactone.

Modification of Acetate Protected Trehalose-Caprolactone with Methacryloyl Chloride.

Figure 11:
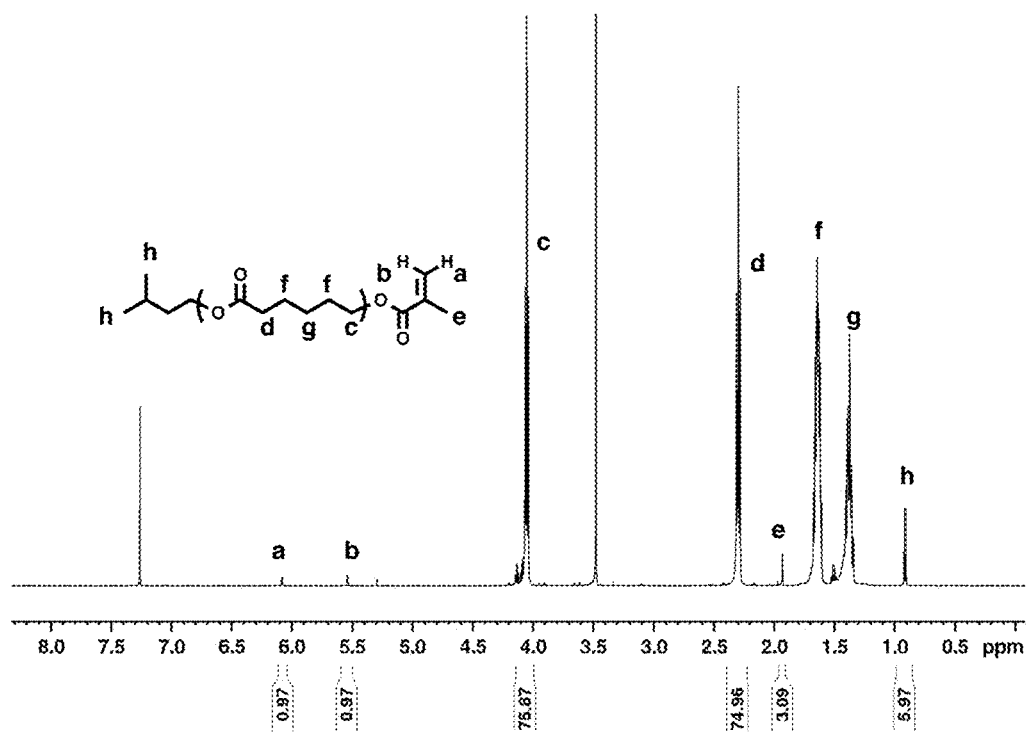
FIG. 11 is a graph showing $^1$H-NMR (500 MHz, CDCl$_3$) of poly(caprolactone) with a methacrylate end group prepared post functionalization.

Acetate-protected trehalose-caprolactone (15 mg) was dissolved in 1 mL anhydrous dichloromethane. Dry triethylamine (21 µL, dried over molecular sieves) was added and the mixture let stir briefly and cooled to 0° C. Methacryloyl chloride (15 µL) was then added and the mixture stirred at 0° C. for 1 hour and then at room temperature. After 28 hours, the mixture was concentrated and the crude solid was re-dissolved in 200 µL DCM and precipitated into 15 mL cold MeOH. The solid was separated by 10 minutes centrifugation and the solution removed. Dissolution and precipitation were repeated and the product was dried in vacuo to reveal a white solid. FIG. 11 shows.

Stabilization of Model Proteins Using Trehalose-Caprolactone as Excipient.

Figure 12A:
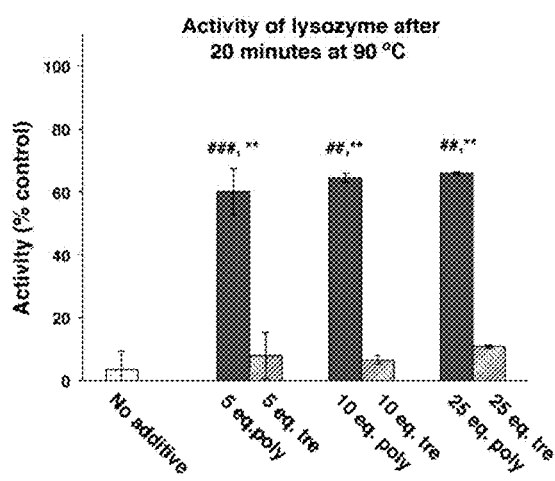
FIG. 12A is a graph showing stabilization of lysozyme.

The ability of these biodegradable trehalose polymers to stabilize proteins was confirmed through heat and lyophilization stress assays. We have previously used trehalose polymers to demonstrate stabilization of lysozyme against heat burden and β-galactosidase (β-Gal) against lyophilization, respectively (Mancini and Maynard, 2012; Lee et al., 2013). Therefore, these proteins were also selected to test the biodegradable trehalose polymers. First, lysozyme was stressed by heating to 90° C. for 20 minutes. To determine the concentration range and effectiveness of the polymer, samples were prepared with 5 to 25 wt eq. of both trehalose-CL as well as trehalose alone. The activity of lysozyme was determined by using a commercially available kit, wherein protein activity is measured by fluorescence resulting from lysis of fluorescein-labeled *Micrococcus lysodeikticus*. Lysozyme samples containing trehalose-CL as an excipient retained up to 66% of native activity, while lysozyme alone displayed 4% retention (FIG. 12a). Trehalose as additive was not significantly different from the negative control.

Figure 12B:
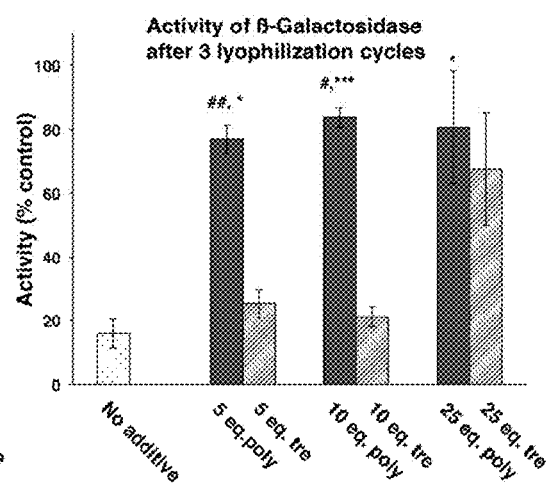
FIG. 12B is a graph showing β-Gal by trehalose-CL. ###: p<0.001 compared to the same wt eq trehalose. ##: p<0.01 compared to the same wt eq trehalose. #: p<0.05 compared to the same wt eq trehalose *: p<0.001 compared to the negative control.: p<0.01 compared to the negative control. * p<0.05 compared to the negative control. White is no additive, dark is adding the trehalose caprolactone polymer, and gray is adding trehalose.

The stabilization of β-Gal against lyophilization stress was also measured. Three 12-hour desiccation cycles were performed with and without trehalose-CL and trehalose as additives. The activity of β-Gal was determined by reaction with ortho-nitrophenol galactose (ONPG). When incubated with β-Gal, release of the yellow-colored o-nitrophenol from ONPG can be monitored at 405 nm. Samples containing trehalose-CL as an excipient maintained up to 84% of native activity, while the unstabilized protein retained only 16% (FIG. 12b). For this protein, high equivalents of trehalose were able to stabilize β-Gal to the same extent as the polymer, up to 67% at 25 equivalents of trehalose.

Trehalose-CL and a styrenyl ether trehalose (SET) polymer previously described were also directly compared in their stabilization of lysozyme (FIG. 13) (Lee et al., 2013). In this test, trehalose-CL maintained up to 61% of lysozyme native activity, while the SET polymer retained up to 67%. Thus, the degradable trehalose glycopolymer was similar in stabilization ability to the non-degradable version.

Experimental Details

Protein Activity

Lysozyme and β-Galactosidase were assayed as previously described (Lee et al., 2013). Briefly, the activity of lysozyme was determined by using a commercially available kit, wherein protein activity is measured by fluorescence resulting from lysis of fluorescein-labeled *Micrococcus lysodeikticus*. The activity of β-Gal was determined by reaction with ortho-nitrophenol galactose (ONPG). When incubated with β-Gal, release of the yellow-colored o-nitrophenol from ONPG can be monitored at 405 nm.

Environmental Stressors

Heat studies with lysozyme were carried out as previously described; lysozyme was heated at 0.02 mg/mL for 20 minutes at 90° C. (Lee et al., 2013). Enzyme solutions were then diluted and activity was assayed using the EnzChek activity kit. Lyophilization studies with β-galactosidase were carried out as previously described; 8-Gal was subjected to three 12 hour lyophliization cycles before dilution. Activity was assayed by monitoring the hydrolysis of o-nitrophenol galactose (ONPG) at 405 nm.

Degradation of Trehalose-Caprolactone Polymer

Figure 14:
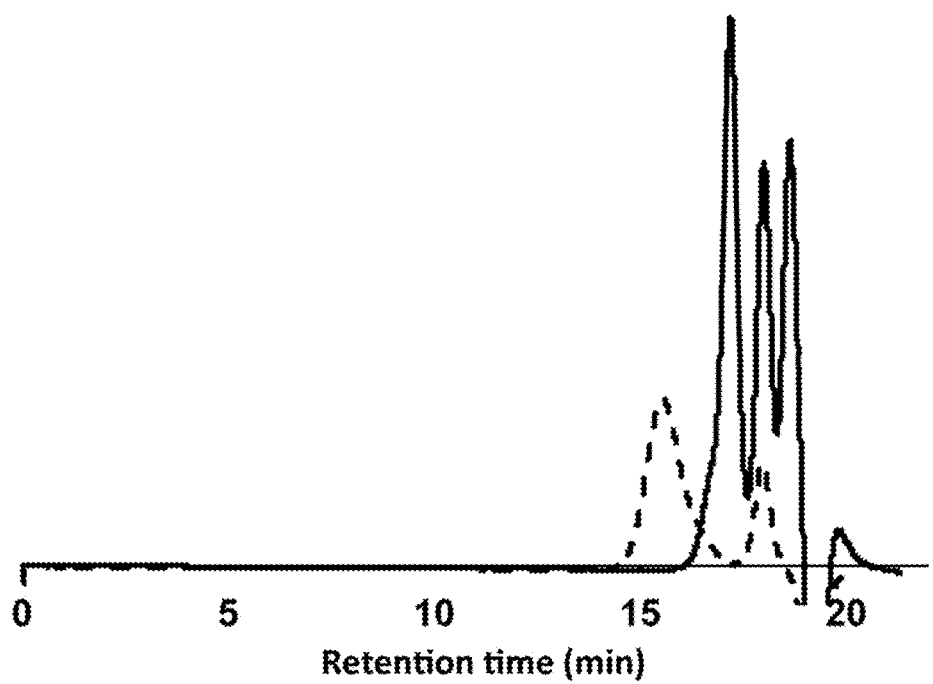
FIG. 14 is a set of graphs showing size exclusion chromatogram of caprolactone-trehalose polymer pre- and post-degradation with 5% KOH.

The degradation of the caprolactone-trehalose polymer upon treatment with 5% KOH was also demonstrated. Analysis by SEC after 24 hours showed a drastic shift toward small molecular weight fragments (Mn=300) with complete loss of polymer (FIG. 14). No further degradation was observed upon longer incubation, implying that these peaks corresponded to the substituted 6-hydroxyl hexanoic acid monomer unit. This data show that the polymers are degradable by ester hydrolysis.

Experimental Details

Degradation of Trehalose-Caprolactone.

In a 1.5 mL Eppendorf tube, trehalose polyester (3 mg) was dissolved in 5% KOH (1 mL) and placed on a rotating plate at 4° C. Aliquots (300 µL) were removed after 1, and 5 days, neutralized with equivalent volumes of 5% HCl, and lyophilized to remove solvent before re-dissolving in SEC mobile phase.

Conjugation of Trehalose-Caprolactone to Lysozyme Via Reductive Amination and Conjugate Stabilization After confirmation that the trehalose-CL polymers were efficient stabilizers as excipients, the polymers were conjugated to lysozyme as a model protein. By using a functional alcohol as ROP initiator, an acetal was installed at the alpha end of the polymer. Acidic hydrolysis exposed the aldehyde, which underwent reductive amination with one or more of the 6 lysine amino acids on lysozyme (FIG. 85, Scheme 4) (Diamond, 1974).

Figure 15:
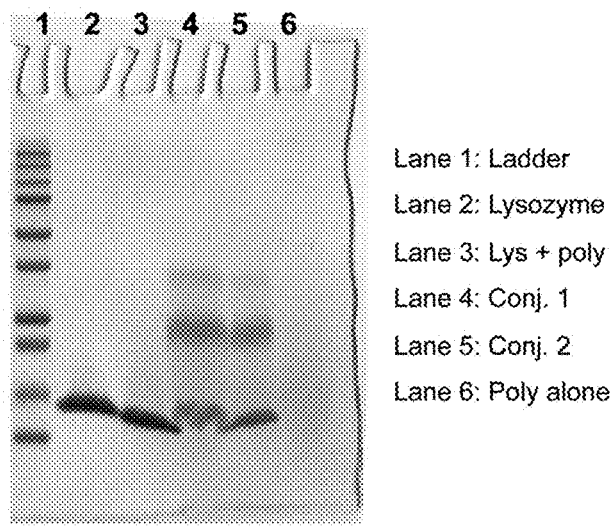
FIG. 15 is a graph showing SDS-PAGE gel depicting conjugation of trehalose-caprolactone polymer to lysozyme.

Conjugates were observed by SDS-PAGE (FIG. 15). A mixture of mono- and bis-conjugate was observed, as reductive amination is not a site-selective conjugation technique (Bentley et al., 1998).

Figure 16:
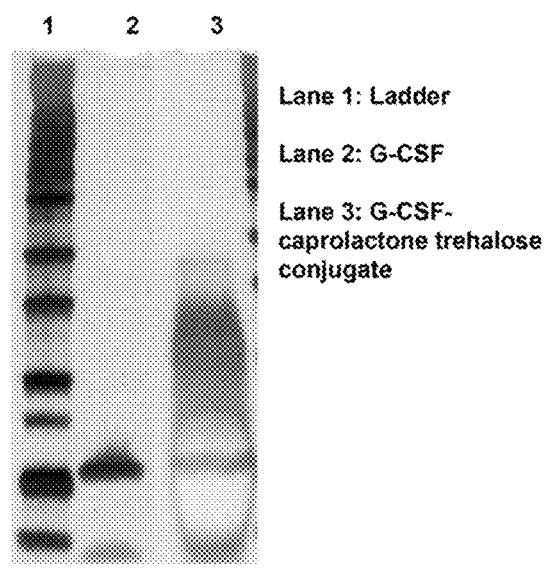
FIG. 16 is a graph showing SDS-PAGE gel with silver stain depicting conjugation of trehalose-caprolactone polymer to G-CSF.

Additionally, the conjugation of the trehalose-caprolactone was carried out with granulyte-stimulating growth factor (G-CSF), an important therapeutic protein (FIG. 16).

Experimental Details

Conjugation to Lysozyme.

Acetal-functionalized trehalose-CL polymer (7 mg) was dissolved in 0.1 M phosphate buffer pH 2.0 (150 µL) and heated to 50° C. for 5 hours. The solution was cooled to room temperature and adjusted to pH 6.0 with 0.2 M Na$_2$PO$_4$ (45 μL). A solution of 3.3 mg/mL lysozyme in water (98 μg, 30 μL) was added and the conjugation mixed at 4° C. for 30 minutes before a solution of 40 mg/mL NaCNBH$_3$ in water (20 μL) was added. The conjugation was then incubated at 21° C. for 19 hours before the crude mixture was concentrated in 3 kD MWCO centrifugal filter. Crude analysis of conjugation yield was performed by SDS-PAGE before the mixture was purified by centrifugal filtration against 30 kD MWCO.

Summary

Protein-polymer conjugates are an important type of therapeutic biological. However, their chronic use poses concerns due to accumulation and immunogenicity in vivo. Additionally, proteins suffer from instability during storage and transport, increasing patient and clinic costs. These trehalose-caprolactone polymers have been shown to stabilize two important enzymes, lysozyme and β-galactosidase, against heat and lyophilization stresses respectively. Additionally, they have been shown to degrade in basic conditions. Finally, the successful conjugation to lysozyme and a therapeutic protein G-CSF has been demonstrated. These materials have the potential to replace PEG as the industry standard for protein-polymer conjugates and overcome previous disadvantages.

Example 2

BMDO Polymers

Background

One method toward the synthesis of biodegradable polymers focuses on the introduction of ester moieties in the polymer backbone via radical ring-opening polymerization (RROP). Cyclic ketene acetals (CKAs) are a well-known class of vinyl monomers, which undergo RROP to produce linear polymers containing esters in the backbone. Some examples of CKAs include 5,6-benzo-2-methylene-1,3-dioxepane (BMDO), 2-methylene-1,3-dioxepane (MDO) and 2-methylene-4-phenyl-1,3-dioxolane (MPDL), as well as other monomers with varied ring size and substitution pattern (Agarwal, 2010). These monomers may polymerize with well-known vinyl monomers such as styrene, methyl methacrylate N-isopropylacrylamide (NIPAAm) and vinyl acetate, among others (Agarwal, 2010; Gomez d'Ayala, et al., 2014). These copolymers have been well documented in the literature and the degradation products resulting from hydrolysis of these copolymers have been shown to be non-cytotoxic (Delplace et al., 2013; Siegwart et al., 2008). While degradable glycopolymers containing galactopyranose moieties have been synthesized by this route (Xiao et al., 2011), no stabilization of proteins was shown and no degradable polymers containing trehalose have yet been synthesized.

Growth factors are important therapeutics. For instance, granulocyte colony-stimulating factor (G-CSF) is a protein-drug for stimulating the growth of neutrophils. Cancer patients treated with chemotherapy are at a high risk to develop neutropenia, or abnormally low levels of neutrophils. G-CSF of the PEGylated form Neulasta are typically administered in patients post-chemotherapy to stimulate bone marrow precursors to form neutrophils and to fight against infection. Specifically, it is important to synthesize degradable and stabilizing polymer-protein conjugates for multiple reasons. Protein therapeutics are susceptible to environmental stressors during transit, decreasing their activity ("FDA Access Data"; www.accessdata.fda.gov).

Additionally, non-biodegradability potentially causes problems in chronic use because PEG has been shown to accumulate in tissue.

Herein, the synthesis of biodegradable trehalose polymers using radical ring-opening polymerization is described. Two approaches are taken to achieve these polymers, using both copolymerization and post-polymerization techniques.

Synthetic Methods

Synthesis of a Degradable Cyclic Ketene Acetal Monomer

First, BMDO and 2-methylene-4-phenyl-1,3-dioxolane (MPDL) were synthesized using known procedures (Bailey and Wu et al., 1982; Bailey and Ni et al., 1982). Bromoacetaldehyde diethyl acetal and benzene dimethanol were condensed using catalytic p-toluenesulfonic acid (TsOH) to yield the brominated BMDO precursor in 76% yield (Scheme 5a; the numericals of compounds are limited in Example 2). Elimination with potassium tert-butoxide and purification by distillation gave BMDO in 87% yield. Similarly, condensation of styrene glycol and bromoacetaldehyde diethyl acetal with catalytic TsOH led to a mixture of cis and trans brominated products, which were not separated and eliminated to lead to the single MPDL product in 40% yield after distillation (Scheme 5b; the numericals of compounds are limited in Example 2).

Scheme 5

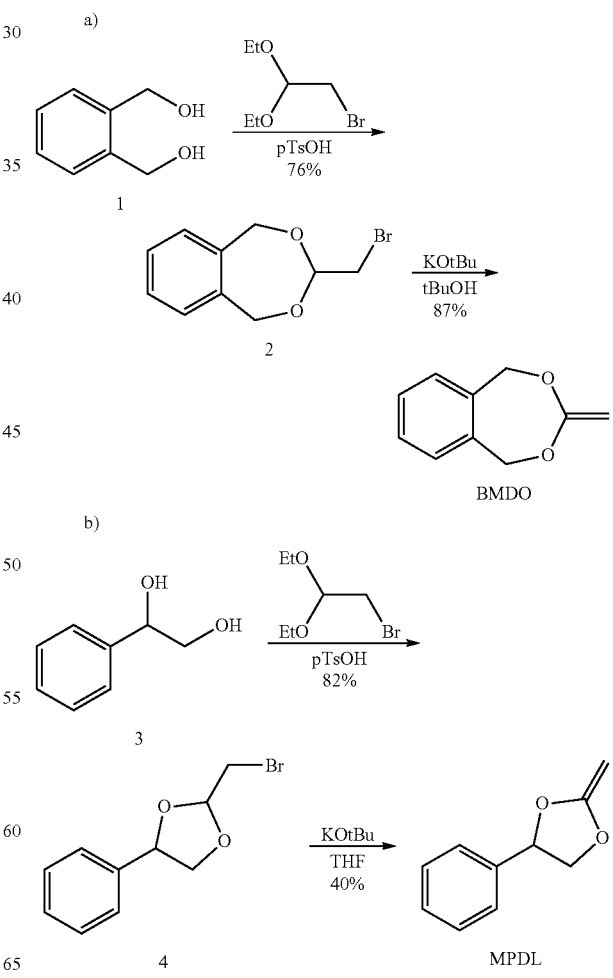

Synthesis of Protected Methacrylate Trehalose Monomer

A three-step procedure was followed to synthesize trimethylsilyl (TMS)-protected methacrylate trehalose monomers (Scheme 6; the numericals of compounds are limited in Example 2). First, trehalose was completely TMS-protected using TMS-Cl in 87% yield, then the primary hydroxyls were selectively removed using mildly basic conditions. Methacryloyl chloride could then be used to install a polymerizable group at one of the free hydroxyls, resulting in TMS-protected monomer 7 in 29% overall yield.

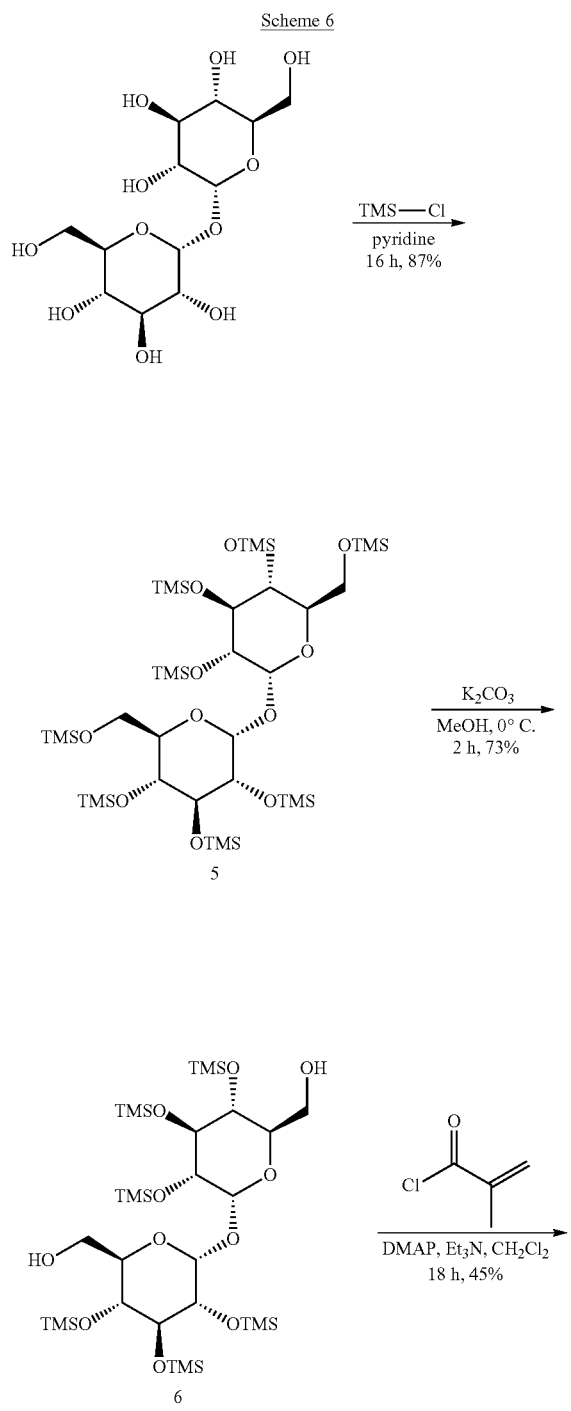

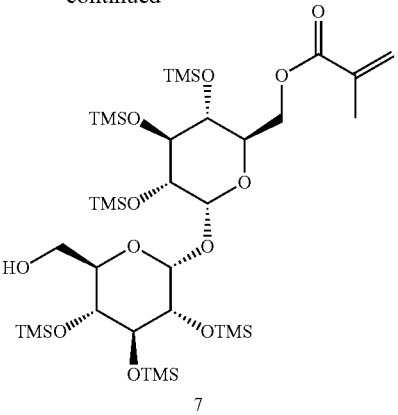

Figure 17:
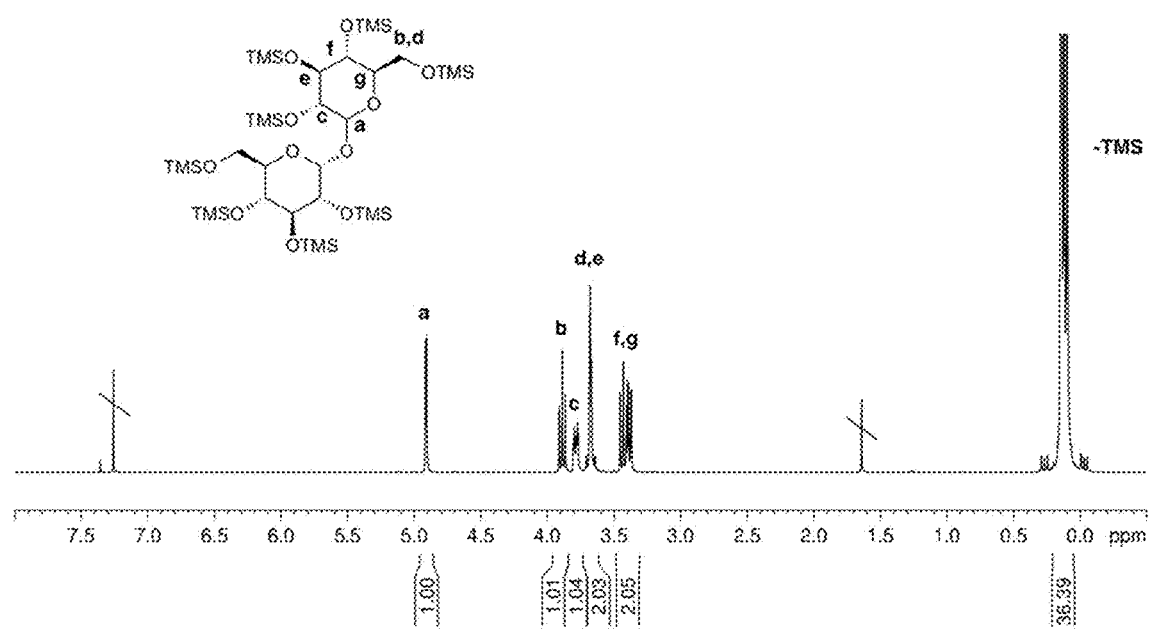
FIG. 17 is a graph showing $^1$H-NMR spectrum (CDCl$_3$) of per-O-(trimethylsilyl)-α,α-trehalose 5.
Figure 18:
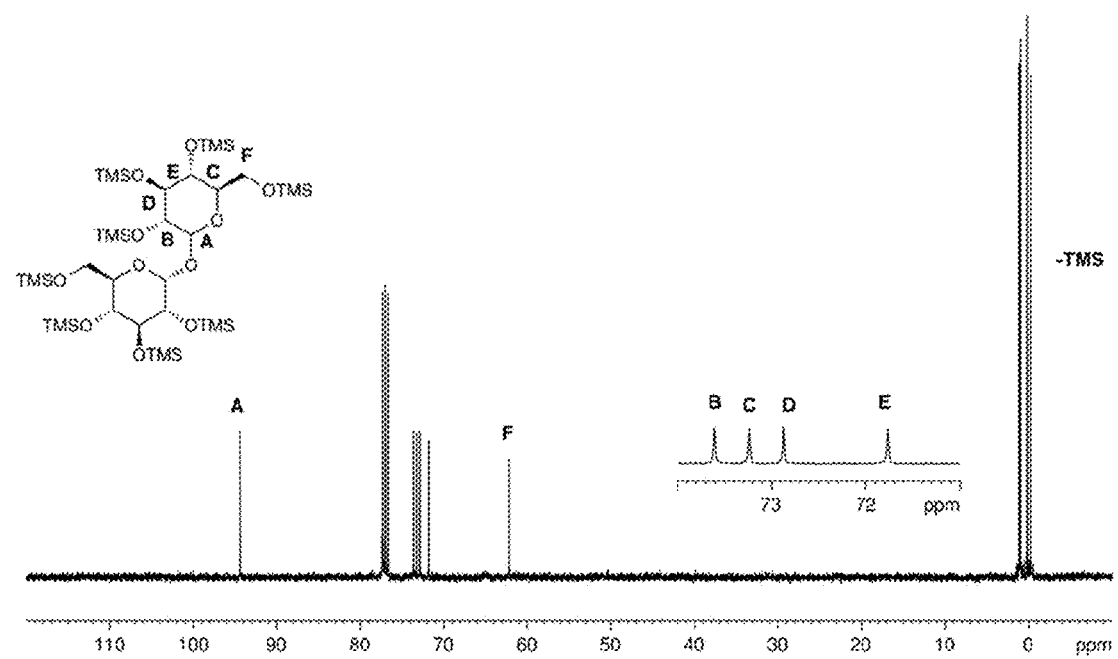
FIG. 18 is a graph showing $^{13}$C-NMR spectrum (CDCl$_3$) of per-O-(trimethylsilyl)-α,α-trehalose 5.

Per-O-(Trimethylsilyl)-α,α-Trehalose 5:

The procedure was adapted from literature (Sizovs et al., 2013). Trehalose (2.0 g, 5.8 mmol) was dissolved in pyridine (50 mL) and let stir 20 minutes until homogeneous. The reaction was cooled to 0° C. and chlorotrimethyl silane (7.11 mL, 56.1 mmol) was added dropwise. The reaction was stirred an additional 30 minutes at 0° C. and warmed to room temperature. After 16 hours, the reaction was cooled again to 0° C. and poured into cold pH 9 carbonate buffer (50 mM, 150 mL). Aqueous workup was performed by extracting with 3×70 mL hexanes. The organic layers were combined and washed with brine (50 mL) then dried over MgSO4. The solvent was removed and the product was freeze-dried from benzene to obtain solid/oil (4.7 g, 5.11 mmol, 87% yield). $^1$H-NMR (400 MHz, CDCl$_3$) δ: 4.91 (d, J=3.2 Hz, 2H), 3.89 (t, J=8.0 Hz, 2H), 3.79 (dt, J=1.4, 9.6 Hz, 2H), 3.68-3.67 (m, 4H), 3.43 (t, J=9.0 Hz, 2H), 3.39 (dd, J=3.2, 9.6 Hz, 2H), 0.14-0.10 (m, 72H). $^{13}$C-NMR (400 MHz, CDCl$_3$) δ=94.4, 73.6, 73.2, 72.9, 71.8, 62.2, 1.2, 0.9, 0.2, −0.3. ESI-MS (MeCN): calculated for $C_{36}H_{86}NaO_{11}Si_8$ [M+Na]$^+$: 941.42, observed: 941.26. FIG. 17 shows $^1$H-NMR spectrum (CDCl$_3$) of per-O-(trimethylsilyl)-α,α-trehalose 5. FIG. 18 shows $^{13}$C-NMR spectrum (CDCl$_3$) of per-O-(trimethylsilyl)-α,α-trehalose 5.

2,3,4,2',3',4'-Hexakis-O-(trimethylsilyl)-α,α-trehalose 6

Figure 19:
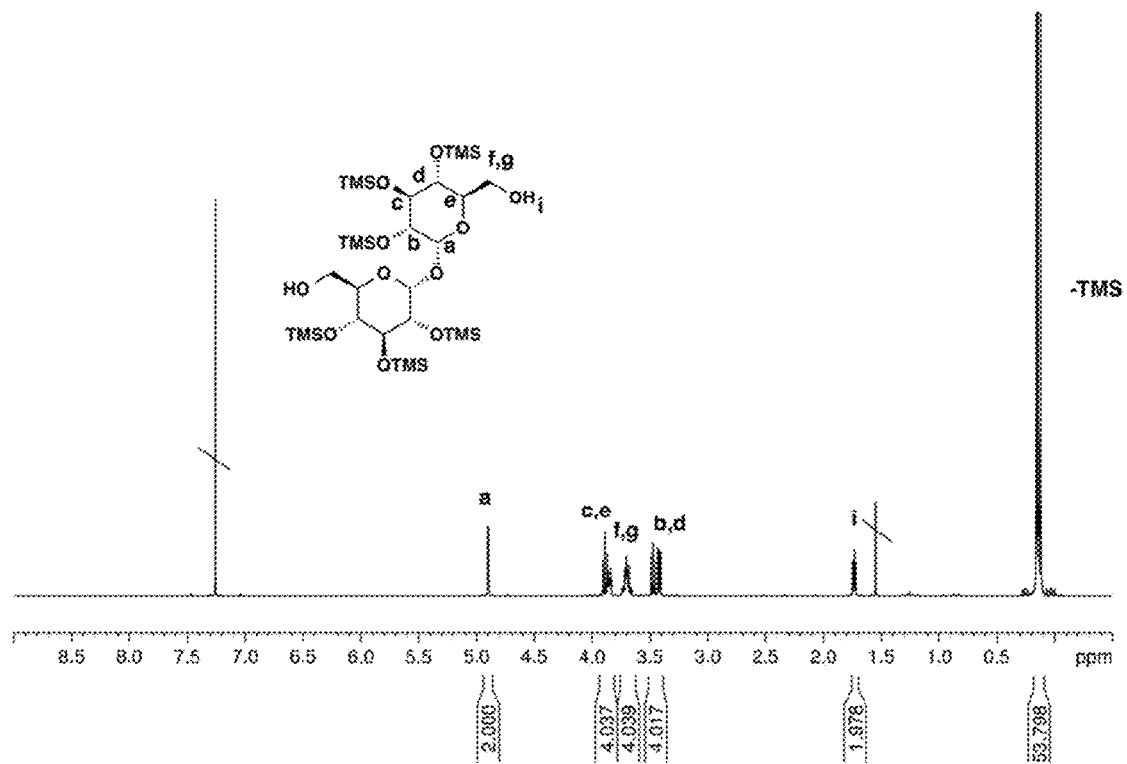
FIG. 19 is a graph showing $^1$H-NMR spectrum (CDCl$_3$) of 2,3,4,2',3',4'-hexakis-O-(trimethyl silyl)-α,α-trehalose 6.
Figure 20:
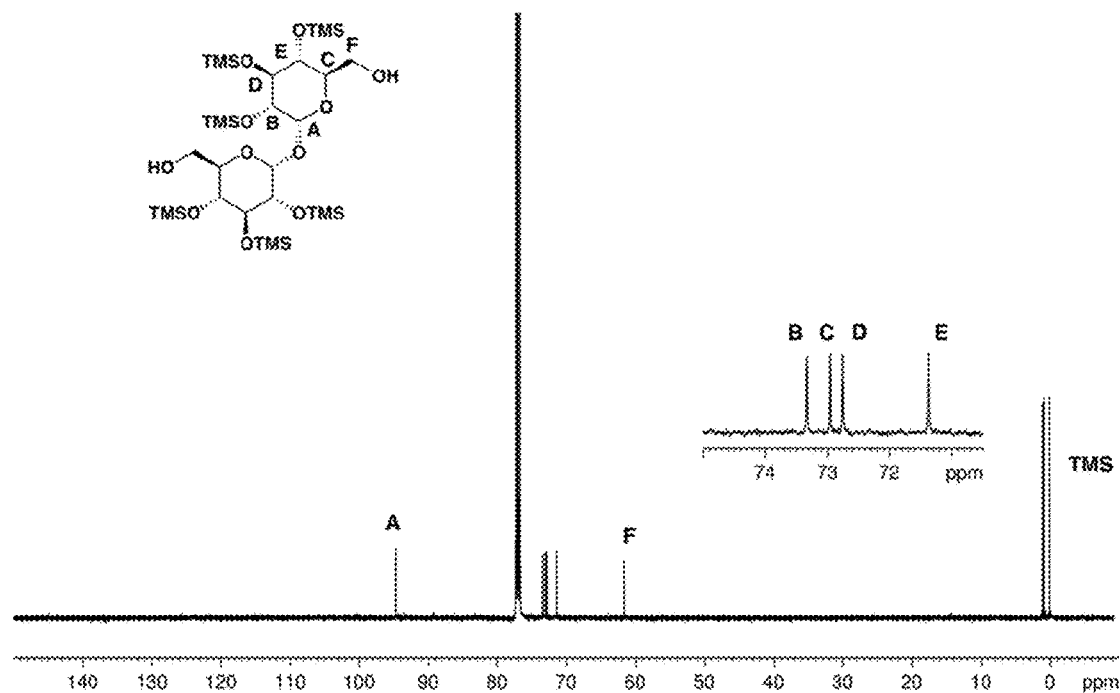
FIG. 20 is a graph showing $^{13}$C-NMR spectrum (CDCl$_3$) of 2,3,4,2',3',4'-hexakis-O-(trimethyl silyl)-α,α-trehalose 6.

The procedure was adapted from a literature procedure (Johnson, 1992). In a dry, 100 mL round bottom flask under argon, 5 (1.0 g, 1.087 mmol) was dissolved in dry methanol (30 mL) and let stir for 30 minutes to dissolve. The reaction was cooled to 0° C. and a suspension of K$_2$CO$_3$ (150 mg, 1.087 mmol) in methanol (30 mL) was added dropwise over 20 minutes. The reaction was stirred at 0° C. for 2 hours. To quench, glacial acetic acid (0.1 mL) was added to neutralize and methanol was removed by rotary evaporation. The crude was re-dissolved in a combination of hexanes and brine and extracted three times with hexanes. The organic layers were combined, dried with Mg$_2$SO$_4$ and solvent was removed in vacuo. The crude solid was purified by silica gel flash chromatography (4:1 hexane: EtOAc) to yield a white solid (651 mg, 0.839 mmol, 77% yield). $^1$H-NMR (500 MHz, CDCl$_3$) δ: 4.90 (d, 2H), 3.91-3.84 (m, 4H), 3.71-3.68 (m, 4H), 3.47 (t, 2H), 3.41 (dd, 2H), 1.73 (dd, 2H). $^{13}$C-NMR (500 MHz, CDCl$_3$) δ: 94.6, 73.3, 72.9, 72.8, 71.4, 61.7, 1.0, 0.9, 0.0. FIG. 19 shows $^1$H-NMR spectrum (CDCl$_3$) of 2,3,4,2',3',4'-Hexakis-O-(trimethylsilyl)-α,α-trehalose 6. FIG. 20 shows $^{13}$C-NMR spectrum (CDCl$_3$) of 2,3,4,2',3',4'-Hexakis-O-(trimethylsilyl)-α,α-trehalose 6.

2,3,4,2',3',4'-Hexakis-O-(trimethylsilyl)-6-O-methacrylate-α,α-trehalose 7

Figure 21:
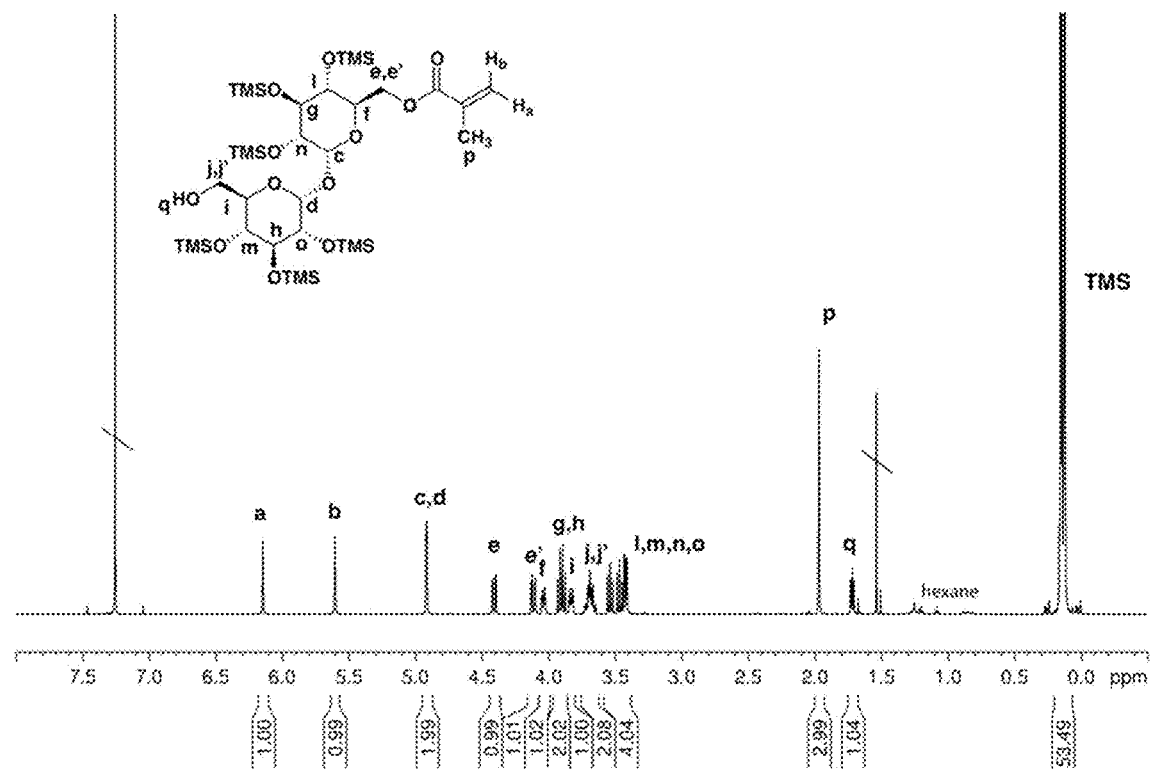
FIG. 21 is a graph showing $^1$H-NMR spectrum (CDCl$_3$) of 2,3,4,2',3',4'-hexakis-O-(trimethylsilyl)-6-O-methacrylate-α,α-trehalose 7.
Figure 22:
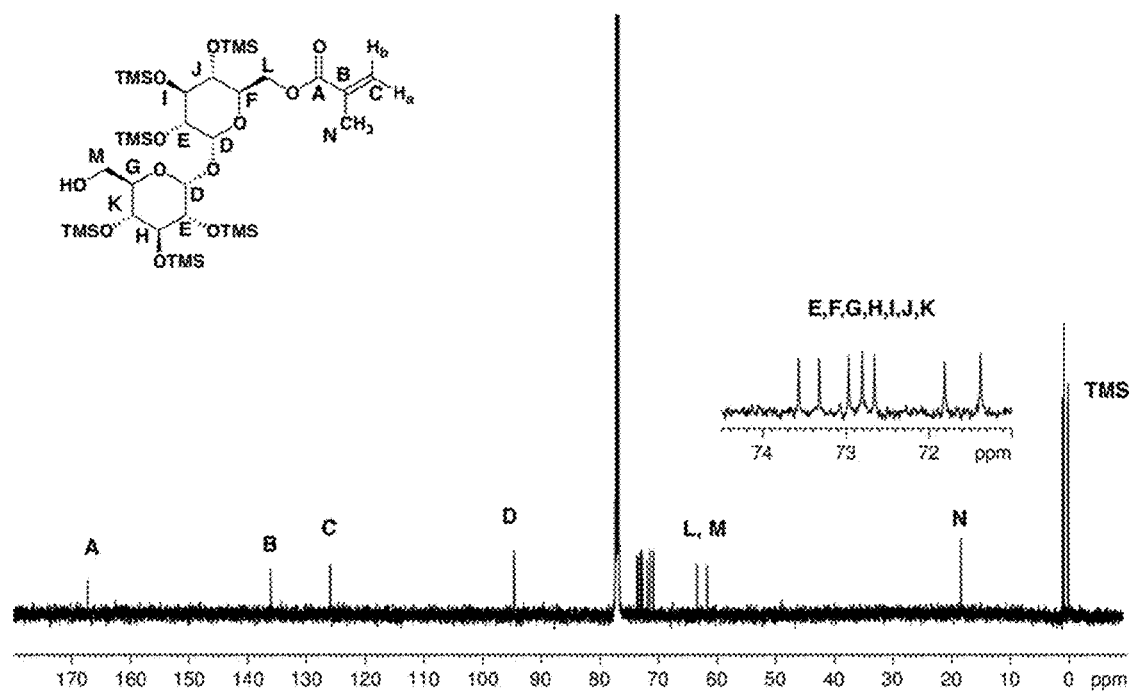
FIG. 22 is a graph showing $^{13}$C-NMR spectrum (CDCl$_3$) of 2,3,4,2',3',4'-hexakis-O-(trimethylsilyl)-6-O-methacrylate-α,α-trehalose 7.

In a dry 2-neck 50 mL flask, 6 (2.70 g, 3.49 mmol) was dissolved in 50 mL dry DCM. DMAP (42.6 mg, 0.35 mmol) was added and the reaction was cooled to 0° C. Next, methacryloyl chloride (426 μL, 4.37 mmol) was dissolved in dry DCM (6 mL). The methacryloyl chloride solution and triethylamine (1.83 mL, 10.48 mmol) was added simultaneously dropwise. The mixture was stirred at 0° C. for 30 minutes, then let warm to room temperature. After 16 hours, the reaction was cooled to 0° C. and poured into cold pH 9 carbonate buffer (400 mL). The layers were separated and the aqueous layer was washed twice with hexanes. The organic layers were combined and washed with brine (50 mL), dried with MgSO4 and purified by silica gel flash chromatography (11:2 hexanes:EtOAc eluent) to yield a white solid (1.34 g, 1.59 mmol, 45% yield). $^1$H-NMR (500 MHz, CDCl3) δ: 6.15 (s, 1H), 5.60 (t, J=1.5 Hz, 1H), 4.92 (d, J=1.5 Hz, 2H), 4.41 (dd, J=12.0, 2.4 Hz, 1H), 4.11 (dd, J=12.1, 3.6 Hz, 1H), 4.04 (dt, J=6.8, 2.7 Hz, 1H), 3.90 (q, J=9.0 Hz, 2H), 3.83 (dt, J=9.4, 3.6 Hz, 1 h), 3.73-3.64 (m, 2H), 3.54 (t, J=9.3 Hz, 2H), 3.47 (t, J=9.3 Hz, 1H), 3.42 (ddd, J=9.3, 3.1, 0.8 Hz, 1H), 1.88 (s, 3H), 1.72 (dd, J=7.5, 5.3 Hz, 1H), 0.16-0.12 (m, 54H). $^{13}$C-NMR (500 MHz, CDCl$_3$): δ=167.24, 136.11, 125.89, 94.60, 94.47, 73.57, 73.33, 72.97, 72.81, 72.65, 71.81, 71.38, 70.80, 18.41, 1.079, 1.014, 0.86, 0.85. ESI-MS (MeCN:CHCl$_3$, 9:1): calculated for C$_{34}$H$_{76}$O$_{13}$Si$_6$ [M+NH$_4$]$^+$: 860.41, observed: 860.23. FIG. 21 shows $^1$H-NMR spectrum (CDCl$_3$) of 2,3,4,2',3',4'-Hexakis-O-(trimethylsilyl)-6-O-methacrylate-α,α-trehalose 7. FIG. 22 shows $^{13}$C-NMR spectrum (CDCl$_3$) of 2,3,4,2',3',4'-Hexakis-O-(trimethylsilyl)-6-O-methacrylate-α,α-trehalose 7.

Copolymerization of BMDO Under RAFT Conditions.

The cyclic ketene monomer BMDO was copolymerized using RAFT to obtain well-defined copolymers. Two methods were followed. In one example, a methacrylate comonomer with a reactive handle for later functionalization was used. In another, TMS-protected methacrylate trehalose was directly used for copolymerization.

In the first example, copolymerization of an alkene-functionalized methacrylate monomer with BMDO followed by thiol-ene modification allowed for later installation of the bulky and hydrophilic trehalose moiety. 3-Butenyl methacrylate (bMA) was synthesized following literature procedures; 3-buten-1-ol was treated with methacryloyl chloride in the presence of triethylamine to give bMA in 53% yield (Campos et al., 2008).

Figure 23:
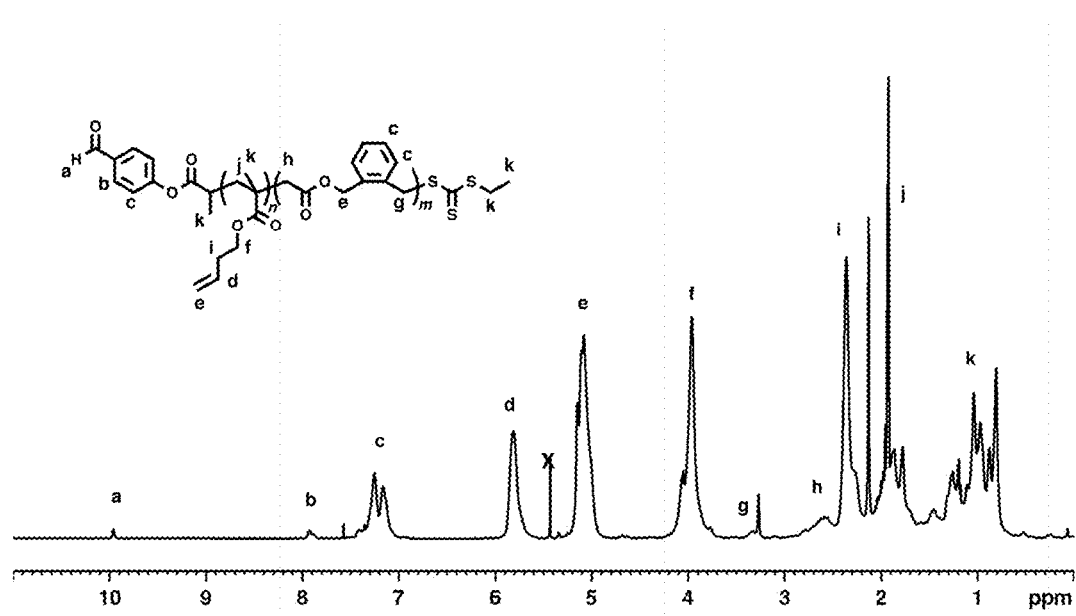
FIG. 23 is a graph showing $^1$H-NMR spectrum (500 MHz, in CD$_3$CN) of BMDO-co-bMA polymer.

BMa and BMDO were then copolymerized using RAFT polymerization (Scheme 7). CKAs are less active monomers than methacrylates and successful incorporation of BMDO into the polymer chain requires a CTA with a slower transfer coefficient, such as a trithiocarbonate. These conditions led to the successful copolymerization of BMDO with bMA (FIG. 23).

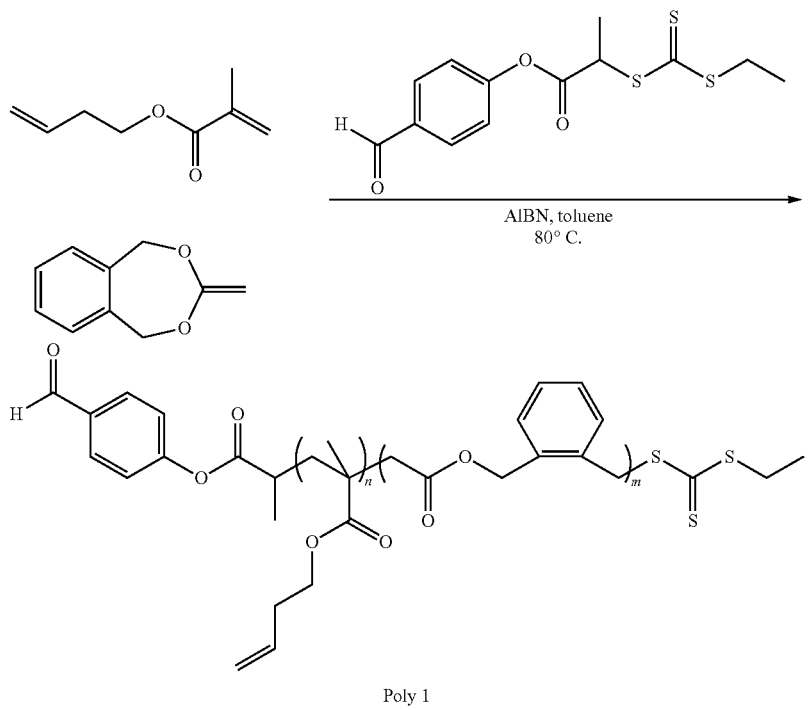

Scheme 7

Poly 1

While the differing monomer reactivities led to low BMDO incorporation in the RAFT copolymer, this is advantageous in the synthesis of a biodegradable trehalose polymer. The majority of the polymer should consist of trehalose units to maintain stabilizing ability. The DMF solvent peak prevented accurate GPC measurement, but the mismatch between CTA and methacrylate monomer required for copolymerization would be expected to result in a broad Đ, typical for improperly controlled BMDO-methacrylate copolymerizations (Decker and Maynard, 2015).

Next, the allyl-functionalized polymer was used as a substrate for a thiol-ene reaction with thiolated trehalose, synthesized as described above.

Scheme 8

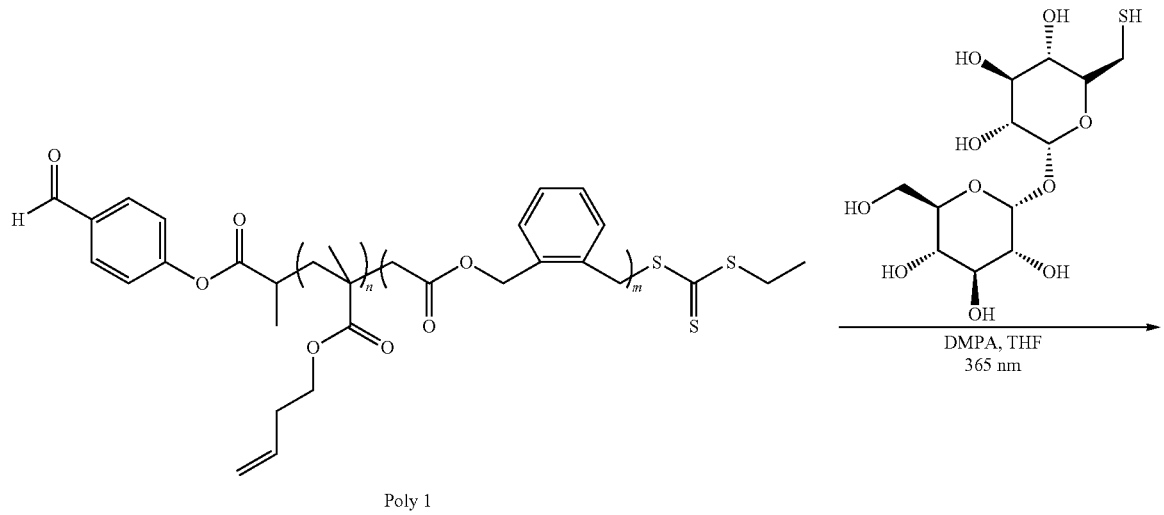

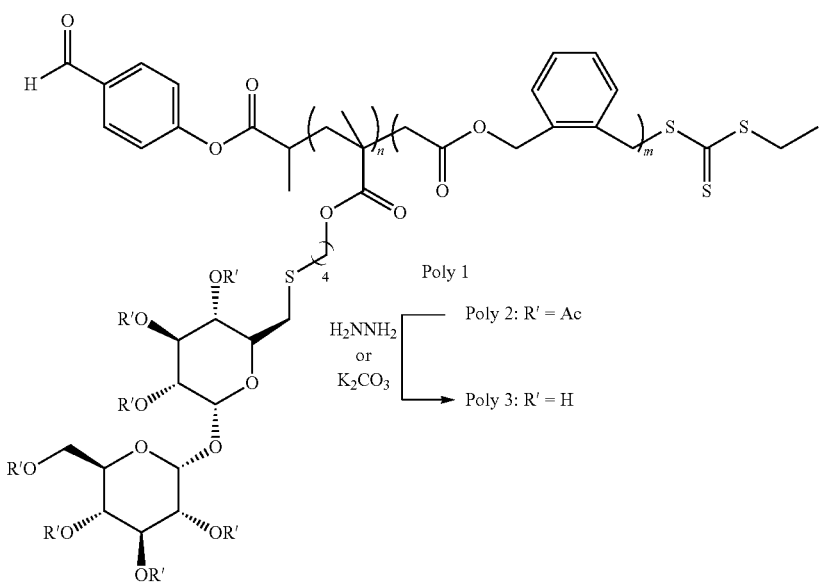

Figure 24:
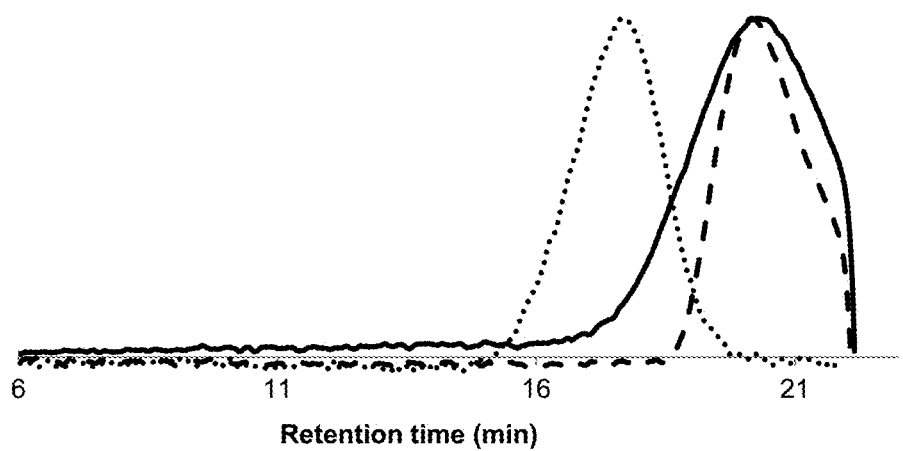
FIG. 24 is a graph showing Gel permeation chromatogram of Poly 1-3. Orange: Poly 1 (poly(BMDO-co-bMA); Blue: Poly2 (poly(BMDO-co-acetate trehalose MA); Green: Poly3 (poly(BMDO-co-trehalose MA).

The successful modification could be followed by gel permeation chromatography (GPC) to ensure that no cleavage of the backbone esters was occurring (FIG. 24).

In the second example, the trehalose-containing methacrylate monomer 4 was directly employed (Scheme 9). Because methyl methacrylate shows a greater tendency to copolymerize with BMDO than styrene, a methacrylate-based trehalose monomer was chosen. Additionally, an amide-containing pyridyl disulfide CTA was used to minimize end-group cleavage during the acidic TMS deprotection.

Scheme 9

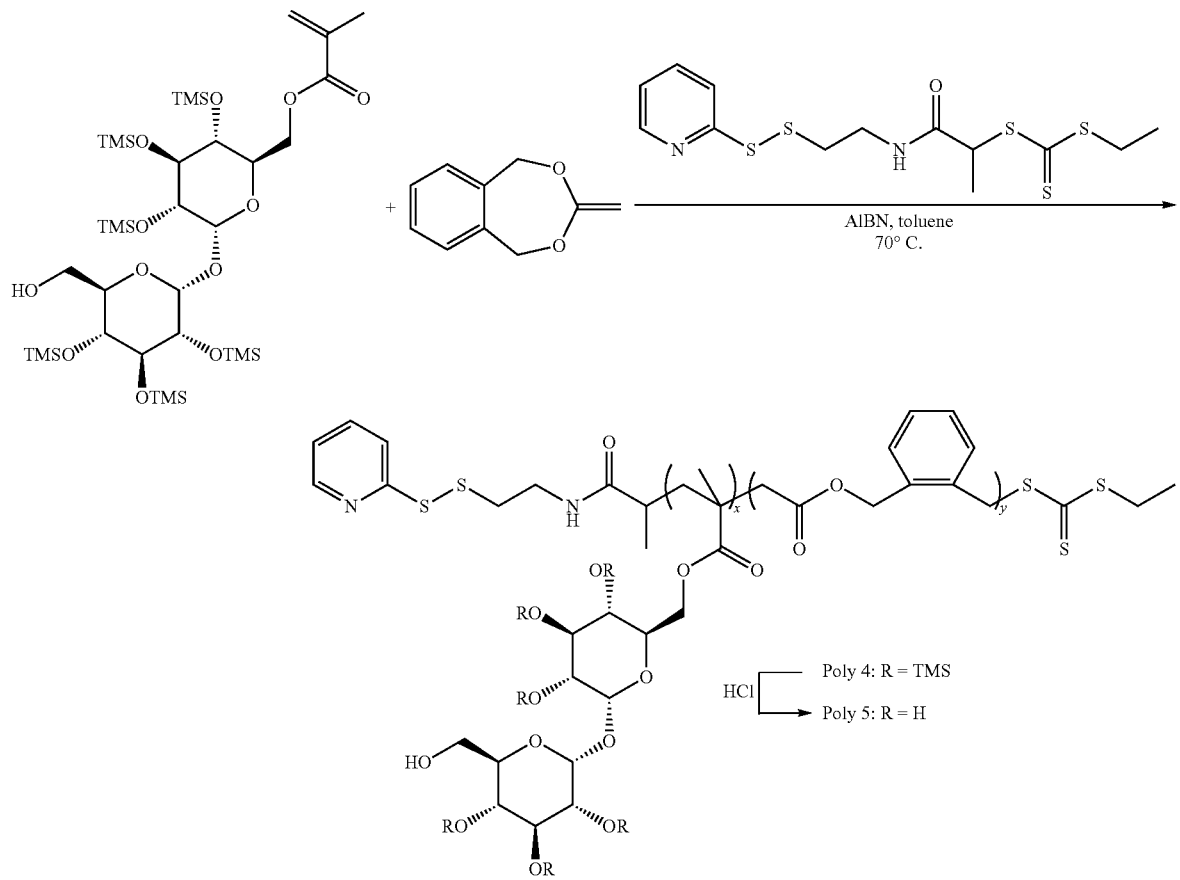

Figure 25:
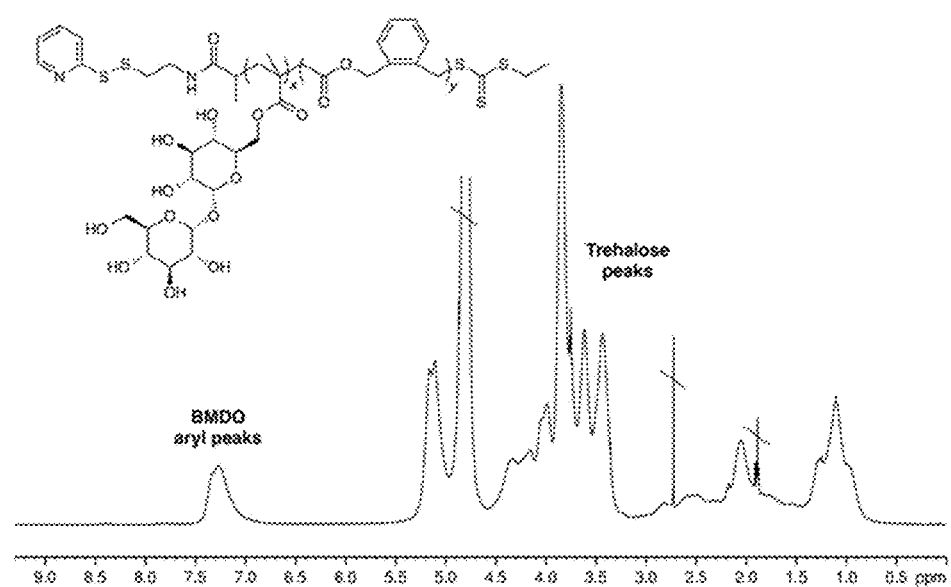
FIG. 25 is a graph showing $^1$H-NMR of trehalose-BMDO copolymer Poly5 showing BMDO aryl peaks and trehalose peaks.

This polymerization was successful and resulted in BMDO incorporation. The $^1$H NMR showed the presence of aryl peaks in the final purified polymer confirming the successful copolymerization of BMDO with the trehalose methacrylate monomer (FIG. 25). BMDO incorporation was calculated to be 28% by comparing the integration of the aryl region at 7.0-7.5 ppm with the trehalose peaks at 3.2-4.5 ppm.

Figure 26:
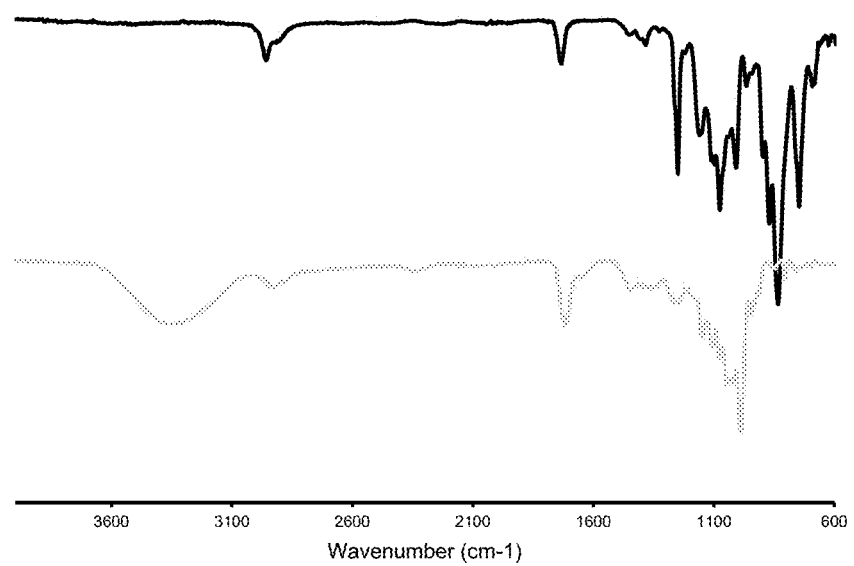
FIG. 26 is a graph showing differences in IR spectra of trehalose-BMDO copolymer Poly4-5 before (black, above) and after (gray, below) removal of TMS protecting groups.

The labile TMS groups were then easily cleaved with dilute acid, as confirmed by infrared spectroscopy (FIG. 26). After deprotection, a broad peak at 3370 cm$^{-1}$ appeared, corresponding to free hydroxyl groups.

Copolymerization of BMDO and 4 Under RAFT Conditions.

Figure 27:
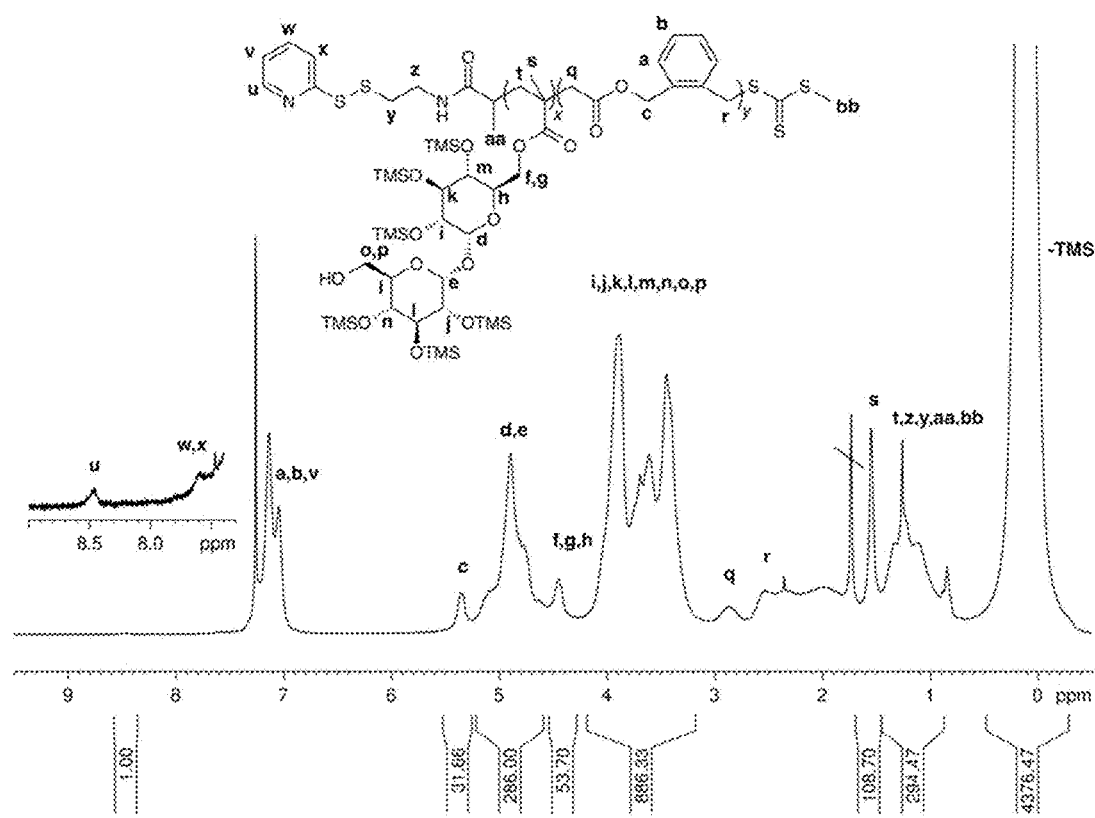
FIG. 27 is a graph showing $^1$H-NMR spectrum (CDCl$_3$) of TMS-trehalose-BMDO copolymer Poly4.
Figure 28:
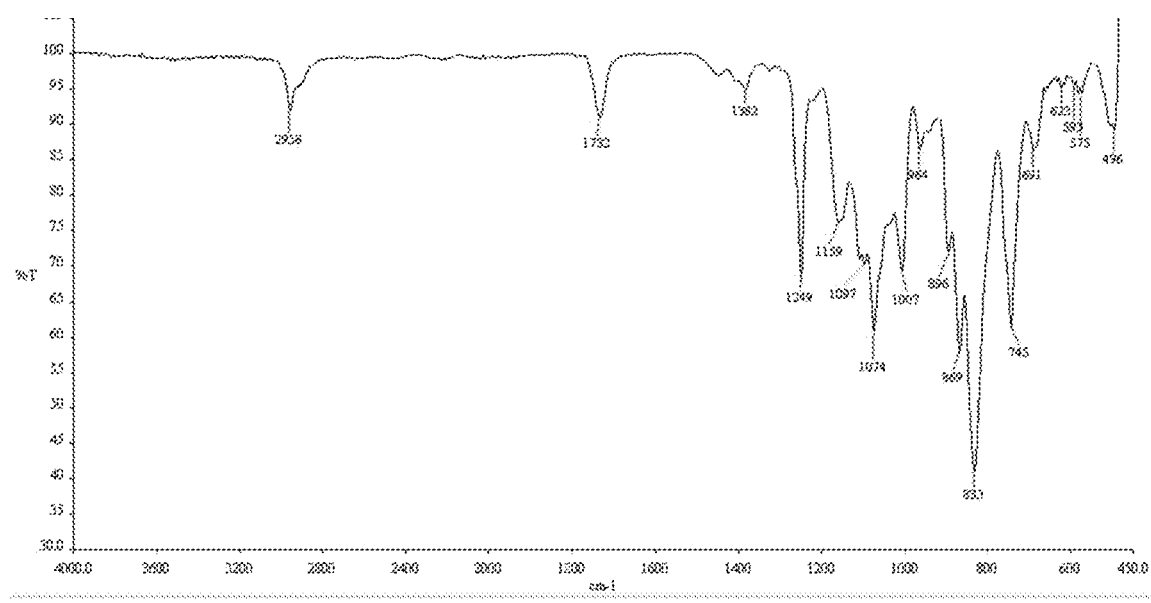
FIG. 28 is a graph showing IR spectrum (neat) of TMS-trehalose-BMDO copolymer Poly4.

In a dry Schlenk flask, 4 (100 mg, 0.12 mmol) was dissolved in dry toluene (80 μL). Then both 9 μL of a stock solution of AIBN (2.8 mg in 500 μL dry toluene) and 15 μL of a stock solution of CTA (2.4 mg in 60 μL dry toluene) were added. BMDO (19.2 mg, 0.12 mmol) was dissolved in toluene (46 μL) and transferred to the Schlenk tube. The Schlenk tube was subjected to five freeze-pump-thaw cycles, until the pressure remained constant at 160 mTorr, then the tube was backfilled with argon and heated to 70° C. After 18 hours, the polymerization was quenched by exposure to oxygen followed by immersion in liquid nitrogen. Percent conversion was assessed by $^1$H-NMR of the crude reaction mixture, which was then purified by precipitating three times from dichloromethane (0.5 mL) into cold methanol (50 mL) to yield a white solid (69.2 mg, 11.6 nmol, 74% recovery). $^1$H-NMR (500 MHz, CDCl$_3$) δ: 8.56-8.42 (s, 1H), 7.68-6.86 (m, 221H), 5.52-5.26 (s, 32H), 5.26-4.55 (m, 286H), 4.56-4.25 (s, 54H), 4.25-3.18 (m, 886H), 3.07-2.70 (s, 44H), 2.70-1.82 (m, 224H), 1.64-1.45 (s, 108H), 1.45-0.91 (m, 294H), 0.47-0.28 (s, 4376H). FT-IR (cm$^{-1}$): 2958, 1732, 1382, 1249, 1159, 1097, 1074, 1007, 964, 896, 869, 833, 745. FIG. 27 shows $^1$H-NMR spectrum (CDCl$_3$) of TMS-trehalose-BMDO copolymer Poly4. FIG. 28 shows IR spectrum (neat) of TMS-trehalose-BMDO copolymer Poly4.

Removal of TMS Groups.

Figure 29:
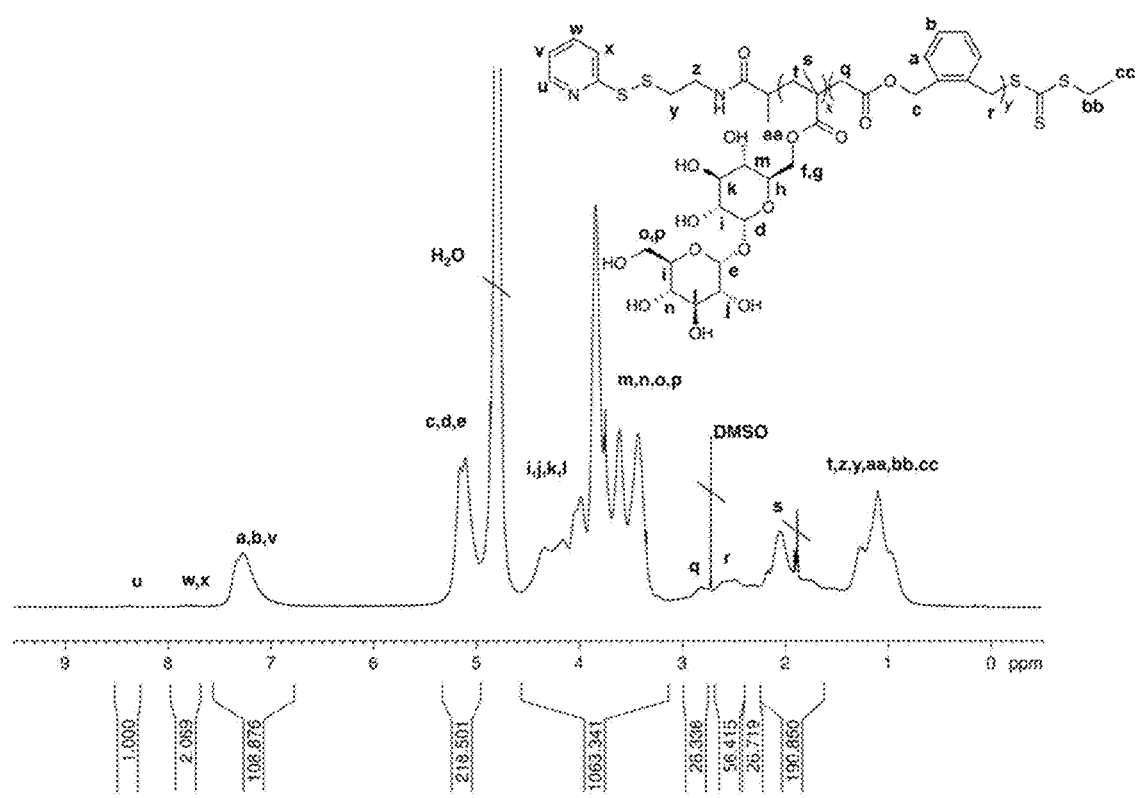
FIG. 29 is a graph showing $^1$H-NMR spectrum (D$_2$O) of trehalose-BMDO copolymer Poly5.
Figure 30:
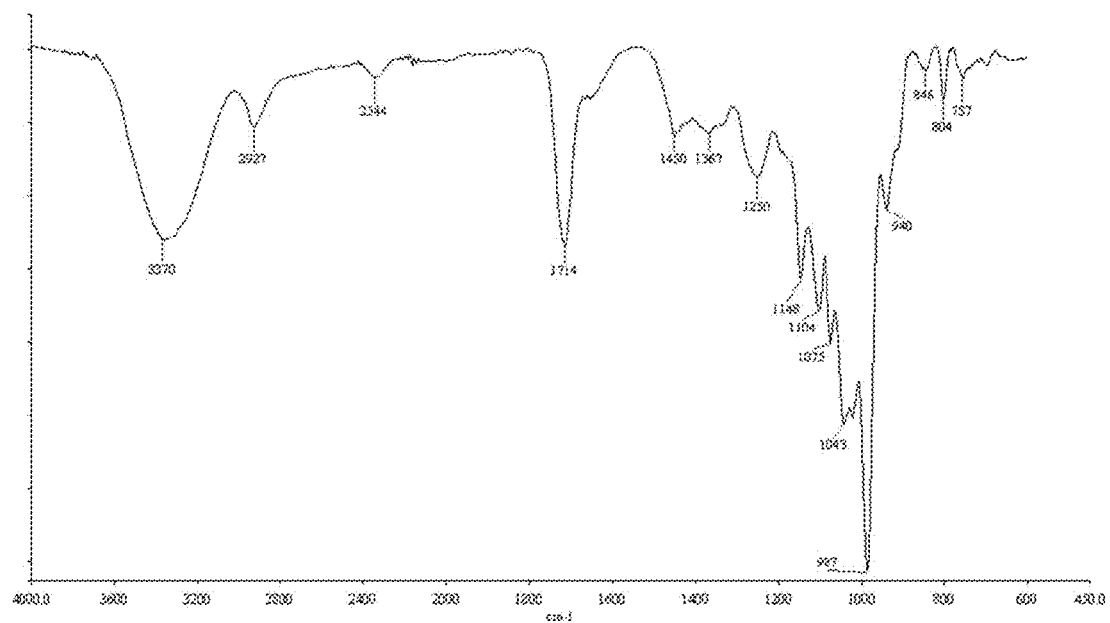
FIG. 30 is a graph showing IR spectrum (neat) of trehalose-BMDO copolymer Poly5.

In a 20 mL scintillation vial, poly(TMS-protected trehalose-co-BMDO) (69 mg) was dissolved in 5:1 THF:MeOH (6 mL) and 1M HCl (0.15 mL) was added. The vial was vortexed and within 3 minutes a white precipitate began to form. The vial was let stand for 10 minutes, then transferred to a falcon tube and centrifuged for 10 minutes. The resulting precipitate was washed three times with 5:1THF:MeOH (6 mL). After the third time, the precipitate was dissolved in 1:1 H$_2$O:MeOH (2 mL) and ultracentrifugation was performed in a 15 mL tube with 3 kD molecular weight cutoff. The polymer was washed once with H$_2$O:MeOH and once with H$_2$O, then lyophilized to remove water to yield a white fluffy solid (32.4 mg, 11.2 mmol, 96% recovery). $^1$H-NMR (500 MHz, D$_2$O) δ: 8.48-8.27 (s, 1H), 7.98-7.69 (s, 2H), 7.56-6.78 (d, 108H), 5.34-4.96 (d, 218H), 4.57-3.14 (m, 1064H), 2.99-2.75 (s, 28H), 2.69-2.40 (m, 56H), 2.40-2.24 (s, 26H), 2.24-1.63 (m, 190H), 1.63-1.46 (s, 24H), 1.43-0.77 (t, 262H). FT-IR (cm$^{-1}$): 3370, 2927, 2344, 1714, 1450, 1367, 1250, 1148, 1104, 1075, 1043, 987, 940. FIG. 29 shows ¹H-NMR spectrum (D$_2$O) of trehalose-BMDO copolymer Poly5. FIG. 30 shows IR spectrum (neat) of trehalose-BMDO copolymer Poly5.

Stabilization of Proteins Using Degradable BMDO-Containing Polymers as Excipients The polymer modified by thiol-ene chemistry (Poly 3) and the polymer formed by direct copolymerization (Poly 5) were assessed for their ability to stabilize proteins as excipients.

In the second example (Poly 5), the resulting deprotected copolymer was then tested for its ability to stabilize proteins against heat stress (FIG. 31) and compared to a methacrylate trehalose hompolymer (i.e. polymer without BMDO) and to no additive. Specifically, model protein lysozyme was stressed at 90° C. for 20 minutes and its bioactivity was reduced to 12% of its original activity when no polymer was added.

Figure 31A:
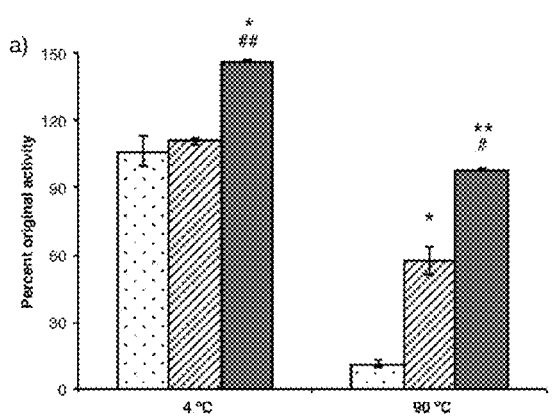
FIG. 31A is a graph showing activity of lysozyme before and after heating at 90° C. for 20 minutes with trehalose homo- and copolymers as excipients (100 wt eq relative to lysozyme).

The trehalose-BMDO copolymer retained 97% lysozyme activity, while the trehalose homopolymer only stabilized lysozyme to 57% of original activity (FIG. 31a). These data indicate that the incorporation of BMDO into the backbone of the trehalose glycopolymer does not adversely affect the polymer's ability to stabilize proteins. In fact, dilution of the trehalose results in a polymer that is a more effective stabilizer of lysozyme. It is known in other systems that diluting sugar moieties along a polymer backbone can lead to increased biological activity (Wada et al., 2011; Kanai et al., 1997; Gestwicki et al., 2002; Ladmiral et al., 2006)).

Figure 31B:
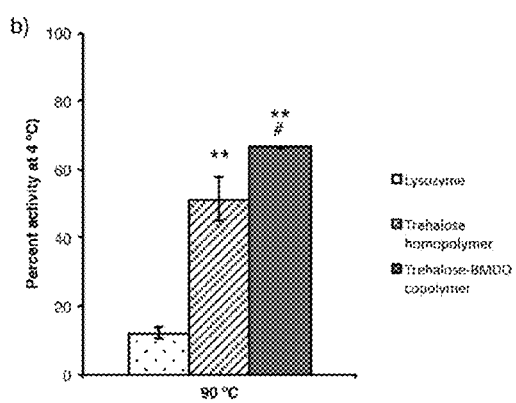
FIG. 31B is a graph showing activity of lysozyme after heat stress with the addition of trehalose homo- and copolymers as excipients, presented as the activity with respect to the original activity of the excipient mixture at 4° C. *=p<0.01, **=p<0.001 in comparison to no additive. #=p<0.01, ##=p<0.001 in comparison to trehalose homopolymer.

In addition to stabilizing lysozyme against heat stress at 90° C., samples with the copolymer as excipient demonstrated increased activity at 4° C. compared to lysozyme alone. This increase has been previously observed for the stabilization of glucose oxidase (GOx) with monomeric trehalose and is thought to be due to the sugar enhancing or stabilizing protein-substrate interactions (Paz-Alfaro et al., 2009). We have ruled out that the polymer itself is a substrate for the assay. Therefore the activity was also presented with respect to the activity of the excipient mixture at 4° C. (FIG. 31b). Represented in this manner, the activity was decreased after heat stress in all cases; yet the trehalose-BMDO copolymers were still statistically better stabilizers (67% activity) than no additive (12% activity) or the homopolymer (51% activity) as shown in FIG. 31b.

Heat Stress of Lysozyme with Trehalose-BMDO Copolymer.

A 0.1 mg/mL lysozyme stock in phosphate buffered saline (PBS) pH 7.4 was prepared and mixed with trehalose-BMDO copolymer (100 eq relative to lysozyme) or methacrylate trehalose homopolymer (100 eq relative to lysozyme). Samples were further diluted to a concentration of 0.021 mg/mL (1 kU/mL) and 20 L aliquots were prepared in 0.5 mL LoBind Eppendorf tubes. Each aliquot was heated to 90° C. for 20 minutes at 500 rpm, then cooled to 4° C. and centrifuged for 1 minute at 10,000 rpm. Samples were stored at 4° C. until activity was evaluated all together using the EnzChek® lysozyme activity assay.

Lysozyme Activity Assay (EnzChek®).

Aliquots containing 20 μL of lysozyme-glycopolymer solution were diluted to 100 μL with PBS pH 7.4. 50 μL of the resulting solution was removed and incubated with 50 μL of *Micrococcus luteus* labeled with FITC (1 mg/mL) at 37° C. for 30 minutes in a 96-well plate. The resulting fluorescence was measured (abs 480 nm/em 530 nm) and quantified relative to a known concentration curve. Statistics to determine significance were calculated using the Students t test; % confidence as +/−=t(standard deviation)/(number of trials)½ with p<1−% confidence/100.

Degradation of Degradable BMDO-Containing Polymers in Basic Conditions

Figure 32:
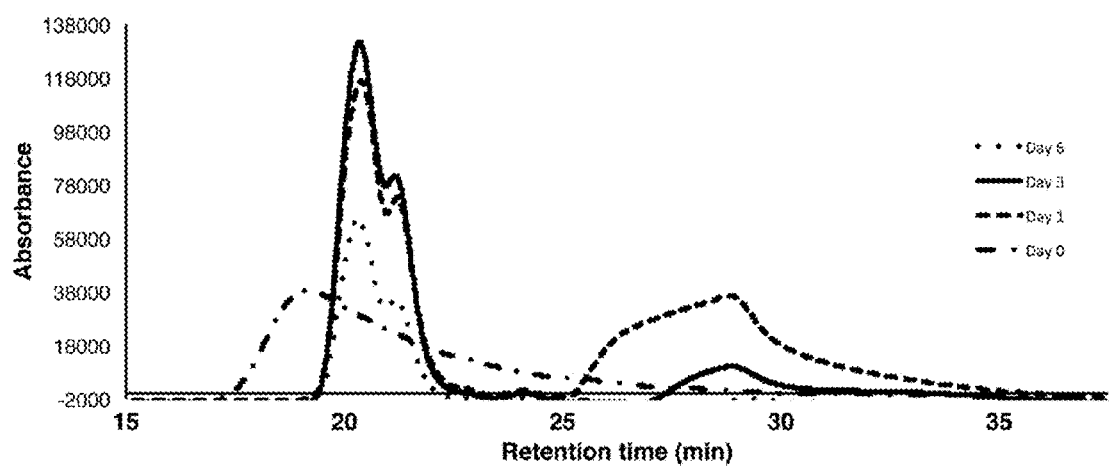
FIG. 32 is a graph showing degradation of trehalose-BMDO copolymer Poly5 in 5% KOH, monitored by gel permeation chromatography (GPC).

Both Poly 3 and Poly 5 were assessed for their ability to degrade under basic conditions. First, Poly 5 was treated with 5% KOH and the molecular weight assessed at intervals between 1 to 5 days. After 1 day, the gel permeation chromatogram showed a significant decrease in molecular weight, with no further change after subsequent days suggesting that the polymer was fully degraded (FIG. 32). In addition, the GPC trace of the degradation products was bimodal, indicating that not all the fragments were the same molecular weight. This would be expected for a random copolymer where degradable units would be placed randomly along the polymer background.

Figure 33:
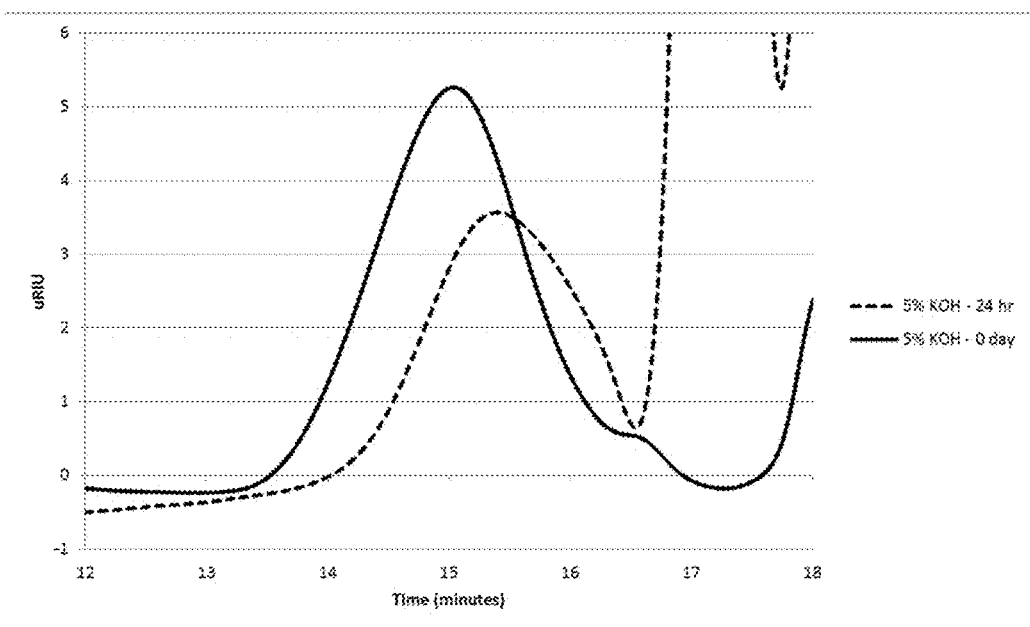
FIG. 33 is a graph showing degradation of Poly3 in 5% KOH.

BMDO-trehalose polymer was dissolved in a 5% KOH solution. Samples were lyophilized, dissolved in the GPC mobile phase, neutralized with HCl, and then analyzed by GPC (FIG. 33).

Degradation of Copolymers Under Basic Conditions.

Trehalose-BMDO copolymer (5 mg) was dissolved in 1.00 mL 5% KOH. The solution was vortexed and placed on Thermoshaker at 23° C. and 1000 rpm. Aliquots (200 μL) were removed and lyophilized at 1, 3, and 5 days.

Scheme 10

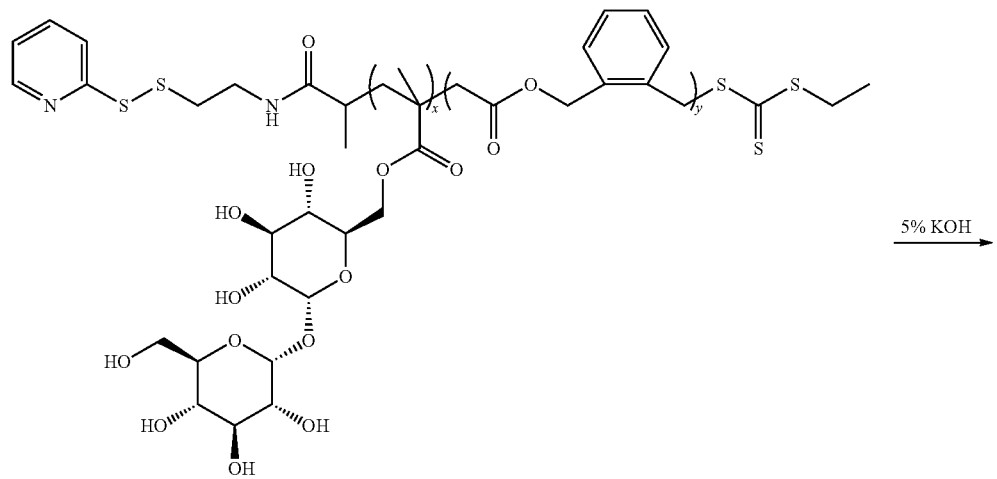

-continued

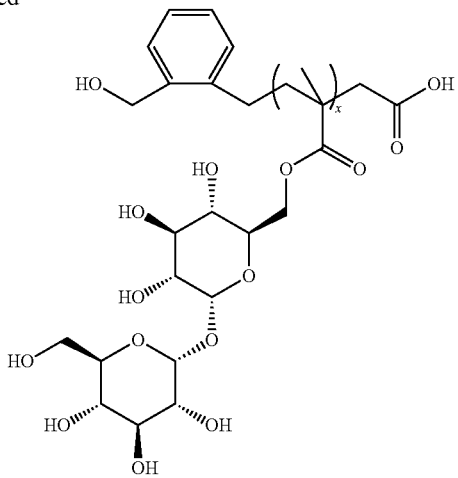

Figure 34:
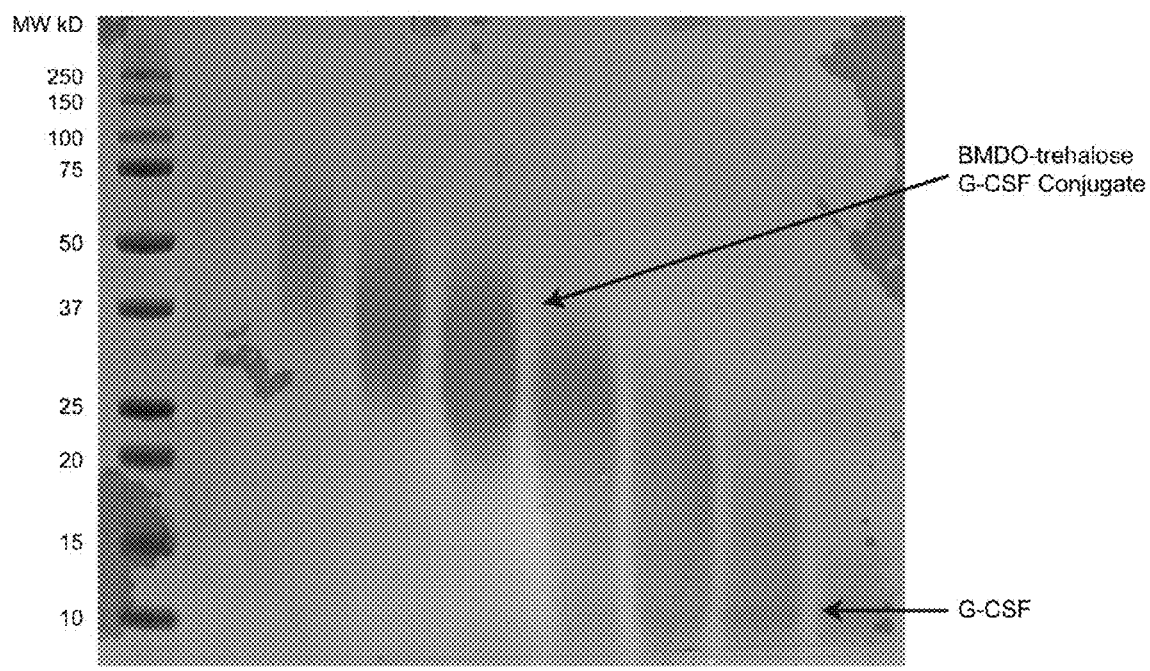
FIG. 34 is a photograph showing SDS-PAGE of FPLC fractions of BMDO-trehalose polymer G-CSF conjugation. Each lane is a successive fraction.

Conjugation of Degradable BMDO-Containing Polymers to G-CSF, a Therapeutic Protein BMDO-trehalose polymer conjugated to G-CSF was made using reductive amination targeting the N-terminal methionine residue of the G-CSF protein. Recombinant human G-CSF (200 μg, 10.6 nmol) was diluted into pH 5.0, 100 mM sodium acetate buffer. BMDO-trehalose polymer (15 mg, 1.07 μmol) and sodium cyanoborohydride (3.84 mg, 61.1 μmol) was added. The conjugation reaction was incubated at 4° C. for 72 hours. The pH was adjusted to 4.0 by the addition of 100 mM HCl and the crude mixture analyzed by SDS-PAGE. The conjugate was then purified by FPLC for separation of free polymer and unconjugated protein (FIG. 34).

In summary, two methods of synthesizing biodegradable trehalose polymers containing BMDO units by RAFT polymerization are presented. The polymers are made by polymerization of a protected monomer or by post-polymerization modification of polymers with reactive pendant units. These polymers were shown to stabilize model proteins as excipients, and to degrade in basic conditions. Additionally, the conjugation to G-CSF as a therapeutic protein was also demonstrated. These conjugates are useful for continuous therapy to impart stabilization without unnecessary accumulation of polymer.

Figure 86:
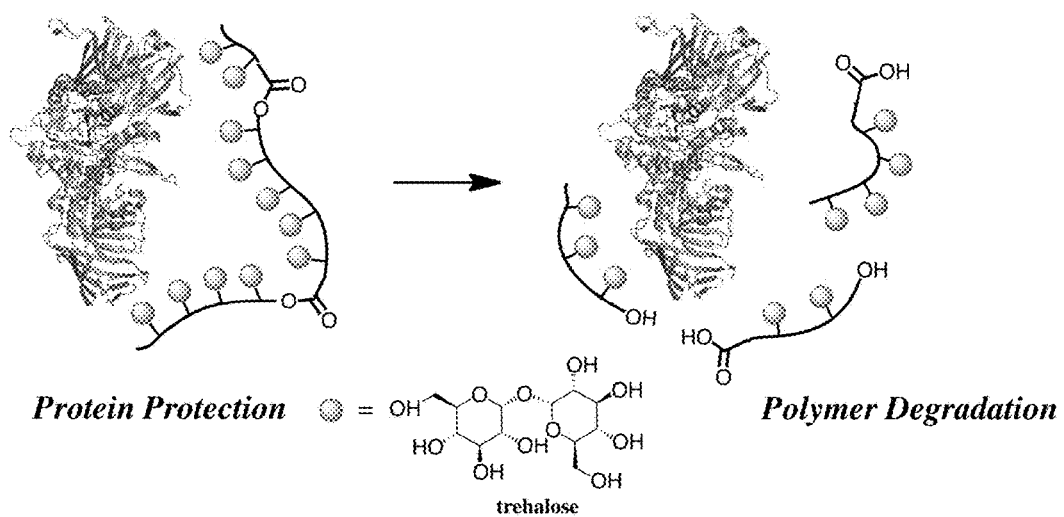
FIG. 86 shows Scheme 11.

We propose synthesizing trehalose glycopolymers that stabilize proteins and other biomolecules to the lyophilization process and also can be degraded through ester hydrolysis (FIG. 86, Scheme 11).

Hypothetical Example 3

The covalent attachment of poly(ethylene glycol) (PEG)-based polymers is known to improve the pharmacokinetics of protein therapeutics through stabilization and improved circulation time (Knop et al., 2010). There are several FDA-approved, PEGylated therapeutic agents on the market (Alconcel et al., 2011). In addition, protein conjugation to branched PEG-like polymers, such as poly(ethylene glycol methyl ether methacrylate) (PEGMA), developed by controlled radical polymerization (CRP) have been shown to improve pharmacokinetics as compared to PEGylation (Gao et al., 2010). Despite these advantages, PEGylation can result in decreased activity of the protein (Robert and Milton, 1998) and long-term treatment with PEGylated therapeutics can result in accumulation in the liver and spleen, hypersensitivity, the development of anti-PEG IgM antibodies, and lysozomal disease syndrome (Markovsky et al., 2012). Therefore, PEG-like polymers, containing a degradable linkage and/or degradable moieties in the backbone, have been sought-after to circumvent these issues (Duro-Castano et al., 2014).

Degradable linkages at the site of attachment between the polymer and protein are often installed so that the protein can be released (hydrolytically, enzymatically, or reductively) from the polymer in-vivo, and thus regain activity (Roberts et al., 2002). Such linkages include maleylamino peptide bonds (Garman and Barret, 1987), carbamate (Veronese et al., 1985), ester (Abuchowski et al., 1985), disulfide (Woghiren et al., 1993), hydrazone (Zalipsky and Menon-Rudolph, 1997), and oxime (Gaertner and Offord, 1996) bonds. For instance, PEG-Intron® was designed with a degradable carbamate linkage to interferon alpha-2b (Kozlowski and Milton, 2001). Roberts and Harris reported PEGylation of lysozyme (Lyz) through a degradable ester linkage; upon hydrolysis of the ester, the activity of Lyz was regained to 60% native activity (Roberts and Harris, 1998). However, the PEG backbone is non-degradable, and thus negative effects associated with polymer accumulation persist. To prevent this accumulation, enzymatically or hydrolytically degradable moieties such as esters (Iha et al., 2010), vinyl ethers (Lundberg et al., 2012), acetals (Dingels et al., 2013), oximes, or urethanes (Yan-Ling et al., 2010), as well as reduction sensitive disulfides (Cerritelli et al., 2007) have been installed in the backbone of PEG. Main-chain degradable PEGs have not yet been conjugated to a protein therapeutic. Several backbone degradable polymer-protein conjugates have been developed. Most of these conjugates consist of sugar-based or sugar-derived polymers such as hydroxyethyl starch (Hey et al., 2012), polysialic acid (Zhang et al., 2010), dextran (Yurkovetskiy et al., 2005) or dextrin (Hardwicke et al., 2008). Recently, ring opening polymerization has been used to synthesize a poly(ε-caprolactone) which was covalently bound to bovine serum albumin (Liu et al., 2014).

CRP offers easy end-group functionalization, well-defined polymer molecular weights, and compatibility with a wide variety of monomers. Therefore, much attention has been paid to the development of CRP techniques as a means to develop well-defined, PEG-like polymer-protein therapeutics (Grover and Maynard, 2010). The backbones of such PEG-like polymers have also been modified with degradable linkages through the coupling of radical ring-opening polymerization (rROP) of cyclic ketene acetals (CKAs) with CRP techniques including atom transfer radical polymerization (ATRP) (Lutz et al., 2007; Riachi et al., 2009) and nitroxide mediated polymerization (NMP) (Delplace et al., 2013). While CKAs have also been polymerized by reversible addition-fragmentation chain-transfer (RAFT) polymerization and macromolecular design via interchange of xanthates (MADIX) as a means of installing degradable units into polymer backbones, these techniques have not yet been applied to PEG-like polymers (Hedir et al., 2014; Siegwart et al., 2008; Kobben et al., 2014). In addition, no degradable polymer, developed by any CRP method, has yet been covalently attached to a protein.

Example 4

Substituted Polyesters by Thiol-Ene Modification: Rapid Diversification for Therapeutic Protein Stabilization Many proteins, especially those used as therapeutics, are unstable to storage and shipping temperatures and must be refrigerated, leading to increased costs in research and industry. Therefore, the design and synthesis of novel protein stabilizers is an important area of investigation. Herein we report new degradable polymers that stabilize proteins to environmental stressors such as refrigeration and elevated temperature that are also degradable. Specifically, polycaprolactones with different pendant groups were synthesized and surveyed for their ability to stabilize an important therapeutic protein to storage and shipping conditions. Ring-opening polymerization (ROP) of an allyl-substituted caprolactone monomer was carried out using the organocatalyst 1,5,7-triazabicyclo[4.4.0]dec-5-ene (TBD) to yield a well-defined, alkene-substituted, degradable polymer, which was used as a common backbone to control for degree of polymerization. Relevant side chains such as trehalose, lactose, glucose, carboxybetaine and oligo(polyethylene glycol) were installed via post-polymerization thiol-ene reactions. These degradable polymers were then employed as excipients for the stabilization of the therapeutic protein granulocyte colony-stimulating factor (G-CSF) against storage at 4° C. and shipping temperatures of 60° C. The best stabilization was observed using the trehalose- and zwitterion-substituted polyesters. Both the trehalose- and carboxybetaine-substituted pCL was further investigated with regard to molecular weight dependence, and it was found that the molecular weight was minimally important for stabilization to refrigeration, but critical for G-CSF stabilization at elevated temperatures. Both high performing zwitterionic and trehalose-substituted polyesters were also degraded and the polymers and degradation products shown to be noncytotoxic. This work provides potential biocompatible polymers for stabilization of the important therapeutic G-CSF, as well as a general platform for the future discovery of new polymeric protein stabilizers.

Introduction

Due to their substrate specificity and biological function, proteins have unique and essential roles in various industries. For example, proteins are used as reagents for improving chemical transformations, as cosmetic additives, as supplements for improving nutrition of animal feed, and as biological therapeutics. However, the stabilization of certain proteins during storage and transport especially those used as therapeutics, can be often critical to maintain structure and activity. Conditions such as UV exposure (Maity et al., 2009), heat (Bischof and He, 2005), lyophilization (Pikal-Cleland AND Carpenter, 2001), and excessive agitation (Sluzky et al., 1991) can lead to protein unfolding, aggregation, or loss of biological activity. Measures to prevent this loss of activity, such as the maintenance of a refrigeration chain for delicate protein therapeutics, increase costs and may still result in inactivated protein.

As a result, a number of compounds are used as excipients or additives to maintain protein activity (Kamerzell et al., 2011). For instance, osmolytes and carbohydrates such as trehalose, sorbitol, and sucrose have been shown to maintain protein activity through preferential hydration or protein interactions (Arakawa and Timasheff, 1985). Arginine, histidine, and other amino acids have also been shown to stabilize proteins through binding interactions, buffering, or hydration mechanisms (Falconer et al., 2011; Arakawa et al., 2007; Chen et al., 2003). Moreover, proteins such as human serum albumin (HSA), have been used as bulking agents or to prevent protein adsorption (Kamerzell et al., 2011). Furthermore, surfactants such as polysorbate (Tween) or modified polysaccharides such as hydroxyethyl starch (HES) have been employed to prevent protein unfolding and aggregation (Kamerzell et al., 2011; Fang et al., 2012; Garzon-Rodriguez et al., 2004). Excipients have also been used in nonbiological therapeutics. For instance, the recently-approved hyperkalemia drug patiromer includes sorbitol in its formulation to improve stability (Montaperto and Gandhi, 2016). However, proteins still suffer from activity loss despite the presence of these excipients, prompting further development of improved materials.

Synthetic polymers comprise another promising class of excipients used to stabilize proteins against environmental stressors. Polymers such as anionic polyacrylate, poly(glutamic acid), carboxylated polyamidosaccharides as well as block copolymers of poly(ethylene glycol (PEG) and poly (histadine) have been shown to stabilize a variety of proteins to stressors such as heat, aggregation, and lyophilization (Martin et al., 2014; Lee et al., 2010; Izaki et al., 2015; Gombotz et al., 1994; Stidham et al., 2014; Taluja et al., 2007). Other charged polymers such as poly(ethyleneimine) or heparin mimicking polymers can stabilize a variety of enzymes or growth factors using electrostatic interactions (Mazzaferro et al., 2010; Andersson and Hatti-Kaul, 1999; Nguyen et al., 2013; Matsusaki et al., 2005). Zwitterions have also been shown to have significant stabilizing ability due to their hydration and protein repulsion properties (Keefe and Jiang, 2012). Additionally, thermoresponsive copolymers have been used for refolding denatured proteins (Yoshimoto et al., 2003). We have previously developed styrene- and methacrylate-based polymers with trehalose side chains and shown that these polymers protect lysozyme, horseradish peroxidase (HRP), and glucose oxidase (GOX) against elevated temperatures both as excipients and as protein-polymer conjugates (Mancini et al., 2012; Lee et al., 2013). And others have investigated use of trehalose in polyacrylamide polymers to inhibit amyloid protein aggregation and in polycationic nanoparticles for delivery of siRNA (Wada et al., 2011; Srinivasachari et al., 2006).

Though synthetic polymers show promise in stabilization of proteins, most are non-degradable and thus will not be cleared from biological systems or will persist in the environment. For instance, poly(ethylene glycol) (PEG) is the most widely used biocompatible polymer, but has been shown to induce the formation of antibodies in 32-46% of patients during a clinical trial because of its persistence in vivo (Hershfield et al., 2014; Armstrong et al., 2007). Additionally, vacuolation in rats has been reported upon injection with high molecular weight (40 kDa) PEG (Rudmann et al., 2013). Small-molecule excipients that have been widely used for therapeutic formulation present other disadvantages. For instance, sorbitol is widely used and effectively maintains protein activity, yet has been shown to result in GI tract complications such as bleeding, ulcers, and necrosis (Abraham et al., 2001). Other high-performing excipients include the nonionic surfactants Tween 20 and Tween 80, which effectively prevent protein aggregation but have been shown to undergo auto-oxidation, resulting in the formation of damaging peroxides (Kerwin, 2008). Therefore, the development of degradable and functional polymers has been a subject of recent interest, especially for biological applications (Pelegri-O'Day et al., 2014; Pelegri-O'Day and Maynard, 2016). Degradable polymers might alleviate immunogenic responses, while also enabling the use of higher molecular weight polymers, which typically cannot be employed due to difficulty in clearance. In addition, enzymes are widely employed in applications such as in detergents or animal feed, where the use of any protein stabilizers must be biodegradable to avoid unwanted environmental buildup. Therefore, there is significant need for well-controlled, homogeneous, and degradable synthetic materials for biological and environmental concerns.

Herein we report the synthesis of degradable stabilizing polyesters using ring-opening polymerization (ROP). The polymers were prepared by first synthesizing alkene-functionalized polycaprolactones, followed by the installation of desired side chains using high-yielding thiol-ene reactions. A variety of materials were easily synthesized by varying mercaptan identity and the resulting materials protected G-CSF against loss of biological activity when added as excipients. We expect that these polymers can function as protein stabilizers in a variety of fields due to their combination of biodegradability and stabilization abilities.

Experimental Details

Materials

All materials and proteins were purchased from Sigma-Aldrich, Acros, or Fisher Scientific and were used without purification unless noted. Trehalose was purchased from The Healthy Essential Management Corporation (Houston, Tex.) and dried with ethanol and kept under vacuum before use. Anhydrous toluene was distilled from CaH2 and stored under argon prior to use. Anhydrous tetrahydrofuran (THF) was distilled from sodium benzophenone and stored under argon prior to use. Allyl-caprolactone was synthesized as previously described 33 and purified by distillation under reduced pressure before use. Thiolated methoxy polyethyleneglycol was synthesized as previously described.34 Thiolactose heptaacetate was synthesized as previously described (Shu et al., 2015; Yu et al., 2010) from commercially available lactosyl bromide. Recombinant human GCSF (herein called G-CSF) expressed in E. coli was a gift of Dr. Uland Lau (UCLA).

Analytical Techniques

NMR spectra were obtained on Bruker AV 500 and DRX 500 MHz spectrometers. 1H-NMR spectra were acquired with a relaxation delay of 2 s for small molecules and 30 s for polymers. Infrared absorption spectra were recorded using a PerkinElmer FT-IR equipped with an ATR accessory. High-resolution mass spectra were obtained on Waters LCT Premier with ACQUITY LC and ThermoScientific Exactive Mass Spectrometers with DART ID-CUBE. Gel Permeation Chromatography (GPC) was conducted on a Shimadzu high performance liquid chromatography (HPLC) system with a refractive index detector RID-10A, one Polymer Laboratories PLgel guard column, and two Polymer Laboratories PLgel 5 µm mixed D columns. Eluent was DMF with LiBr (0.1 M) at 50° C. (flow rate: 0.80 mL/min). Calibration was performed using near-monodisperse PMMA standards from Polymer Laboratories. Size Exclusion Chromatography (SEC) was conducted on a Shimadzu HPLC system with a refractive index detector RID-10A, one Tosoh TSKGel guard column, and one Tosoh TSKGel G4000PW column. Eluent was 0.3 M NaNO3+20 mM phosphate buffer pH 7+20% MeCN at 25° C. (flow rate 0.7 mL/min). Calibration was performed using near-monodisperse PEG standards from Polymer Laboratories. Matrix-assisted laser desorption/ionization (MALDI) was carried out on a Bruker Ultraflex. Solutions of trans-2-[3-(4-tert-butylphenyl)-2-methyl-2-propylidene]malonitrile (DCTB) as a matrix (20 mg/mL in THF), sodium trifluoroacetate (0.33 mg/mL in THF) as a cationizing agent, and polymer (1 mg/mL in THF) were mixed then added to the target to prepare a thin matrix/analyte film.

Representative Ring-Opening Polymerization (pCL-Allyl$_{40}$)

For the synthesis of pCL-allyl$_{40}$, a 1.5 mm glass sample vial was equipped with a stir bar and 2-34 Å molecular sieves and the setup was flame-dried. A 0.1 M solution of triazabicyclodecene in toluene (480 µL, 24 µmol, 2.5 mol %) and a solution of 15% v/v 3-methylbutanol in toluene (12.6 µL, 17 µmol, 1 equivalent) were added and the initiator-catalyst mixture was allowed to stir for 30 minutes at 21° C. before adding allyl-caprolactone monomer (150 mg, 973 µmol, 56 equivalents) via nitrogen-purged syringe. The reaction mixture was stirred at 21° C. and aliquots were removed for $^1$H-NMR analysis via nitrogen-purged syringe. After the desired conversion was achieved, the reaction was quenched with AcOH and the crude mixture purified by silica gel column chromatography (eluent EtOAc in hexanes 15-50%) to give the polymer as a colorless oil (100.5 mg). MN (GPC)=4700 Da, Đ=1.17. $^1$H-NMR (500 MHz in CDCl$_3$) δ: 5.75-5.67 (m, 36H), 5.06-5.00 (m, 72H), 4.11-4.10 (m, 72H), 3.63-3.61 (m, 2H), 2.44-2.31 (m, 72H), 2.24-2.19 (m, 36H), 1.67-1.45 (m, 144H), 1.36-1.30 (m, 72H), 0.92-0.91 (d, J=7 Hz, 6H). IR: ν=3077, 2941, 2863, 1729, 1642, 1444, 1417, 1392, 1364, 1234, 1162, 1135, 1064, 994, 915, 736OAc.

Representative Synthesis of Functional Polyesters Via Thiol-Ene Reaction (pCL-trehaloseOAc$_{40}$)

For the synthesis of pCL-trehaloseOAc$_{40}$, in a 1.5 mm glass sample vial, pCL-allyl$_{40}$ (12 mg, 2.1 µmol, 77 µmol alkene groups) was dissolved in anhydrous THF (300 µL). Thiolated trehalose A (162 mg, 249 µmol, 3 equivalents per alkene) and 2,2-dimethoxy-2-phenylacetophenone (DMPA) (11 mg, 42 µmol, 0.5 equivalents per alkene) were added and the vial was sealed with a septum, degassed by sparging for 10 minutes, and exposed to a handheld UV lamp (λ=365 nm) for 4 hours. The crude solution was then precipitated into cold MeOH (protected sugars) or dialyzed in MeOH (PEG and zwitterion precursor) to yield the desired functional polyester (53.1 mg, 1.7 µmol, 79%). MN (GPC)=28400 Da, Đ=1.06. 1H-NMR (500 MHz in CDCl$_3$) δ: 5.47 (q, 86H), 5.30-5.26 (m, 86H), 5.13-5.10 (m, 44H), 5.06-4.97 (m, 129H), 4.24-4.20 (m, 43H), 4.06-4.00 (m, 215H), 2.62-2.47 (m, 172H), 2.34-2.27 (m, 43H), 2.15-2.00 (m, 903H), 1.68-1.58 (m, 215H), 1.55-1.42 (m, 172H), 1.34-1.26 (m, 86H), 0.93 (d, J=6.5 Hz, 6H).

pCL-glucoseOAc$_{40}$: MN (GPC)=22300 Da, Đ=1.06. $^1$H-NMR (500 MHz in CDCl3) δ: 5.23 (t, 39H), 5.09 (t, 39H), 4.99 (t, 39H), 4.52-4.45 (d, 39H), 4.25 (dd, 39H), 4.16-4.10 (d, 78H), 4.07-3.97 (m, 78H), 3.75-3.69 (m, 39H), 2.73-2.60 (m, 78H), 2.37-2.28 (m, 39H), 2.13-1.97 (m, 468H), 1.70-1.42 (m, 312H), 1.38-1.24 (m, 78H), 0.93 (d, J=6.5 Hz, 6H).

pCL-lactoseOAc$_{40}$: MN (GPC)=28900 Da, Đ=1.07. $^1$H-NMR (500 MHz in CDCl3) δ: 5.36 (d, 37H), 5.27 (t, 37H), 5.09 (t, 37H), 4.99-4.86 (m, 74H), 4.53-4.40 (m, 111H), 4.18-3.95 (m, 185H), 3.91-3.84 (t, 37H), 3.82-3.73 (t, 37H), 3.66-3.55 (m, 37H), 2.69-2.56 (m, 74H), 2.35-2.24 (m, 37H), 2.18-1.90 (m, 777H), 1.71-1.40 (m, 370H), 1.34-1.21 (m, 74H), 0.92 (d, J=6.5 Hz, 6H).

pCL-PEG$_{40}$: MN (GPC)=23600 Da, Đ=1.07. $^1$H-NMR (500 MHz in CDCl$_3$) δ: 4.11-3.98 (m, 78H), 3.74-3.51 (m, 1225H), 3.38 (s, 117H), 2.69 (t, 78H), 2.53 (t, 78H), 2.36-2.29 (m, 39H), 1.71-1.42 (m, 332H), 1.36-1.25 (m, 78H), 0.93 (d, J=6.5 Hz, 6H).

Representative Deprotection of Acetylated Glycopolymers (pCL-Trehalose$_{80}$)

For the synthesis of pCL-trehalose$_{80}$, in a 20 mL screw-top vial, pCL-trehaloseOAc$_{80}$ (16.8 mg, 0.3 μmol, 145 μmol acetate groups) was dissolved in CHCl$_3$:MeOH 1:1 (2 mL). K$_2$CO$_3$ (20 mg, 148 μmol, 1 equivalent per acetate group) was added, and the suspension was let stir at room temperature for 3 hours, during which time a white precipitate formed. The organic solvents were removed and the solid was dissolved in H2O, neutralized with 2M HCl and dialyzed against 3.5 kD MWCO in 50% MeOH, switching to 100% H$_2$O after 24 hours. The resulting solution was removed from the dialysis tubing and lyophilized, yielding a fluffy white solid (6.3 mg, 0.16 μmol, 60% yield). MN (GPC)=17000 Da, Đ=1.39. 1H-NMR (500 MHz in CDCl3) δ: 5.12-4.95 (d, 160H), 4.14-3.88 (s, 320H), 3.89-3.56 (m, 400H), 3.54-3.42 (s, 320H), 3.36-3.16 (m, 160H), 2.94-2.78 (s, 80H), 2.65-2.42 (m, 240H), 2.36-2.22 (s, 80H), 1.78-1.35 (m, 480H), 1.31-1.09 (s, 160H), 0.82 (s, 6H). IR: ν=3339, 2931, 1726, 1367, 1264, 1146, 1102, 1030, 991, 942, 841, 804, 731.

pCL-glucose$_{40}$: MN (GPC)=18300 Da, Đ=1.09. 1H-NMR (500 MHz in CDCl3) δ: 4.38 (d, 32H), 4.01 (s, 64H), 3.74 (d, 32H), 3.60 (s, 32H), 3.40-2.37 (m, 96H), 3.19 (t, 32H), 2.63 (s, 64H), 2.31 (s, 32H), 1.59-1.42 (m, 256H), 1.29-1.17 (m, 64H), 0.84 (d, J=6.5 Hz, 6H).

pCL-lactose$_{40}$: MN (GPC)=16900 Da, Đ=1.17. $^1$H-NMR (500 MHz in CDCl$_3$) δ: 4.38 (dd, 70H), 4.06-3.93 (s, 70H), 3.90-3.78 (m, 70H), 3.74-3.41 (m, 280H), 3.26 (t, 32H), 2.70-2.58 (m, 70H), 2.35-2.27 (m, 35H), 2.04-1.98 (m, 35H), 1.62-1.41 (m, 280H), 1.30-1.19 (m, 70H), 0.84 (d, J=6.5 Hz, 6H).

Synthesis of pCL-Zwitterion$_{40}$

In a 1.5 mm glass sample vial, pCL-allyl$_{40}$ (15 mg, 2.5 μmol, 96 μmol alkene groups) was dissolved in MeOH:DCM (1:1, 400 μL total). Dimethylaminoethanethiol hydrochloride (41 mg, 288 μmol, 3 equivalents per alkene) and DMPA (12 mg, 48 μmol, 0.5 equivalents per alkene) were added and the vial sealed with a septum, degassed by sparging for 10 minutes, and exposed to a handheld UV lamp (λ=365 nm) for 4 hours. The crude solution was opened to air and volatiles removed under reduced pressure. A solution of saturated sodium bicarbonate (3 mL) was then added to the vial and let stir for 1 hour. The aqueous layer was extracted with dichloromethane (3×10 mL) and the organic layers combined and dried using MgSO4. Solvent was removed in vacuo, and thorough removal of water was ensured by freeze-drying from benzene. The resulting oil was dissolved in anhydrous acetonitrile (2 mL) and t-butyl bromoacetate (57 μL, 384 μmol, 4 equivalents per amine) was added. The reaction mixture was stirred at 50° C. for 17 hours. The crude was let cool to room temperature and the acetonitrile was removed in vacuo. Trifluoroacetic acid (TFA, 0.5 mL) was then added and the reaction mixture let stir at room temperature for 3.5 hours. TFA was removed in vacuo and the crude material was dissolved in MeOH:H$_2$O 1:1 and dialyzed against 3.5 kD MWCO dialysis tubing, switching to 100% H$_2$O after 24 hours. The resulting solution was filtered and lyophilized to remove water, yielding a white fluffy solid (18.2 mg, 1.5 μmol, 60% yield). MN (GPC)=5100 Da, Đ=1.19. 1H-NMR (500 MHz in CDCl3) δ: 4.07-3.96 (s, 78H), 3.84-3.77 (s, 78H), 3.76-3.65 (m, 78H), 3.23-3.09 (s, 234H), 2.89-2.76 (m, 78H), 2.61-2.47 (m, 78H), 2.39-2.27 (m, 39H), 1.78-1.41 (m, 312H), 1.33-1.16 (s, 78H), 0.84 (d, J=6 Hz, 6H). IR: ν=2944, 2861, 1721, 1626, 1457, 1385, 1325, 1250, 1163, 1059, 1006, 960, 886, 799, 715.

G-CSF Stabilization Studies: G-CSF samples (25 μL) were prepared in 10 mM acetate buffer, pH 4.0 at 1 μg/mL with 100 equivalents polymer additive by weight. Samples were stored at 4° C. for 90 minutes or 60° C. for 30 minutes and then were diluted with cold RPMI-1640 medium+10% FBS (735 μL). The samples were then further diluted with RPMI-1640+10% FBS to a final concentration of 1 ng/mL. G-CSF bioactivity was then assayed in a NFS-60 mouse myelogenous leukemia lymphoblast cell line. NFS-60 cells were cultured in RPMI-1640 medium supplemented with 10% FBS and 2 ng/mL interleukin-3 (IL-3) at 37° C./5% CO2. NFS-60 cells were passaged at least three times before used in proliferation experiments. Prior to treating NFS-60 cells with G-CSF samples, NFS-60 cells were collected and resuspended in RPMI-1640 with 10% FBS (without additional growth factors). Cells were plated in the internal wells of a 96 well plate at a density of 20,000 cells per well in 50 μL of medium. G-CSF solution (50 μL) was then added to provide a final concentration of 0.5 ng/mL and total well volume of 100 μL. Following 48 h incubation at 37° C./5% CO2, CellTiter-Blue viability assay was performed to measure cell proliferation. All experimental groups were normalized to the control of the control of media alone without G-CSF addition. All p values were calculated using the independent Student's t test assuming unequal variances.

Results

The nature of the degradable polymer backbone was an important consideration in the design of a modular system for protein stabilization. We have previously observed that trehalose polymers with hydrophobic backbones have demonstrated good protein stabilization (Lee et al., 2013) and hypothesized that the nonionic surfactant character of these materials was an important contributor to their desirable properties (Kamerzell et al., 2011). Therefore, the FDA-approved polymer poly(caprolactone) (pCL) was selected because of its hydrophobic and biodegradable nature. Previous examples have introduced functional side chains onto pCL using a variety of post-polymerization click chemistries to avoid chemical incompatibilities with ROP conditions and also to minimize steric interference during polymerization. For instance, aminooxy-functionalized PEG chains have been added to ketone-modified pCL through oxime click chemistry, resulting in graft copolymers (Taniguchi et al., 2005). Alkyne- and alkene-functionalized valero- and caprolactone monomers have been synthesized and polymerized to yield polyesters with reactive handles for later installation of PEG and peptide side-chains (Parrish et al., 2002; Parrish et al., 2005). We chose to synthesize the polyester backbone with reactive alkene side chains and use it as a common precursor to introduce stabilizing functionalities via post-polymerization thiol-ene reactions. Thiol-ene is a particularly attractive type of "click" modification because it combines efficiency, a metal-free nature, and a tolerance of both water and oxygen (Lowe, 2010; Hoyle and Bowman, 2010). Using this type of chemistry allows for the ready introduction of different functional, potentially stabilizing moieties onto the polymer side-chains by using a variety of mercaptans (FIG. 1). Additionally, with this post polymerization approach, the backbone length would be the same between the different classes to rule out differences in stabilizing ability due to changes in degree of polymerization.

Synthesis of a Library of Functionalized Polyesters

The desired alkene-functionalized caprolactone monomer was synthesized by adding allyl bromide to CL in the presence of n-butyl lithium following a literature procedure 33 and polymerized using ROP to produce polymers. A degree of polymerization (DP) of 40 was targeted because it would result in functionalized polymers with molecular weights between 20.9 and 12.8 kD. The organic catalyst 1,5,7-triazabicyclo[4.4.0]dec-5-ene (TBD) was used due to its fast polymerization kinetics at room temperature and narrow dispersity (Đ) for the ROP of functional lactones (Pratt, et al., 2006; Lohmeijer, et al., 2006; Silvers et al., 2012; Kamber et al., 2007). The initiator 3-methyl-1-butanol was employed because its distinctive $^1$H-NMR peaks allowed for good characterization (Stevens et al., 2013). Using a monomer concentration of 2 M, high conversion and good control over molecular weight was achieved, with Đ=1.08, a degree of polymerization (DP) of 36, and a number average molecular weight of 5,600 Da by $^1$H NMR and 5,400 by gel permeation chromatography (pCL-allyl$_{40}$, Table 1). Initially, polymers were purified by dialysis in DCM/MeOH. However, polymers purified using this method had unidentified impurities, which resulted in significant loss of protein activity in later experiments (data not shown). Purification by silica gel column chromatography successfully removed the impurities, and subsequent polymers were therefore purified using this method.

The allylated polymers were then used in radical thiol-ene reactions to install the desired pendant stabilizing groups (Scheme 12). The photoinitiator 2,2-dimethoxyphenylacetophenone (DMPA) was used because of its demonstrated high efficiency in photoinitiated thiol-ene reactions (Campos et al., 2008). A series of easily accessible thiols (A-D) were selected containing sugars or oligo(PEG) that as small molecules are known stabilizing excipients (Kamerzell et al., 2011). Thiolated trehalose was synthesized in five steps and 53% overall yield from trehalose using trityl and acetate protecting groups (Scheme 1). Briefly, mono-hydroxyl trehalose heptaacetate was synthesized as previously described (Lee et al., 2013). A tosylate ester was installed and displaced using potassium thioacetate. Selective cleavage of the thioester using hydrazine acetate then led to thiolated trehalose A. Thiolated lactose C and D were synthesized as previously described.

Scheme 12. Synthetic scheme of thiol-ene modification of pCL-allyl polymers with acetyl-trehalose, acetyl-glucose, acetyl-lactose and PEG thiols, followed by deprotection of the acetylated sugars.

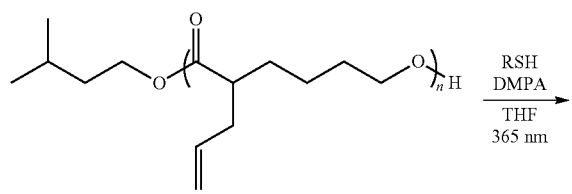

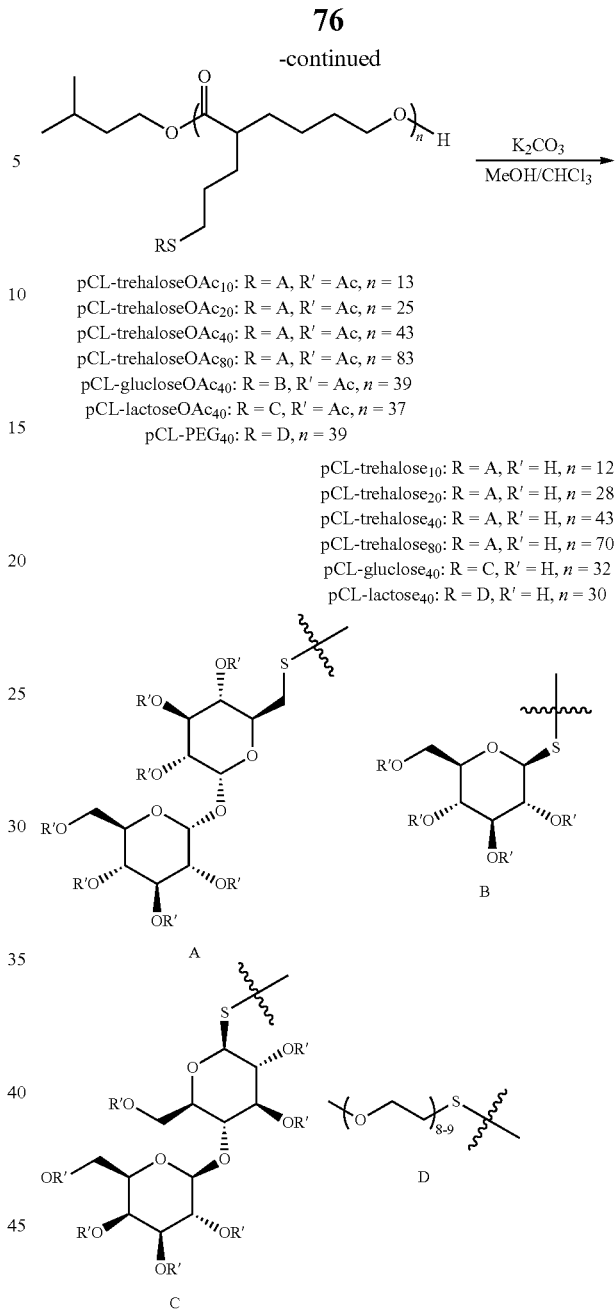

Figure 36A:
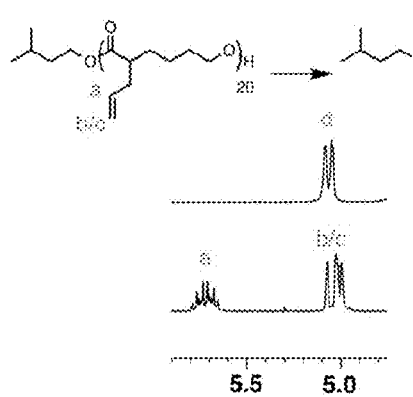
FIG. 36A is a graph showing characterization of trehalose modification of pCL using thiol-ene chemistries. The $^1$HNMR traces before and after modification showing a disappearance of the alkene resonance peaks at 5.0 and 5.7 ppm and the appearance of resonance peaks corresponding to trehalose anomeric protons.
Figure 36B:
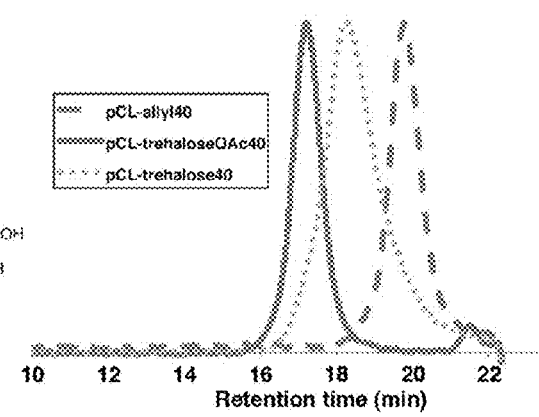
FIG. 36B is a graph showing characterization of trehalose modification of pCL using thiol-ene chemistries. GPC characterization of pCL-allyl40 before and after modification showing a shift towards a higher molecular weight species. After deprotection of the trehalose, a shift towards a lower molecular weight species was observed showing complete modification and deprotection of the polymer.

Use of acetate-protected saccharide mercaptans was found to be important for good miscibility between the pCL backbone and the thiol, giving clean conversion to the acetylated glycopolymers. In all cases, three equivalents of thiol per alkene were used to ensure complete reaction of the alkene side-chains. After polymer modification, removal of the acetate esters using potassium carbonate in MeOH/CHCl$_3$ (Lee et al., 2013) or hydrazine hydrate (Aoi et al., 1994; Takasu and Kojima, 2010; Dong et al., 2004; Takasu et al., 2002) led to the desired glycopolymers without hydrolysis of the polyester backbone. Complete modification was confirmed by disappearance of the alkene peaks in the $^1$H-NMR (representative data in FIG. 36a) as well as clean shifts in GPC molecular weight (representative data in FIG. 36b).

The carboxybetaine zwitterionic pCL polymer was synthesized taking inspiration from a literature procedure for a non-degradable polymer (Scheme 13) (Aapro et al., 2006). 2-(Dimethylamino)ethanethiol hydrochloride was added to the pCL-allyl$_{40}$ backbone polymer using photoinitiated thiol-ene conditions and subsequently treated with sodium bicarbonate to neutralize the hydrochloride salt. Exposure to t-butyl bromoacetate quaternized the amine and hydrolysis of the t-butyl ester with trifluoroacetic acid led to the formation of the zwitterion. No acidic backbone scission was observed by GPC or 1H-NMR analysis.

Scheme 13. Synthetic scheme for the synthesis of zwitterionic polymer pCL-zwitterion$_{40}$.

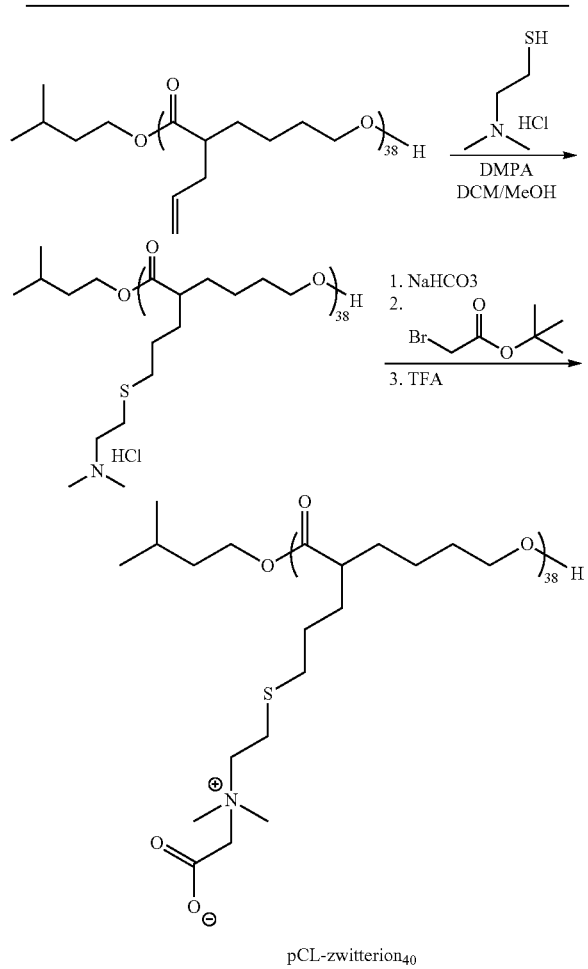

pCL-zwitterion$_{40}$

All polymers were characterized by GPC and $^1$H-NMR to determine molecular weight and dispersity (Table 1). When analyzed by $^1$H-NMR, slight variations in DP were observed between the substituted pCLs, despite use of a common alkene-substituted backbone. This is unlikely to be due to chain scission, as the library of substituted pCL all gave narrow molecular weight distributions between 1.19 and 1.07 and the peak shapes were generally well-defined and symmetrical (FIGS. 59, 65, 66 and 78). Using poly(methyl methacrylate) standards, the MN by GPC for the DMF-soluble polymers varied from 12.7 to 23.6 kD. The zwitterionic material was not DMF-soluble and was instead analyzed using PEG standards, making direct molecular weight comparison difficult. However, because a post-polymerization approach was used to synthesize these materials, the same backbone was used to construct all polymers in the study. Therefore, while the molecular weight varied due to side chain identity, the DP of all polymers (i.e. backbone length) compared is identical.

TABLE 1

Molecular weights and GPC data for the library of polyesters (DP40)

| | Polymer | DP$^b$ | Mn ($^1$H-NMR) | Mn (GPC) | Đ |
|---|---|---|---|---|---|
| Protected SP$^a$ | pCL-allyl$_{40}$ | 36 | 5600 | 5400 | 1.08 |
| | pCL-trehalose-OAc$_{40}$ | 43 | 34700 | 28400 | 1.06 |
| | pCL-glucose-OAC$_{40}$ | 39 | 20300 | 22300 | 1.06 |
| | pCL-lactose-OAC$_{40}$ | 37 | 29900 | 28900 | 1.07 |
| Deprotected | pCL-trehalose-OH$_{40}$ | 36 | 18500 | 12700 | 1.17 |
| | pCL-glucose$_{40}$ | 32 | 11300 | 18300 | 1.09 |
| | pCL-lactose$_{40}$ | 35 | 18000 | 16900 | 1.17 |
| | pCL-PEG$_{40}$ | 39 | 20400 | 23600 | 1.07 |
| | pCL-zwitterion$_{40}$ | 39 | 12500 | 5100$^c$ | 1.19$^c$ |

$^a$Starting polymer
$^b$By $^1$H-NMR analysis
$^c$GGPC run in buffer/MeCN with PEG standards Assessment of Stabilizing Ability Next the ability of the polymer to protect protein activity against environmental stressors was assessed. The therapeutic protein granulocyte colony-stimulating factor (G-CSF) was selected to compare excipient efficacy due to its clinical importance. G-CSF is FDA-approved as filgrastim and lenograstim and is used therapeutically to increase neutrophil granulocyte count during chemotherapy (Aapro et al., 2006). G-CSF is highly unstable at physiological pH and is therefore stored at pH 4.0; still at this pH the protein readily degrades upon storage or subjection to heat (Krishnan et al., 2002). The side chain identity was varied to determine the relative stabilizing ability of the functional groups. To investigate storage at refrigeration temperatures, pCL polymers were added to G-CSF at 100 weight equivalents to protein and the protein was stored for 90 minutes at 4° C. at 1 μg/mL and pH 4.0. Protein activity was determined by measuring cell proliferation in murine myeloid leukemia NFS-60 cells, which is enhanced in the presence of GCSF, and compared to the proliferation of freshly diluted protein (Shirafuji et al., 1989).

After stressing, G-CSF with no additive only exhibited 133±6% cell proliferation, a drastic reduction compared to fresh G-CSF (FIG. 37a). Addition of the pCL-glucose and pCL-lactose polymers was not statistically different than no additive, indicating that for this protein, the polymers were not effective stabilizers. Interestingly, when the pCL-PEG polymer was added to the G-CSF solution, significantly lower proliferation was observed; only 16±7% of the native activity was retained. PEG has been shown to associate with hydrophobic moieties on the protein surface due to its amphiphilic nature (Wu et al., 2014), and has been previously observed to lower protein thermal stability (Jayaraman et al., 2004). A similar mechanism may be a factor for the destabilizing affect of this pCL-PEG polymer. Both the zwitterionic and trehalose side chains significantly outperformed the other polymers, stimulating 171±7% and 168±3% cell proliferation, respectively. Both stabilizing polymers were not statistically different than the fresh sample, indicating that both are equally effective at preventing G-CSF activity loss under these conditions. G-CSF was also stressed at 60° C. for 30 minutes; this is representative of the maximum temperature inside truck and shipping containers during transport (Young, 2002). As expected, G-CSF lost more than 95% of the native activity after heating; addition of the pCL-PEG polymer was not statistically different than no additive and only exhibited 2±3% of the native activity (FIG. 37b). The pCL-glucose and the pCL-lactose polymers were moderately stabilizing, retaining 12±2% and 36±7% of G-CSF activity, respectively. Addition of the trehalose (133±8%)) and zwitterionic (179±3%) side chain polymers resulted in the highest cell proliferation and the pCL-zwitterion$_{80}$ was not statistically different than the fresh sample. The greater than 100% activity shown by the zwitterionic polymer might be due to stabilization against manipulation at room temperature and 37° C. during the assay preparation. We observed that at the zwitterionic polymers retained greater activity than the trehalose side chain polymers. Since one hypothesis of why trehalose provides stabilization is due to clustering of the sugar around flexible polar residues on the protein surface (Katyal and Deep, 2014; Fedorov et al., 2011), we included a larger trehalose CL polymer (preparation vide infra) in the heat study. In this case, a 40 kDa pCL-trehalose polymer gave 105±14% stabilization and was statistically the same as the zwitterionic polymer, showing that the larger trehalose pCL stabilizes as well as the zwitterionic polymer and suggesting a molecular weight dependence of the trehalose polymer stabilization ability.

Testing of Different Molecular Weights

Figure 46:
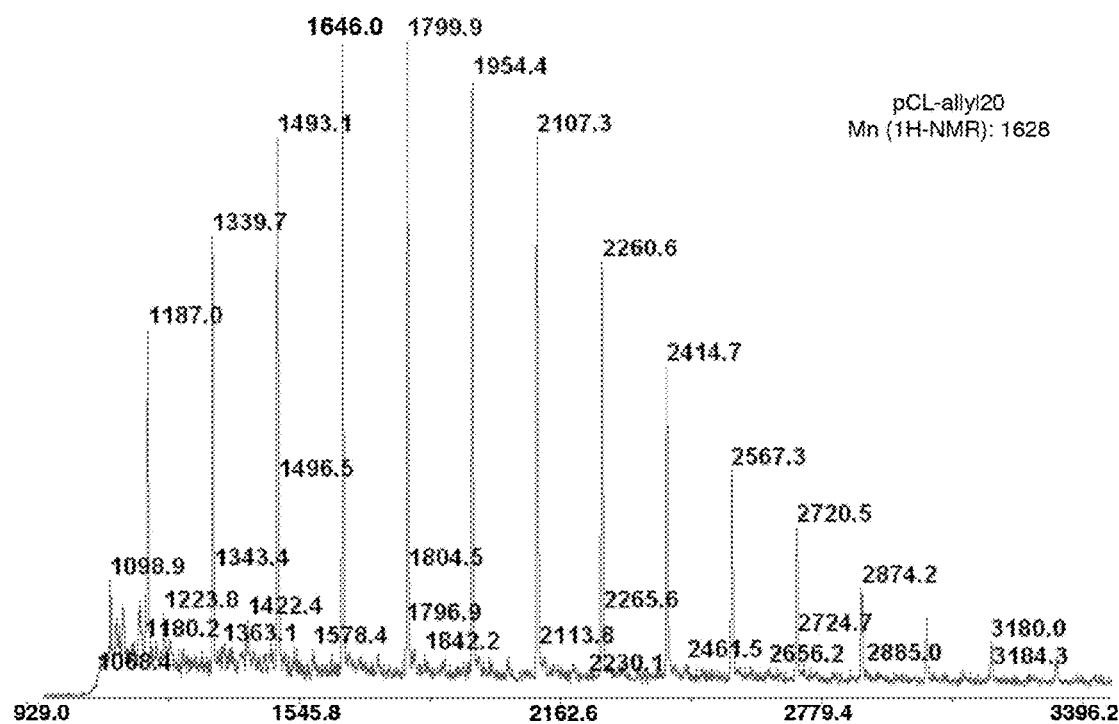
FIG. 46 is a graph showing Matrix-assisted laser desorption/ionization (MALDI) chromatogram of pCL-allyl$_{10}$.
Figure 47:
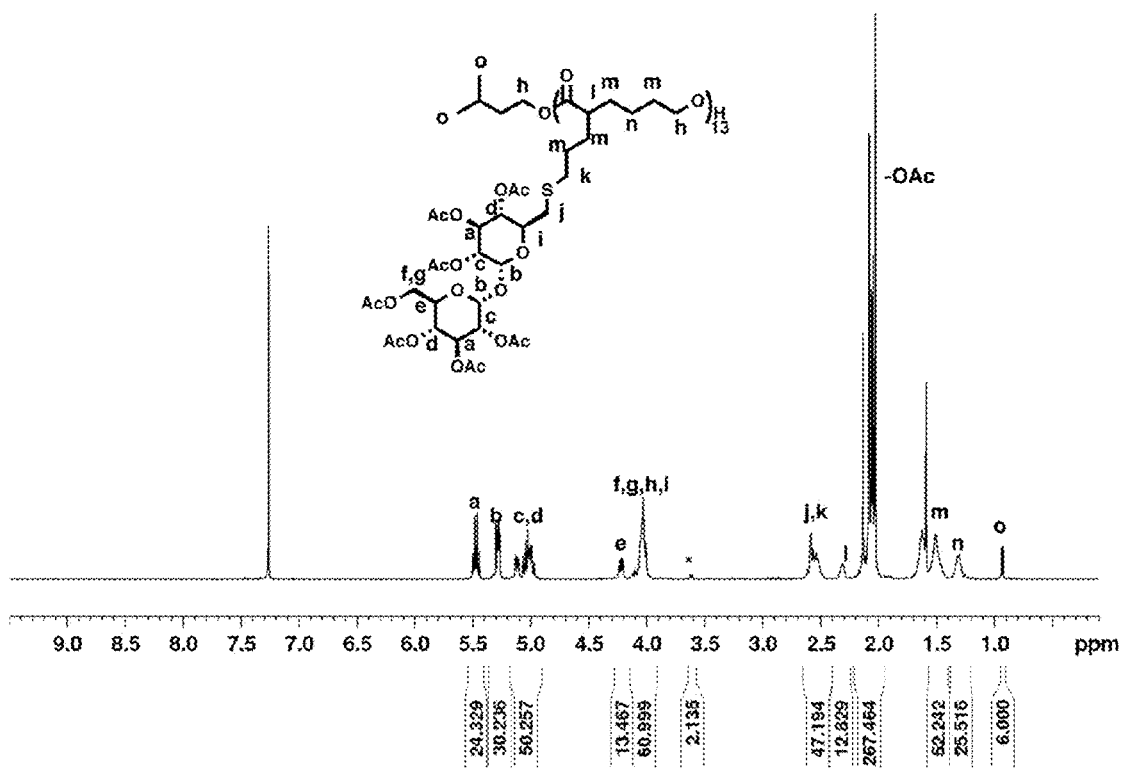
FIG. 47 is a graph showing $^1$H-NMR spectrum of pCL-trehaloseOAc$_{10}$ (CDCl$_3$, 500 MHz). *=protons from terminal unit on polymer.
Figure 48:
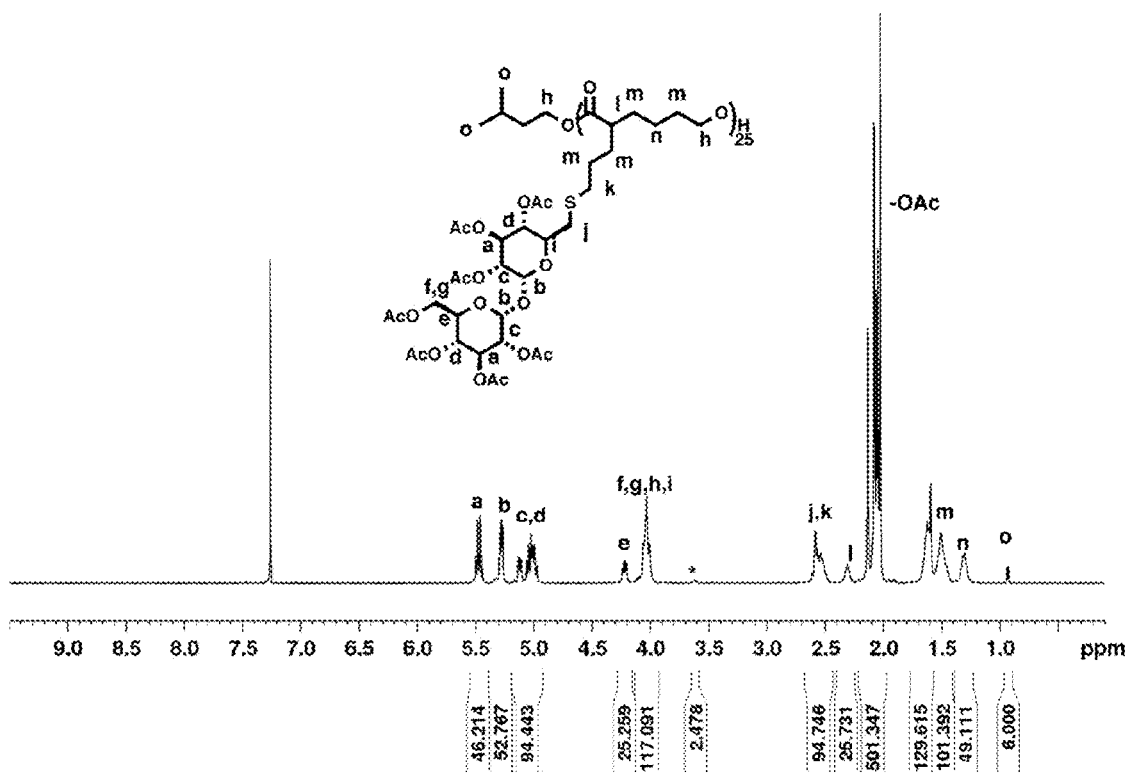
FIG. 48 is a graph showing $^1$H-NMR spectrum of pCL-trehaloseOAc$_{20}$ (CDCl$_3$, 500 MHz). *=protons from terminal unit on polymer.
Figure 49:
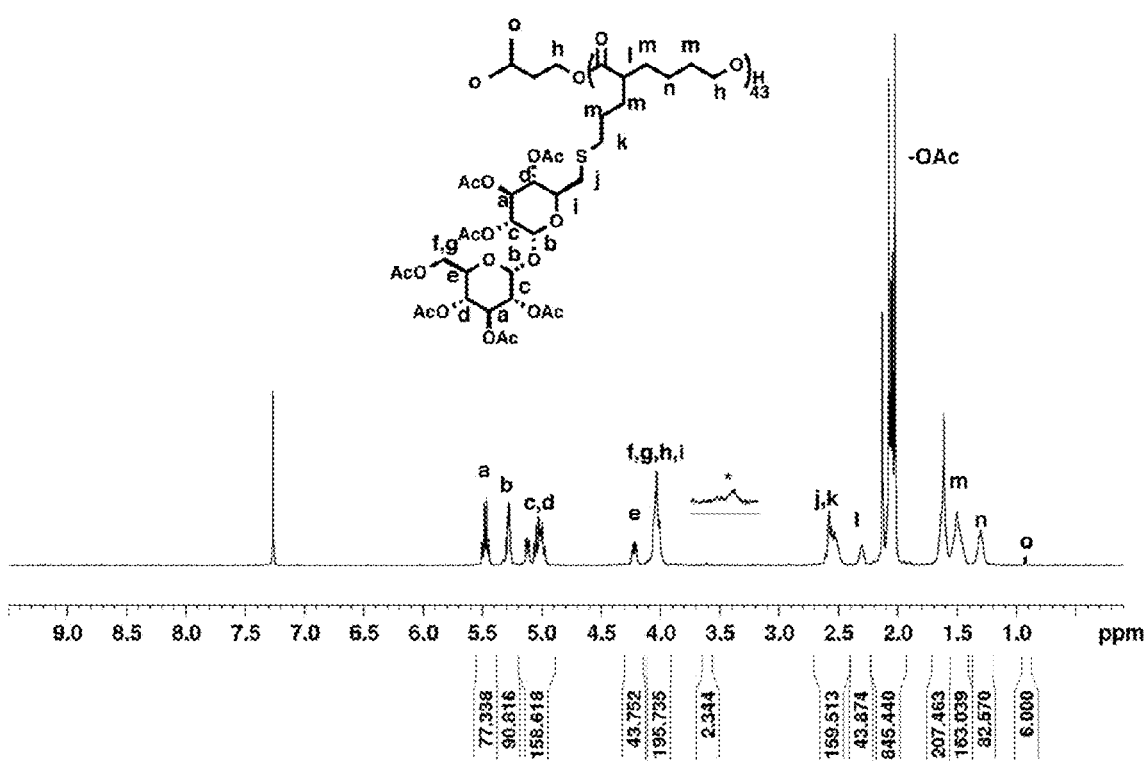
FIG. 49 is a graph showing $^1$H-NMR spectrum of pCL-trehaloseOAc$_{40}$ (CDCl$_3$, 500 MHz). *=protons from terminal unit on polymer.
Figure 50:
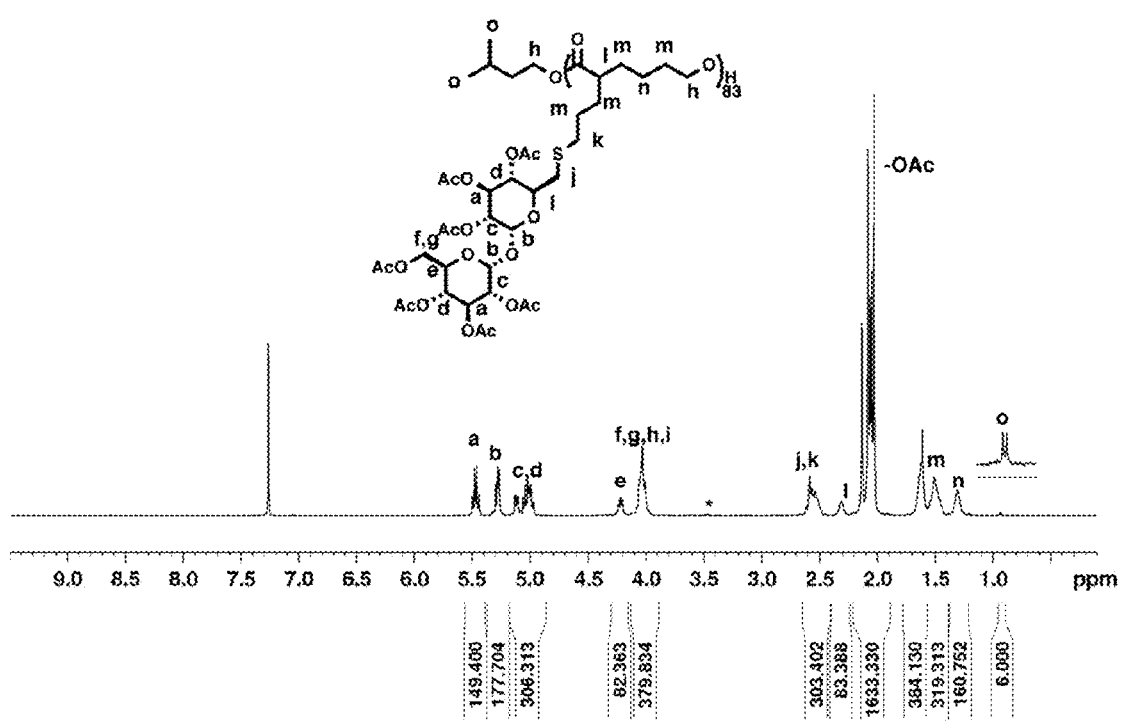
FIG. 50 is a graph showing $^1$H-NMR spectrum of pCL-trehaloseOAc$_{80}$ (CDCl$_3$, 500 MHz). *=protons from terminal unit on polymer.
Figure 51:
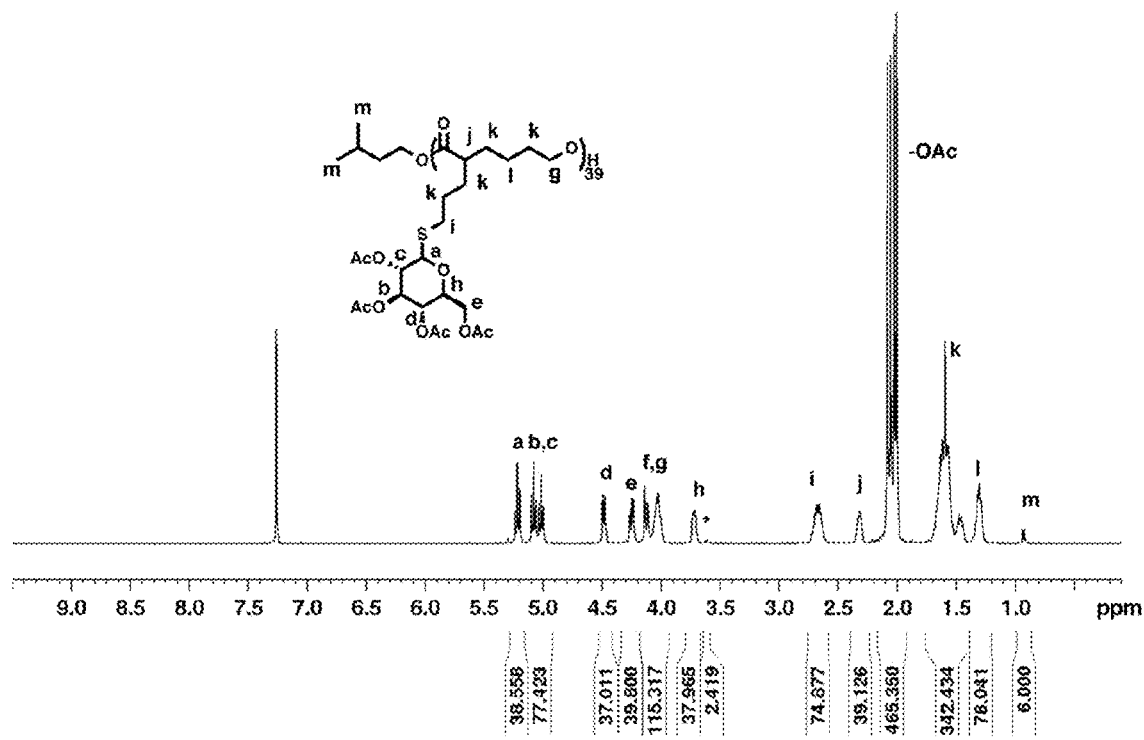
FIG. 51 is a graph showing $^1$H-NMR spectrum of pCL-glucose OAc$_{40}$ (CDCl$_3$, 500 MHz). *=protons from terminal unit on polymer.
Figure 52:
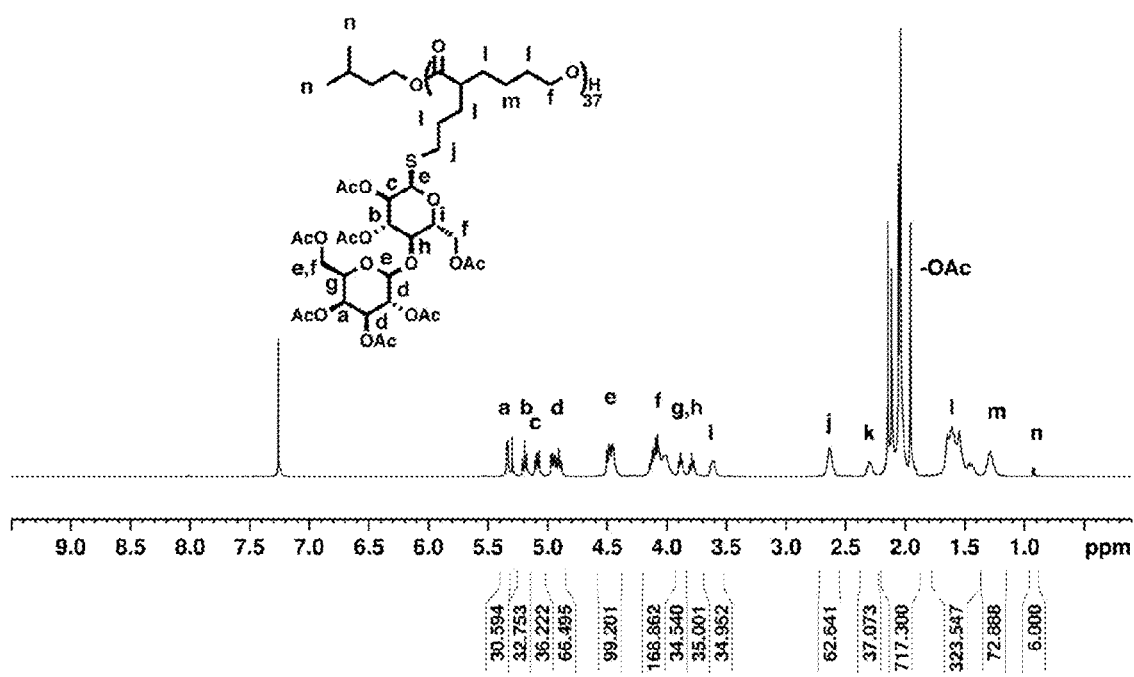
FIG. 52 is a graph showing $^1$H-NMR spectrum of pCL-lactose OAc$_{40}$ (CDCl$_3$, 500 MHz). *=protons from terminal unit on polymer.
Figure 53:
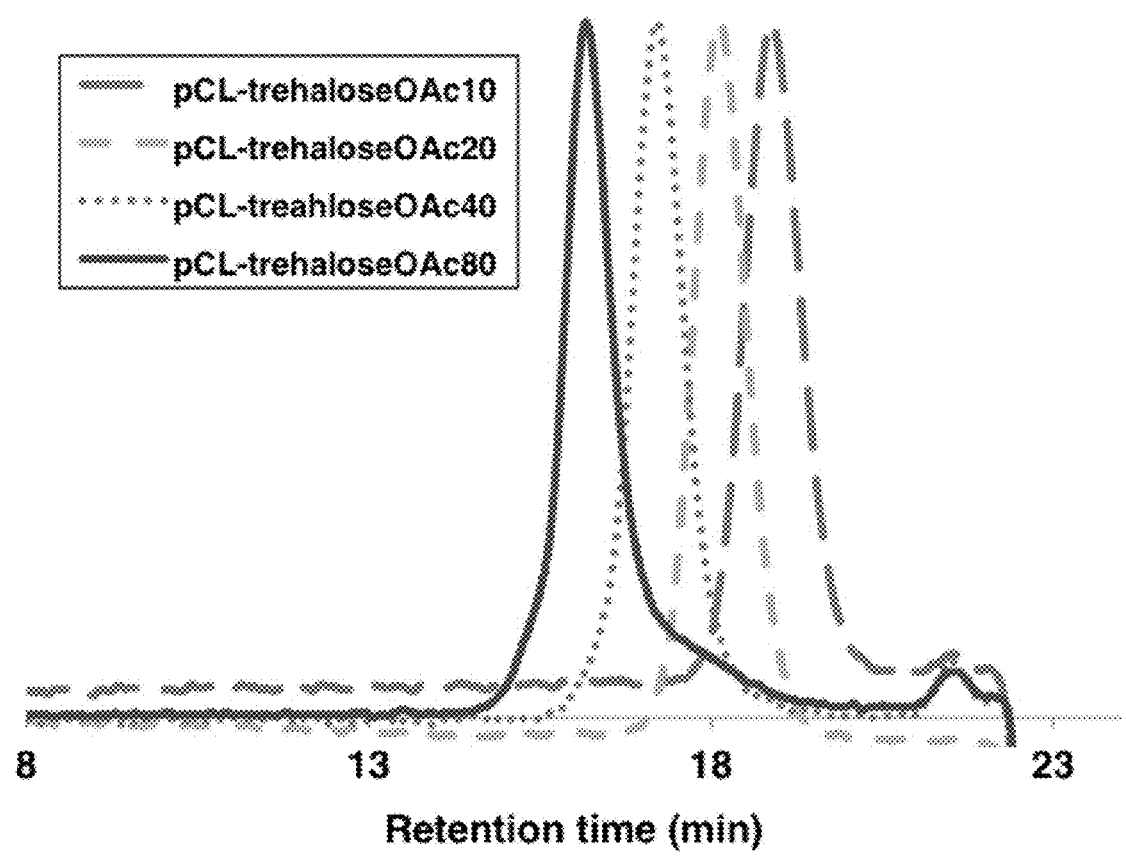
FIG. 53 is a graph showing gel permeation chromatograms of pCL-trehaloseOAc$_{10}$, pCL-trehaloseOAc$_{20}$, pCL-trehaloseOAc$_{40}$, pCL-trehaloseOAc$_{80}$.
Figure 54:
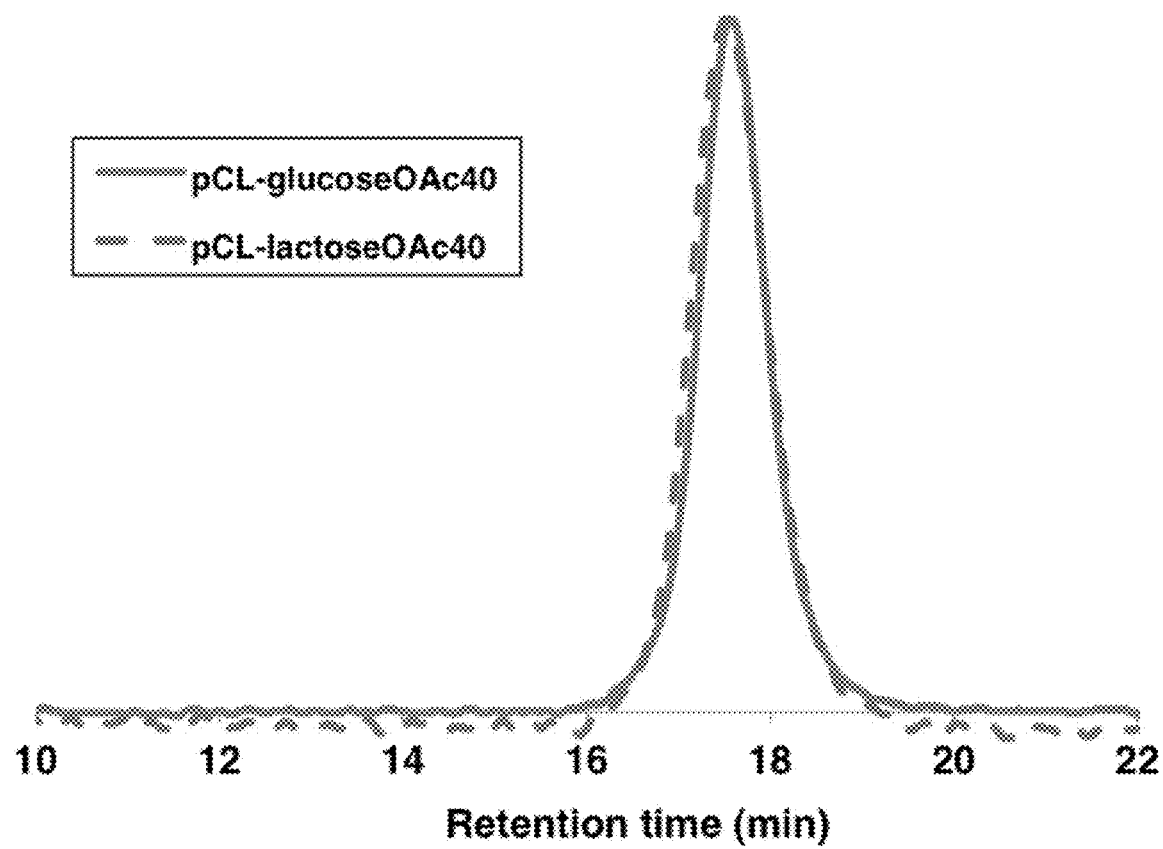
FIG. 54 is a graph showing gel permeation chromatograms of pCL-glucoseOAc$_{40}$, pCL-lactoseOAc$_{40}$.
Figure 55:
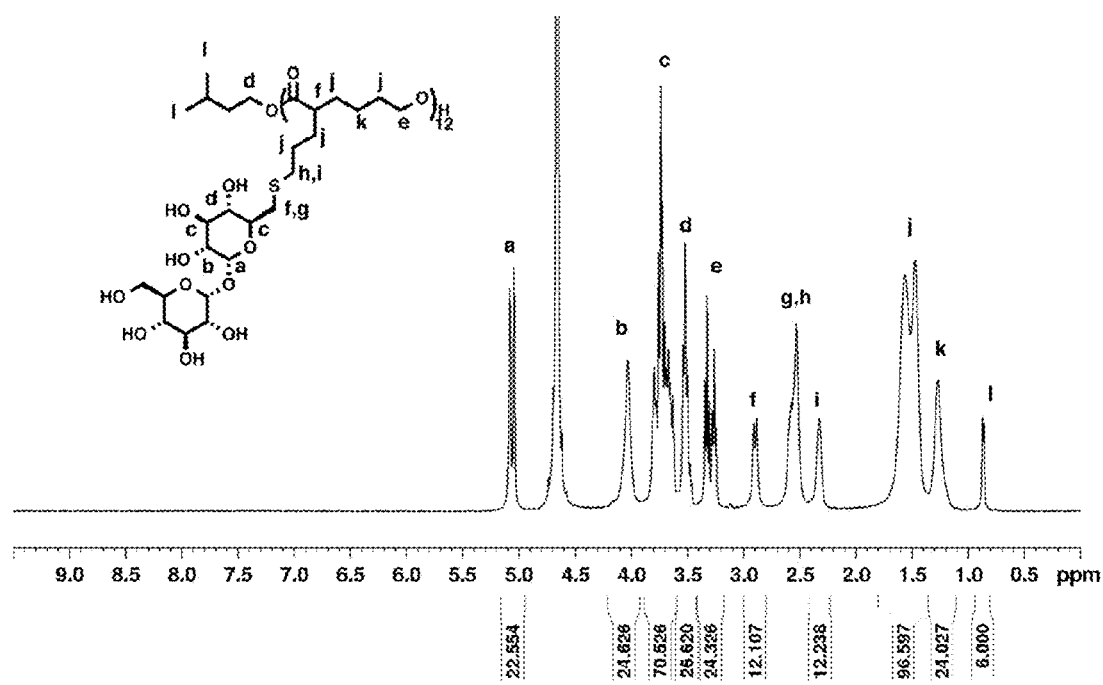
FIG. 55 is graph showing $^1$H-NMR spectrum of pCL-trehalose$_{10}$ (D$_2$O, 500 MHz).
Figure 56:
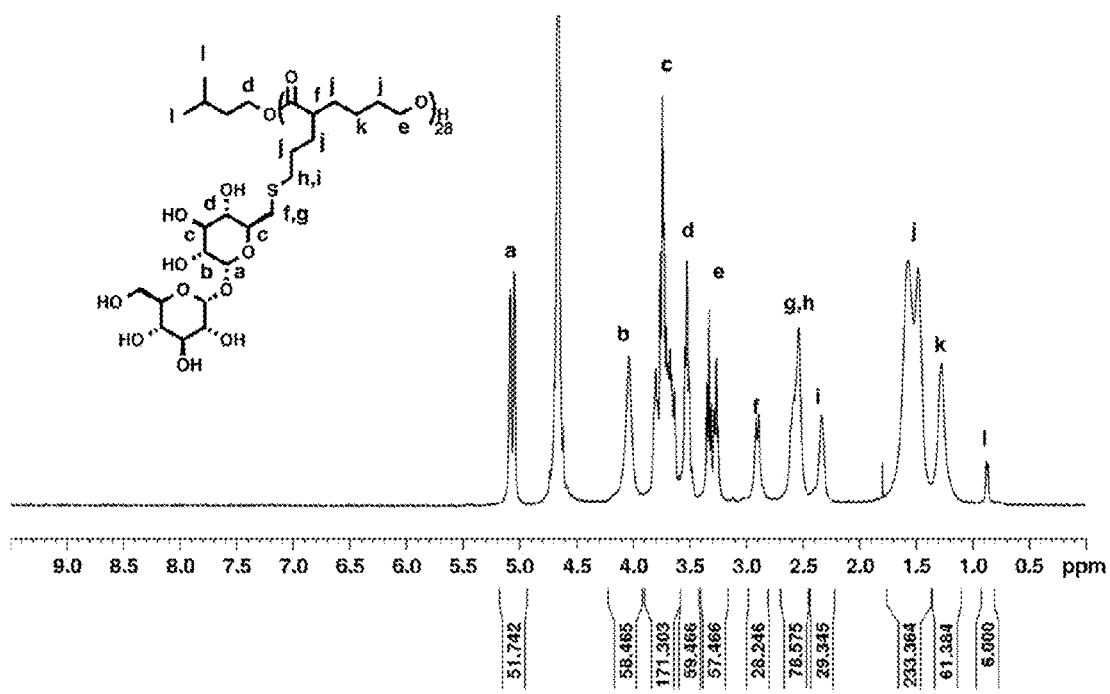
FIG. 56 is a graph showing $^1$H-NMR spectrum of pCL-trehalose$_{20}$ (D$_2$O, 500 MHz).
Figure 57:
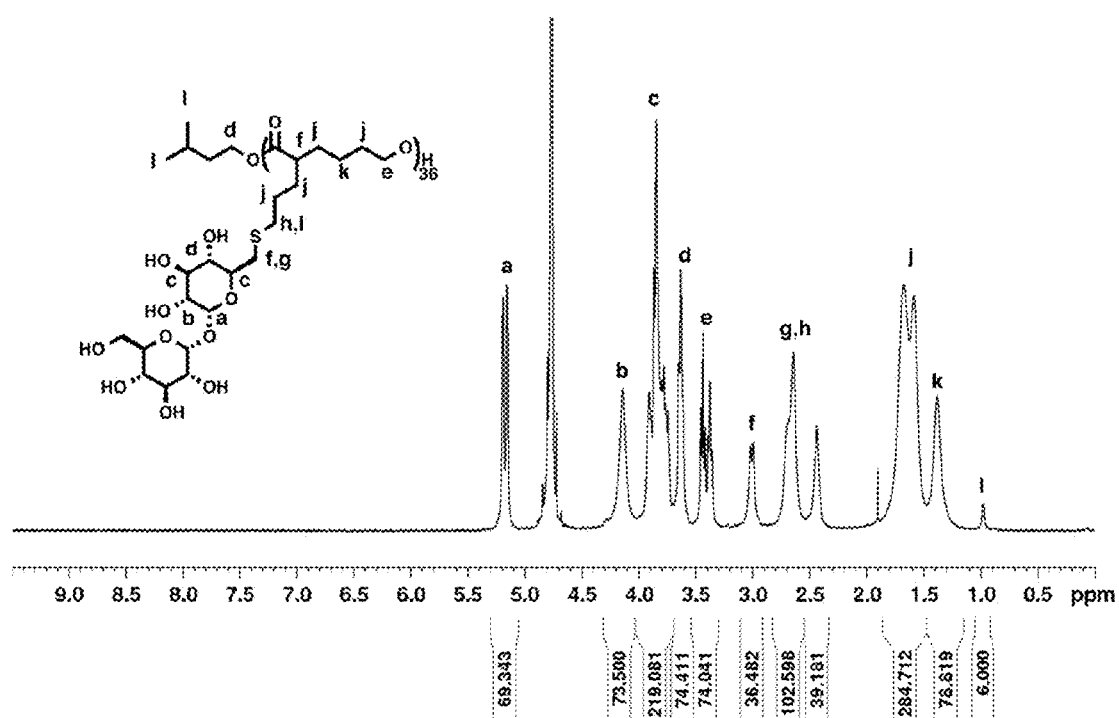
FIG. 57 is a graph showing $^1$H-NMR spectrum of pCL-trehalose$_{40}$ (D$_2$O, 500 MHz).
Figure 58:
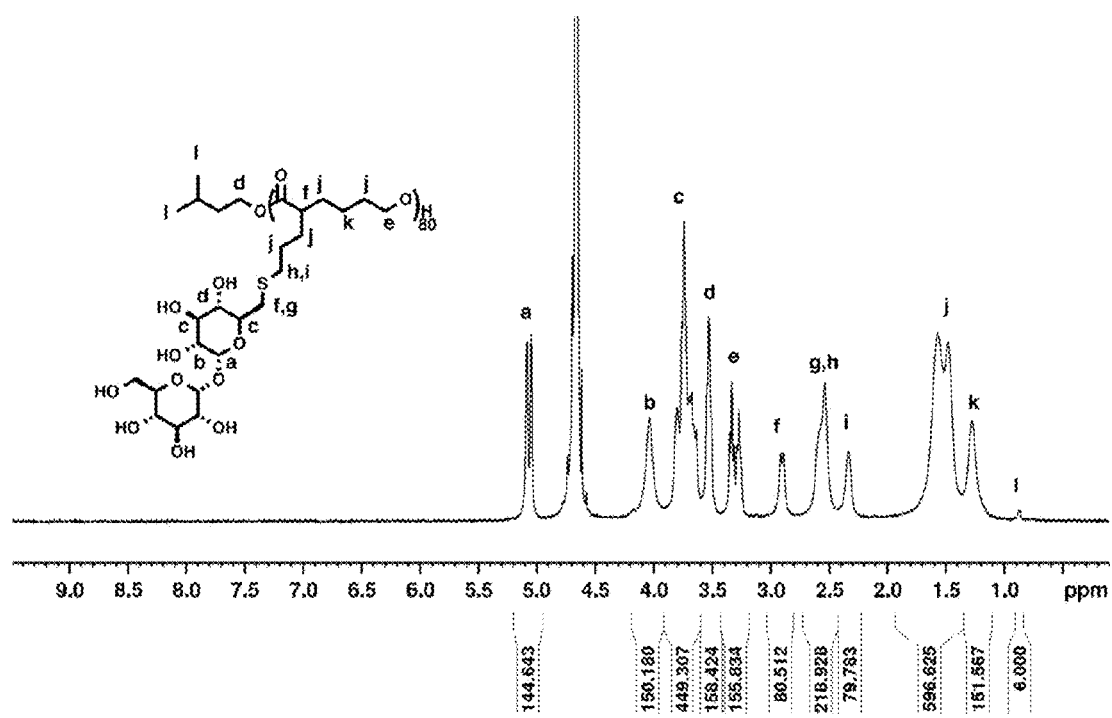
FIG. 58 is a graph showing $^1$H-NMR spectrum of pCL-trehalose$_{80}$ (D$_2$O, 500 MHz).
Figure 59:
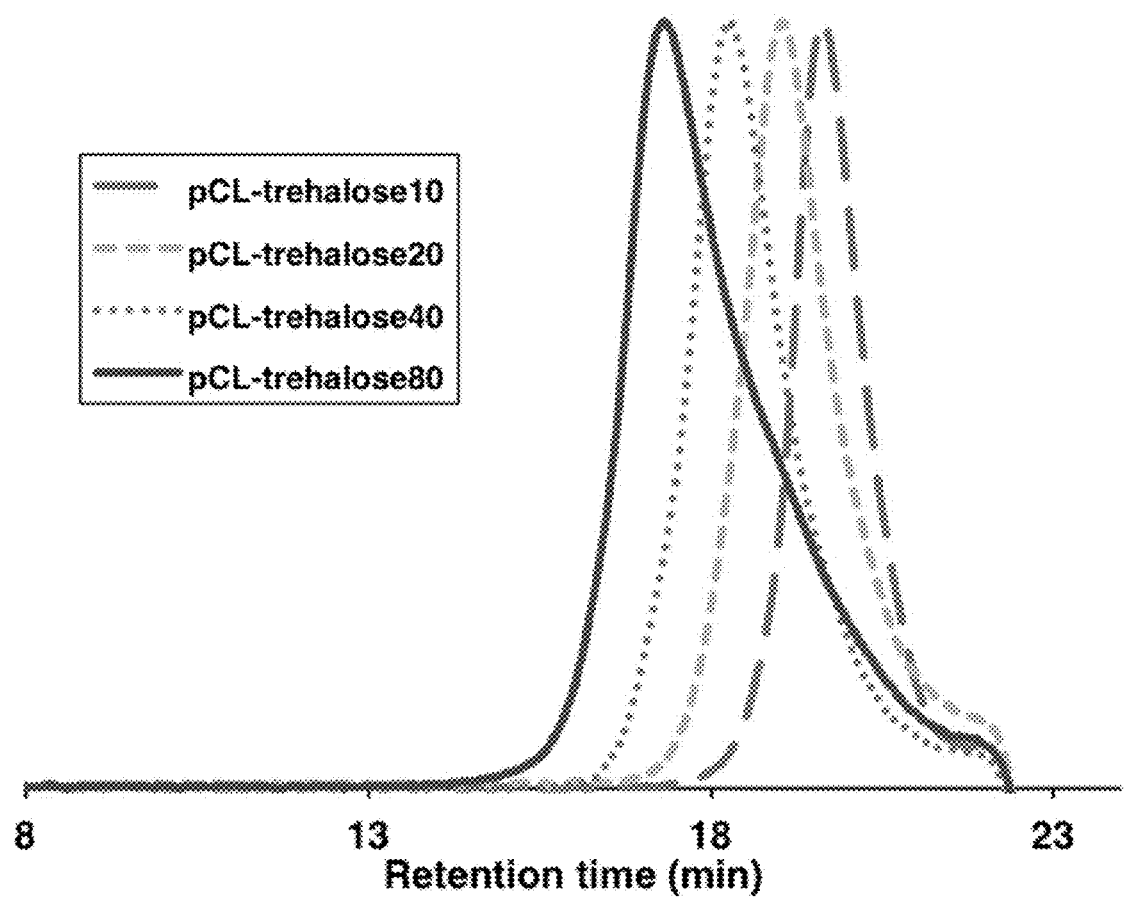
FIG. 59 is a graph showing gel permeation chromatograms of pCL-trehalose$_{10}$, pCL-trehalose$_{20}$, pCL-trehalose$_{40}$, pCLtrehalose$_{80}$.
Figure 67A:
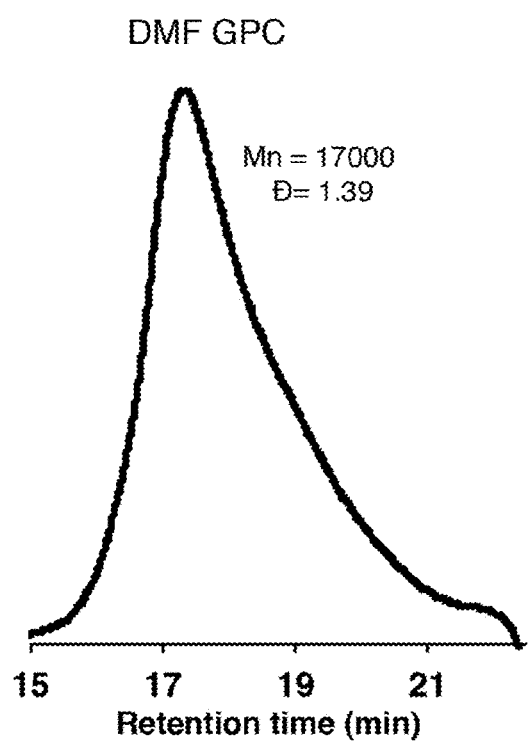
FIG. 67A is a graph showing comparison of gel permeation chromatography (DMF).
Figure 67B:
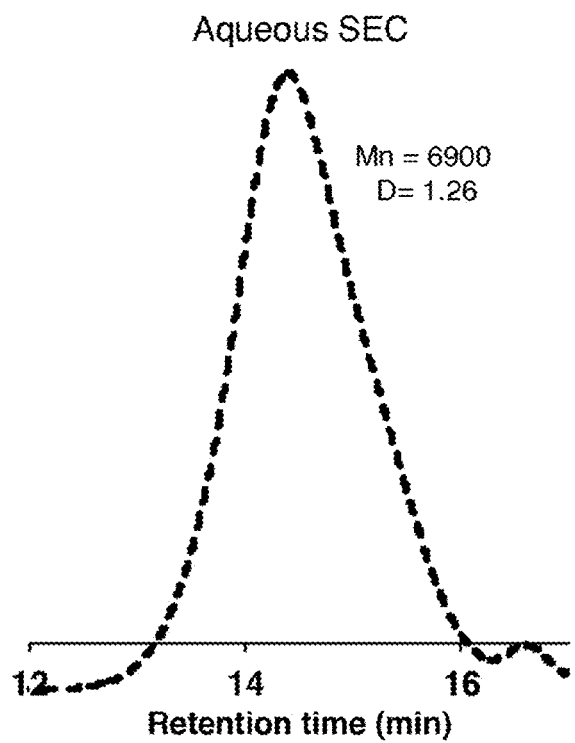
FIG. 67B is a graph showing size exclusion chromatography (aqueous) traces for pCL-trehalose$_{80}$.
Figure 68:
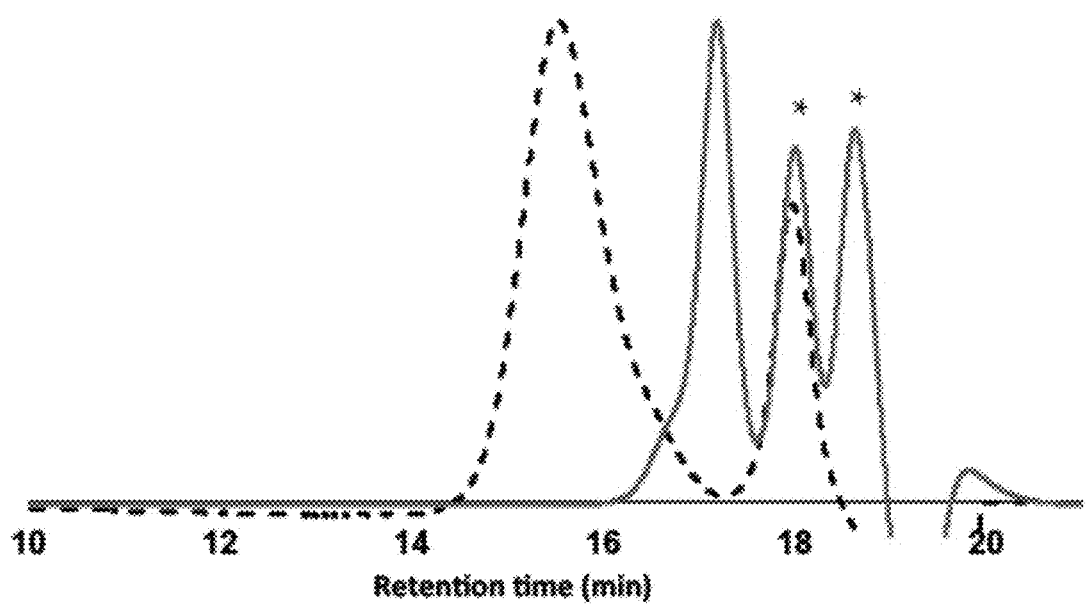
FIG. 68 is a graph showing size exclusion chromatogram of pCL-trehalose$_{20}$ (black dashed line) and basic degradation products (red solid line). Peaks due to salts in the buffer indicated with *.

To further test this potential molecular weight dependence, various CL trehalose polymer sizes were synthesized. Using previously optimized ROP conditions, well-defined pCL-allyl polymers were synthesized with DP between 10 and 80 and Đ<1.25 (Table 2). These DPs were selected so that after modification with thiolated trehalose, the molecular weight of the pCL-trehalose polymers would be between 5 and 40 kDa, assuming quantitative conversion. For the smallest pCL-allyl polymer, matrix assisted laser desorption ionization (MALDI) was used to confirm the molecular weight (FIG. 46). Modification was again carried out using photoinitiated thiol-ene chemistry, yielding a series of trehalose-modified pCL polymers. This series demonstrated increased dispersity (Đ) with increasing molecular weight. At high molecular weights (Table 2, pCL-trehalose$_{80}$) Đ was increased to 1.39 and the GPC molecular weight was correspondingly lower than that predicted by $^1$H-NMR. The peak shape was also asymmetrical and extended toward the low molecular weight side (FIG. 67a). To confirm that this peak broadening was not due to hydrolysis of the backbone esters, the molecular weight of pCL-trehalose$_{80}$ was also measured on an aqueous size exclusion chromatography (SEC) system (FIG. 67b). In aqueous solution, no asymmetry was observed and the calculated dispersity was lower (1.26). The dragging observed at high molecular weights was therefore hypothesized to be a result of interactions with the stationary phase of the GPC column. Similarly, a series of pCL-zwitterion polymers were synthesized using photoinitiated thiol-ene chemistry on the pCL-allyl backbones. Analysis by GPC showed that they were well-defined and demonstrated clear shifts in molecular weight with increasing pCL-allyl DP (Table 2).

TABLE 2

Molecular weights and GPC data for the library of pCL-trehalose and pCL-zwitterion polymers with variable DP.

|  | Polymer | Mn ($^1$H-NMR) | Mn (GPC) | Đ |
| --- | --- | --- | --- | --- |
| Starting Polys | pCL-allyl$_{10}$ | 1600 | ND$^a$ | ND$^a$ |
|  | pCL-allyl$_{20}$ | 3600 | 2400 | 1.21 |
|  | pCL-allyl$_{40}$$^c$ | 5600 | 5400 | 1.08 |
|  | pCL-allyl$_{80}$ | 12400 | 12200 | 1.08 |

TABLE 2-continued

Molecular weights and GPC data for the library of pCL-trehalose and pCL-zwitterion polymers with variable DP.

|  | Polymer | Mn ($^1$H-NMR) | Mn (GPC) | Đ |
| --- | --- | --- | --- | --- |
| Trehalose-OAc | pCLtrehalose-OAc$_{10}$ | 10600 | 9600 | 1.07 |
|  | pCL-trehalose-OAc$_{20}$ | 20200 | 15400 | 1.06 |
|  | pCL-trehalose-OAc$_{40}$$^b$ | 34700 | 28400 | 1.06 |
|  | pCL-trehalose-OAc$_{80}$ | 67000 | 53100 | 1.06 |
| Trehalose-OH | pCL-trehalose-OH$_{10}$ | 6200 | 5600 | 1.09 |
|  | pCL-trehalose-OH$_{20}$ | 14400 | 8100 | 1.15 |
|  | pCL-trehalose-OH$_{40}$$^b$ | 18500 | 12700 | 1.17 |
|  | pCL-trehalose-OH$_{80}$ | 41000 | 17000 | 1.39 |
| Zwitterions | pCL-zwitterion$_{10}$ | 3200 | 1700$^c$ | 1.17$^c$ |
|  | pCL-zwitterion$_{20}$ | 6400 | 3000$^c$ | 1.12$^c$ |
|  | pCL-zwitterion$_{40}$$^b$ | 12400 | 5100$^c$ | 1.19$^c$ |
|  | pCL-zwitterion$_{80}$ | 25400 | 8900$^c$ | 1.19$^c$ |

$^a$Too small for GPC analysis
$^b$Same entry as in Table 1
$^c$GGPC run in buffer/MeCN with PEG standards Both sets of polymeric backbones were then subjected to the same stability tests using 100 weight equivalents of polymer.

First the trehalose polymers were tested and a very slight dependence of protein activity on molecular weight was observed upon storage at 4° C. (FIG. 38a). Larger polymers offered improved stabilization compared to smaller polymers, but there was no significant difference between the stabilizing effects of DP40 and DP80 polymers, or between the DP10 and DP20 polymers. The series of pCL-trehalose polymers were also used as stabilizers against 60° C. heating (FIG. 38b). In this case, a drastic molecular weight dependence was observed, with the pCL-trehalose$_{80}$ polymer exhibiting the highest cell proliferation. It should be noted, that despite the increase in molecular weight, the concentration of stabilizing units in solution remained constant at 69 weight equivalents of trehalose or 190 µM, indicating that the observed changes in stabilizing ability were solely due to the molecular weights of the polymers.

Figure 38C:
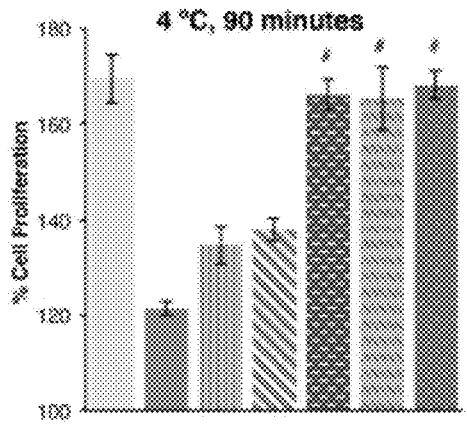
FIG. 38C is a graph showing Effect of pCL-trehalose molecular weight on G-CSF stabilization ability and shows effect of pCLzwitterion molecular weight on G-CSF stabilization at pH 4.0 to storage at 4° C. for 90 minutes.
Figure 38D:
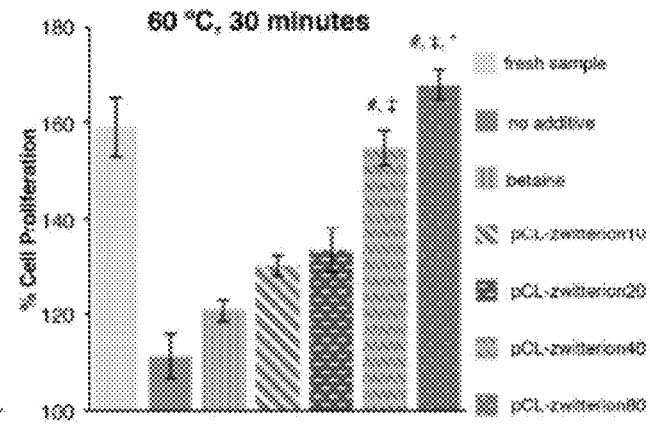
FIG. 38D is a graph showing Effect of pCL-trehalose molecular weight on G-CSF stabilization ability and shows GCSF stabilization to thermal stress at 60° C. for 30 minutes. Data shown as the average of six experimental repeats and six well repeats with standard deviation. All trehalose polymers exhibited statistically significant stabilization (p<0.05) relative to no stabilizing additive. A dependence on molecular weight was also observed in that greater molecular weight polymers showed greater stabilization (#=p<0.01 relative to pCL-trehalose$_{10}$ and pCL-trehalose20, **=p<0.001 relative to pCL-trehalose40, Student's t-test).

Similar experiments were carried out using the zwitterionic backbone. Upon exposure to the milder 4° C. stressor, only a moderate dependence on molecular weight was observed (FIG. 38c). While the pCL-zwitterion$_{10}$ polymer sample exhibited reduced cell proliferation, there was no statistical difference between the DP20, DP40, and DP80 polymers. They were statistically the same as the fresh sample, indicating the presence of a molecular weight threshold for complete stabilization ability. However, when the protein was heated to 60° C. for 30 minutes, separation between the polymer additives was observed (FIG. 38d). At this temperature, the performance of the DP20, DP40 and DP80 polymers was significantly different to each other, and only the two largest polymers retained comparable activity to the pristine sample.

Figure 79:
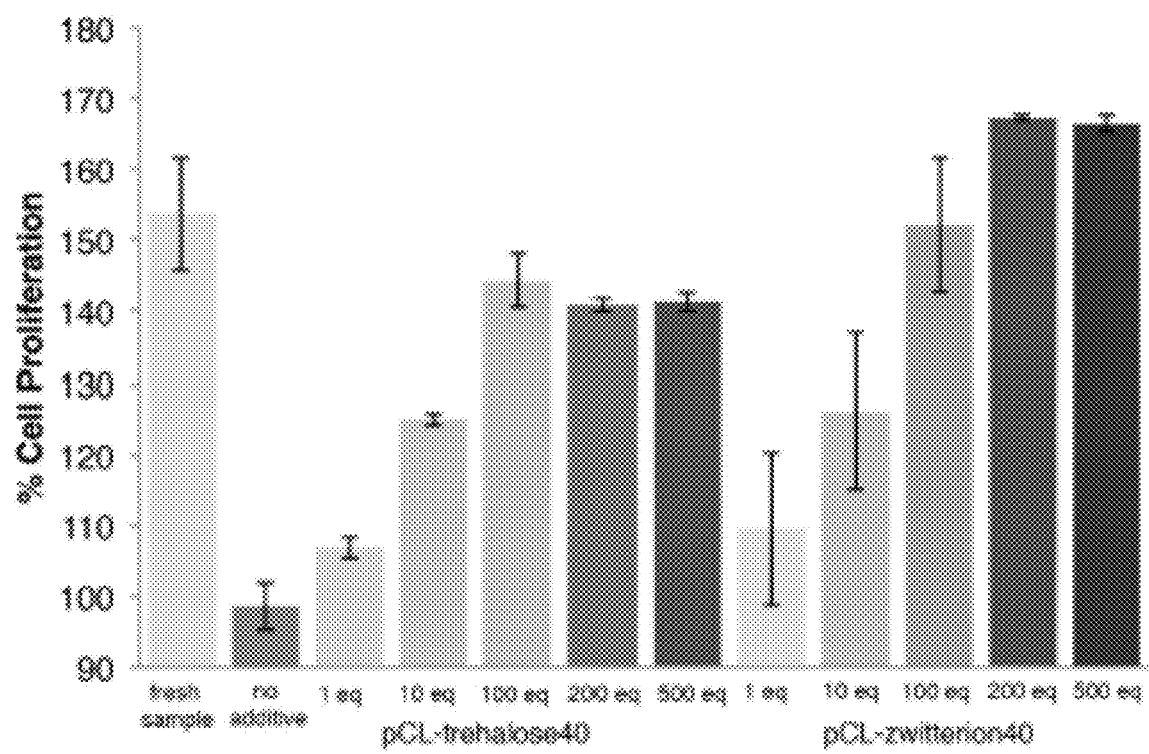
FIG. 79 is a graph showing dependence on G-CSF stabilization on polymeric equivalents of pCL-trehalose$_{40}$ and pCL-zwitterion$_{40}$ against heating at 60° C. for 30 minutes.

Additional experiments were carried out to better understand the observed dependence on molecular weight. To determine if shorter polymers could demonstrate improved stabilization at higher weight equivalents, we stressed G-CSF at 60° C. for 30 minutes and added pCL-trehalose$_{40}$ and pCLzwitterion$_{40}$, varying the amount of polymer in solution between 1 and 500 weight equivalents (FIG. 79). We were curious to determine if the DP 40 polymers would match the stabilizing performance of higher molecular weight DP 80 polymers when more weight equivalents were used. Instead, there was a distinct plateau, and for both polymers only 100 weight equivalents were required to see the best stabilization, without further improvement at the higher concentrations tested. This is strong evidence that the number of repeat units on the polymer chain has a distinct effect on the polymer's stabilizing ability. Trehalose has been previously shown to demonstrate a clustering effect in computational studies, self-organizing near polar residues on proteins (Fedorov et al., 2011). The molecular weight trends observed support a multivalency effect in these materials, where increased equivalents offer inferior protection compared to a preorganized or pre-grouped set of stabilizing units. This sort of molecular weight effect has been previously reported in other systems (Lees, et al., 1994).

Figure 74:
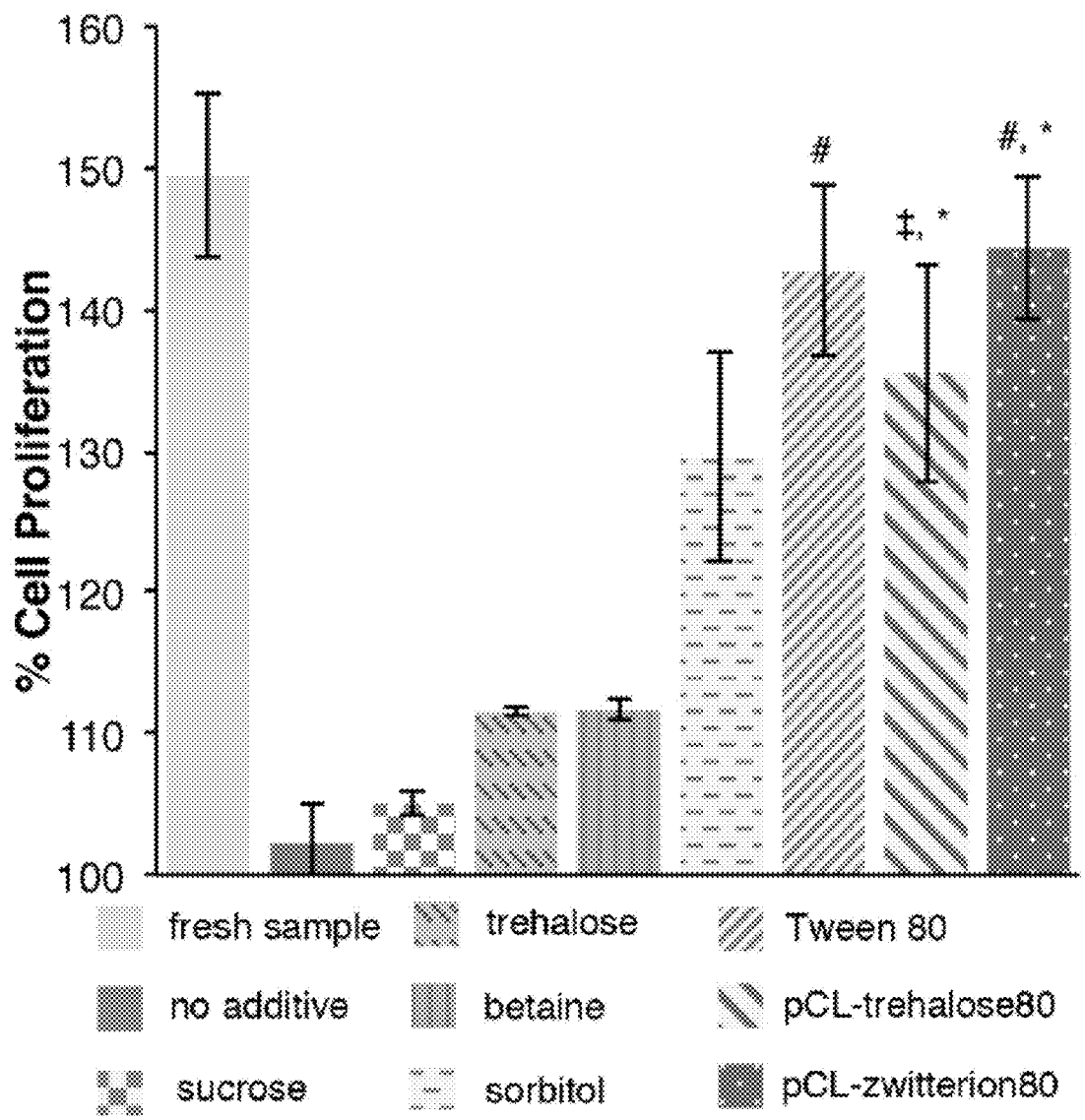
FIG. 74 is a graph showing Stabilization of G-CSF against thermal stress at 60° C. for 30 minutes and comparison of pCL-trehalose$_{80}$ and pCL-zwitterion$_{80}$ with relevant small molecule controls. Data shown as the average of three experimental repeats and six well repeats. #=no statistical difference from the fresh control (p>0.05). ‡=no statistical difference from sorbitol (p>0.05). *=no statistical difference from Tween (p>0.05).
Figure 75:
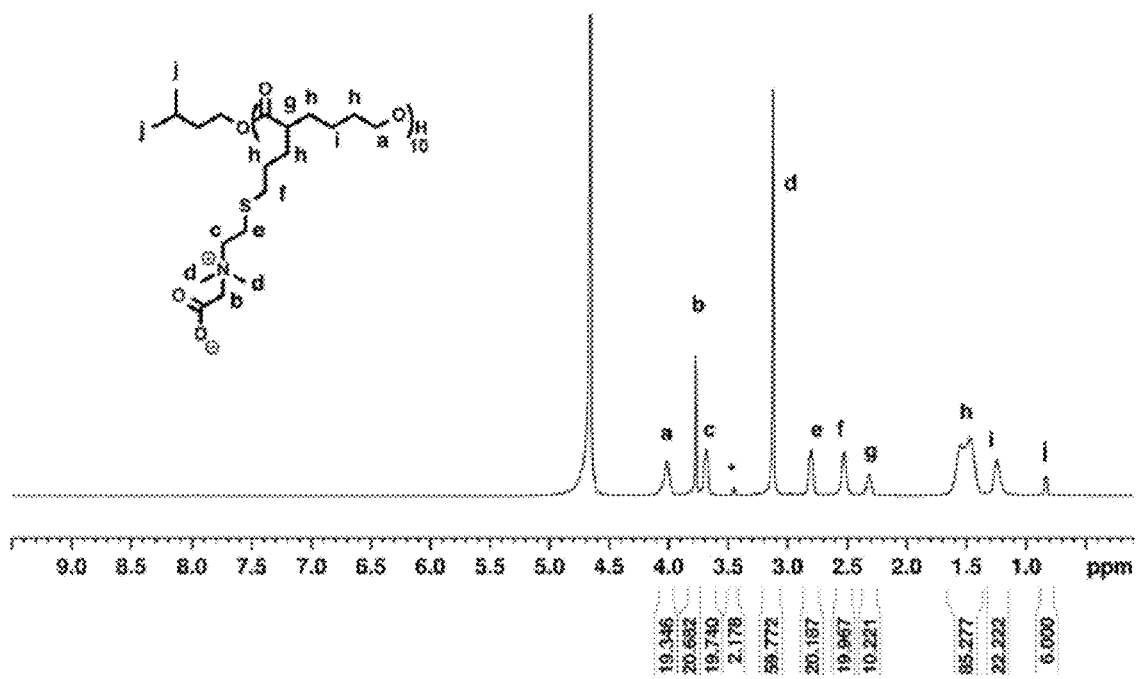
FIG. 75 is a graph showing $^1$H-NMR spectrum of pCL-zwitterion$_{10}$ (D$_2$O, 500 MHz). *=protons from terminal unit on polymer.

The stabilizing abilities of the pCL polymers to protect G-CSF from 60° C. thermal stress were additionally compared to commonly used small-molecule excipients: sucrose, trehalose, betaine, sorbitol and polysorbate 80 (FIG. 74). These compounds were chosen to represent the materials present in the high-performing pCL scaffolds, with the addition of sorbitol and polysorbate 80 (Tween 80), which are used industrially in the formulation of Neupogen (therapeutic GCSF) (Alebouyeh et al., 2016) and sucrose, which is a widely used excipient (Kamerzell et al., 2011). The pCL-trehalose$_{80}$ and pCL-zwitterion$_{80}$ polymers were selected because they were the highest-performing pCL polymers in the experiments described above and were added at 100 weight equivalents. Small molecules were added to be equivalent to the concentration of stabilizing units in the pCL-zwitterion$_{80}$ polymer except for Tween 80, which was added at 100 weight equivalents because of its larger molecular weight, similar to the CL polymers. After heating to 60° C. for 30 minutes, sucrose, betaine and sorbitol had little stabilizing effect and the cell proliferation was low. However, the sorbitol and Tween 80 maintained high protein activity that was statistically equivalent to pCL-trehalose$_{80}$, and pCL-zwiterion$_{80}$, respectively. The results show that the degradable polymers with DP of 80 are as good as the currently utilized additives for therapeutic G-CSF and better than other common protein excipients at the concentrations tested.

Figure 80:
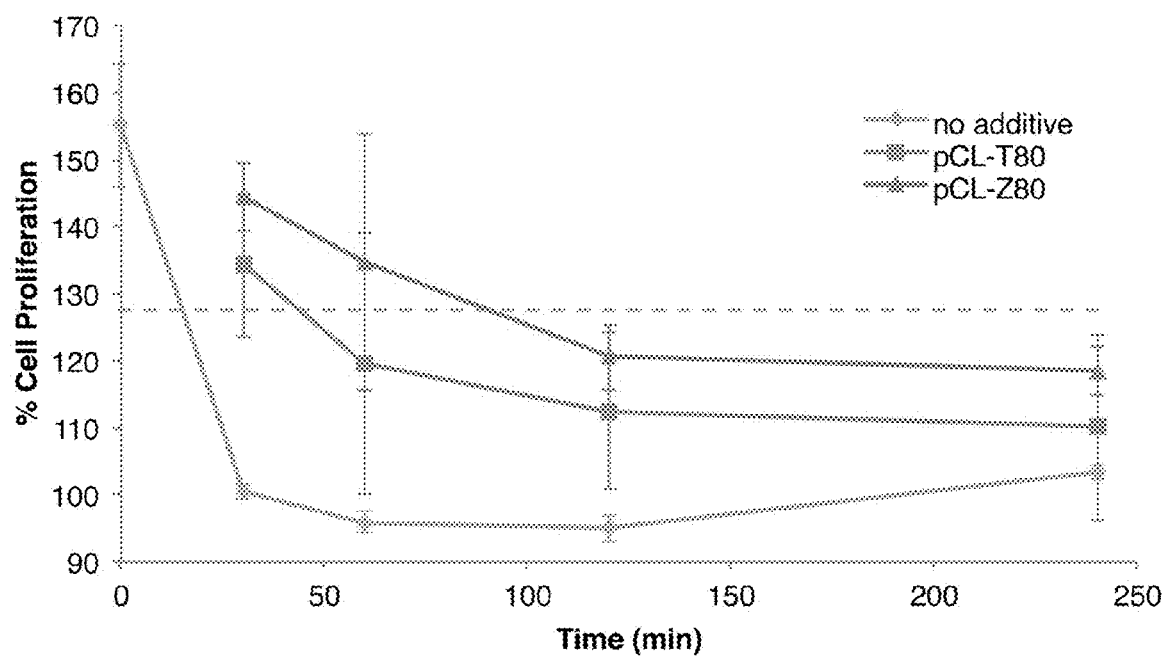
FIG. 80 is a graph showing timecourse of G-CSF activity in the presence of 100 weight equivalents of pCL-trehalose$_{80}$ and pCL-zwitterion$_{80}$ when heated at 60° C.

Additionally, the half-life of G-CSF at 60° C. was tested with the DP80 polymers as excipients (FIG. 80). When the pCL-trehalose$_{80}$ polymer was added, G-CSF retained 50% of the native activity until 48 minutes of heating, whereas when the pCL-zwitterion$_{80}$ polymer was used, the half-life was calculated to be 90 minutes, almost double. In contrast, with no additive G-CSF was already inactive after 30 minutes (first time point tested). This data shows that that both pCL scaffolds, especially the zwitterion-substituted polymer, provide a significant increase in thermal stability.

Degradation and Biological Compatibility

Figure 82A:
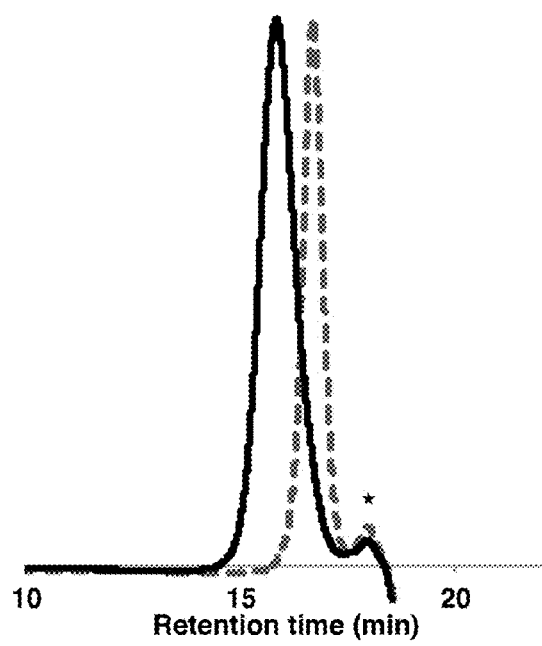
FIG. 82A is a set of graphs showing size exclusion chromatogram of the degradation of pCL-trehalose$_{10}$. Polymer is indicated by the black solid line and basic degradation products are indicated by the red dashed line. Peaks due to salts in the buffer indicated with *.
Figure 82B:
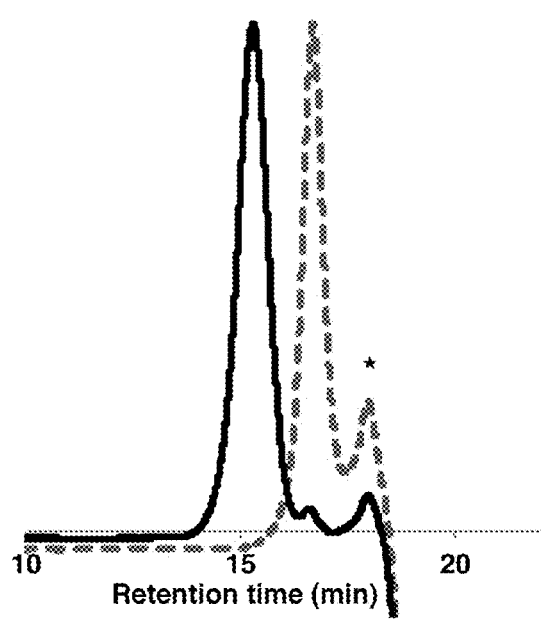
FIG. 82B is a set of graphs showing size exclusion chromatogram of the degradation of pCLzwitterion$_{20}$. Polymer is indicated by the black solid line and basic degradation products are indicated by the red dashed line. Peaks due to salts in the buffer indicated with *.

To confirm that the polycaprolactone was still degradable, pCL-trehalose$_{20}$ pCL-trehalose$_{40}$ and pCL-zwitterion$_{40}$ was treated with 5% KOH to hydrolytically cleave the backbone esters (Scheme 14). The molecular weight of the polymeric materials was determined post cleavage by aqueous SEC (FIG. 82). Complete shift in molecular weight towards a lower molecular weight species was observed after 24 hours, confirming hydrolytic degradation. No hydrolytic degradation was observed under more moderate degradation conditions (cell media at 37° C.) for up to 49 days, consistent with the slow hydrolysis rates observed for polycaprolactone in vivo (Woodruff and Hutmacher, 2010).

Figure 83:
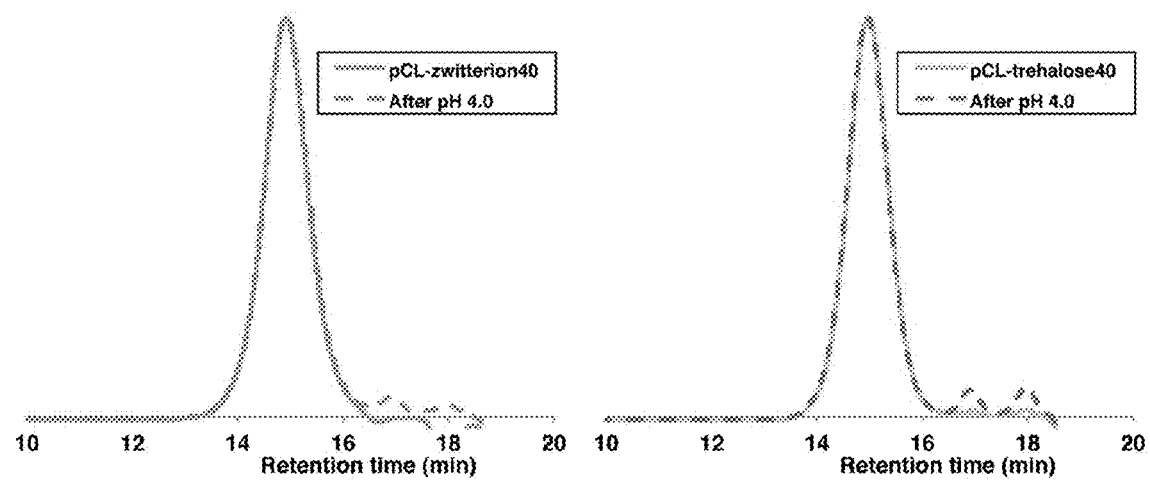
FIG. 83 is a set of graphs showing size exclusion chromatograms of pCL-trehalose$_{40}$ and pCL-zwitterion$_{40}$ before and after exposure to pH 4.0 at 60° C. for 30 minutes.

Additionally, experiments were carried out to confirm that the pCL polymers remained stable at the acidic conditions of the cell assay. pCL-trehose and -zwitterion polymers were heated to 60° C. for 30 minutes to mimic the thermal stress conditions, then buffer was removed and the materials analyzed by GPC (FIG. 83). No shift was observed in the chromatogram, confirming that the polymers were intact throughout the experiment.

Scheme 14. Basic hydrolysis of pCL-trehalose$_{10}$ and pCL-zwitterion$_{20}$

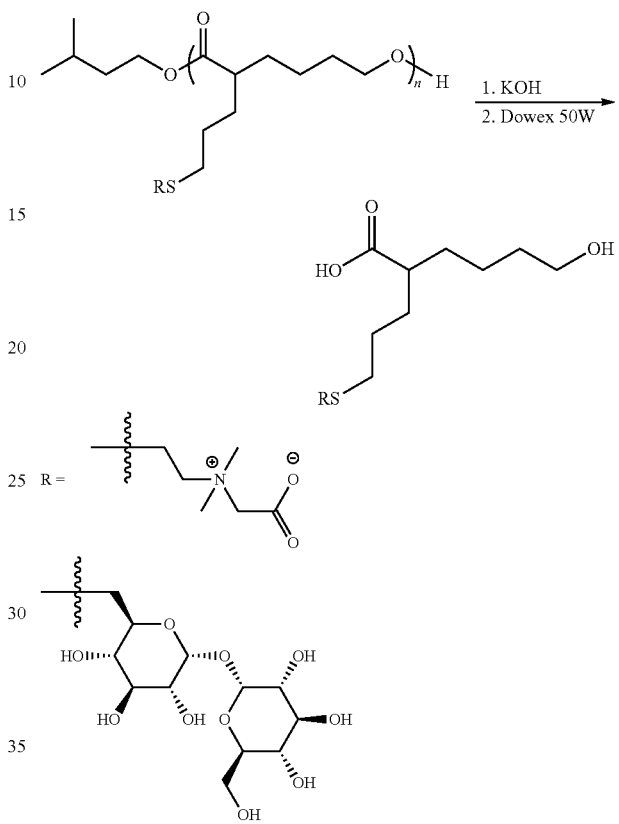

Figure 84:
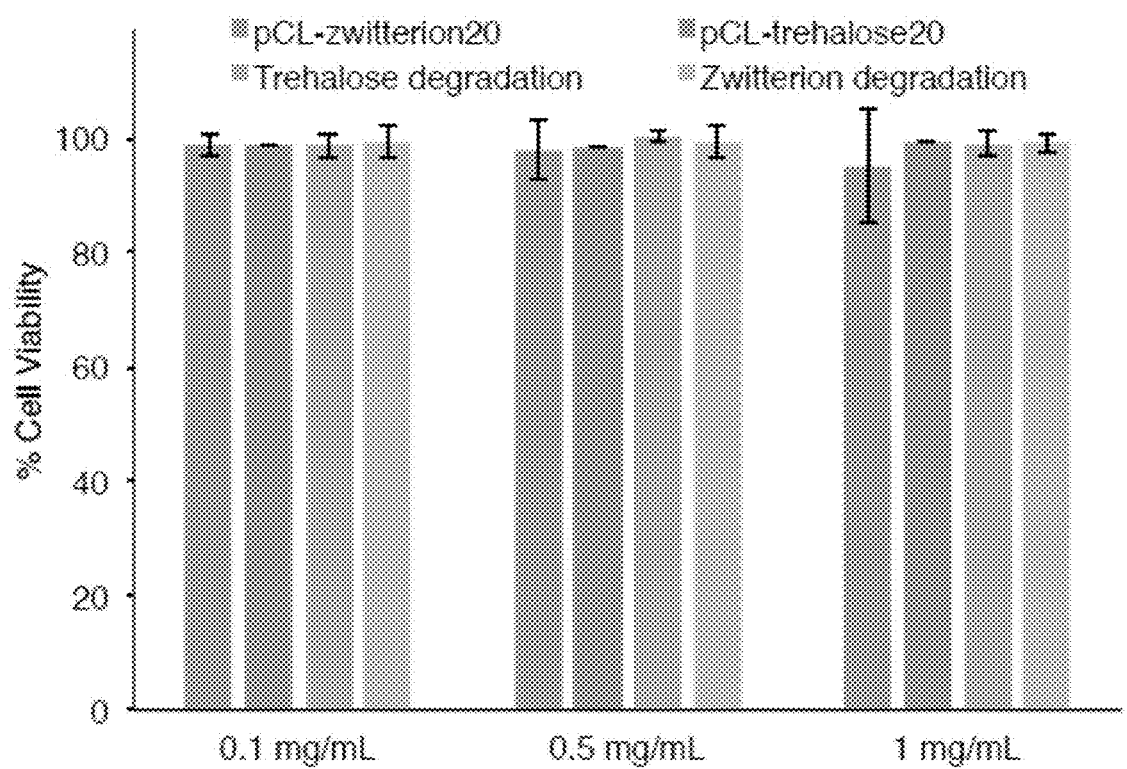
FIG. 84 is a graph showing cytotoxicity assay of pCL-trehalose$_{20}$, pCl-zwitterion$_{20}$, and their basic degradation products with HUVECs. Data shown as the average of three experimental repeats with standard deviation. There is no statistical difference between groups.

Additionally, cytotoxicity and biocompatibility of the trehalose based polycaprolactone polymers were assessed in human umbilical vein endothelial cells (HUVECs) as a primary, non-cancerous cell line. HUVECs were cultured in the presence of pCL-trehalose$_{10}$ and pCL-trehalose$_{20}$, pCL-zwitterion$_{20}$, and the polymeric degradation products. Compared to the control, no reduction in cell viability was observed upon addition of either polymer (pCL-trehalose and pCL-zwitterion) or polymeric degradation products, up to 1 mg/mL, confirming that the glycopolyesters and their eventual degradation products are noncytotoxic (FIG. 84).

Analysis of the substituted pCL polymers using transmission electron microscopy (TEM) indicated the presence of aggregated structures in both samples of pCL-zwitterion$_{80}$ and pCL-trehalose$_{80}$ alone and in the presence of G-CSF (FIG. 81). This self-assembly may play an important role in the mechanism of stabilization and shows that the polymers are nonionic surfactants, an important class of excipients (Kamerzell et al., 2011). Similar aggregates have been observed for tyloxapol, a polymeric material with an aryl backbone and poly(ethylene oxide) side chains that is structurally similar to the pCL polymers (Regev and Zana, 1999). We additionally investigated the osmolyte character of the synthesized materials using differential scanning calorimetry (DSC). Both polymers changed the enthalpy of melting and crystallization of water (Table 3) suggesting the polymers are able to depress ice formation (Lee et al., 2013).

Discussion

We have demonstrated that a biodegradable backbone can be transformed into a library of potential protein stabilizers using thiol-ene chemistry. This approach allows us to survey the effectiveness of various side chains without complications due to differences in the number of backbone repeat units. We tested five relevant side chains: three sugars, oligoPEG and a zwitterion. Yet, one can readily envision that synthesis of larger libraries of side chains using this approach. To investigate side chain effectiveness, the therapeutic protein G-CSF was stabilized against refrigeration and heat, two stresses that are relevant to the storage and shipping of many proteins. For example, for example, nearly 80% of current protein therapeutics need to be refrigerated (Leader et al., 2008). This temperature requirement causes inconvenience and increased costs to patients and may make some therapeutics impossible for use in parts of the world that do not have an effective cold chain. In addition, in some industries such as personal care where products are stored at room temperature, the instability of some proteins of interest may preclude their use.

We found that pCL with trehalose- and zwitterion-substituted side chains were the most effective stabilizers to G-CSF to room temperature storage and heating, with the zwitterion polymers as the most effective over different time and molecular weight ranges. Activity loss in G-CSF has been reported to be a result of both methionine oxidation and aggregation (Krishnan et al., 2002; Pan et al., 2006; Yin et al., 2005). Trehalose as an excipient has been shown to have no effect on methionine oxidation of G-CSF, presumably because it is preferentially excluded from the protein surface, but has been shown to broadly inhibit aggregation of various proteins (Yin et al., 2005; Ohtake and Wang, 2011). The nonionic surfactant tween has been shown to reduce G-CSF aggregation through micelle formation (Niven et al., 1996). Initial analysis by TEM and DSC suggest that the trehalose and zwitterion-substituted polymers form structured aggregates alone and in the presence of G-CSF likely due to the non-ionic surfactant character of the polymers. Additionally, the materials have the capability to reduce the enthalpy of water crystallization and melting, equivalent to the thermodynamic effects that have been previously observed for their constituent side chain materials. Many current studies of osmolyte-protein interactions hypothesize that their stabilizing effect is in fact due to water-osmolyte interactions (Bruzdziak et al., 2013; Street et al., 2006), and the pCL materials are likely to be similar to small-molecule osmolytes in this manner. The materials therefore combine two different classes of known excipients.

We also found the polymers to be as good as excipients currently used in the formulation for Neulasta, a therapeutic G-CSF. However, as has been previously noted, sorbitol and polysorbate both present downsides to large-scale and repeated applications in therapeutics. Namely, sorbitol has been linked to GI tract problems and polysorbate has been shown to undergo auto-oxidation (Abraham et al., 2001; Kerwin, 2008). The substituted pCL polymers offer equivalent stabilities, and may be potential alternatives to the clinically used additives for G-CSF.

Although we looked at G-CSF, it should be possible to utilize this library approach to investigate a wide variety of proteins, and the outcome may be different depending on the individual protein degradation mechanism and the stress imposed. Using versatile thiol-ene strategy it should be possible to readily alter the polymer side chains to identify stabilizers for a wide variety of stressors. Additionally, molecular weight dependence was surveyed using the trehalose side chain. Many common polymer excipients are commercially available in a variety of molecular weights, such as PEG, polysorbate, and tween. The use of controlled ring-opening polymerization allows for the rapid synthesis of a variety of molecular weights to compare to commercially available additives. As we have demonstrated, the effect of molecular weight on stabilization can be quite significant and the ability to add molecular weight variation to a library of polymeric stabilizers is significant. Additionally, the excellent control provided by ROP conditions allows for delicate tuning of the hydrolytic stability and degradability through selection of a variety of cyclic monomers or even using copolymerization. We anticipate this will greatly expand the possible applications for these materials, and this work is underway.

Importantly compared to most other stabilizers, these polymers are degradable, which is critical for many applications. For example in medical excipients, polymers need to be degraded and/or secreted from the body. For homecare or food applications, polymers that sustain in the environment cause pollution and toxicity issues (Gross and Kalra, 2002), and degradable stabilizers are required for a sustainable future. Although we have chosen a polycaprolactone backbone, it should be possible to utilize a wide variety of different backbones and a similar approach, thus tuning the time to degradation.

Figure 60:
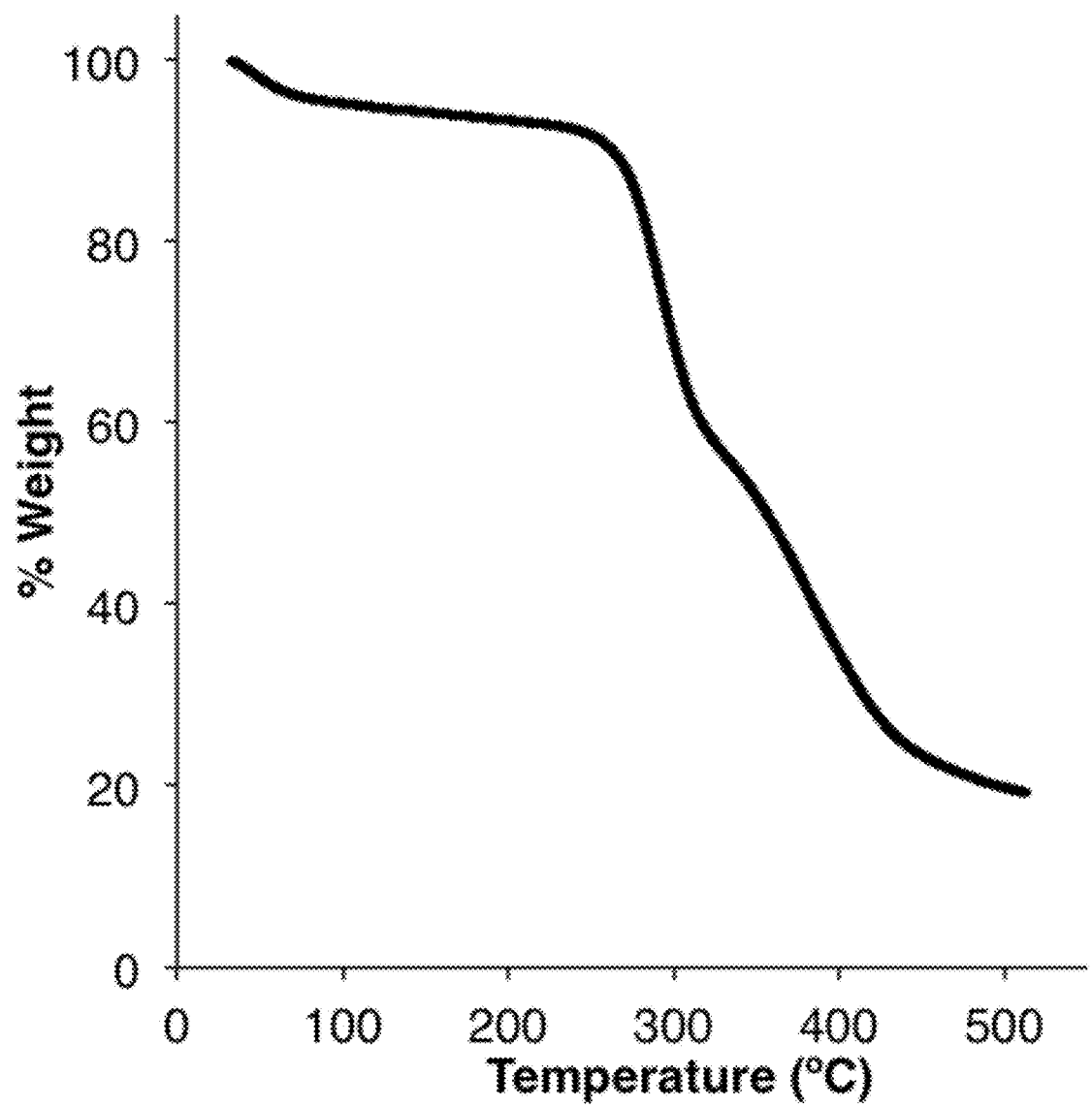
FIG. 60 is a graph showing thermal gravimetric analysis (TGA) chromatogram of pCL-trehalose$_{20}$.
Figure 61:
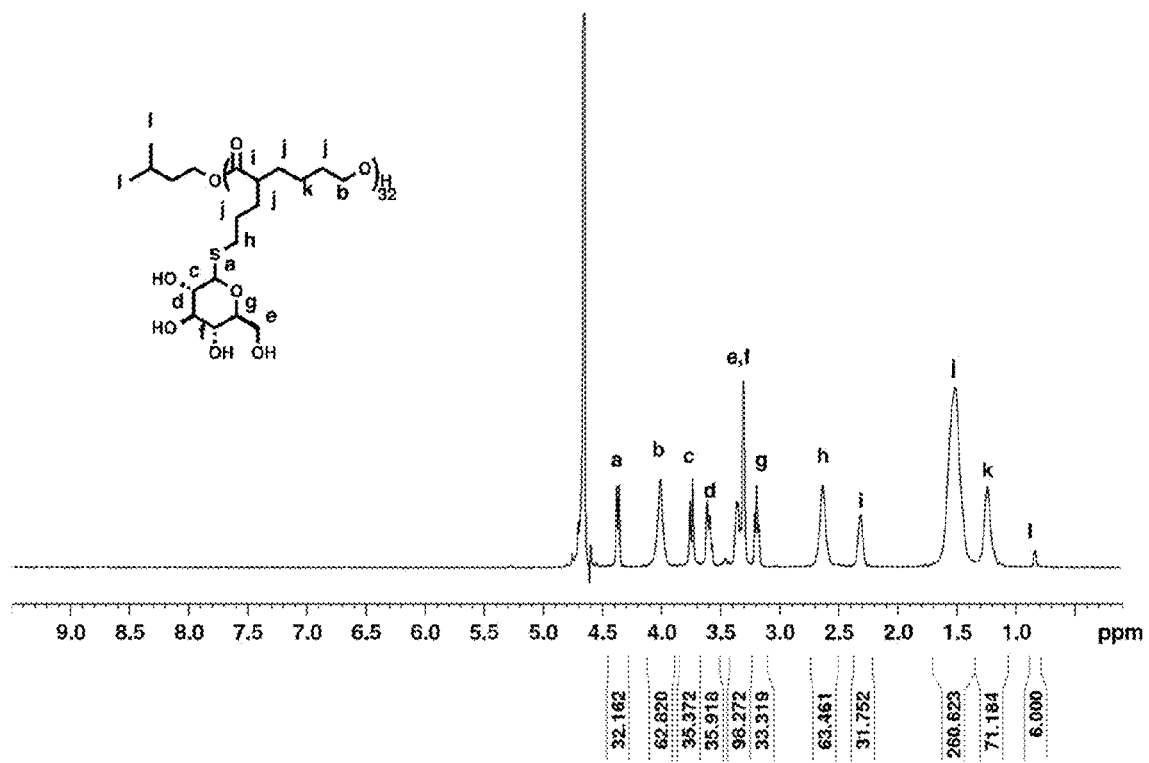
FIG. 61 is a graph showing $^1$H-NMR spectrum of pCL-glucose$_{40}$ (D$_2$O, 500 MHz).
Figure 62:
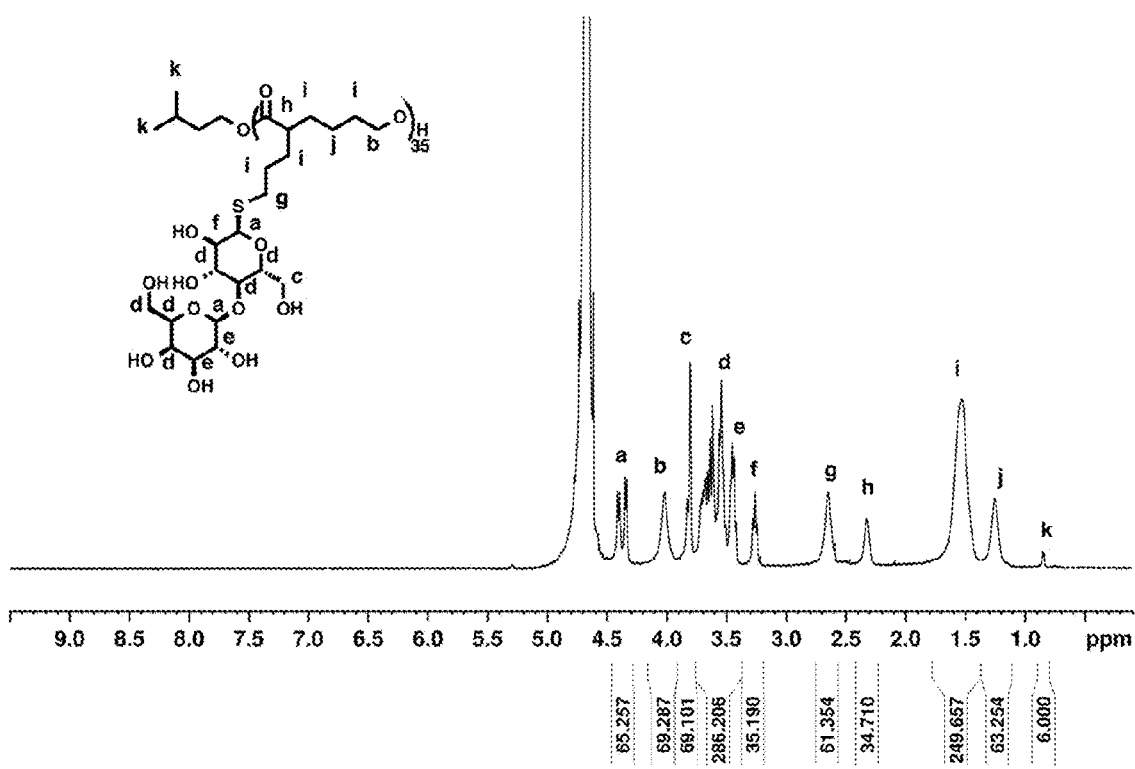
FIG. 62 is a graph showing $^1$H-NMR spectrum of pCL-lactose$_{40}$ (D$_2$O, 500 MHz).
Figure 63:
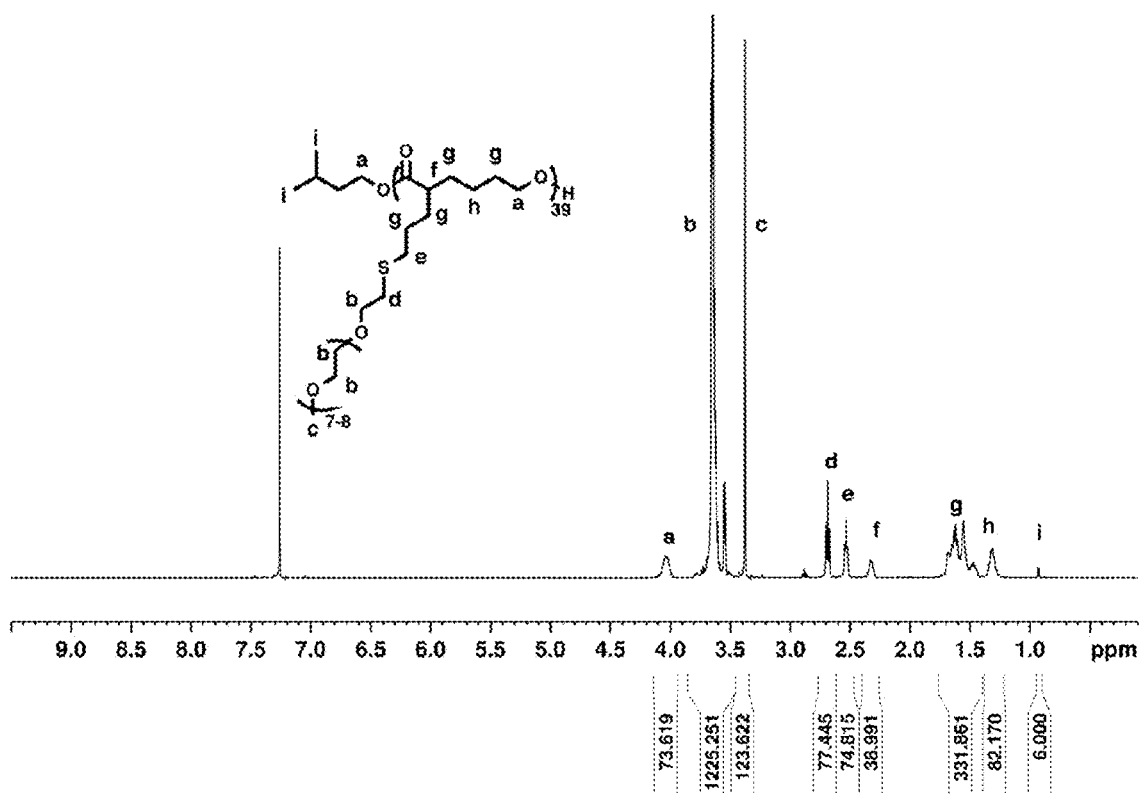
FIG. 63 is a graph showing $^1$H-NMR spectrum of pCL-PEG$_{40}$ (CDCl$_3$, 500 MHz).
Figure 64:
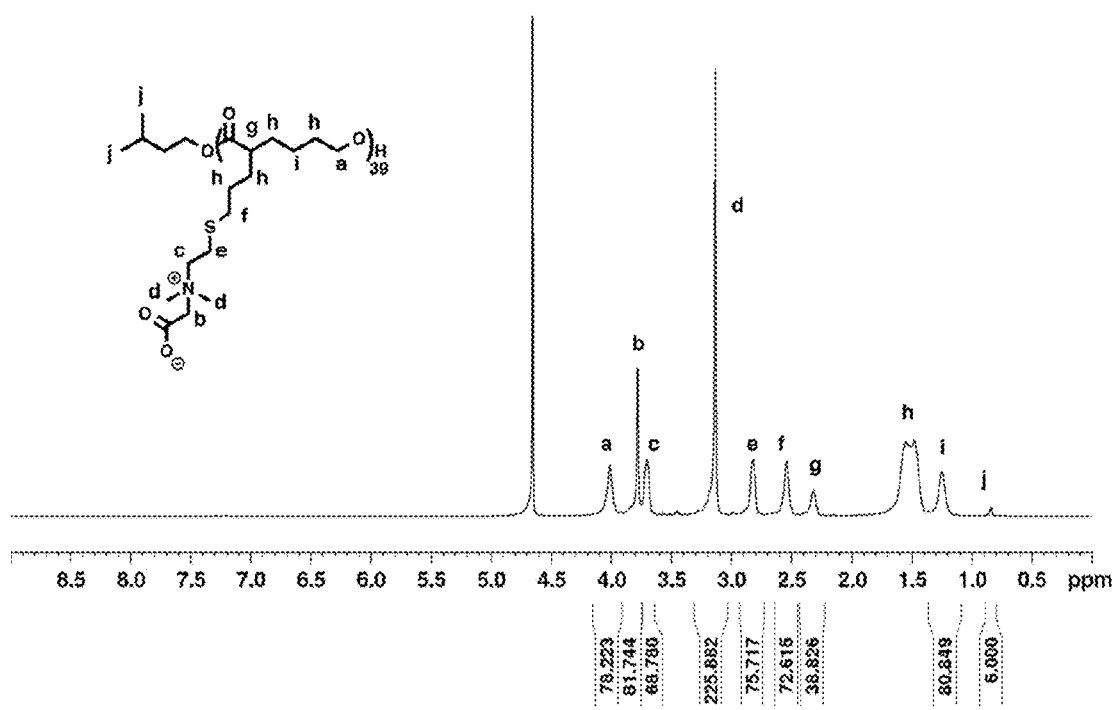
FIG. 64 is a graph showing $^1$H-NMR spectrum of pCL-zwitterion$_{40}$ (D$_2$O, 500 MHz).
Figure 65:
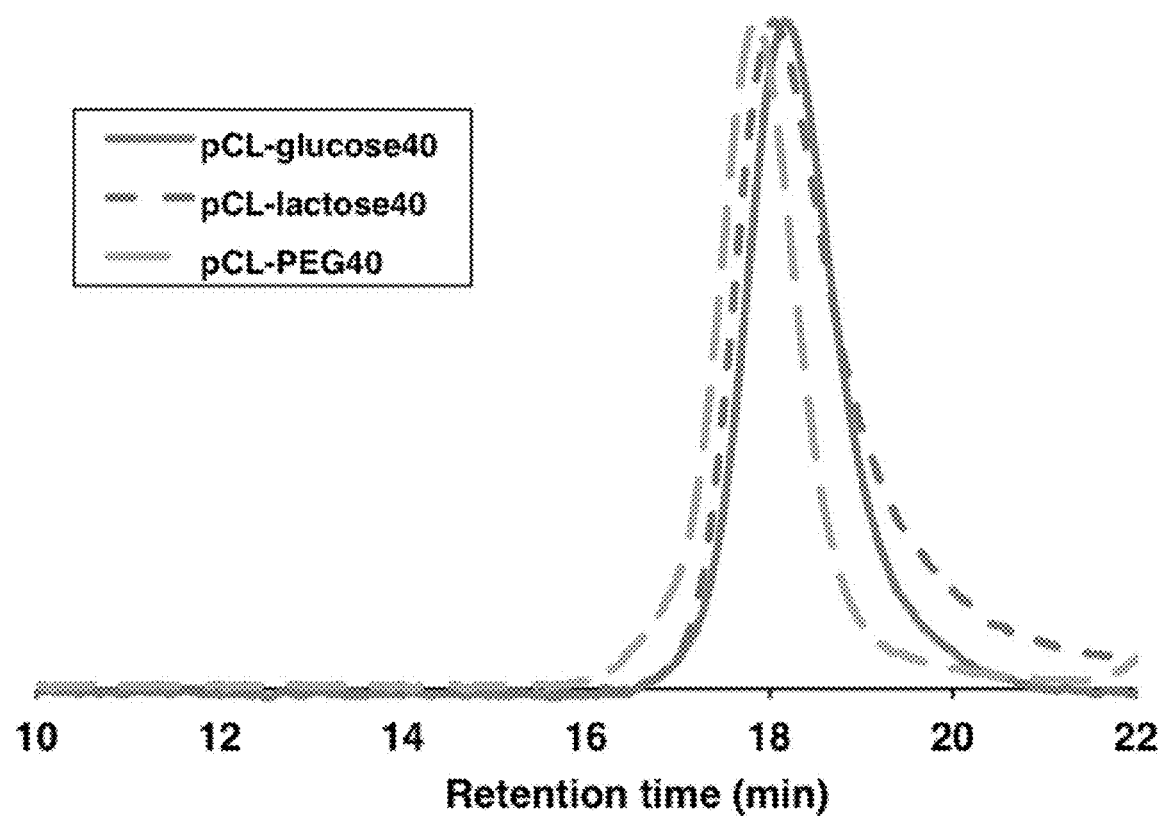
FIG. 65 is a graph showing gel permeation chromatograms of pCL-glucose$_{40}$, pCL-lactose$_{40}$, pCL-PEG$_{40}$.
Figure 66:
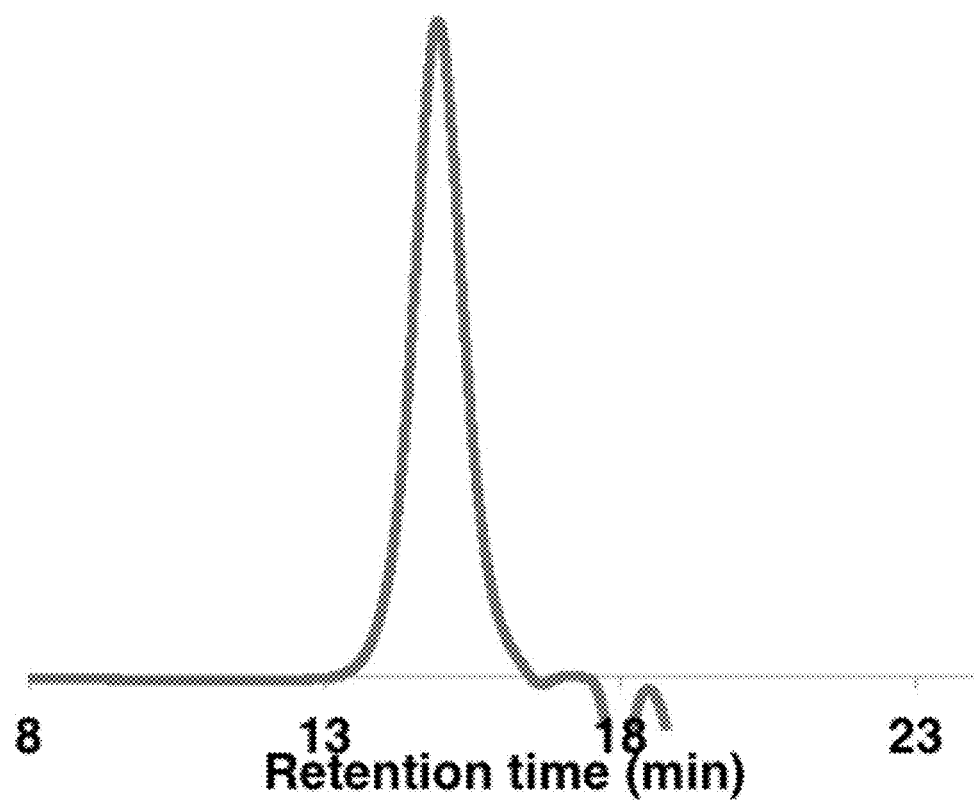
FIG. 66 is a graph showing size exclusion chromatogram of pCL-zwitterion$_{40}$.

These polymers are designed to act as excipients. Polymers have benefits as excipients because they exhibit closely spaced groupings of functional groups, increasing the effective concentration of those functionalities and improving stabilization (Lees et al., 1994). Additionally, polymers have the advantage of easy tunability based on monomer identity, molecular weight, and comonomer incorporation, and may be used as bulk materials for processed materials. As such, polymers and polyesters are widely used in biomedical applications. For example, polycaprolactone is FDA-approved as a copolymer with glycolide in the absorbable suture Monocryl (Bezwada et al., 1995). We have previously shown that polystyrene with trehalose side chains stabilizes proteins in the solid state (Bat et al., 2015). Therefore, it may also be possible to utilize these substituted pCL polymers as solid-state protein stabilizers for a myriad of applications where degradability is required. Thermal gravimetric analysis (TGA) has shown that pCL-trehalose$_{20}$ is stable to over 250° C. when heated (FIG. 60), permitting use of these materials at high temperature. Furthermore, polymers such as PEG have been conjugated to proteins to increase their in vivo stability via enhanced pharmacokinetic effects (Pelegri-O'Day et al., 2014; Caliceti and Veronese, 2003). It should be possible to conjugate these polymers to a variety of proteins to additionally stabilize them to environmental stressors. For example, scheme 4 (FIG. 85) shows conjugation of trehalose-caprolactone to lysozyme via reductive amination and conjugate stabilization.

Conclusions

A series of alkene-functionalized polyesters were synthesized by organocatalyzed ring-opening polymerization. Post-polymerization thiol-ene modification with a series of thiols led to well-defined trehalose-, lactose-, glucose-, PEG- and zwitterion-based biodegradable polyesters. These biodegradable stabilizers were investigated as to their ability to protect the therapeutic protein G-CSF from storage and heat stressors. Side chains containing trehalose and a zwitterionic carboxybetaine were found to be the most effective at maintaining G-CSF activity. Molecular weight studies of pCL-trehalose and pCLzwitterion were explored and the polymers were shown to have moderate molecular weight dependence to refrigeration, where larger polymers (molecular weight 18,500 and 40,000) demonstrated greater protein stabilization to heat. Both high-performing polymer scaffolds and their degradation products were also not cytotoxic up to at least 1 mg/mL. These materials could be used for stabilization of protein activity in therapeutic and industrial applications, leading to improved performance and lowered cost.

Synthesis and Characterization of Small Molecules

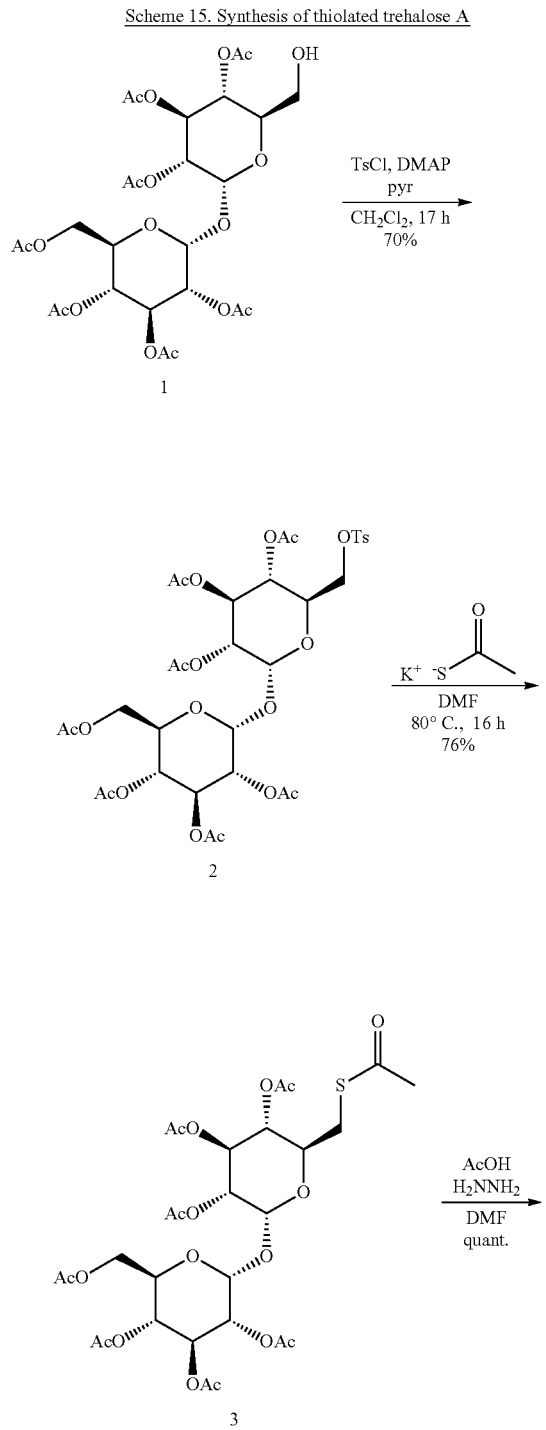

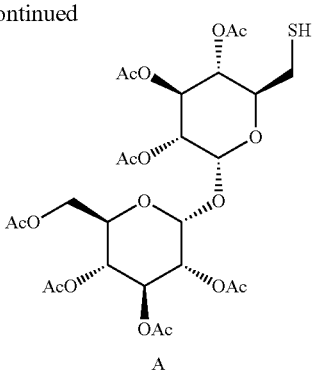

Synthesis of Tosylated Trehalose 2

In a two-neck round bottom flask, monohydroxylheptaacetyltrehalose 1 (Lee et al., 2013) (1.54 g, 2.42 mmol) was dissolved in anhydrous $CH_2Cl_2$ (15 mL) under argon. 4-Dimethylaminopyridine (59 mg, 0.48 mmol) and anhydrous pyridine (580 µL, 7.26 mmol) were added and the reaction solution cooled to 0° C. in an ice-water bath. Tosyl chloride (1.38 g, 7.26 mmol) was added slowly as a solid and the solution stirred for an additional 20 minutes at 0° C. before warming to room temperature and stirring for 14 hours. The crude mixture was diluted with additional $CH_2Cl_2$ (40 mL) and washed with water (2×50 mL) and brine (50 mL). The organic layer was then dried with $MgSO_4$ and concentrated in vacuo. The crude solid was purified by silica gel flash column chromatography (eluent 5:1 $CH_2Cl_2$:EtOAc) to obtain a crispy white solid (1.34 g, 1.70 mmol, 70%). $^1$H-NMR (500 MHz in CDCl3) δ: 7.74 (d, J=8.3 Hz, 2H), 7.34 (d, J=8 Hz, 2H), 5.47-5.41 (m, 2H), 5.14 (d, J=3.9 Hz, 1H), 5.05-5.01 (m, 3H), 4.93-4.89 (m, 2H), 4.21 (dd, J=12.1 Hz, 6.7 Hz, 1H), 4.14-3.94 (m, 5H), 2.44 (s, 3H), 2.09 (s, 3H), 2.06 (s, 3H), 2.05 (s, 3H), 2.03 (s, 3H), 2.02 (s, 3H), 2.01 (s, 3H), 2.00 (s, 3H). 13C NMR: (500 MHz in CDCl3) δ: 169.0, 169.9, 169.6, 169.6, 169.5, 169.5, 145.3, 132.4, 129.9, 128.0, 92.8, 92.3, 70.0, 69.7, 69.7, 69.3, 68.6, 68.4, 68.2, 68.1, 67.5, 61.7, 21.7, 20.7, 20.7, 20.6, 20.6, 20.6, 20.5. IR: ν=2950, 1744, 1432, 1368, 1221, 1190, 1177, 1138, 1079, 1035, 1016, 988, 911, 862, 805 cm$^{-1}$. HRMS-ESI (m/z) [M+H2O]+ calcd for C33H44O21S, 808.2096; found 808.2226.

Synthesis of Thioacetylated Trehalose 3

In a two-neck round bottom flask, tosylated trehalose 2 (2.38 g, 3.01 mmol) was dissolved in anhydrous DMF (12 mL) under argon. Potassium thioacetate (1.03 g, 9.03 mmol) was added and the reaction solution heated to 70° C. for 18 hours. After cooling to room temperature, DMF was removed in vacuo. The crude brown solid was dissolved in $CH_2Cl_2$ and washed with water, sat. $NaHCO_3$ (2×), water, and brine. The organic layer was dried with MgSO4 and concentrated in vacuo. The crude oil was purified by silica gel flash column chromatography (eluent 1:1 hexanes:EtOAc) to obtain 3 as a light tan solid (1.59 g, 2.29 mmol, 76%). 1H NMR: (500 MHz in CDCl3) δ: 5.47 (t, J=10 Hz, 2H), 5.28 (dd, J=4, 14 Hz, 2H), 5.07-4.96 (m, 4H), 4.19 (dd, J=6, 12 Hz, 1H), 4.04 (dd, J=2, 12 Hz, 1H), 3.98-3.95 (m, 1H), 3.87 (ddd, J=2.6, 7.8, 10.2 Hz, 1H), 3.17 (dd, J=2.5, 14.5 Hz, 1H), 2.96 (dd, J=8, 14 Hz, 1H), 2.34 (s, 3H), 2.10 (s, 3H), 2.08 (s, 3H), 2.08 (s, 3H), 2.07 (s, 3H), 2.04 (s, 3H), 2.03 (s, 3H), 2.02 (s, 3H). $^{13}$C NMR: (500 MHz, CDCl$_3$) δ: 194.7, 170.6, 169.9, 169.9, 169.9, 169.8, 169.7, 169.6, 91.4, 91.2, 70.9, 70.1, 70.0, 69.8, 69.6, 69.3, 68.6, 68.2, 61.8, 30.4, 29.8, 20.7, 20.7, 20.6, 20.6, 20.6. IR: ν=2957, 1746, 1694, 1431, 1367, 1212, 1161, 1134, 1034, 981, 962, 900, 803 cm$^{-1}$. HRMS-ESI (m/z) [M+Na]$^+$ calculated for C28H38NaO18S, 717.1677, found 717.1650.

Synthesis of Selectively Deprotected Thiolated Trehalose A

In a 20 mL screw-top vial, thioacetylated trehalose 3 (1.5 g, 2.16 mmol) was dissolved in DMF (22 mL) under argon. Acetic acid (122 µL, 2.14 mmol) was added and the solution was stirred for 10 minutes. Hydrazine hydrate (70-82% in $H_2O$, 131 µL, 2.14 mmol) was then added and the reaction solution was stirred at 21° C. for a further 2 hours. Acetone (200 µL, 2.72 mmol) was added to quench the reaction, and the crude product was poured into $H_2O$ and extracted with EtOAc. The organic layer was washed with brine (2×), dried over MgSO4, and solvent removed in vacuo to obtain 4 as a light tan solid (1.52 g, quantitative yield). $^1$H NMR: (500 MHz in $CDCl_3$) δ: 5.49 (t, J=10 Hz, 2H), 5.31 (t, J=4 Hz, 2H), 5.11-5.00 (m, 4H), 4.22 (dd, J=12, 5.5 Hz, 1H), 4.03-3.97 (m, 3H), 2.63-2.55 (m, 2H), 2.13 (s, 3H), 2.09 (s, 6H), 2.07 (s, 3H), 2.05 (s, 3H), 2.03 (s, 3H), 2.03 (s, 3H), 1.68 (dd, J=10, 7 Hz, 1H). 13C NMR: (500 Hz, $CDCl_3$) δ: 170.6, 170.0, 169.7, 169.7, 169.6, 92.2, 91.9, 71.2, 70.7, 70.0, 70.0, 69.9, 69.4, 68.6, 68.2, 61.8, 25.8, 21.0, 20.7, 20.7, 20.6, 20.6. IR: ν=2962, 1746, 1669, 1435, 1368, 1215, 1166, 1137, 1033, 984, 964, 904, 804, 722, 659 $cm^{-1}$. HRMS-ESI (m/z) [M+Na]+ calcd for C26H36NaO17S, 675.1571; found 675.1624.

Basic Hydrolysis and Degradation

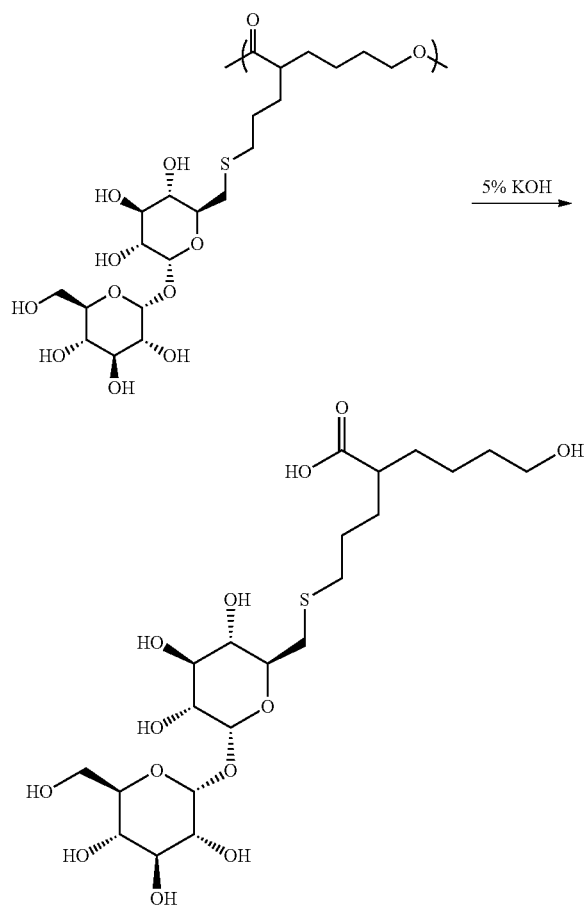

pCL-trehalose$_{30}$ (3 mg) was dissolved in 5% aqueous KOH (1 mL) and placed on a rotating place at 4° C. Aliquots (300 µL) were removed after 24 hours, lyophilized to remove solvent, and analyzed by aqueous SEC to assess degradation.

Cytotoxicity

The cell compatibility of the pCL-trehalose$_{10}$, pCL-trehalose$_{20}$, pCL-zwitterion$_{20}$, and the degraded polymeric products was evaluated in human umbilical vein endothelial cells (HUVECs, ATCC) using a LIVE-DEAD viability/cytotoxicity assay (Invitrogen). HUVECs were cultured in endothelial cell growth medium (ATCC) supplemented with 100 unit/mL penicillin and 100 µg/mL streptomycin. At passage 6 the cells were trypsinized and resuspended in supplemented growth medium and then seeded in 48-well plates at a density of 5,000 cells/well in 200 µL medium. After 48 hours, culture medium was replaced with 200 µL of the working medium (endothelial cell growth medium with penicillin and streptomycin) containing polymer concentrations of 0.1, 0.5 and 1 mg/mL. Polymer solutions were sterile filtered prior to use and endothelial cell growth medium without polymers was used as a control. After incubation for 24 hours at 37° C./5% $CO_2$, the medium was aspirated out of the wells and 125 µL of the LIVE/DEAD reagent (2 µM calcein AM and 4 µM ethidium homodimer-1) was added. The plate was incubated for 15 minutes and then images were captured on an Axiovert 200 microscope with an AxioCam MRm camera and FluoArc mercury lamp. The number of live and dead cells were counted using ImageJ software and percent cell viability was calculated by dividing the number of live cells by the total number of cells.

Transmission Electron Microscopy (TEM)

Solutions were prepared for TEM by preparing polymer solutions (2 mg/mL) and G-CSF solutions (0.3 mg/mL) in 10 mM acetate buffer, pH 4.0. The solutions were mixed 1:1 and 3.0 µL of the resulting solution was added to TEM grids that had been pre-treated using a glow discharge unit (Pelco easiGlow). Samples were then stained using a 1% uranyl acetate solution, blotted dry, and imaged using a FEI Tecnai T12 cryo-electron microscope. Micrographs were recorded using a Gatan 4 megapixel CCD camera (2 k by 2 k).

Differential Scanning Calorimetry (DSC)

Solutions of trehalose, betaine, pCL-trehalose$_{80}$, and pCL-zwitterion$_{80}$ were made at 1 mol % of the stabilizing unit (trehalose or betaine) and analyzed by DSC (TA Instruments Q2000). Runs were carried out using two heat/cool cycles from −40° C. to 40° C. at 10° C. and values were taken from the second run.

TABLE 3

Changes in melting and crystallization enthalpy of water upon addition of 1 mol % trehalose, trehalose repeating units in pCL-trehalose$_{80}$, betaine, or zwitterionic repeating units in pCL-zwitterion$_{80}$.

| Sample | $H_m$ | $\Delta H_m$ | $H_c$ | $\Delta H_c$ |
|---|---|---|---|---|
| Water | 296.5 | | −252.2 | |
| Trehalose | 249.1 | −47.4 | −229.9 | 22.3 |
| T80 | 115.9 | −180.6 | −96.3 | 155.9 |
| Betaine | 198.1 | −98.4 | −179 | 73.2 |
| Z80 | 16.41 | −280.09 | −23.4 | 228.8 |

Example 5

There is considerable interest in proteins, as therapeutics and as biochemical and chemical reagents (Robert et al., 2002; Harris and Chess, 2003; Alconcel et al., 2011). However, most are inherently unstable and degrade upon storage, transport and use, necessitating regulated temperatures, controlled salvation, and addition of carrier molecules that may need to be removed (Bays et al., 2009; Mateo et al., 2000; Lyczak and Morrison, 1994; Syed et al., 1997; Cohen et al., 1991; Abuchowski et al., 1977). Proteins are also known to denature due to physical or chemical stresses such as desiccation (Wang, 2000), heat (Oobatake and Ooi, 1993), light (Maity et al., 2009), and pH change (Chi et al., 2003) further complicating application of certain biomolecules. While attachment of poly(ethylene glycol) (PEG) to proteins has been widely used to increase in vitro and in vivo stability for therapeutic proteins by reducing access of proteolytic enzymes and screening through the renal filtration systems (Lyczak and Morrison, 1994; Syed et al., 1997; Cohen et al., 1991), PEGylation alone does not normally significantly increase protein stability to temperature, desiccation, and storage. The non-biodegradability of PEG is also a drawback of its use.

PEGylation of proteins has been shown to lead to accumulation of the conjugates and vacuolation (Besheer et al., 2013). Additionally, most conjugates display lower activity than the native protein due to steric hindrance of the active site (Molineaux, 2004). Degradable polymers would stabilize a protein during storage and transport and then degrade in biological conditions to expose a fully active protein.

A degradable polymer containing esters in the backbone that stabilizes proteins to environmental stressors when added to proteins is disclosed. The polymer is composed of side chains that have trehalose and are significantly better than trehalose alone at the same concentration. Stabilization of a protein to desiccation and heat is demonstrated herein. Additionally, the polymer is degradable and reduction of molecular weight after treatment with base is demonstrated.

The application may also include, but is not limited to stabilization of proteins, enzymes, antibodies, DNA, siRNA, peptides, drugs, or conjugates to heat, desiccation, light, storage, exposure to enzymes, and pH changes. Commercial applications of this invention include, but are not limited to, stabilization of proteins, enzymes, antibodies, DNA, siRNA, peptides, drugs, or conjugates thereof utilized as therapeutics, biochemical reagents, chemical reagents and nutrients. The polymer may be added to a solution or powder form of the biomolecule alone or as part of a formulation. The polymer may also be attached to a protein or other biomolecule covalently to form a conjugate. Unconjugated polymer may be added to the polymer conjugate as additional excipient.

Conjugate: The following summarizes journal articles on degradable polymers conjugated to proteins.

To our knowledge, only two examples of degradable polymers synthesized by controlled polymerization methods exist and covalently conjugated to proteins in the literature. Poly(PEGMA-co-BMDO) was synthesized using RAFT, shown to degrade under basic conditions, and conjugated to lysozyme through a reductively pyridyl disulfide end-group (Decker and Maynard, 2015). A maleimide-functionalized polycaprolactone was synthesized and conjugated to BSA through thiol-ene chemistries (Liu et al., 2014). This amphiphillic self-assembled into micelles for delivery of hydrophobic drugs. However, other known degradable polymers such as hydroxyethyl starch (HES) (Hey et al., 2012), polysialic acid (Jain et al., 2003), and dextrin (Hardwicke et al., 2011) have been conjugated to proteins and shown some stabilizing ability against environmental stressors.

Previous trehalose polymers have been shown to be superior to free trehalose as stabilizing agents for proteins. These polymers containing side-chain trehalose moieties can be synthesized using controlled polymerization techniques in order to install a protein-reactive end-group onto the polymer. However, these trehalose polymers, as well as PEG and polymeric PEG alternatives, suffer from non-degradability in vivo. Similarly, there are no examples of zwitterion polymers attached to proteins that are degradable. This invention combines the advantages of polymeric trehalose previously described with hydrolytically degradable ester units in the backbone in order to eliminate problems of vacuolation and accumulation in the body with repeated protein polymer conjugation dosage. Additionally, the activity of protein-polymer conjugates is usually considerably decreased when compared to native proteins. The conjugation of a degradable polymer to a protein may enable safe storage and transport, while degrading into short molecular weights in vivo and maintaining high therapeutic activity.

This invention may be best implemented in practice as the polymer attached to proteins utilized as drugs. Addition of the unconjugated polymer to proteins alone or combination with other formulation agents is another best use of this invention. The polymer may also be employed to stabilize proteins used solely for research purposes.

Invention Details

The degradable glycopolymers are synthesized using post-polymerization modification of a biodegradable allylated polymer backbone. Allylated caprolactone is synthesized and polymerized to yield a polyester with pendant allyl groups.

Scheme 17. Synthesis of poly(allyl-caprolactone).

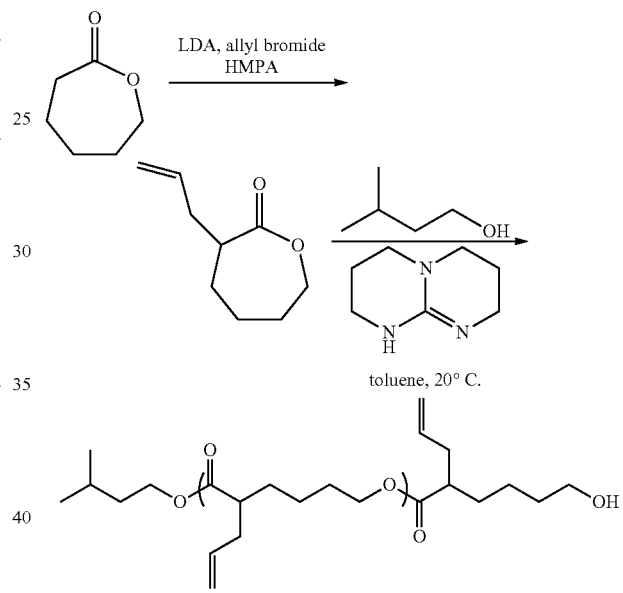

Figure 76:
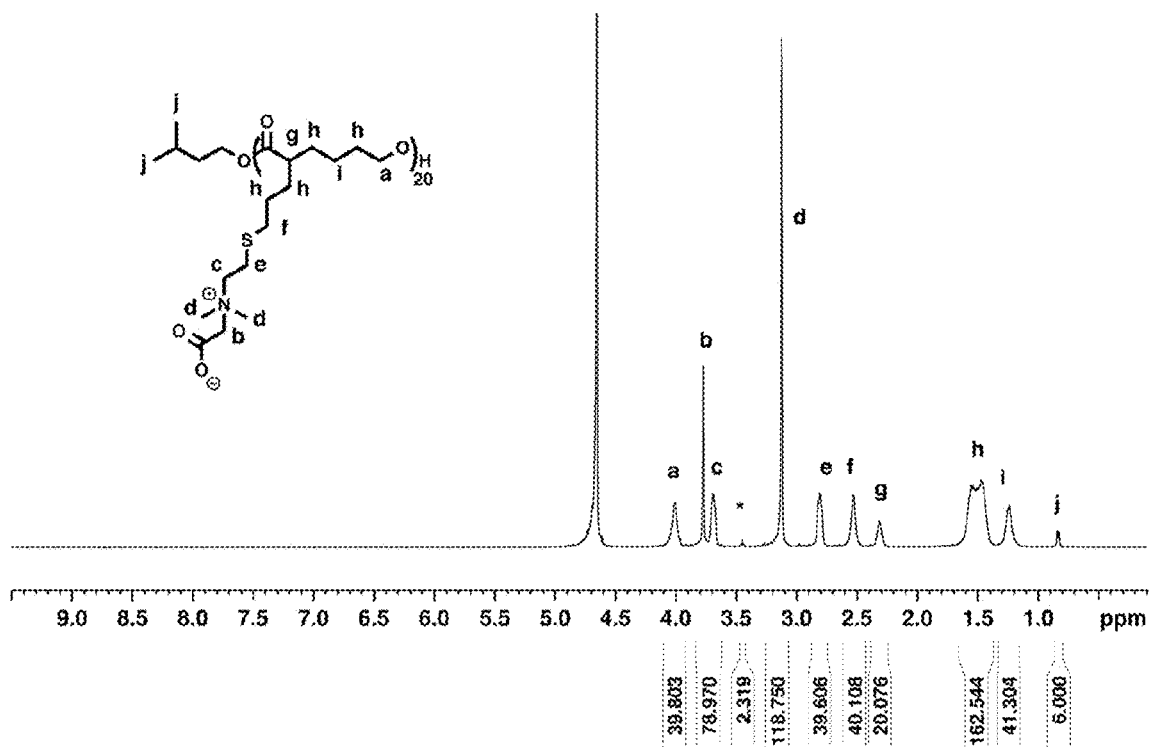
FIG. 76 is a graph showing $^1$H-NMR spectrum of pCL-zwitterion$_{20}$ (D$_2$O, 500 MHz). *=protons from terminal unit on polymer.
Figure 77:
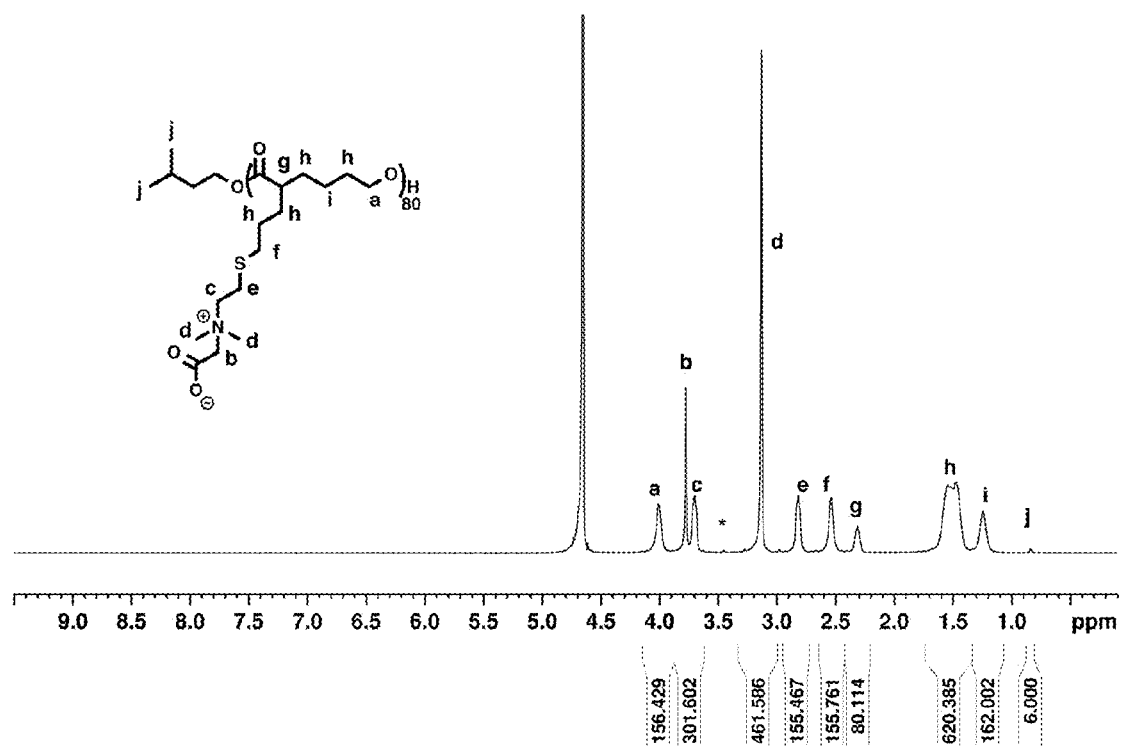
FIG. 77 is a graph showing $^1$H-NMR spectrum of pCL-zwitterion$_{80}$ (D$_2$O, 500 MHz). *=protons from terminal unit on polymer.
Figure 78:
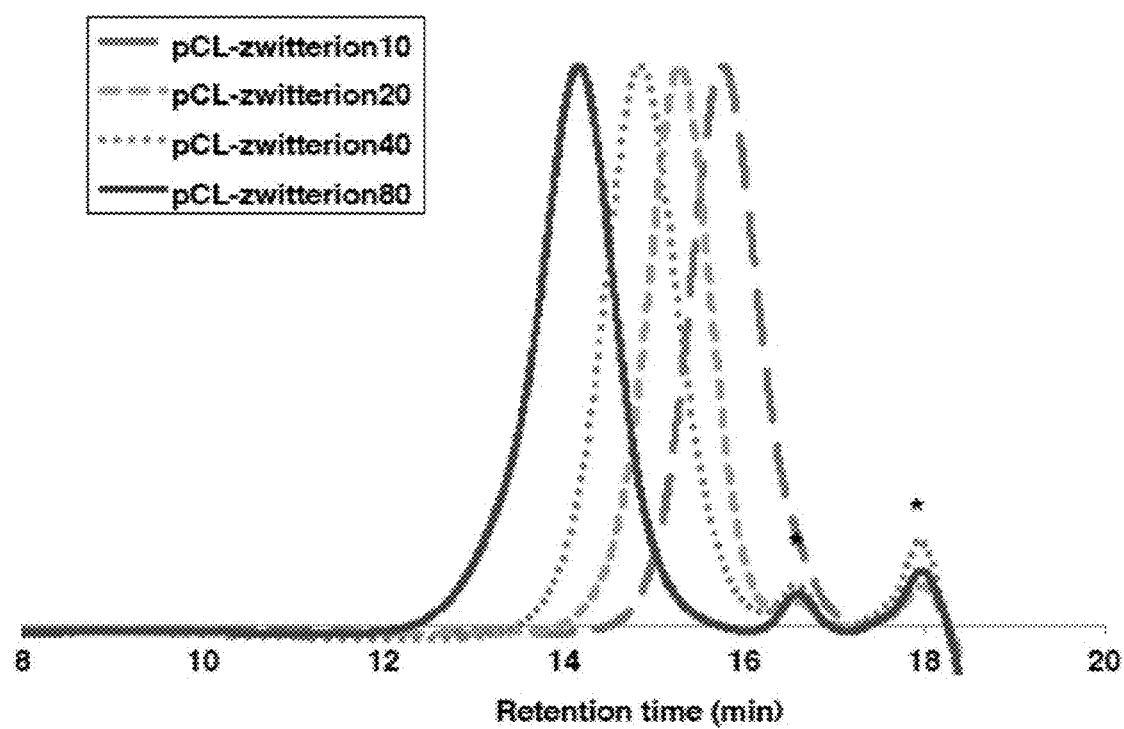
FIG. 78 is graph showing size exclusion chromatograms of pCL-zwitterion$_{10}$, pCL-zwitterion$_{20}$, pCL-zwitterion$_{40}$, pCL-zwitterion$_{80}$. Peaks due to salts in the buffer indicated with *.

The initiator may also contain a protected functional group such as an acetal, which can be hydrolyzed under acidic conditions to yield a protein-reactive aldehyde for conjugation. FIG. 76 shows $^1$H-NMR spectrum of poly(allyl-caprolactone). FIG. 77 shows GPC trace of poly(allyl-caprolactone).

Thiolated trehalose was then synthesized for use in thiol-ene post-polymerization modification.

Scheme 18. Synthesis of thiolated trehalose.

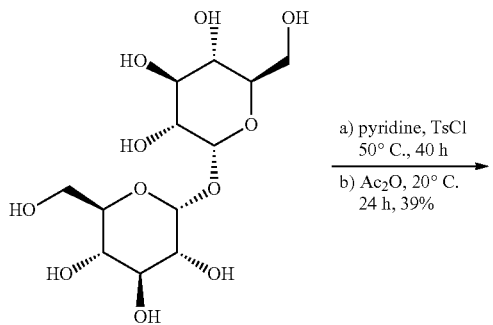

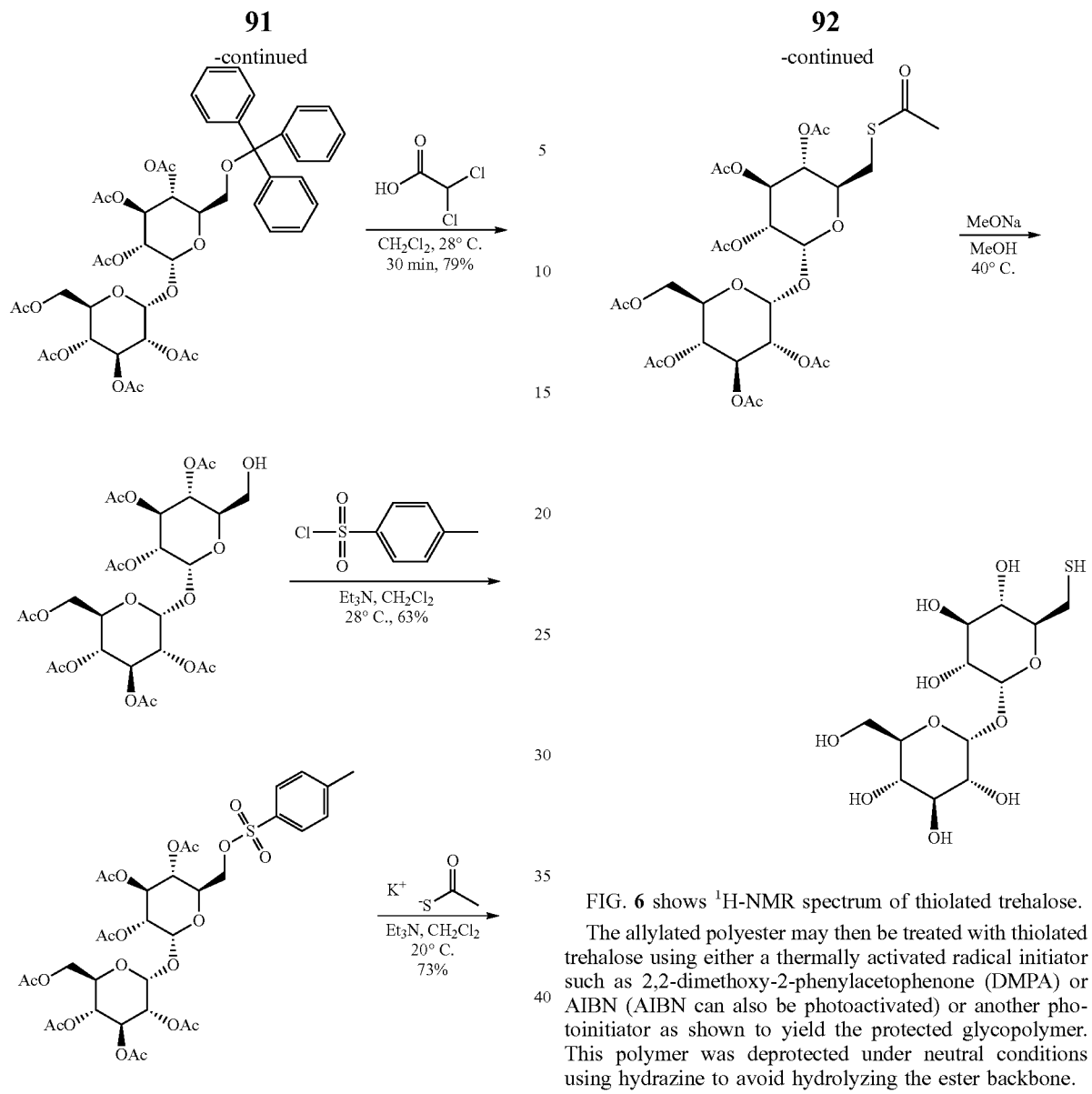

FIG. 6 shows ¹H-NMR spectrum of thiolated trehalose.

The allylated polyester may then be treated with thiolated trehalose using either a thermally activated radical initiator such as 2,2-dimethoxy-2-phenylacetophenone (DMPA) or AIBN (AIBN can also be photoactivated) or another photoinitiator as shown to yield the protected glycopolymer. This polymer was deprotected under neutral conditions using hydrazine to avoid hydrolyzing the ester backbone.

Scheme 19. Synthesis of trehalose polyester.

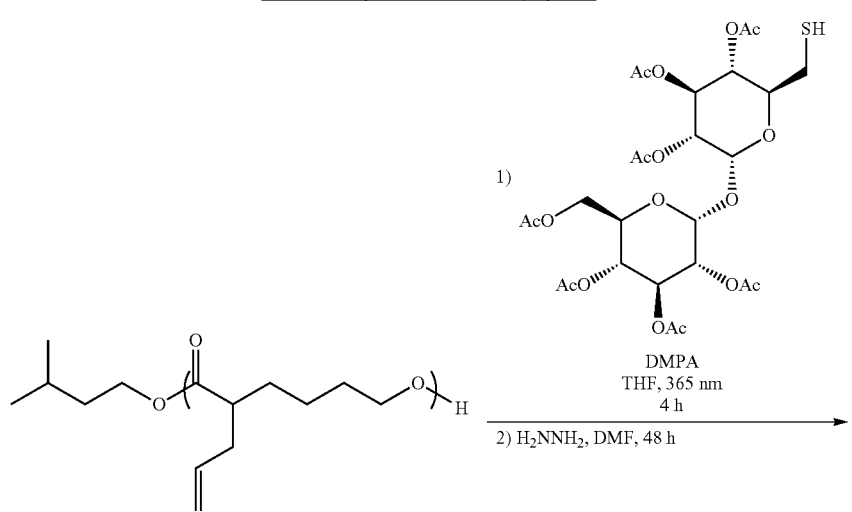

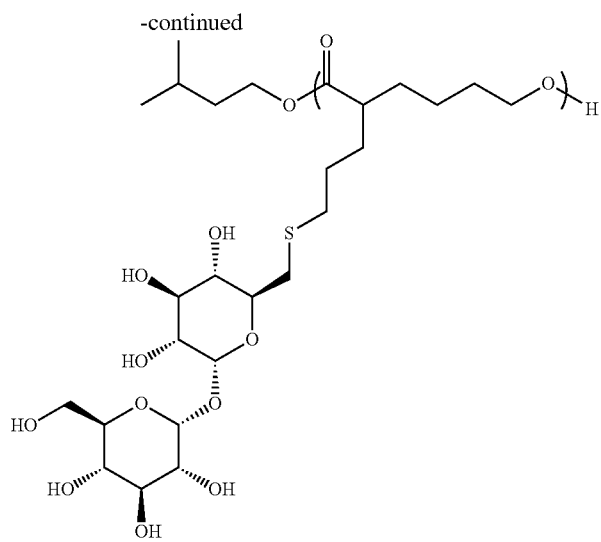

FIGS. 47-52 show $^1$H-NMR spectrum of protected trehalose polyesters.

FIGS. 55-58 show $^1$H-NMR spectrum of deprotected trehalose polyesters.

Stabilization Property

Figure 13:
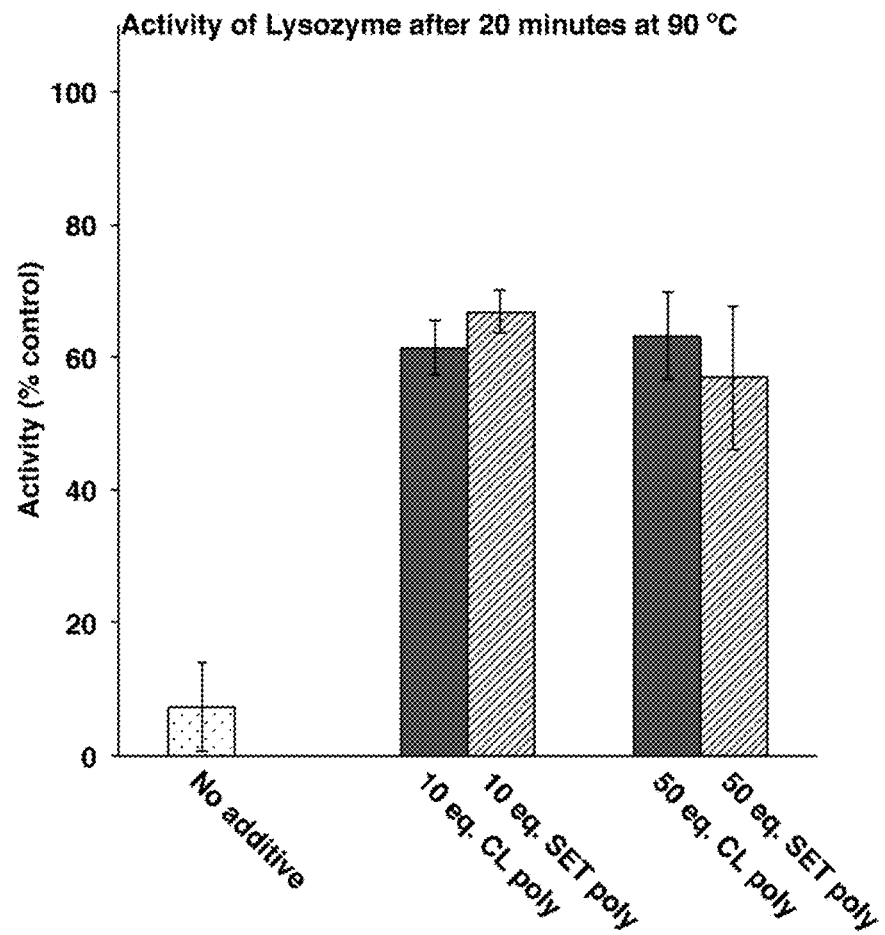
FIG. 13 is a graph showing comparison of trehalose-caprolactone polymer (dark) and styrenyl ether trehalose polymer (SET poly; gray) in the stabilization of lysozyme. *: p<0.001 compared to the negative control.: p<0.01 compared to the negative control. White is no additive.

The ability of this degradable trehalose polymer to stabilize proteins against environmental stressors was then investigated. Lysozyme was heated to 90° C. for 20 minutes with either trehalose polyester, styrenyl ether trehalose polymer, or no excipient. The activity of the stressed samples were measured and the trehalose polyester was shown to be equivalent to trehalose side-chain polymers already described. FIGS. 12 and 13 show stabilization of lysozyme against heat stress by trehalose polyester.

Lyophilization was also tested as an environmental stressor. β-Galactosidase underwent three cycles of lyophilization with either trehalose or trehalose polyester as excipient. The activity of the stressed samples was measured and was shown to be superior to the identical weight equivalent of trehalose. FIG. 12 shows stabilization of β-Galactosidase against lyophilization stress by trehalose polyester.

A second degradable trehalose polymer could also be prepared by copolymerizing allylated methacrylate with a well-known biodegradable monomer, BMDO. This polymer could then undergo thiol-ene chemistry in a similar manner to the caprolactone in order to install trehalose side-chains.

Scheme 20. Synthesis of BMDO-co-trehalose polymer.

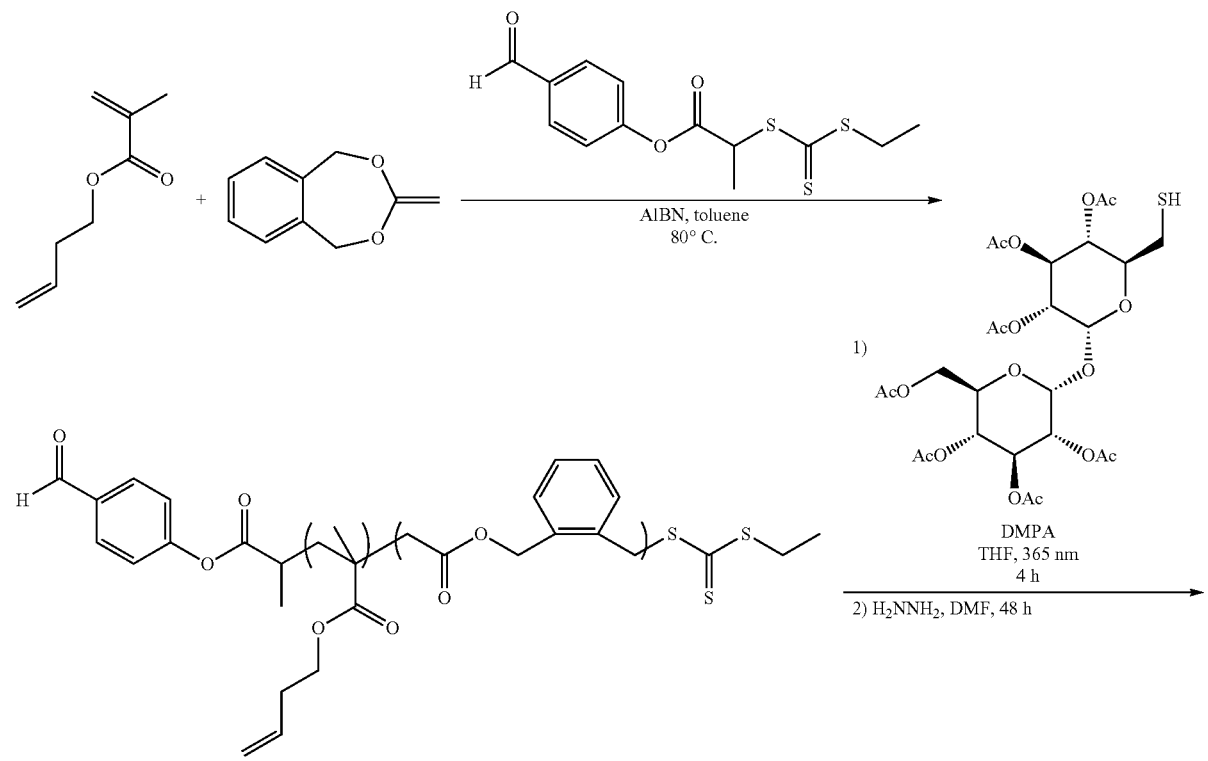

-continued

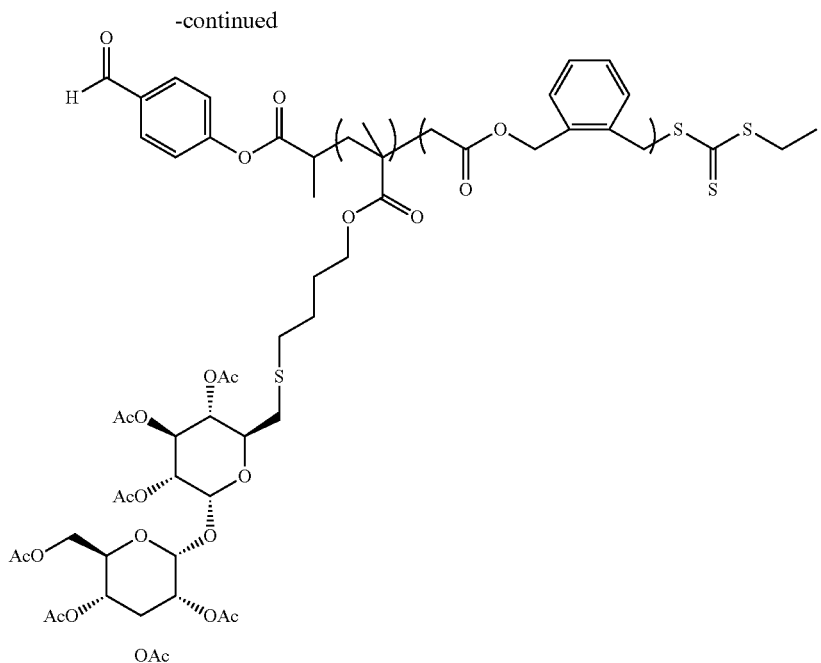

FIG. 29 shows ¹H-NMR spectrum of BMDO-co-allyl methacrylate polymer.

Example 6

Functionalization of the End Groups for PCL Trehalose or Zwitterion Polymers Applicants also demonstrate that the end groups of p(CL-zwitterion) and p(CL-trehalose) polymers can be functionalized.

For example, the end groups of p(CL-zwitterion) and p(CL-trehalose) polymers can be functionalized by azide groups.

Scheme 21: Synthesis of azide funcationalized p(CL-zwitterion) and p(CL-trehalose) polymers.

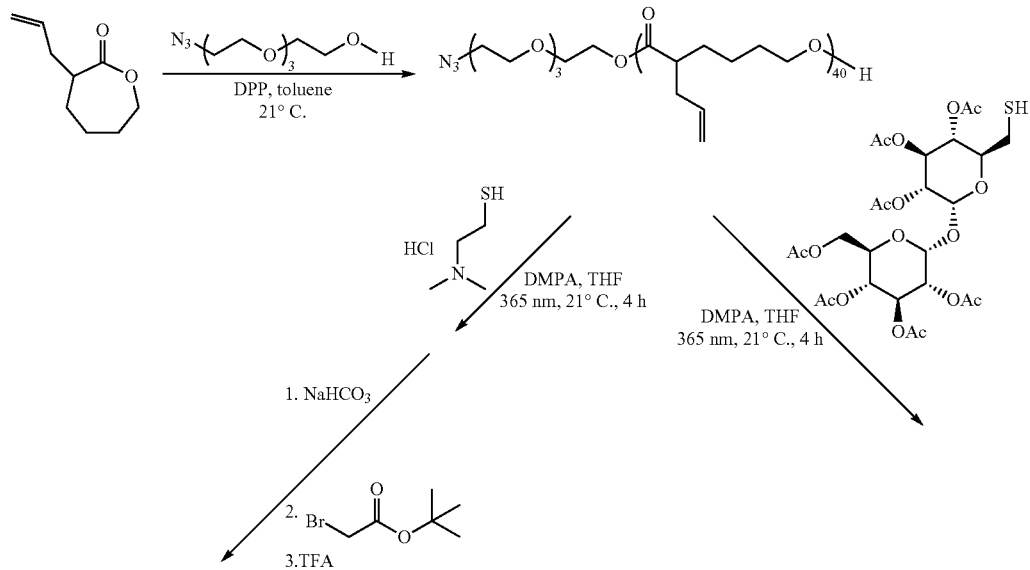

-continued

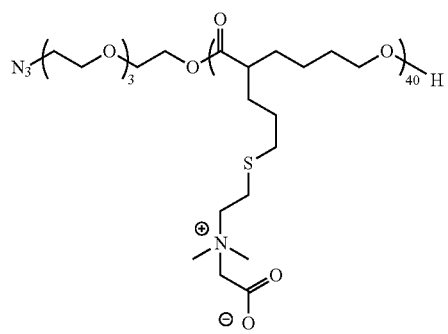
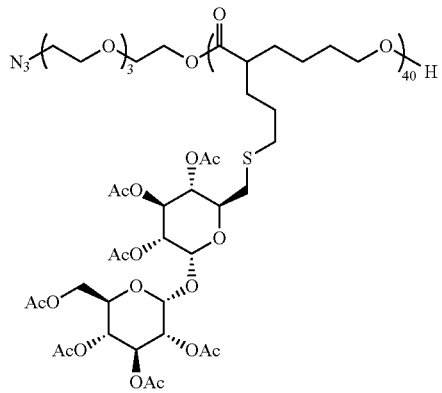

Scheme 21 shows the synthesis of azide functionalized p(CL-zwitterion) and p(CL-trehalose) polymers.

Specifically, azide functionalized p(CL) polymers can be synthesized.

Scheme 22: Synthesis of azide functionalized p(CL)$_{40}$

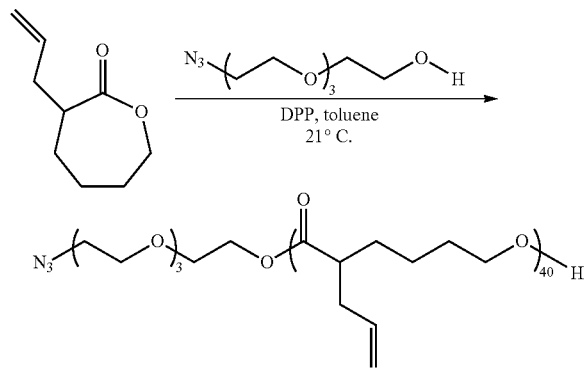

As an example, scheme 22 shows the synthesis of azide functionalized p(CL)$_{40}$.

Representative Ring-Opening Polymerization

To synthesize p(CL)$_{40}$, in an inert atmosphere a 1.5 mm sample vial was charged with a stir bar and a solution of 7.5% v/v N$_3$-PEG$_4$-OH in toluene (30 μL stock, 2.54 mg N$_3$-PEG$_4$-OH, 11.6 μmol, 1 equivalent) and a 0.12 M solution of diphenylphosphate in toluene (264 L stock, 8.11 mg DPP, 32.4 μmol, 2.8 equivalent) were added to the vial and allowed to stir for 30 minutes at 21° C. To this solution, allyl-caprolactone (106.9 mg, 693.2 μmol, 60 equivalent) was added, and the reaction progress was monitored by taking aliquots for $^1$H-NMR analysis. After the target monomer conversion was obtained, the reaction was removed from inert atmosphere and quenched with acetic acid (20 μL) and triethylamine (20 μL). The crude mixture was purified by silica gel column chromatography (eluent ethyl acetate/hexanes, 15-50%) to obtain the polymer, resulting in a colorless oil (79.9 mg).

PCL zwitterion polymers with azide functionalization can also be produced.

Scheme 23: Azide functionalization of p(CL)$_{40}$ with zwitterion

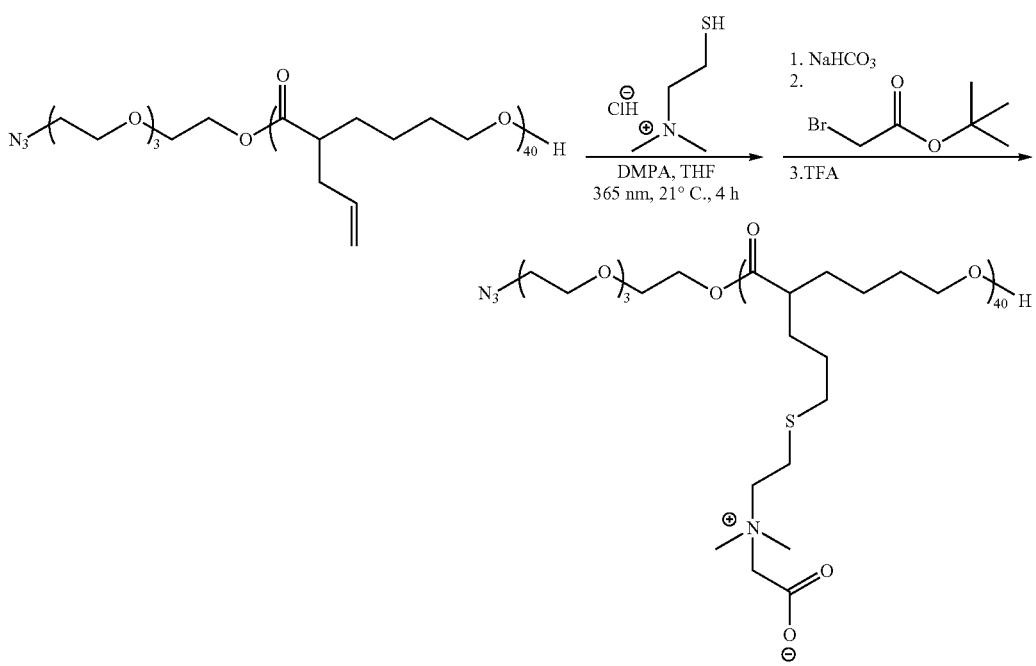

Scheme 23 shows azide functionalization of p(CL)$_{40}$ with zwitterion.

Similarly, azide functionalization of p(CL)$_{40}$ with thiolated trehalose can also be produced.

Scheme 24: Azide functionalization of p(CL)$_{40}$ with thiolated trehalose

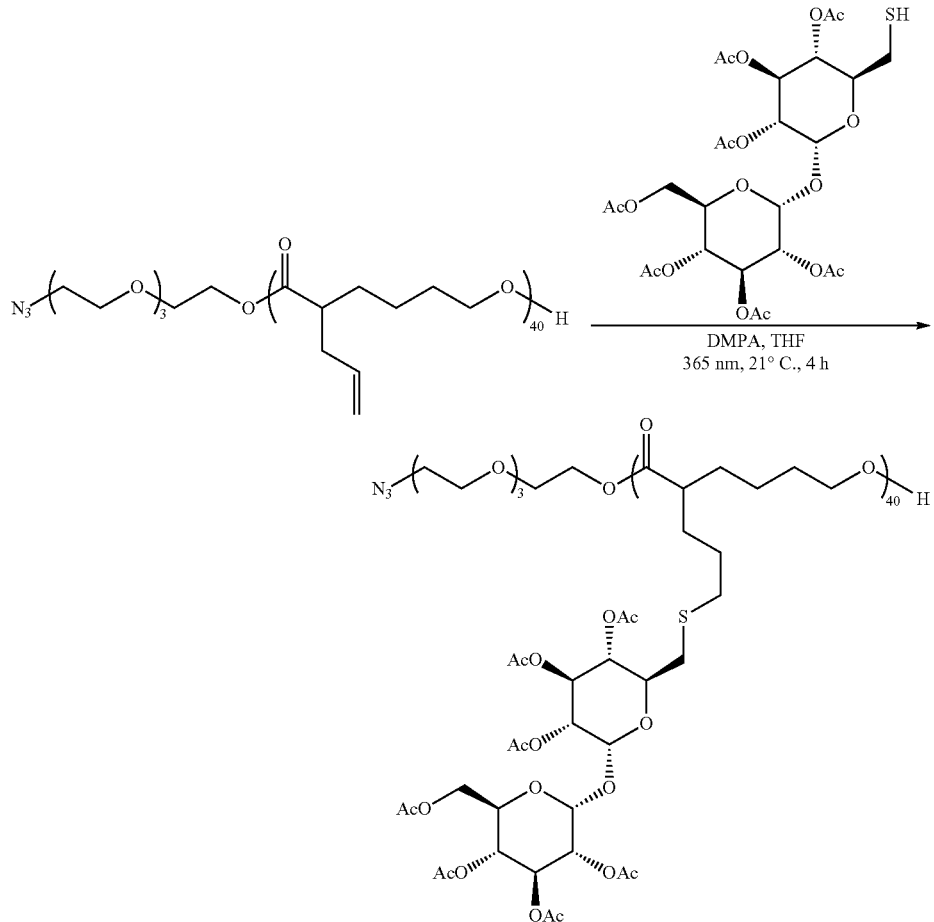

Scheme 24 shows azide functionalization of p(CL)$_{40}$ with thiolated trehalose.

Representative Functionalization of p(CL) Polymers by Thiol-Ene Reaction

For the synthesis of p(CL-trehaloseOAc), p(CL)$_{40}$ (16.5 mg, 2.646 µmol, 105.84 µmol C=C, 1 equivalent C=C) was dissolved in a 1.5 mL sample vial with tetrahydrofuran (THF, 300 µL). Thiolated trehalose (205 mg, 314.1 µmol, 3 equivalent to C=C) and 2,2-dimethoxy-2-phenylacetophenone (14 mg, 54.6 µmol, 0.52 equivalent to C=C) were stirred in. The solution was then sealed with a septum, sparged for 10 minutes under argon, and exposed to a handheld UV lamp ($\lambda$=365 nm) for 4 hours. To purify the functionalized polymer, crude solutions were precipitated dropwise into cold methanol (protected trehalose) or dialyzed in methanol and water (zwitterion).

FIGS. 15 and 16 show a lysozyme conjugate with the trehalose pCL polymer. FIG. 10 shows an acetal end functionalized pCL polymer and FIG. 11 shows poly(caprolactone) with a methacrylate end group prepared post functionalization. The data shows that pCL polymers could both react with amines or could additionally react with any free cysteines on biomolecules.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Agarwal, S. *Polym. Chem.* 2010, 1, 953-964.
2. Roy, I. and Jain, N. K. *Protein Science,* 2009, 24-36.
3. Mancini, R. J.; Lee, J.; Maynard, H. D. *J. Am. Chem. Soc.,* 2012, 134, 8474-8479.
4. Lee, J.; Lin, E.-W.; Lau, U. Y.; Hedrick, J. L.; Bat, E.; Maynard, H. D. *Biomacromolecules,* 2013, 14, 2561-2569.
5. Siegwart, D. J.; Bencherif, S. A.; Srinivasan, A.; Hollinger, J. O.; Matyjaszewski, K. *J. Biomed. Mater.* 2008, 87, 345-58.
6. Knop, K.; Hoogenboom, R.; Fischer, D.; Schubert, U. S. *Angew. Chem. Int. Ed.* 2010, 49, 6288.

7. Alconcel, S. N. S.; Baas, A. S.; Maynard, H. D. *Polymer Chemistry* 2011, 2, 1442.
8. Gao, W.; Liu, W.; Christensen, T.; Zalutsky, M. R.; Chilkoti, A. *Proceedings of the National Academy of Sciences* 2010, 107, 16432.
9. Roberts, M. J.; Milton Harris, J. *J. Journal of Pharmaceutical Sciences* 1998, 87, 1440.
10. Markovsky, E.; Baabur-Cohen, H.; Eldar-Boock, A.; Omer, L.; Tiram, G.; Ferber, S.; Ofek, P.; Polyak, D.; Scomparin, A.; Satchi-Fainaro, R. *Journal of Controlled Release* 2012, 161, 446.
11. Duro-Castano, A.; Conejos-Sanchez, I.; Vicent, M. *Polymers* 2014, 6, 515.
12. Roberts, M. J.; Bentley, M. D.; Harris, J. M. *Advanced Drug Delivery Reviews* 2002, 54, 459.
13. Garman, A. J.; Barret Kalindjian, S. *FEBS Letters* 1987, 223, 361.
14. Veronese, F. M.; Largajolli, R.; Boccu, E.; Benassi, C. A.; Schiavon, O. *Appl Biochem Biotechnol* 1985, 11, 141.
15. Abuchowski, A.; Kazo, G. M.; Verhoest Jr, C. R.; Van Es, T.; Kafkewitz, D.; Nucci, M. L.; Viau, A. T.; Davis, F. F. *Cancer Biochemistry Biophysics* 1984, 7, 175.
16. Woghiren, C.; Sharma, B.; Stein, S. *Bioconjugate Chemistry* 1993, 4, 314.
17. Zalipsky, S.; Menon-Rudolph, S. In *Poly(ethylene glycol)*; American Chemical Society: 1997; Vol. 680, p 318.
18. Gaertner, H. F.; Offord, R. E. *Bioconjugate Chemistry* 1996, 7, 38.
19. Kozlowski, A.; Milton Harris, J. *J. Journal of Controlled Release* 2001, 72, 217.
20. Iha, R. K.; van Horn, B. A.; Wooley, K. L. *Journal of Polymer Science Part A: Polymer Chemistry* 2010, 48, 3553.
21. Lundberg, P.; Lee, B. F.; van den Berg, S. A.; Pressly, E. D.; Lee, A.; Hawker, C. J.; Lynd, N. A. *ACS Macro Lett.* 2012, 1, 1240.
22. Dingels, C.; Muller, S. S.; Steinbach, T.; Tonhauser, C.; Frey, H. *Biomacromolecules* 2013, 14, 448.
23. Yan-Ling, L.; Yun-Fei, N.; Feng, X.; Ya-Shao, C.; Pei, Z. *Journal of Biomaterials Science—Polymer Edition* 2010, 21, 1143.
24. Cerritelli, S.; Velluto, D.; Hubbell, J. A. *Biomacromolecules* 2007, 8, 1966.
25. Hey, T.; Knoller, H.; Vorstheim, P. In *Therapeutic Proteins*; Wiley-VCH Verlag GmbH & Co. KGaA: 2012, p 117.
26. Zhang, R.; Jain, S.; Rowland, M.; Hussain, N.; Agarwal, M.; Gregoriadis, G. *Journal of Diabetes Science and Technology* 2010, 4, 532.
27. Yurkovetskiy, A.; Choi, S.; Hiller, A.; Yin, M.; McCusker, C.; Syed, S.; Fischman, A. J.; Papisov, M. I. *Biomacromolecules* 2005, 6, 2648.
28. Hardwicke, J.; Ferguson, E. L.; Moseley, R.; Stephens, P.; Thomas, D. W.; Duncan, R. *Journal of Controlled Release* 2008, 130, 275.
29. Liu, Z.; Dong, C.; Wang, X.; Wang, H.; Li, W.; Tan, J.; Chang, J. *ACS Applied Materials & Interfaces* 2014, 6, 2393.
30. Grover, G. N.; Maynard, H. D. *Current Opinion in Chemical Biology* 2010, 14, 818.
31. Lutz, J.-F.; Andrieu, J.; Uzgtin, S.; Rudolph, C.; Agarwal, S. *Macromolecules* 2007, 40, 8540.
32. Riachi, C.; Schuiwer, N.; Klok, H.-A. *Macromolecules* 2009, 42, 8076.
33. Delplace, V.; Tardy, A.; Harrisson, S.; Mura, S.; Gigmes, D.; Guillaneuf, Y.; Nicolas, J. *Biomacromolecules* 2013, 14, 3769.
34. Hedir, G. G.; Bell, C. A.; Ieong, N. S.; Chapman, E.; Collins, I. R.; O'Reilly, R. K.; Dove, A. P. *Macromolecules* 2014.
35. Siegwart, D. J.; Bencherif, S. A.; Srinivasan, A.; Hollinger, J. O.; Matyjaszewski, K. *Journal of Biomedical Materials Research* Part A 2008, 87A, 345.
36. Kobben, S.; Ethirajan, A.; Junkers, T. *Journal of Polymer Science Part A: Polymer Chemistry* 2014, n/a.
37. Xu, N.; Wang, R.; Du, F.-S.; Li, Z.-C. *J Polym Sci Pol Chem* 2009, 47, 3583.
38. Li, L.; Wang, J.; Obrinske, M.; Milligan, I.; O'Hara, K.; Bitterman, L.; Du, W. *Chemical Communications* 2015, 51, 6972.
39. Li, L.; Xu, Y.; Milligan, I.; Fu, L.; Franckowiak, E. A.; Du, W. *Angewandte Chemie—International Edition* 2013, 52, 13699.
40. Congdon, T.; Wilmet, C.; Williams, R.; Polt, J.; Lilliman, M.; Gibson, M. I. *European Polymer Journal* 2015, 62, 352.
41. Li, F.; Pei, D. F.; Huang, Q. R.; Shi, T. F.; Zhang, G. *Carbohyd Polym* 2014, 99, 728.
42. Xiao, N.; Liang, H.; Lu, J. *Soft Matter* 2011, 7, 10834.
43. Evaluate Ltd. Drug sales database, http://www.evaluategroup.com.
44. Pfister, D.; Morbidelli, M. *J. Controlled Release* 2014, 180, 134.
45. Besheer, A.; Liebner, R.; Meyer, M.; Winter, G. In *Tailored Polymer Architectures for Pharmaceutical and Biomedical Applications*; Scholz, C., Kressler, J., Eds.; Amer Chemical Soc: Washington, 2013; Vol. 1135, p 215.
46. Pelegri-O'Day, E. M.; Lin, E.-W.; Maynard, H. D. *J. Am. Chem. Soc.* 2014, 136, 14323.
47. Chi, E. Y.; Krishnan, S.; Randolph, T. W.; Carpenter, J. F. *Pharm. Res.* 2003, 20, 1325.
48. "FDA Access Data", http://www.accessdata.fda.gov
49. Leader, B.; Baca, Q. J.; Golan, D. E. *Nat. Rev. Drug Discovery* 2008, 7, 39.
50. Keefe, A. J.; Jiang, S. *Nat. Chem.* 2012, 4, 59.
51. Nguyen, T. H.; Kim, S.-H.; Decker, C. G.; Wong, D. Y.; Loo, J. A.; Maynard, H. D. *Nat. Chem.* 2013, 5, 221.
52. Lee, J.; Lin, E.-W.; Lau, U. Y.; Hedrick, J. L.; Bat, E.; Maynard, H. D. *Biomacromolecules* 2013, 14, 2561.
53. Bat, E.; Lee, J.; Lau, U. Y.; Maynard, H. D. *Nature Communications* 2015, 6.
54. Lee, J.; Ko, J. H.; Lin, E.-W.; Wallace, P.; Ruch, F.; Maynard, H. D. *Polym. Chem.* 2015, 6, 3443.
55. Jain, N. K.; Roy, I. *Protein Sci.* 2009, 18, 24.
56. Congdon, T.; Notman, R.; Gibson, M. I. *Biomacromolecules* 2013, 14, 1578.
57. Stidham, S. E.; Chin, S. L.; Dane, E. L.; Grinstaff, M. W. *Journal of the American Chemical Society* 2014, 136, 9544.
58. Hu, J.; Zhao, W.; Gao, Y.; Sun, M.; Wei, Y.; Deng, H.; Gao, W. *Biomaterials* 2015, 47, 13.
59. Hardwicke, J.; Moseley, R.; Stephens, P.; Harding, K.; Duncan, R.; Thomas, D. W. *Mol. Pharmaceutics* 2010, 7, 699.
60. Hardwicke, J. T.; Hart, J.; Bell, A.; Duncan, R.; Thomas, D. W.; Moseley, R. *J. Controlled Release* 2011, 152, 411.
61. Decker, C. G.; Maynard, H. D. *European Polymer Journal* 2015, 65, 305.
62. Slavin, S.; Burns, J.; Haddleton, D. M.; Becer, C. R. *European Polymer Journal* 2011, 47, 435.
63. Campos, L. M.; Killops, K. L.; Sakai, R.; Paulusse, J. M. J.; Damiron, D.; Drockenmuller, E.; Messmore, B. W.; Hawker, C. J. *Macromolecules* 2008, 41, 7063.

64. Ende, A. E. v. d.; Kravitz, E. J.; Harth, E. *Journal of the American Chemical Society* 2008, 130, 8706.
65. Silvers, A. L.; Chang, C.-C.; Emrick, T. *J Polym Sci Pol Chem* 2012, 50, 3517.
66. Parrish, B.; Quansah, J. K.; Emrick, T. *Journal of Polymer Science Part A: Polymer Chemistry* 2002, 40, 1983.
67. Parrish, B.; Breitenkamp, R. B.; Emrick, T. *Journal of the American Chemical Society* 2005, 127, 7404.
68. Pratt, R. C.; Lohmeijer, B. G. G.; Long, D. A.; Waymouth, R. M.; Hedrick, J. L. *Journal of the American Chemical Society* 2006, 128, 4556.
69. Lohmeijer, B. G. G.; Pratt, R. C.; Leibfarth, F.; Logan, J. W.; Long, D. A.; Dove, A. P.; Nederberg, F.; Choi, J.; Wade, C.; Waymouth, R. M.; Hedrick, J. L. *Macromolecules* 2006, 39, 8574.
70. Wang, R.; Chen, W.; Meng, F.; Cheng, R.; Deng, C.; Feijen, J.; Zhong, Z. *Macromolecules* 2011, 44, 6009.
71. Takasu, A.; Houjyou, T.; Inai, Y.; Hirabayashi, T. *Biomacromolecules* 2002, 3, 775.
72. Diamond, R. *J. Mol. Biol.* 1974, 82, 371.
73. Bentley, M. D.; Roberts, M. J.; Harris, J. M. *J. Pharm. Sci.* 1998, 87, 1446.
74. Gomez d'Ayala, G.; Malinconico, M.; Laurienzo, P.; Tardy, A.; Guillaneuf, Y.; Lansalot, M.; D'Agosto, F.; Charleux, B. *J. Polym. Sci., A, Polym. Chem.* 2014, 52, 104.
75. Bailey, W. J.; Wu, S. R.; Ni, Z. *Makromolekulare Chemie-Macromolecular Chemistry and Physics* 1982, 183, 1913.
76. Bailey, W. J.; Ni, Z.; Wu, S. R. *Macromolecules* 1982, 15, 711.
77. Sizovs, A.; Xue, L.; Tolstyka, Z. P.; Ingle, N. P.; Wu, Y.; Cortez, M.; Reineke, T. M. *Journal of the American Chemical Society* 2013, 135, 15417.
78. Johnson, D. A. *Carbohydr. Res.* 1992, 237, 313.
79. Wada, M.; Miyazawa, Y.; Miura, Y. *Polymer Chemistry* 2011, 2, 1822.
80. Kanai, M.; Mortell, K. H.; Kiessling, L. L. *J. Am. Chem. Soc.* 1997, 119, 9931.
81. Gestwicki, J. E.; Cairo, C. W.; Strong, L. E.; Oetjen, K. A.; Kiessling, L. L. *J. Am. Chem. Soc.* 2002, 124, 14922.
82. Ladmiral, V.; Mantovani, G.; Clarkson, G. J.; Cauet, S.; Irwin, J. L.; Haddleton, D. M. *J. Am Chem Soc* 2006, 128, 4823.
83. Paz-Alfaro, K. J.; Ruiz-Granados, Y. G.; Uribe-Carvajal, S.; Sampedro, J. G. *Journal of Biotechnology* 2009, 141, 130.
84. Maity, H.; O'Dell, C.; Srivastava, A.; Goldstein, *J. Curr. Pharm. Biotechnol.* 2009, 10, 761.
85. Bischof, J. C.; He, X. M. In Cell Injury: Mechanisms, Responses, and Repair; Lee, R. C., Despa, F., Hamann, K. J., Eds. 2005; Vol. 1066, p 12.
86. Pikal-Cleland, K. A.; Carpenter, J. F. *J. Pharm. Sci.* 2001, 90, 1255.
87. Sluzky, V.; Tamada, J. A.; Klibanov, A. M.; Langer, R. *Proc. Natl. Acad. Sci. U.S.A* 1991, 88, 9377.
88. Kamerzell, T. J.; Esfandiary, R.; Joshi, S. B.; Middaugh, C. R.; Volkin, D. B. *Adv. Drug Delivery Rev.* 2011, 63, 1118.
89. Arakawa, T.; Timasheff, S. N. *Biophys. J.* 1985, 47, 411.
90. Falconer, R. J.; Chan, C.; Hughes, K.; Munro, T. P. *J. Chem. Technol. Biotechnol.* 2011, 86, 942.
91. Arakawa, T.; Tsumoto, K.; Kita, Y.; Chang, B.; Ejima, D. *Amino Acids* 2007, 33, 587.
92. Chen, B.; Bautista, R.; Yu, K.; Zapata, G. A.; Mulkerrin, M. G.; Chamow, S. M. *Pharm. Res.* 2003, 20, 1952.
93. Fang, W.-J.; Qi, W.; Kinzell, J.; Prestrelski, S.; Carpenter, J. F. *Pharm. Res.* 2012, 29, 3278.
94. Garzon-Rodriguez, W.; Koval, R. L.; Chongprasert, S.; Krishnan, S.; Randolph, T. W.; Warne, N. W.; Carpenter, J. F. *J. Pharm. Sci.* 2004, 93, 684.
95. Martin, N.; Ma, D.; Herbet, A.; Boquet, D.; Winnik, F. M.; Tribet, C. *Biomacromolecules* 2014, 15, 2952.
96. Lee, E.-H.; Tsujimoto, T.; Uyama, H.; Sung, M.-H.; Kim, K.; Kuramitsu, S. *Polym. J.* 2010, 42, 818.
97. Izaki, S.; Kurinomaru, T.; Handa, K.; Kimoto, T.; Shiraki, K. *J. Pharm. Sci.* 2015, 104, 2457.
98. Gombotz, W. R.; Pankey, S. C.; Phan, D.; Drager, R.; Donaldson, K.; Antonsen, K. P.; Hoffman, A. S.; Raff, H. V. *Pharm. Res.* 1994, 11, 624.
99. Taluja, A.; Bae, Y. H. *Mol. Pharmaceutics* 2007, 4, 561.
100. Mazzaferro, L.; Breccia, J. D.; Andersson, M. M.; Hitzmann, B.; Hatti-Kaul, R. *Int. J. Biol. Macromol.* 2010, 47, 15.
101. Andersson, M. A.; Hatti-Kaul, R. *J. Biotechnol.* 1999, 72, 21.
102. Matsusaki, M.; Serizawa, T.; Kishida, A.; Akashi, M. *Biomacromolecules* 2005, 6, 400.
103. Yoshimoto, N.; Hashimoto, T.; Felix, M. M.; Umakoshi, H.; Kuboi, R. *Biomacromolecules* 2003, 4, 1530.
104. Srinivasachari, S.; Liu, Y.; Zhang, G.; Prevette, L.; Reineke, T. M. *J. Am. Chem. Soc.* 2006, 128, 8176.
105. Hershfield, M. S.; Ganson, N. J.; Kelly, S. J.; Scarlett, E. L.; Jaggers, D. A.; Sundy, J. S. *Arthritis Res. Ther.* 2014, 16.
106. Armstrong, J. K.; Hempel, G.; Koling, S.; Chan, L. S.; Fisher, T.; Meiselman, H. J.; Garratty, G. *Cancer* 2007, 110, 103.
107. Rudmann, D. G.; Alston, J. T.; Hanson, J. C.; Heidel, S. *Toxicol. Pathol.* 2013, 41, 970.
108. Pelegri-O'Day, E. M.; Maynard, H. D. *Acc. Chem. Res.* 2016, 49, 1777.
109. Erdem, S. S.; Nesterova, I. V.; Soper, S. A.; Hammer, R. P. *J. Org. Chem.* 2009, 74, 9280.
110. Shu, P.; Zeng, J.; Tao, J.; Zhao, Y.; Yao, G.; Wan, Q. *Green Chem.* 2015, 17, 2545.
111. Yu, M.; Yang, Y.; Han, R.; Zheng, Q.; Wang, L.; Hong, Y.; Li, Z.; Sha, Y. *Langmuir* 2010, 26, 8534.
112. Taniguchi, I.; Mayes, A. M.; Chan, E. W. L.; Griffith, L. G. *Macromolecules* 2005, 38, 216.
113. Lowe, A. B. *Polym. Chem.* 2010, 1, 17.
114. Hoyle, C. E.; Bowman, C. N. *Angew. Chem. Int. Ed.* 2010, 49, 1540.
115. Kamber, N. E.; Jeong, W.; Waymouth, R. M.; Pratt, R. C.; Lohmeijer, B. G. G.; Hedrick, J. L. *Chem. Rev.* 2007, 107, 5813.
116. Stevens, D. M.; Watson, H. A.; LeBlanc, M.-A.; Wang, R. Y.; Chou, J.; Bauer, W. S.; Harth, E. *Polym. Chem.* 2013, 4, 2470.
117. Aoi, K.; Tsutsumiuchi, K.; Okada, M. *Macromolecules* 1994, 27, 875.
118. Takasu, A.; Kojima, H. *J. Polym. Sci., Part A: Polym. Chem.* 2010, 48, 5953.
119. Dong, C. M.; Faucher, K. M.; Chaikof, E. L. *J. Polym. Sci., Part A: Polym. Chem.* 2004, 42, 5754.
120. Cao, Z.; Yu, Q.; Xue, H.; Cheng, G.; Jiang, S. *Angew. Chem. Int. Ed.* 2010, 49, 3771.
121. Aapro, M. S.; Cameron, D. A.; Pettengell, R.; Bohlius, J.; Crawford, J.; Ellis, M.; Kearney, N.; Lyman, G. H.; Tjan-Heijnen, V. C.; Walewski, J.; Weber, D. C.; Zielinski, C.; Eortc, G. C. *Eur. J. Cancer* 2006, 42, 2433.

122. Krishnan, S.; Chi, E. Y.; Webb, J. N.; Chang, B. S.; Shan, D. X.; Goldenberg, M.; Manning, M. C.; Randolph, T. W.; Carpenter, J. F. Biochemistry 2002, 41, 6422.
123. Shirafuji, N.; Asano, S.; Matsuda, S.; Watari, K.; Takaku, F.; Nagata, S. Exp. Hematol. 1989, 17, 116.
124. Wu, J.; Zhao, C.; Lin, W.; Hu, R.; Wang, Q.; Chen, H.; Li, L.; Chen, S.; Zheng, J. J. Mater. Chem. B 2014, 2, 2983.
125. Jayaraman, S.; Gantz, D. L.; Gursky, O. Biochemistry 2004, 43, 5520.
126. Young, D. ISTA Temperature Project—Data Summary; International Safe Transit Association: East Lansing, Mich., 2002
127. Katyal, N.; Deep, S. Physical Chemistry Chemical Physics 2014, 16, 26746.
128. Fedorov, M. V.; Goodman, J. M.; Nerukh, D.; Schumm, S. Phys. Chem. Chem. Phys. 2011, 13, 2294.
129. Woodruff, M. A.; Hutmacher, D. W. Prog. Polym. Sci. 2010, 35, 1217.
130. Leader, B.; Baca, Q. J.; Golan, D. E. Nat. Rev. Drug Discovery 2008, 7, 21.
131. Pan, B.; Abel, J.; Ricci, M. S.; Brems, D. N.; Wang, D. I. C.; Trout, B. L. Biochemistry 2006, 45, 15430.
132. Yin, J.; Chu, J. W.; Ricci, M. S.; Brems, D. N.; Wang, D. I. C.; Trout, B. L. Pharm. Res. 2005, 22, 141.
133. Ohtake, S.; Wang, Y. J. J. Pharm. Sci. 2011, 100, 2020.
134. Niven, R. W.; Prestrelski, S. J.; Treuheit, M. J.; Ip, A. Y.; Arakawa, T. Int. J. Pharm. 1996, 127, 191.
135. Chen, S. F.; Zheng, J.; Li, L. Y.; Jiang, S. Y. J. Am. Chem. Soc. 2005, 127, 14473.
136. Shao, Q.; Jiang, S. Y. Adv. Mater. 2015, 27, 15.
137. Gross, R. A.; Kalra, B. Science 2002, 297, 803.
138. Lees, W. J.; Spaltenstein, A.; Kingerywood, J. E.; Whitesides, G. M. J. Med. Chem. 1994, 37, 3419.
139. Bezwada, R. S.; Jamiolkowski, D. D.; Lee, I. Y.; Agarwal, V.; Persivale, J.; Trenkabenthin, S.; Erneta, M.; Suryadevara, J.; Yang, A.; Liu, S. Biomaterials 1995, 16, 1141.
140. Caliceti, P.; Veronese, F. M. Adv. Drug Deliv. Rev. 2003, 55, 1261.
141. Harris, J. M. & Chess, R. B. Effect of pegylation on pharmaceuticals. Nat Rev Drug Discov 2, 214-221 (2003).
142. Bays, E., Tao, L., Chang, C. W. & Maynard, H. D. Synthesis of Semitelechelic Maleimide Poly(PEGA) for Protein Conjugation by RAFT Polymerization. Biomacromolecules 10, 1777-1781 (2009).
143. Mateo, C. et al. Removal of amphipathic epitopes from genetically engineered antibodies: Production of modified immunoglobulins with reduced immunogenicity. Hybridoma 19, 463-471 (2000).
144. Lyczak, J. B. & Morrison, S. L. Biological and Pharmacokinetic Properties of a Novel Immunoglobulin-Cd4 Fusion Protein. Archives of Virology 139, 189-196 (1994).
145. Syed, S., Schuyler, P. D., Kulczycky, M. & Sheffield, W. P. Potent antithrombin activity and delayed clearance from the circulation characterize recombinant hirudin genetically fused to albumin. Blood 89, 3243-3252 (1997).
146. Cohen, S., Yoshioka, T., Lucarelli, M., Hwang, L. H. & Langer, R. Controlled Delivery Systems for Proteins Based on Poly(Lactic Glycolic Acid) Microspheres. Pharmaceutical Research 8, 713-720 (1991).
147. Abuchowski, A., Mccoy, J. R., Palczuk, N. C., Vanes, T. & Davis, F. F. Effect of Covalent Attachment of PolyethyleneGlycol on Immunogenicity and Circulating Life of Bovine Liver Catalase. Journal of Biological Chemistry 252, 3582-3586 (1977).
148. Wang, W. Lyophilization and development of solid protein pharmaceuticals. International Journal of Pharmaceutics 203, 1-60 (2000).
149. Oobatake, M. & Ooi, T. HYDRATION AND HEAT-STABILITY EFFECTS ON PROTEIN UNFOLDING. Prog. Biophys. Mol. Biol. 59, 237-284 (1993).
150. Maity, H., O'Dell, C., Srivastava, A. & Goldstein, J. Effects of Arginine on Photostability and Thermal Stability of IgG1 Monoclonal Antibodies. Curr. Pharm. Biotechnol. 10, 761-766 (2009).
151. Molineaux, G. Curr. Pharm. Design. 2004, 11, 1235.
152. Decker. C. G.; Maynard, H. D. Eur. Polym. J. 2015, in press.
153. Jain, S.; Hreczuk-Hirst, D. H.; McCormack, B.; Mital, M.; Epenetos, A.; Laing, P.; Gregoriadis, G. Biochim. Biophys. Acta 2003, 1622, 42.
154. Montaperto, A. G.; Gandhi, M. A.; Gashlin, L. Z.; Symoniak, M. R. Curr. Med. Res. Opin. 2016, 32, 155.
155. Abraham, S. C.; Bhagavan, B. S.; Lee, L. A.; Rashid, A.; Wu, T. T. Am. J. Surg. Pathol. 2001, 25, 637.
156. Kerwin, B. A. J. Pharm. Sci. 2008, 97, 2924.
157. Alebouyeh, M.; Tahzibi, A.; Yaghoobzadeh, S.; Zahedy, E. T.; Kiumarsi, S.; Soltanabad, M. H.; Shahbazi, S.; Amini, H. Biologicals 2016, 44, 150.
158. Regev, O.; Zana, R. J. Colloid Interface Sci. 1999, 210, 8.
159. Bruzdziak, P.; Panuszko, A.; Stangret, J. J. Phys. Chem. B 2013, 117, 11502.
160. Street, T. O.; Bolen, D. W.; Rose, G. D. Proc. Natl. Acad. Sci. U.S.A 2006, 103, 13997.

What is claimed is:

1. A biodegradable trehalose or zwitterion polymer, wherein the polymer consists of the general structure:

$$R'\text{-}[DG\text{-}CR^1R^2\text{—}CR^3R^4\text{—}CR^5R^6\text{—}CR^7R^8\text{—}CR^9R^{10}]_m\text{—}R''$$

wherein $R^1$-$R^{10}$ are independently selected from hydrogen or a side chain comprising at least one carbon atom, and wherein at least one of $R^1$-$R^{10}$ is a side chain comprising trehalose, -L-trehalose, -zwitterion or -L-zwitterion, wherein L is a linker molecule that links trehalose or zwitterion to the polymer through the reaction of at least one of the trehalose hydroxyl groups (—OH) or through one end of the zwitterion, wherein DG is a biodegradable group, and wherein R' and R" are end groups, and wherein m≥1.

2. The polymer of claim 1, wherein R' and R" are independently comprising —H, —Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

3. The polymer of claim 1, wherein R' and R" are independently comprising —H, -Alkyl, -Alkenyl, -Alkynyl, azide or biomolecules.

4. The polymer of claim 1, wherein DG comprises at least one ester group.

5. The polymer of claim 1, wherein DG is an ester group in the backbone of the polymer.

6. The polymer of claim 1, the linking molecules L are methylene groups —$(CH_2)_n$— (n=1-1000).

7. The polymer of claim 6, wherein the linking molecules L are methylene groups —$(CH_2)_n$— (n=1-10).

8. The polymer of claim 1, wherein the polymer is

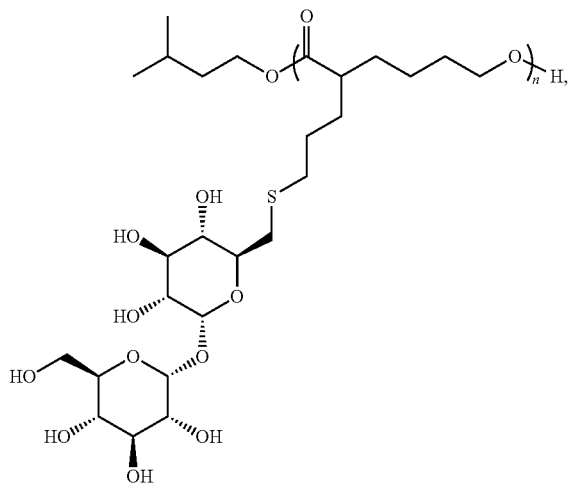

wherein n=1-10000.

9. The polymer of claim 1, wherein the polymer is

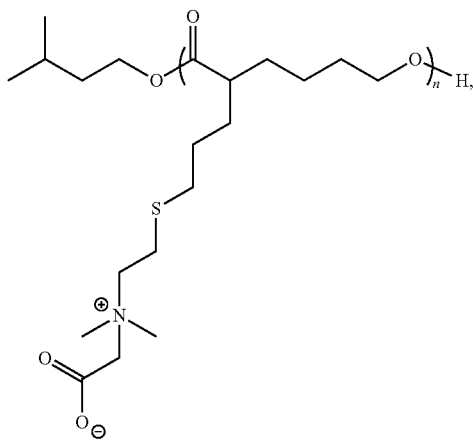

wherein n=1-10000.

10. A biodegradable trehalose or zwitterion polymer, wherein the polymer consists of the general structure: R'—[OOC—$CR^1R^2$—$(CH_2)_m]_n$—OR",
wherein m=0-10, n=1-10000 and $R^1$ and $R^2$ are independently selected from hydrogen or a side chain comprising at least one carbon atom, wherein at least one of $R^1$ and $R^2$ is a side chain comprising -trehalose, -L-trehalose, -zwitterion or -L-zwitterion, wherein L is a linker molecule that links the trehalose or zwitterion to the polymer through the reaction of at least one of the trehalose hydroxyl groups (—OH) or through one end of the zwitterion,
wherein R' and R" are end groups.

11. The polymer of claim 10, wherein R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

12. The polymer of claim 10, wherein R' and R" are independently comprising —H, -Alkyl, -Alkenyl, -Alkynyl, azide or biomolecules.

13. The polymer of claim 10, the linking molecules L are methylene groups —$(CH_2)_n$— (n=1-1000).

14. The polymer of claim 13, wherein the linking molecules L are methylene groups —$(CH_2)_n$— (n=1-10).

15. A biodegradable zwitterion polymer, wherein the polymer consists of the general structure: R—[OOC—$CR^1R^2$—$(CH_2)_m]_n$—OR",
wherein m=0-10, n=1-10000 and $R^1$ and $R^2$ are independently selected from hydrogen or a side chain comprising at least one carbon atom, wherein at least one of $R^1$ and $R^2$ is a side chain comprising -zwitterion or -L-zwitterion, wherein L is a linker molecule that links zwitterion to the polymer through one end of the zwitterion electrical charges,
wherein R' and R" are end groups.

16. The polymer of claim 15, wherein R' and R" are independently comprising —H, -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, azide or biomolecules.

17. The polymer of claim 15, wherein R' and R" are independently comprising —H, -Alkyl, -Alkenyl, -Alkynyl, azide or biomolecules.

18. The polymer of claim 15, the linking molecules L are methylene groups —$(CH_2)_n$— (n=1-1000).

19. The polymer of claim 18, wherein the linking molecules L are methylene groups —$(CH_2)_n$— (n=1-10).

20. The polymer of claim 15, where the zwitterion is an amino acid derivative.

* * * * *

UNITED STATES PATENT AND TRADEMARK OFFICE
CERTIFICATE OF CORRECTION

PATENT NO. : 10,273,333 B2  
APPLICATION NO. : 15/394483  
DATED : April 30, 2019  
INVENTOR(S) : Maynard et al.

Page 1 of 1

It is certified that error appears in the above-identified patent and that said Letters Patent is hereby corrected as shown below:

On the Title Page

Under item (12) "Maynard" should read --Maynard et al.--

Item (72), Inventor: add --Emma M. Pelegri-O'Day, Los Angeles, CA (US)--

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*